US007897762B2

(12) United States Patent
Flynn et al.

(10) Patent No.: US 7,897,762 B2
(45) Date of Patent: Mar. 1, 2011

(54) KINASE INHIBITORS USEFUL FOR THE TREATMENT OF PROLIFERATIVE DISEASES

(75) Inventors: Daniel L. Flynn, Lawrence, KS (US); Peter A. Petillo, Lawrence, KS (US); Michael D. Kaufman, Lawrence, KS (US); William C. Patt, Lawrence, KS (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 174 days.

(21) Appl. No.: 11/854,293

(22) Filed: Sep. 12, 2007

(65) Prior Publication Data

US 2009/0099190 A1 Apr. 16, 2009

Related U.S. Application Data

(60) Provisional application No. 60/844,552, filed on Sep. 14, 2006.

(51) Int. Cl.
*A61K 31/519* (2006.01)
*C07D 487/04* (2006.01)
(52) U.S. Cl. .................................. 544/256; 514/262.1
(58) Field of Classification Search .................. 544/256; 514/262.1
See application file for complete search history.

(56) References Cited

U.S. PATENT DOCUMENTS

| 6,150,373 | A | 11/2000 | Harris et al. |
| 7,112,676 | B2 | 9/2006 | Dermatakis et al. |
| 2004/0019210 | A1 | 1/2004 | Chivikas Connolly et al. |
| 2005/0222177 | A1 | 10/2005 | Sim et al. |
| 2006/0004011 | A1 | 1/2006 | Ladouceur et al. |
| 2008/0114006 | A1 | 5/2008 | Flynn et al. |

FOREIGN PATENT DOCUMENTS

| WO | WO 99/32111 | 7/1999 |
| WO | WO 99/32455 | 7/1999 |
| WO | WO 01/19828 | 3/2001 |
| WO | WO 03/068223 | 8/2002 |
| WO | WO 2004/061084 | 7/2004 |
| WO | WO 2006/071940 | 7/2006 |
| WO | WO 2006/081034 | 8/2006 |
| WO | WO 2008/051757 | 5/2008 |

OTHER PUBLICATIONS

Peyssonnaux, C. et al, "The Raf/MEK/ERK pathway: new concepts of activation," *Biol. Cell* (2001) 93: 53-62.
Bolton et al, "Chapter 17. Ras Oncogene Directed Approaches in Cancer Chemotherapy," *Ann. Rep. Med. Chem.* (1994) 29: 165-174.
Magnuson et al, "The Raf-1 serine/threonine protein kinase," *Seminars in Cancer Biology.* (1994) 5: 247-253.
Avruch, J. et al., "Ras Activation of the Raf Kinase: Tyrosine Kinase Recruitment of the MAP Kinase Cascade," *Recent Prog. Horm. Res.* (2001) 56: 127-155.
Kolch, W., "Meaningful relationships: the regulation of the Ras/Raf/MEK/ERK pathway by protein interactions," *Biochem. J.* (2000) 351: 289-305.
Davies, H. et al, "Mutations of the BRAF gene in human cancer," *Nature* (Jun. 2002) 417: 949-954.
Lowinger et al, "Design and Discovery of Small Molecules Targeting Raf-1 Kinase," *Current Pharmaceutical Design* (2002) 8: 2269-2278.
Dumas, J. et al, "Recent developments in the discovery of protein kinase inhibitors from the urea class," *Current Opinion in Drug Discovery & Development* (2004) 7 (5): 600-616.
Wan, P.T.C. et al, "Mechanism of Activation of the RAF-ERK Signaling Pathway by Oncogenic Mutations of B-RAF," *Cell* (Mar. 2004) 116: 855-867.
Huse, M. et al, "The Conformational Plasticity of Protein Kinases," *Cell* (May 2002) 109: 275-282.
Ettmayer et al, "Lessons Learned from Marketed and Investigational Prodrugs," *J. Med. Chem* (May 2004) 47 (10): 2393-2404.
Lorenzi et al, "Amino Acid Ester Prodrugs of 2-Bromo-5,6-dichloro-1-($\beta$-D-ribofuranosyl)benzimidazole Enhance Metabolic Stability in Vitro and In Vivo," *J. Pharm. Exp. Therpeutics* (2005) 314 (2): 883-890.
Chan et al, "Copper promoted C-N and C-O bond dross-coupling with phenyl and pyridylboronates," *Tetrahedron Lett.* (2003) 44: 3863-3865.
Chan et al, "New N- and O-Arylations with Phenylboronic Acids and Cupric Acetate," *Tetrahedron Lett.* (1998) 39: 2933-2936.
Chan, D. M. T., "Promotion of Reaction of N-H Bonds with Triatylbismuth and Cupric Acetate," *Tetrahedron Lett.* (1996) 37 (50): 9013-9016.
Seto, et al, "2-Substituted-4-aryl-6,7,8,9-tetrahydro-5$H$-pyrimido [4,5-$b$] [1,5]oxazocin-5-one as a structurally new NK$_1$ antagonist," *Biorg. Med. Chem. Lett.* (2005) 15: 1485-1488.

(Continued)

*Primary Examiner* — Rebecca L Anderson
*Assistant Examiner* — Samantha L Shterengarts
(74) *Attorney, Agent, or Firm* — James J. Sales

(57) ABSTRACT

The present invention relates to novel kinase inhibitors and modulator compounds useful for the treatment of various diseases. More particularly, the invention is concerned with such compounds, kinase/compound adducts, methods of treating diseases, and methods of synthesis of the compounds. Preferably, the compounds are useful for the modulation of kinase activity of Raf kinases and disease polymorphs thereof. Compounds of the present invention find utility in the treatment of mammalian cancers and especially human cancers including but not limited to malignant melanoma, colorectal cancer, ovarian cancer, papillary thyroid carcinoma, non small cell lung cancer, and mesothelioma. Compounds of the present invention also find utility in the treatment of rheumatoid arthritis and retinopathies including diabetic retinal neuropathy and macular degeneration.

93 Claims, No Drawings

OTHER PUBLICATIONS

Pierrat et al, "Solid Phase Synthesis of Pyridine-Based Derivatives from a 2-Chloro-5-Bromopyridine Scaffold," *J. Comb. Chem.* (2005) 7 (6): 879-886.

Kroon et al, "Deazapurine derivatives XV. Syntheses of some mono- and difluoroimidazo[4,5-*b*]- and -4,5-*c*lpyridines," *Recueil des Travaux Chimiques des Pays-Bas* (Jun. 1976) 95: 127-129.

O'Brien, et al, "Pyrimidines. XVI. 2,4,5-Triaminopyrimidines and Related Compounds," *J. Med Chem.* (Jan. 1966) 9:121-126.

Schindler, et al, "Structural Mechanism for STI-571 Inhibition of Abelson Tyrosine Kinase," *Science* (Sep. 2000) 289: 1938-1942.

SEQUENCE LISTING

<160> NUMBER OF SEQ ID NOS: 2

<210> SEQ ID NO 1
<211> LENGTH: 294
<212> TYPE: PRT
<213> ORGANISM: Homo sapiens
<220> FEATURE:
<221> NAME/KEY: MISC_FEATURE
<223> OTHER INFORMATION: B-Raf(V600E)

<400> SEQUENCE: 1

Glu Asp Arg Asn Arg Met Lys Thr Leu Gly Arg Arg Asp Ser Ser Asp
1               5                   10                  15

Asp Trp Glu Ile Pro Asp Gly Gln Ile Thr Val Gly Gln Arg Ile Gly
            20                  25                  30

Ser Gly Ser Phe Gly Thr Val Tyr Lys Gly Lys Trp His Gly Asp Val
        35                  40                  45

Ala Val Lys Met Leu Asn Val Thr Ala Pro Thr Pro Gln Gln Leu Gln
    50                  55                  60

Ala Phe Lys Asn Glu Val Gly Val Leu Arg Lys Thr Arg His Val Asn
65                  70                  75                  80

Ile Leu Leu Phe Met Gly Tyr Ser Thr Lys Pro Gln Leu Ala Ile Val
                85                  90                  95

Thr Gln Trp Cys Glu Gly Ser Ser Leu Tyr His His Leu His Ile Ile
            100                 105                 110

Glu Thr Lys Phe Glu Met Ile Lys Leu Ile Asp Ile Ala Arg Gln Thr
        115                 120                 125

Ala Gln Gly Met Asp Tyr Leu His Ala Lys Ser Ile Ile His Arg Asp
    130                 135                 140

-continued

```
Leu Lys Ser Asn Asn Ile Phe Leu His Glu Asp Leu Thr Val Lys Ile
145                 150                 155                 160

Gly Asp Phe Gly Leu Ala Thr Glu Lys Ser Arg Trp Ser Gly Ser His
                165                 170                 175

Gln Phe Glu Gln Leu Ser Gly Ser Ile Leu Trp Met Ala Pro Glu Val
            180                 185                 190

Ile Arg Met Gln Asp Lys Asn Pro Tyr Ser Phe Gln Ser Asp Val Tyr
        195                 200                 205

Ala Phe Gly Ile Val Leu Tyr Glu Leu Met Thr Gly Gln Leu Pro Tyr
    210                 215                 220

Ser Asn Ile Asn Asn Arg Asp Gln Ile Ile Phe Met Val Gly Arg Gly
225                 230                 235                 240

Tyr Leu Ser Pro Asp Leu Ser Lys Val Arg Ser Asn Cys Pro Lys Ala
                245                 250                 255

Met Lys Arg Leu Met Ala Glu Cys Leu Lys Lys Lys Arg Asp Glu Arg
            260                 265                 270

Pro Leu Phe Pro Gln Ile Leu Ala Ser Ile Glu Leu Leu Ala Arg Ser
        275                 280                 285

Leu Pro Lys Ile His Arg
    290

<210> SEQ ID NO 2
<211> LENGTH: 333
<212> TYPE: PRT
<213> ORGANISM: Homo sapiens
<220> FEATURE:
<221> NAME/KEY: MISC_FEATURE
<223> OTHER INFORMATION: MEK1

<400> SEQUENCE: 2

Met Glu Leu Lys Asp Asp Asp Phe Glu Lys Ile Ser Glu Leu Gly Ala
1               5                   10                  15

Gly Asn Gly Gly Val Val Phe Lys Val Ser His Lys Pro Ser Gly Leu
            20                  25                  30

Val Met Ala Arg Lys Leu Ile His Leu Glu Ile Lys Pro Ala Ile Arg
        35                  40                  45

Asn Gln Ile Ile Arg Glu Leu Gln Val Leu His Glu Cys Asn Ser Pro
    50                  55                  60

Tyr Ile Val Gly Phe Tyr Gly Ala Phe Tyr Ser Asp Gly Glu Ile Ser
65                  70                  75                  80

Ile Cys Met Glu His Met Asp Gly Gly Ser Leu Asp Gln Val Leu Lys
                85                  90                  95

Lys Ala Gly Arg Ile Pro Glu Gln Ile Leu Gly Lys Val Ser Ile Ala
            100                 105                 110

Val Ile Lys Gly Leu Thr Tyr Leu Arg Glu Lys His Lys Ile Met His
        115                 120                 125

Arg Asp Val Lys Pro Ser Asn Ile Leu Val Asn Ser Arg Gly Glu Ile
    130                 135                 140

Lys Leu Cys Asp Phe Gly Val Ser Gly Gln Leu Ile Asp Ser Met Ala
145                 150                 155                 160

Asn Ser Phe Val Gly Thr Arg Ser Tyr Met Ser Pro Glu Arg Leu Gln
                165                 170                 175

Gly Thr His Tyr Ser Val Gln Ser Asp Ile Trp Ser Met Gly Leu Ser
            180                 185                 190

Leu Val Glu Met Ala Val Gly Arg Tyr Pro Ile Pro Pro Pro Asp Ala
        195                 200                 205
```

```
Lys Glu Leu Glu Leu Met Phe Gly Cys Gln Val Glu Gly Asp Ala Ala
    210             215                 220

Glu Thr Pro Pro Arg Pro Arg Thr Pro Gly Arg Pro Leu Ser Ser Tyr
225             230                 235                 240

Gly Met Asp Ser Arg Pro Pro Met Ala Ile Phe Glu Leu Leu Asp Tyr
                245                 250                 255

Ile Val Asn Glu Pro Pro Pro Lys Leu Pro Ser Gly Val Phe Ser Leu
            260             265                 270

Glu Phe Gln Asp Phe Val Asn Lys Cys Leu Ile Lys Asn Pro Ala Glu
        275             280                 285

Arg Ala Asp Leu Lys Gln Leu Met Val His Ala Phe Ile Lys Arg Ser
    290             295                 300

Asp Ala Glu Glu Val Asp Phe Ala Gly Trp Leu Cys Ser Thr Ile Gly
305             310             315                 320

Leu Asn Gln Pro Ser Thr Pro Thr His Ala Ala Gly Val
                325             330
```

KINASE INHIBITORS USEFUL FOR THE TREATMENT OF PROLIFERATIVE DISEASES

CROSS-REFERENCE TO RELATED APPLICATIONS

This application claims the benefit of Provisional Application 60/844,552 filed Sep. 14, 2006. This application is incorporated by reference herein.

FIELD OF THE INVENTION

The present invention relates to novel kinase inhibitors and modulator compounds useful for the treatment of various diseases. More particularly, the invention is concerned with such compounds, methods of treating diseases, and methods of synthesis of the compounds. Preferably, the compounds are useful for the modulation of kinase activity of Raf kinases and disease polymorphs thereof.

BACKGROUND OF THE INVENTION

Several members of the protein kinase family have been clearly implicated in the pathogenesis of various proliferative diseases and thus represent important targets for treatment of these diseases. Some of the proliferative diseases relevant to this invention include cancer, rheumatoid arthritis, atherosclerosis, and retinopathies. Important examples of kinases which have been shown to cause or contribute to the pathogenesis of these diseases including, but not limited to, are BRaf, CRaf, Abl, KDR(VEGF), EGFR/HER1, HER2, HER3, cMET, FLT-3, PDGFR-a, PDGFR-b, p38, cKIT, and JAK2.

A major signaling pathway downstream of cell surface growth factor receptor activation is the Ras-RAF-MEK-ERK-MAP kinase pathway (Peyssonnaux, C. et al, *Biol. Cell* (2001) 93: 53-62, Cancers arise when mutations occur in one or more of the proteins involved in this signaling cascade. Cell proliferation and differentiation become dysregulated and cell survival mechanisms are activated which allow unregulated cancer cells to override protective programmed cell death surveillance. Mutations in the p21-Ras protein have been shown to be a major cause of dysregulation of this signaling pathway, leading to the development of human cancers. P21-Ras mutations have been identified in approximately 30% of human cancers (Bolton et al, *Ann. Rep. Med. Chem.* (1994) 29: 165-174). Cancer-causing mutations in the P21-Ras protein lead to a constitutively active signaling cascade, causing unregulated activation of the downstream components of the RAF-MEK-ERK-MAP kinase pathway (Magnuson et al., *Semin. Cancer Biol.* (1994) 5: 247-253). The three RAF kinases which participate in this signaling cascade are known as ARAF, BRAF, and CRAF (Peyssonnaux, C. et al, *Biol. Cell* (2001) 93: 53-62; Avruch, J., *Recent Prog. Horm. Res.* (2001) 56: 127-155; Kolch, W., *Biochem. J.* (2000) 351: 289-305). These RAF kinase isoforms are all activated by Ras, and thus are activated in cancers that result from mutated and upregulated p21-Ras protein activity. In addition to activation of this signaling cascade at the initial p21-Ras protein level, mutations have also been found in BRAF kinase which results in activation of the cascade downstream from p21-Ras (Davies, H., et al, *Nature* (2002) 417: 949-954). A dominant single site mutation at position 600 in the BRAF kinase was shown to be particularly aggressive and linked to approximately 80% of the observed human malignant melanomas. This mutation substitutes the negatively charged amino acid glutamic acid for the normally occurring neutral amino acid valine. This single site mutation is sufficient to render the mutated BRAF kinase constitutively active, resulting in signaling pathway dysregulation and human cancer. Hence small molecule inhibitors of BRAF kinase are a rational approach to the treatment of human malignancy, whether the signaling mutation is at the level of the upstream p21-Ras protein or at the level of BRAF kinase.

The majority of small molecule kinase inhibitors that have been reported have been shown to bind in one of three ways. Most of the reported inhibitors interact with the ATP binding domain of the active site and exert their effects by competing with ATP for occupancy. Other inhibitors have been shown to bind to a separate hydrophobic region of the protein known as the "DFG-in-conformation" pocket, and still others have been shown to bind to both the ATP domain and the "DFG-in-conformation" pocket. Examples specific to inhibitors of RAF kinases can be found in Lowinger et al, *Current Pharmaceutical Design* (2002) 8: 2269-2278; Dumas, J. et al., *Current Opinion in Drug Discovery & Development* (2004) 7: 600-616; Dumas, J. et al, WO 2003068223 A1 (2003); Dumas, J., et al, WO 9932455 A1 (1999), and Wan, P. T. C., et al, *Cell* (2004)116: 855-867.

Physiologically, kinases are regulated by a common activation/deactivation mechanism wherein a specific activation loop sequence of the kinase protein binds into a specific pocket on the same protein which is referred to as the switch control pocket (see Flynn, D. et al WO 2004/061084 for further details). Such binding occurs when specific amino acid residues of the activation loop are modified for example by phosphorylation, oxidation, or nitrosylation. The binding of the activation loop into the switch pocket results in a conformational change of the protein into its active form (Huse, M. and Kuriyan, J. *Cell* (109) 275-282.)

SUMMARY OF THE INVENTION

Compounds of the present invention find utility in the treatment of mammalian cancers and especially human cancers including but not limited to malignant melanoma, colorectal cancer, ovarian cancer, papillary thyroid carcinoma, lung cancers, kidney cancers, pancreatic cancer, glioblastomas, myeloproliferative diseases, and mesothelioma. Compounds of the present invention also find utility in the treatment of inflammatory diseases including rheumatoid arthritis, retinopathies including diabetic retinal neuropathy and macular degeneration, cardiovascular disease and metabolic diseases.

DESCRIPTION OF THE PREFERRED EMBODIMENTS

The following descriptions refer to various compounds and moieties thereof.

Carbocyclyl refers to carbon rings taken from cyclopropyl, cyclobutyl, cyclopentyl, cyclohexyl, cycloheptanyl, cyclooctanyl, norboranyl, norborenyl, bicyclo[2.2.2]octanyl, and bicyclo[2.2.2]octenyl;

Halogen refers to fluorine, chlorine, bromine and iodine;

Aryl refers to monocyclic or fused bicyclic ring systems characterized by delocalized π electrons (aromaticity) shared among the ring carbon atoms of at least one carbocyclic ring; preferred aryl rings are taken from phenyl, naphthyl, tetrahydronaphthyl, indenyl, and indanyl;

Heteroaryl refers to monocyclic or fused bicyclic ring systems characterized by delocalized π electrons (aromaticity) shared among the ring carbon or heteroatoms including nitrogen, oxygen, or sulfur of at least one carbocyclic or heterocyclic ring; heteroaryl rings are taken from, but not limited to, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, triazinyl, indolyl, indolinyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, pyrazolopyridinyl, imidazolonopyridinyl, thiazolopyridinyl, thiazolonopyridinyl, oxazolopyridinyl, oxazolonopyridinyl, isoxazolopyridinyl, isothiazolopyridinyl, triazolopyridinyl, imidazopyrimidinyl, pyrazolopyrimidinyl, imidazolonopyrimidinyl, thiazolopyridiminyl, thiazolonopyrimidinyl, oxazolopyridiminyl, oxazolonopyrimidinyl, isoxazolopyrimidinyl, isothiazolopyrimidinyl, triazolopyrimidinyl, dihydropurinonyl, pyrrolopyrimidinyl, purinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalaziniyl, benzodioxyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, or benzoxazopinyl;

Heterocyclyl refers to monocyclic rings containing carbon and heteroatoms taken from oxygen, nitrogen, or sulfur and wherein there is not delocalized π electrons (aromaticity) shared among the ring carbon or heteroatoms; heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl;

Poly-aryl refers to two or more monocyclic or fused aryl bicyclic ring systems characterized by delocalized π electrons (aromaticity) shared among the ring carbon atoms of at least one carbocyclic ring wherein the rings contained therein are optionally linked together;

Poly-heteroaryl refers to two or more monocyclic or fused bicyclic systems characterized by delocalized π electrons (aromaticity) shared among the ring carbon or heteroatoms including nitrogen, oxygen, or sulfur of at least one carbocyclic or heterocyclic ring wherein the rings contained therein are optionally linked together, wherein at least one of the monocyclic or fused bicyclic rings of the poly-heteroaryl system is taken from heteroaryl as defined broadly above and the other rings are taken from either aryl, heteroaryl, or heterocyclyl as defined broadly above;

Poly-heterocyclyl refers to two or more monocyclic or fused bicyclic ring systems containing carbon and heteroatoms taken from oxygen, nitrogen, or sulfur and wherein there is not delocalized π electrons (aromaticity) shared among the ring carbon or heteroatoms wherein the rings contained therein are optionally linked, wherein at least one of the monocyclic or fused bicyclic rings of the poly-heteroaryl system is taken from heterocyclyl as defined broadly above and the other rings are taken from either aryl, heteroaryl, or heterocyclyl as defined broadly above;

Lower alkyl refers to straight or branched chain C1-C6alkyls;

Substituted in connection with a moiety refers to the fact that a further substituent may be attached to the moiety to any acceptable location on the moiety.

The term salts embraces pharmaceutically acceptable salts commonly used to form alkali metal salts of free acids and to form addition salts of free bases. The nature of the salt is not critical, provided that it is pharmaceutically-acceptable. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, and heterocyclyl containing carboxylic acids and sulfonic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methane sulfonic, ethanesulfonic, 2-hydroxyethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid. Suitable pharmaceutically-acceptable salts of free acid-containing compounds of the invention include metallic salts and organic salts. More preferred metallic salts include, but are not limited to appropriate alkali metal (group Ia) salts, alkaline earth metal (group IIa) salts and other physiological acceptable metals. Such salts can be made from aluminum, calcium, lithium, magnesium, potassium, sodium and zinc. Preferred organic salts can be made from primary amines, secondary amines, tertiary amines and quaternary ammonium salts, including in part, tromethamine, diethylamine, tetra-N-methylammonium, N,N'-dibenzylethylenediamine, chloroprocaine, choline, diethanolamine, ethylenediamine, meglumine (N-methylglucamine) and procaine.

The term prodrug refers to derivatives of active compounds which revert in vivo into the active form. For example, a carboxylic acid form of an active drug may be esterified to create a prodrug, and the ester is subsequently converted in vivo to revert to the carboxylic acid form. See Ettmayer et. al, *J. Med. Chem,* 2004, 47(10), 2393-2404 and Lorenzi et. al, *J. Pharm. Exp. Therapeutics,* 2005, 883-8900 for reviews.

1. First Aspect of the Invention—Compounds, Preparations and Methods

In the first aspect of the invention, compounds are of the formula Ia

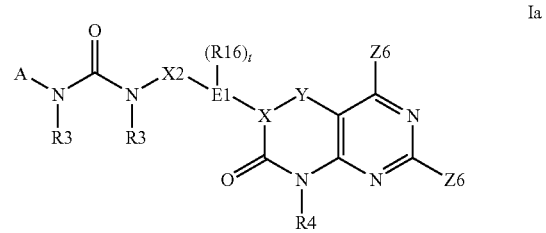

wherein X—Y in order is C=N or N—CH2;

wherein E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;

wherein A is selected from the group consisting of phenyl, naphthyl, C3-C8-carbocyclyl, indanyl, tetralinyl, indenyl, G1, G2, G3, G4 and —CHR4R8;

G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl;

G2 is a fused bicyclic heteroaryl taken from the group consisting of indolyl, indolinyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, pyrazolopyridinyl, imidazolonopyridinyl, thiazolopyridinyl, thiazolonopyridinyl, oxazolopyridinyl, oxazolonopyridinyl, isoxazolopyridinyl, isothiazolopyridinyl, triazolopyridinyl, imidazopyrimidinyl, pyrazolopyrimidinyl, imidazolonopyrimidinyl, thiazolopyridiminyl, thiazolonopyrimidinyl, oxazolopyridiminyl, oxazolonopyrimidinyl, isoxazolopyrimidinyl, isothiazolopyrimidinyl, triazolopyrimidinyl, dihydropurinonyl, pyrrolopyrimidinyl, purinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, and benzoxazepinyl;

G3 is a non-fused bicyclic heteroaryl taken from the group consisting of pyridylpyridiminyl pyrimidinylpyrimidinyl, oxazolylpyrimidinyl, thiazolylpyrimidinyl, imidazolylpyrimidinyl, isoxazolylpyrimidinyl, isothiazolylpyrimidinyl, pyrazolylpyrimidinyl, triazolylpyrimidinyl, oxadiazoylpyrimidinyl, thiadiazoylpyrimidinyl, morpholinylpyrimidinyl, dioxothiomorpholinylpyrimidinyl, and thiomorpholinylpyrimidinyl;

G4 is a heterocyclyl taken from the group consisting of oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl;

the A ring may be optionally substituted with one or more —X1-A1 moieties;

X1 is selected from the group consisting of —(CH$_2$)$_n$—(O)$_r$—(CH$_2$)$_n$—, —(CH$_2$)$_n$—(NR3)$_r$-(CH$_2$)$_n$—, —(CH$_2$)$_n$—(S)$_r$—(CH$_2$)$_n$—, —(CH$_2$)$_n$—(C═O)$_r$—(CH$_2$)$_n$—, —(CH$_2$)—(C(═O)—NR3)$_r$-(CH$_2$)$_n$—, and —(CH$_2$))—(SO$_2$—NR3)$_r$-(CH$_2$)$_n$—, wherein any of the alkylenes may be straight or branched chain;

X2 is selected from the group consisting of C1-C6alkyl, branched C2-C6alkyl, and a direct bond wherein E1 is directly linked to the NR3 group of formula Ia;

A1 is selected from the group consisting of hydrogen, aryl, G1, G2, G3, G4, C1-C6 alkyl, branched C3-C8alkyl, R19 substituted C3-C8-carbocyclyl, fluoroC1-C6alkyl wherein the alkyl is fully or partially fluorinated, halogen, cyano, hydroxyl, —N(R4)$_2$, —R5, —C(O)N(R4)$_2$, C(O)R5, C1-C6alkoxy, and fluoroC1-C6alkoxy wherein the alkyl group is fully or partially fluorinated;

When A and A1 have one or more substitutable sp2-hybridized carbon atom, each respective sp2 hybridized carbon atom may be optionally substituted with a Z1 or Z3 substituent;

when A and A1 have one or more substitutable sp3-hybridized carbon atom, each respective sp3 hybridized carbon atom may be optionally substituted with a Z2 or R3 substituent;

when A and A1 have one or more substitutable nitrogen atom, each respective nitrogen atom may be optionally substituted with a Z4 substituent;

each Z1 is independently and individually selected from the group consisting of hydrogen, hydroxyC1-C6alkyl, C1-C6alkoxy, C1-C6 alkoxyC1-C6alkyl, (R4)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—C(═O)—, (R4)$_2$N—C(═O)—, (R4)$_2$N—CO—C1-C6alkyl-, C1-C6alkoxycarbonyl-, -carboxyC1-C6alkyl, C1-C6alkoxycarbonylC1-C6alkyl, (R3)$_2$NSO$_2$—, —SOR3, (R4)$_2$NSO$_2$—, —SO$_2$R3, —SOR4, —C(═O)R6, —C(═NOH)R6, —C(═NOR3)R6, —(CH$_2$)$_n$N(R4)C(O)R8, —(CH$_2$)$_n$-G1, —(CH$_2$)$_n$-G4, phenoxy, —(CH$_2$), —O—(CH$_2$)$_n$-G1, —(CH$_2$)$_n$—O—(CH$_2$)$_n$-G4, —(CH$_2$), —NR3-(CH$_2$)$_n$-aryl, —(CH$_2$), —NR3-(CH$_2$)$_n$-G1, —(CH$_2$), —NR3-(CH$_2$)$_n$-G4, —S(O)$_2$R5, —N═S(O)R6R8, —S(O)(═NR3)R6, —(CH$_2$)$_n$NHC(O)NHS(O)$_2$R8, —(CH$_2$)$_n$NHS(O)$_2$NHC(O)R8, —C(O)NHS(O)$_2$R8, —S(O)$_2$NHC(O)R8, —(CH$_2$)$_n$NHC(O)(CH$_2$)$_n$R5, —(CH$_2$)$_n$NHS(O)$_2$(CH$_2$)$_n$R5, —(CH$_2$)$_n$C(O)NH(CH$_2$)$_q$R5, —(CH$_2$)$_n$C(O)R5, —(CH$_2$)$_n$OC(O)R5, —(CH$_2$)$_n$S(O)$_2$NH(CH$_2$)$_q$R5, —CH(OH)(CH$_2$)$_p$R5, —CH(OH)CH(OH)R4, —(CH$_2$)$_n$N(R4)$_2$, —(CH$_2$)$_n$R5, —C(═NH)R5, —C(═NH)N(R4)$_2$, —C(═NOR3)R5, —C(═NOR3)N(R4)$_2$, and —NHC(═NH)R8;

in the event that Z1 contains an alkyl or alkylene moiety, such moieties may be further substituted with one or more C1-C6alkyls;

each Z2 is independently and individually selected from the group consisting of hydrogen, aryl, C1-C6alkyl, C3-C8carbocyclyl, hydroxyl, hydroxyC1-C6alkyl-, cyano, (R3)$_2$N—, (R4)$_2$N—, (R4)$_2$NC1-C6alkyl-, (R4)$_2$NC2-C6alkylN(R4)-(CH$_2$)$_n$—, (R4)$_2$NC2-C6alkylO-(CH$_2$)$_n$—, (R3)$_2$N—C(═O)—, (R4)$_2$N—C(═O)—, (R4)$_2$N—CO—C1-C6alkyl-, carboxyl, carboxyC1-C6alkyl, C1-C6alkoxycarbonyl, C1-C6alkoxycarbonylC1-C6alkyl, (R3)$_2$NSO$_2$—, (R4)$_2$NSO$_2$—, —SO$_2$R5, —SO$_2$R8, —(CH$_2$)$_n$N(R4)C(O)R8, —C(O)R8, ═O, ═NOH, ═N(OR6), —(CH$_2$)$_n$-G1, —(CH$_2$)$_n$-G4, —(CH$_2$)$_n$—O—(CH$_2$)$_n$-G1, —(CH$_2$)$_n$—O—(CH$_2$)$_n$-G4, —(CH$_2$)$_n$—NR3-(CH$_2$)$_n$-aryl, —(CH$_2$)$_n$—NR3-(CH$_2$)$_n$-G1, —(CH$_2$)$_n$—NR3-(CH$_2$)$_n$-G4, —(CH$_2$)$_n$NHC(O)NHS(O)$_2$R8, —(CH$_2$)$_n$NHS(O)$_2$NHC(O)R8, —C(O)NHS(O)$_2$R8, —(CH$_2$)NHC(O)(CH$_2$)$_n$R5, —(CH$_2$)$_n$NHS(O)$_2$R5, —(CH$_2$)$_n$C(O)NH(CH$_2$)$_q$R5, —(CH$_2$)$_n$C(O)R5, —(CH$_2$)$_n$OC(O)R5, and —(CH$_2$)$_n$R5;

in the event that Z2 contains an alkyl or alkylene moiety, such moieties may be further substituted with one or more C1-C6alkyls;

each Z3 is independently and individually selected from the group consisting of H, C1-C6alkyl, branched C3-C7alkyl, C3-C8carbocyclyl, halogen, fluoroalkyl wherein the alkyl moiety can be partially or fully fluorinated, cyano, hydroxyl, methoxy, oxo, (R3)$_2$N—C(═O)—, (R4)$_2$N—C(═O)—, —NNR3-(CH(═O)R8, (R3)$_2$NSO$_2$—, (R4)$_2$NSO$_2$—, —N(R4)SO$_2$R5, —N(R4)SO$_2$R8, —(CH$_2$)$_n$—N(R3)$_2$, —(CH$_2$)$_n$—N(R4)$_2$, —O—(CH$_2$)$_q$—N(R4)$_2$, —O—(CH$_2$)$_q$—O-alkyl, —N(R3)-(CH$_2$)$_q$—O-alkyl, —N(R3)-(CH$_2$)$_q$—N(R4)$_2$, —O—(CH$_2$)$_q$—R5, N(R3)-(CH$_2$)$_q$—R5, —C(═O)R5, —C(═O)R8, and nitro;

in the event that Z3 contains an alkyl or alkylene moiety, such moieties may be further substituted with one or more C1-C6alkyls;

each Z4 is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C1-C6alkyl, carboxyC1-C6alkyl, C1-C6alkoxycarbonylC1-C6alkyl, —C2-C6alkylN(R4)C(O)R8, R8—C(=NR3)-, —SO$_2$R8, —COR8, —(CH$_2$)$_n$-G1, —(CH$_2$)$_n$-G4, —(CH$_2$)$_q$—O—(CH$_2$)$_n$-G1, —(CH$_2$)$_q$—O—(CH$_2$)$_n$-G4, —(CH$_2$)$_q$—NR3-(CH$_2$)$_n$-G1, —(CH$_2$)$_q$—NR3-(CH$_2$)$_n$-G4, —(CH$_2$)$_q$NHC(O)(CH$_2$)$_n$R5, —(CH$_2$)$_q$C(O)NH(CH$_2$)$_q$R5, —(CH$_2$)$_q$C(O)R5, —(CH$_2$)$_q$OC(O)R5, —(CH$_2$)$_q$R5, —(CH$_2$)$_q$NR4(CH$_2$)$_q$R5, and —(CH$_2$)$_q$O(CH$_2$)$_q$R5;

in the event that Z4 contains an alkyl or alkylene moiety, such moieties may be further substituted with one or more C1-C6alkyls;

each Z6 is independently and individually selected from the group consisting of H, C1-C6alkyl, branched C3-C7alkyl, hydroxyl, C1-C6alkoxy, —OR4, C1-C6alkylthio, (R3)$_2$N—, (R4)$_2$N—, —N(R3)COR8, —N(R4)COR8, —N(R3)SO$_2$R6-, —CON(R3)$_2$, —CON(R4)$_2$, —COR5, —SO$_2$N(R4)$_2$, halogen, fluoroC1-C6alkyl wherein the alkyl is fully or partially fluorinated, cyano, fluoroC1-C6alkoxy wherein the alkyl is fully or partially fluorinated, —O—(CH$_2$)$_q$—N(R4)$_2$, —N(R3)-(CH$_2$)$_q$—N(R4)$_2$, —O—(CH$_2$)$_q$—O-alkyl, —N(R3)-(CH$_2$)$_q$—O-alkyl, —O—(CH$_2$)$_q$—R5, —N(R3)-(CH$_2$)$_q$—R5, —(NR3)$_r$—, —(CH$_2$)$_n$—R17, —(O)$_r$—R17, —(S)$_r$—R17, and —(CH$_2$)$_r$—R17;

in the event that Z6 contains an alkyl or alkylene moiety, such moieties may be further substituted with one or more C1-C6alkyls;

wherein each R3 is independently and individually selected from the group consisting of H, C1-C6alkyl, branched C3-C7alkyl, C3-C8carbocyclyl, and Z3-substituted phenyl;

each R4 is independently and individually selected from the group consisting of H, C1-C6alkyl, hydroxyC1-C6alkyl, dihydroxyC1-C6alkyl, C1-C6alkoxyC1-C6alkyl, branched C3-C7alkyl, branched hydroxyC1-C6alkyl, branched C1-C6alkoxyC1-C6alkyl, branched dihydroxyC1-C6alkyl, —(CH$_2$)$_p$—N(R7)$_2$, —(CH$_2$)$_p$—R5, —(CH$_2$)$_p$—C(O)N(R7)$_2$, —(CH$_2$)$_n$C(O)R5, —(CH$_2$)$_n$—C(O)OR3, C3-C8carbocyclyl, hydroxyl substituted C3-C8-carbocyclyl, alkoxy substituted C3-C8-carbocyclyl, dihydroxy substituted C3-C8-carbocyclyl, and —(CH$_2$),—R17;

each R5 is independently and individually selected from the group consisting of

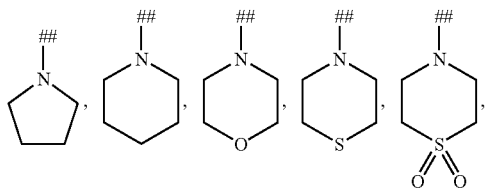

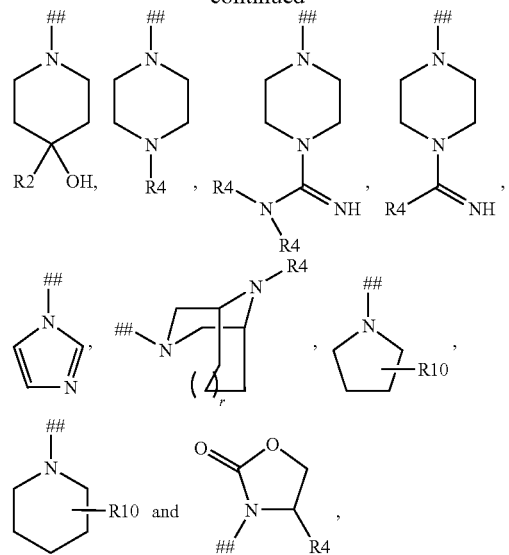

and wherein the symbol (##) is the point of attachment of the R5 moiety;

each R6 is independently and individually selected from the group consisting of C1-C6alkyl, branched C3-C7alkyl, C3-C8carbocyclyl, phenyl, G1, and G4;

each R7 is independently and individually selected from the group consisting of H, C1-C6alkyl, hydroxyC2-C6alkyl, dihydroxyC2-C6alkyl, C1-C6alkoxyC2-C6alkyl, branched C3-C7alkyl, branched hydroxyC2-C6 alkyl, branched C1-C6alkoxyC2-C6alkyl, branched dihydroxyC2-C6alkyl, —(CH$_2$)$_q$—R5, —(CH$_2$)$_n$—C(O)R5, —(CH$_2$)$_n$—C(O)OR3, C3-C8carbocyclyl, hydroxyl substituted C3-C8carbocyclyl, alkoxy substituted C3-C8carbocyclyl, dihydroxy substituted C3-C8carbocyclyl, and —(CH$_2$)$_n$—R17;

each R8 is independently and individually selected from the group consisting of C1-C6alkyl, branched C3-C7alkyl, fluoroalkyl wherein the alkyl moiety is partially or fully fluorinated, C3-C8carbocyclyl, Z3-substituted phenyl, Z3-substituted phenyl C1-C6alkyl, Z3-substituted G1, Z3-substituted G1-C1-C6alkyl, Z2-substituted G4, Z2-substituted G4-C1-C6alkyl, OH, C1-C6alkoxy, N(R3)$_2$, N(R4)$_2$, and R5;

each R10 is independently and individually selected from the group consisting of CO$_2$H, CO$_2$C1-C6alkyl, CO—N(R4)$_2$, OH, C1-C6alkoxy, and —N(R4)$_2$;

R16 is independently and individually selected from the group consisting of hydrogen, C1-C6alkyl, branched C3-C7alkyl, C3-C8carbocyclyl, halogen, fluoroalkyl wherein the alkyl moiety can be partially or fully fluorinated, cyano, hydroxyl, C1-C6alkoxy, C1-C6fluoroalkoxy wherein the alkyl moiety can be partially or fully fluorinated, —N(R3)$_2$, —N(R4)$_2$, C2-C3alkynyl, and nitro;

each R17 is taken from the group comprising phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, oxetanyl, azetadinyl, tetrahydrofuranyl, oxazolinyl, oxazolidinyl, pyranyl, thiopyranyl, tetrahydropyranyl, dioxalinyl, azepinyl, oxepinyl, diazepinyl, pyrrolidinyl, and piperidinyl;

wherein R17 can be further substituted with one or more Z2, Z3 or Z4 moieties;

R19 is H or C1-C6 alkyl;

wherein two R3 or R4 moieties are independently and individually taken from the group consisting of C1-C6alkyl and branched C3-C6alkyl, hydroxyalkyl, and alkoxyalkyl and are attached to the same nitrogen atom, said moieties may cyclize to form a C3-C7 heterocyclyl ring;

and k is 1 or 2; n is 0-6; p is 1-4; q is 2-6; r is 0 or 1; t is 1-3.

1.1 Compounds of Formula Ia which Exemplify Preferred E1-X2 Moieties

In an embodiment of section 1, preferred compounds have the structures of formula Ib

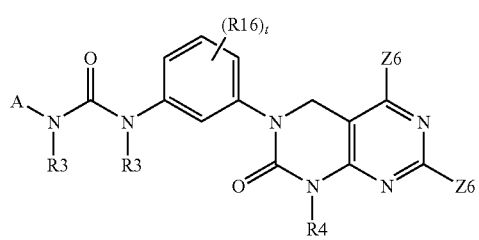

Ib

1.2 Compounds of Formula Ia which Exemplify Preferred A Moieties

In an embodiment of section 1.1, preferred compounds have the structures of formula Ic

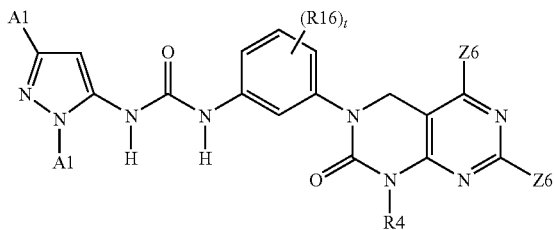

Ic

1.3 Compounds of Formula Ia which Exemplify Preferred A1 Moieties

In an embodiment of section 1.2, preferred compounds have the structures of formula Id

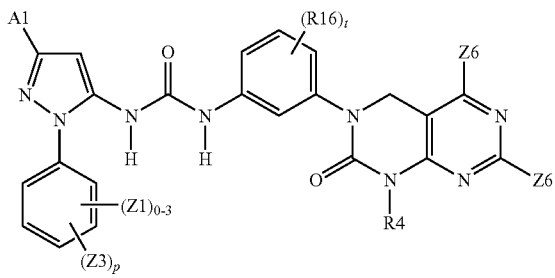

Id wherein A1 is selected from the group consisting of branched C3-C8alkyl, R19 substituted C3-C8carbocyclyl, C1-C6alkyl, fluoroC1-C6alkyl wherein the alkyl is fully or partially fluorinated, Z3-substituted phenyl, and Z3-substituted G1; and wherein R16 is C1-C6alkyl, cyano, —CCH, or halogen.

1.3a Compounds of Formula Id which Exemplify More Preferred X2-E1 Moieties

In an embodiment of section 1.3, preferred compounds have the structures of formula Ie

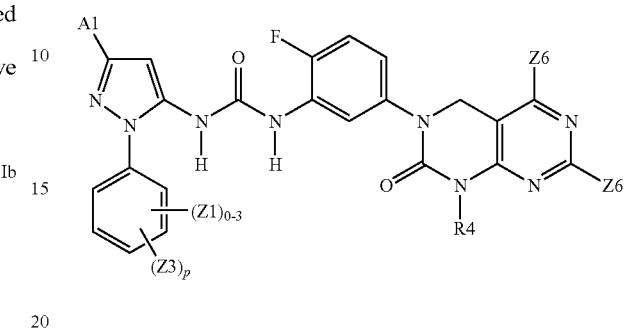

Ie

1.3b Additional Compounds of Formula Id which Exemplify More Preferred X2-E1 Moieties In another embodiment of section 1.3, preferred compounds have the structures of formula If

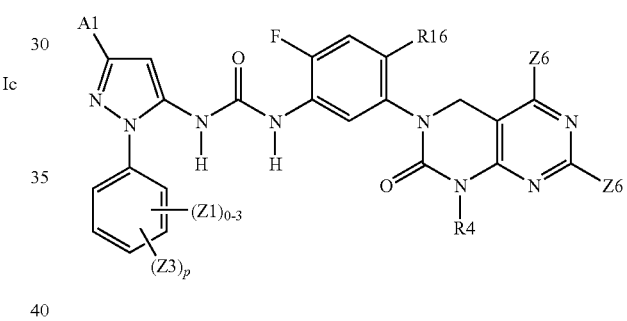

If wherein R16 is methyl, cyano, —CCH, fluorine or chlorine.

1.4 Compounds of Formula Ia which Exemplify Additional Preferred A1 Moieties In a different embodiment of section 1.2, additional preferred compounds have the structures of formula Ig

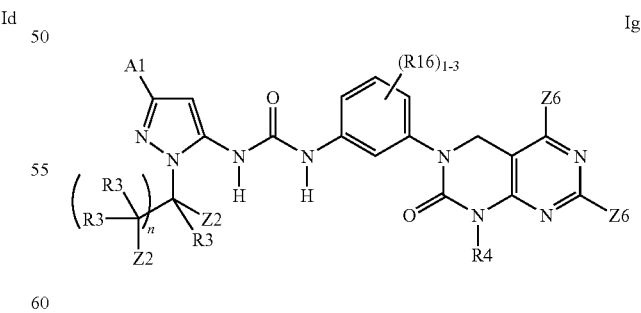

Ig wherein A1 is selected from the group consisting of branched C3-C8alkyl, R19 substituted C3-C8-carbocyclyl, C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

1.4a Additional Compounds of Formula Ig which Exemplify More Preferred X2-E1 Moieties In an embodiment of section 1.4, preferred compounds have the structures of formula Ih

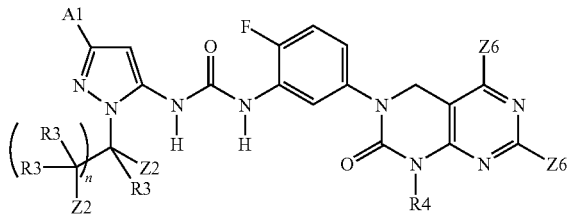

Ih

1.4b Additional Compounds of Formula Ig which Exemplify More Preferred X2-E1 Moieties In another embodiment of section 1.4, preferred compounds have the structures of formula Ii

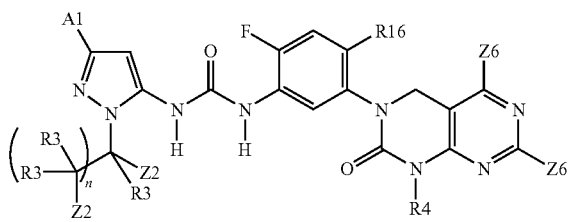

Ii wherein R16 is C1-C6alkyl, cyano, —CCH, fluorine or chlorine.

1.5 Compounds of Formula Ia which Exemplify Additionally Preferred A Moieties In a different embodiment of section 1.1, additional preferred compounds have the structures of formula Ij

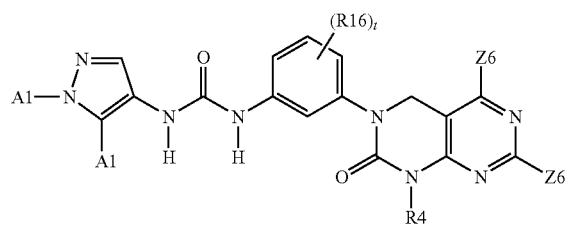

Ij wherein A1 is selected from the group consisting of branched Z2-substituted C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, cyano, —CCH, or halogen.

1.5a Additional Compounds of Formula Ij which Exemplify More Preferred X2-E1 Moieties In an embodiment of section 1.5, preferred compounds have the structures of formula Ik

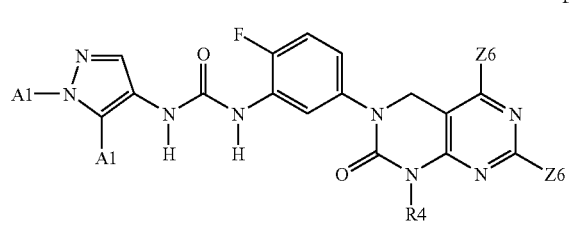

Ik

1.5b Additional Compounds of Formula Ij which Exemplify More Preferred X2-E1 Moieties In another embodiment of section 1.5, preferred compounds have the structures of formula Il

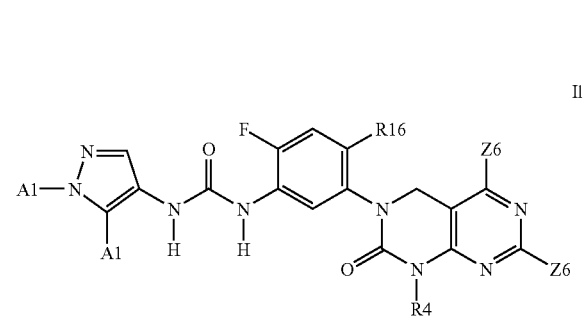

Il and wherein R16 is methyl, cyano, —CCH, fluorine or chlorine.

1.6 Compounds of Formula Ia which Exemplify Additionally Preferred A Moieties In a different embodiment of section 1.1, additional preferred compounds have the structures of formula Im

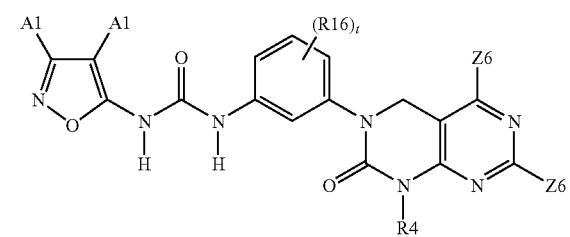

Im wherein A1 is selected from the group consisting of hydrogen, Z2-substituted branched C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, cyano, —CCH, or halogen.

1.6a Additional Compounds of Formula Im which Exemplify More Preferred X2-E1 Moieties In an embodiment of section 1.6, preferred compounds have the structures of formula In

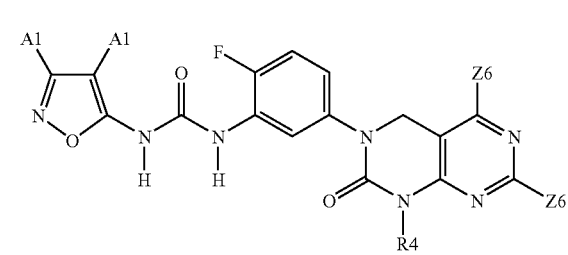

In

1.6b Additional Compounds of Formula Im which Exemplify More Preferred X2-E1 Moieties In another embodiment of section 1.6, preferred compounds have the structures of formula Io

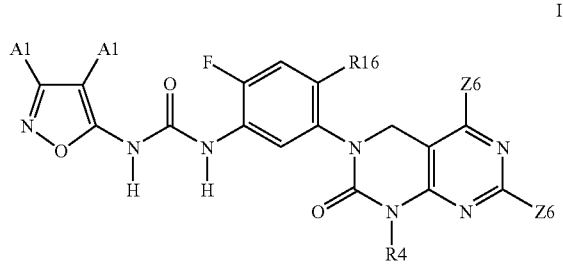

Io wherein R16 is C1-C6alkyl, cyano, —CCH, fluorine or chlorine.

1.7 Compounds of Formula Ia which Exemplify Additionally Preferred A Moieties In a different embodiment of section 1.1, additional preferred compounds have the structures of formula Ip Ip

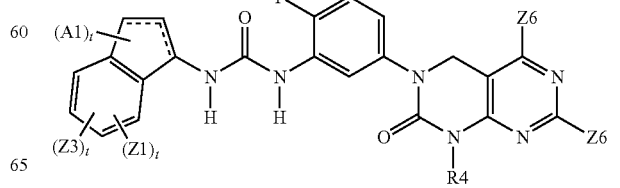

wherein A1 is selected from the group consisting of Z2-substituted branched C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, cyano, —CCH, or halogen.

1.7a Additional Compounds of Formula Ip which Exemplify More Preferred X2-E1 Moieties In an embodiment of section 1.7, preferred compounds have the structures of formula Iq Iq

1.7b Additional Compounds of Formula Ip which Exemplify More Preferred X2-E1 Moieties In another embodiment of section 1.7, preferred compounds have the structures of formula Ir

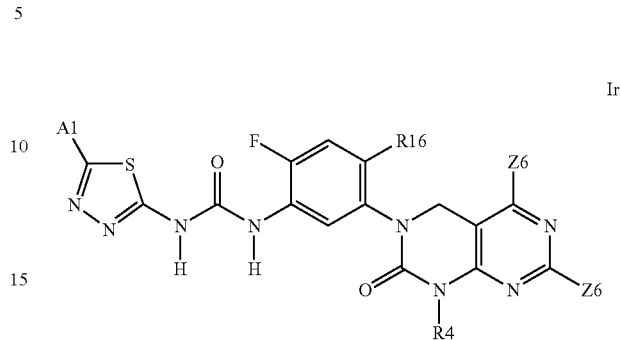

Ir and wherein R16 is methyl, cyano, —CCH, fluorine or chlorine.

1.8 Compounds of Formula Ia which Exemplify Additionally Preferred A Moieties In a different embodiment of section 1.1, additional preferred compounds have the structures of formula Is

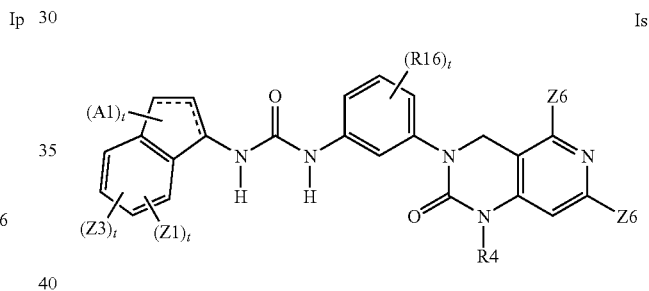

Is wherein the hashed bond is a saturated or unsaturated bond;
and wherein A1 is selected from the group consisting of hydrogen, Z2-substituted branched C3-C8alkyl, R19 substituted C3-C8carbocyclyl, Z2-substituted C1-C6alkyl, halogen, fluoroC1-C6alkyl, cyano, C1-C6alkoxy, fluoroC1-C6alkoxy, fluoroC1-C6alkyl wherein the alkyl is fully or partially fluorinated, Z3-substituted phenyl, and Z3-substituted G1;
and wherein R16 is C1-C6alkyl, cyano, —CCH, or halogen.

1.8a Additional Compounds of Formula Is which Exemplify More Preferred X2-E1 Moieties In an embodiment of section 1.8, preferred compounds have the structures of formula It

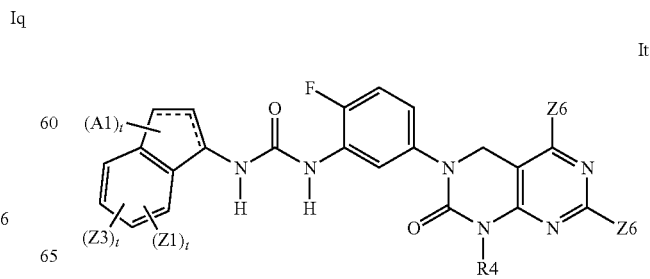

It 1.8b Additional Compounds of Formula Is which Exemplify More Preferred X2-E1 Moieties In another embodiment of section 1.8, preferred compounds have the structures of formula Iu

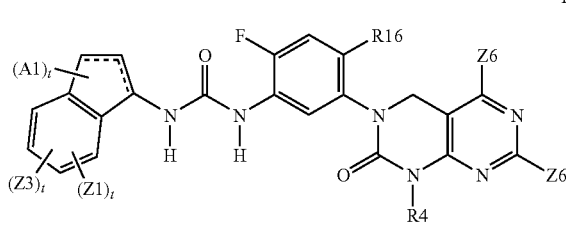

Iu wherein R16 is methyl, cyano, —CCH, fluorine or chlorine.

1.9 Compounds of Formula Ia which Exemplify Additionally Preferred A Moieties

In a different embodiment of section 1.1, additional preferred compounds have the structures of formula Iv

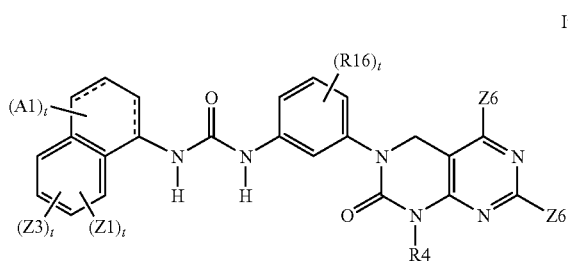

Iv wherein the bashed bond is a saturated or unsaturated bond; and wherein A1 is selected from the group consisting of hydrogen, Z2-substituted branched C3-C8alkyl, R19 substituted C3-C8carbocyclyl, Z2-substituted C1-C6alkyl, halogen, fluoroC1-C6alkyl, cyano, C1-C6alkoxy, fluoroC1-C6alkoxy, fluoroC1-C6alkyl wherein the allyl is fully or partially fluorinated, Z3-substituted phenyl, and Z3-substituted C1;
and wherein R16 is C1-C6alkyl, cyano, —CCH, or halogen.

1.9a Additional Compounds of Formula Iv which Exemplify More Preferred X2-E1 Moieties In an embodiment of section 1.9, preferred compounds have the structures of formula Iw

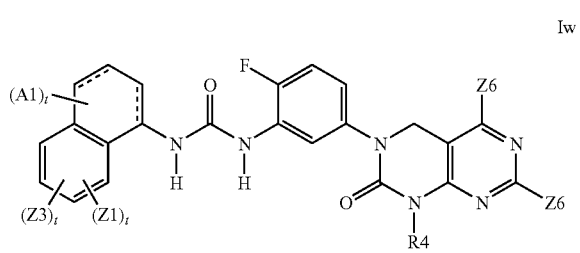

Iw 1.9b Additional Compounds of Formula Iv which Exemplify More Preferred X2-E1 Moieties In another embodiment of section 1.9, preferred compounds have the structures of formula Ix

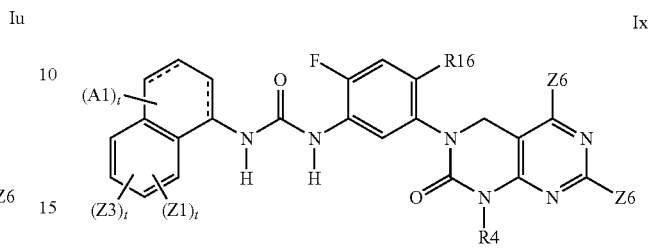

Ix wherein R16 is C1-C6alkyl, cyano, —CCH, fluorine or chlorine.

1.10 Compounds of Formula Ia which Exemplify Additionally Preferred A Moieties

In a different embodiment of section 1.1, additional preferred compounds have the structures of formula Iy

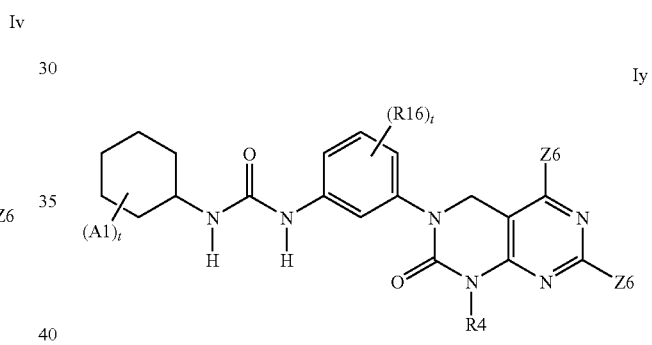

Iy wherein A1 is selected from the group consisting of Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, cyano, —CCH, or halogen.

1.10a Additional Compounds of Formula Iy which Exemplify More Preferred X2-E1 Moieties In an embodiment of section 1.10, preferred compounds have the structures of formula Iz

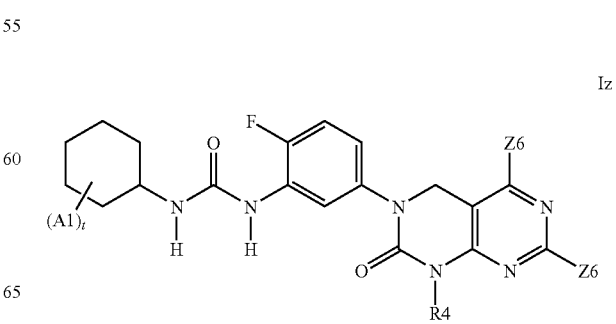

Iz

1.10b Additional Compounds of Formula Iy which Exemplify More Preferred X2-E1 Moieties In another embodiment of section 1.10, preferred compounds have the structures of formula Iaa

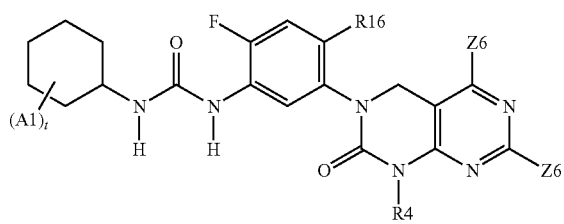

Iaa wherein R16 is C1-C6alkyl, cyano, —CCH, fluorine or chlorine.

1.11 Compounds of Formula Ia which Exemplify Additionally Preferred A Moieties In a different embodiment of section 1.1, additional preferred compounds have the structures of formula Ibb

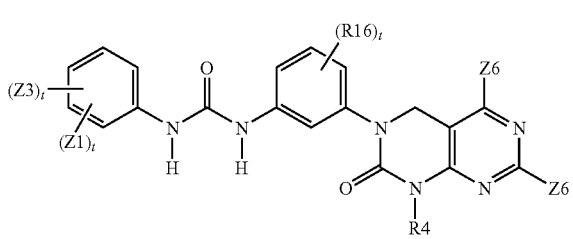

Ibb wherein R16 is C1-C6alkyl, cyano, —CCH, or halogen.

1.11a Additional Compounds of Formula Ibb which Exemplify More Preferred X2-E1 Moieties In an embodiment of section 1.11, preferred compounds have the structures of formula Icc

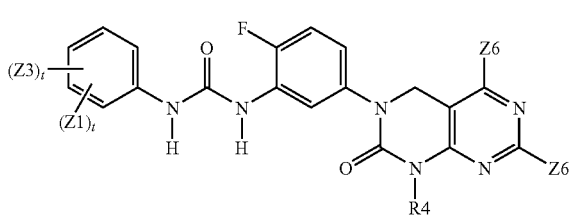

Icc

1.11b Additional Compounds of Formula Ibb which Exemplify More Preferred X2-E1 Moieties In another embodiment of section 1.11, preferred compounds have the structures of formula Idd

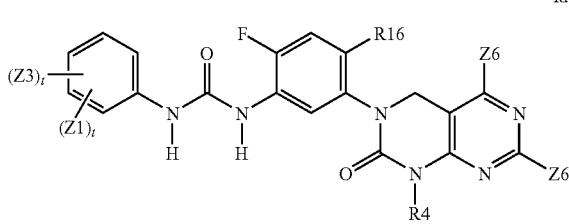

Idd wherein R16 is C1-C6alkyl, cyano, —CCH, fluorine or chlorine.

1.12 Compounds of Formula Ia which Exemplify Additionally Preferred A Moieties In a different embodiment of section 1.1, additional preferred compounds have the structures of formula Iee

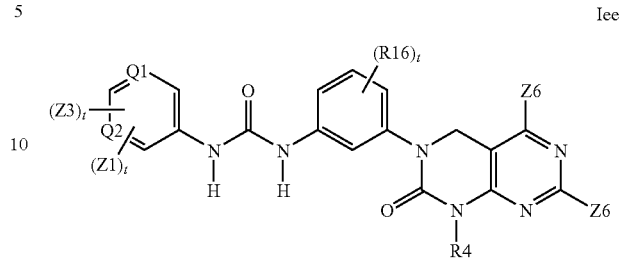

Iee wherein Q1 and Q2 individually and independently taken from the group consisting of N and CH;
and wherein R16 is C1-C6alkyl, cyano, —CCH, or halogen.

1.12a Additional Compounds of Formula Iee which Exemplify More Preferred X2-E1 Moieties In an embodiment of section 1.12 preferred compounds have the structures of formula Iff

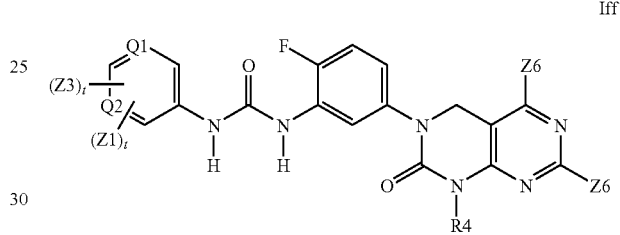

Iff

1.12b Additional Compounds of Formula Iee which Exemplify More Preferred X2-E1 Moieties In another embodiment of section 1.12, preferred compounds have the structures of formula Igg

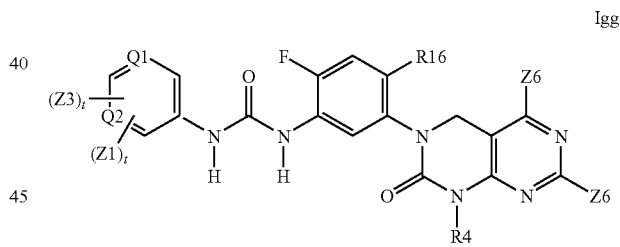

Igg wherein R16 is C1-C6alkyl, cyano, —CCH, fluorine or chlorine.

1.13 Compounds of Formula Ia which Exemplify Additionally Preferred A Moieties In a different embodiment of section 1.1, additional preferred compounds have the structures of formula Ihh

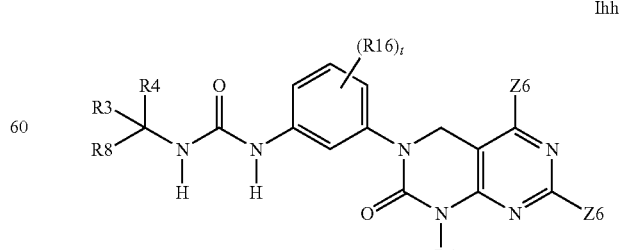

Ihh and wherein R16 is C1-C6alkyl, cyano, —CCH, or halogen.

1.13a Additional Compounds of Formula Ihh which Exemplify More Preferred X2-E1 Moieties In an embodiment of section 1.13, preferred compounds have the structures of formula Iii

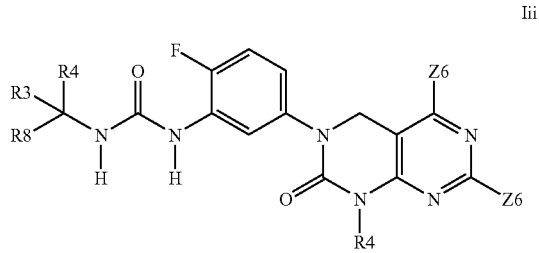

Iii

1.13b Additional Compounds of Formula Ihh which Exemplify More Preferred X2-E1 Moieties In another embodiment of section 1.13, preferred compounds have the structures of formula Ijj

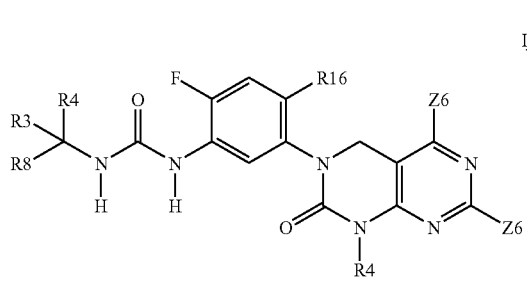

Ijj and wherein R16 is methyl, cyano, —CCH, fluorine or chlorine.

1.14 Compounds of Formula Ia which Exemplify Additionally Preferred A Moieties In a different embodiment of section 1.1, additional preferred compounds have the structures of formula Ikk

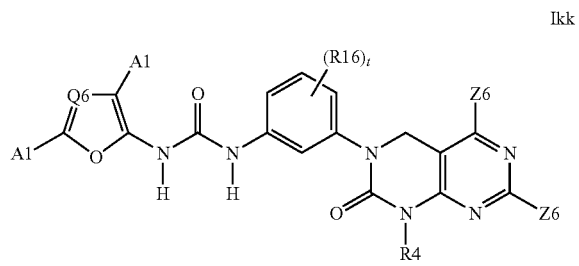

Ikk wherein Q6 is N or C-A1;
wherein A1 is selected from the group consisting of hydrogen, Z2-substituted branched C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, cyano, —CCH, or halogen.

1.14a Additional Compounds of Formula Ikk which Exemplify More Preferred X2-E1 Moieties In an embodiment of section 1.14, preferred compounds have the structures of formula Ill

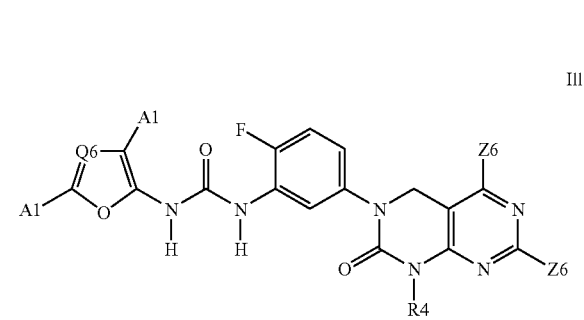

Ill

1.14b Additional Compounds of Formula Ikk which Exemplify More Preferred X2-E1 Moieties In another embodiment of section 1.14, preferred compounds have the structures of formula Imm

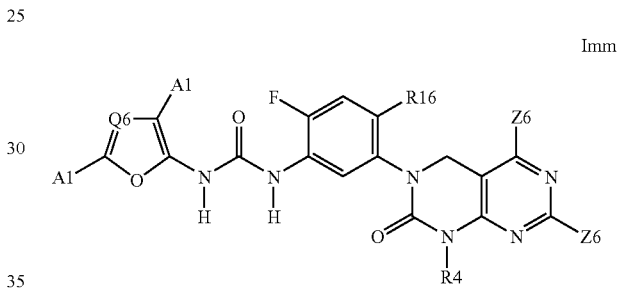

Imm wherein R16 is C1-C6alkyl, cyano, —CCH, fluorine or chlorine.

1.15 Compounds of Formula Ia which Exemplify Additionally Preferred A Moieties In a different embodiment of section 1.1, additional preferred compounds have the structures of formula Inn

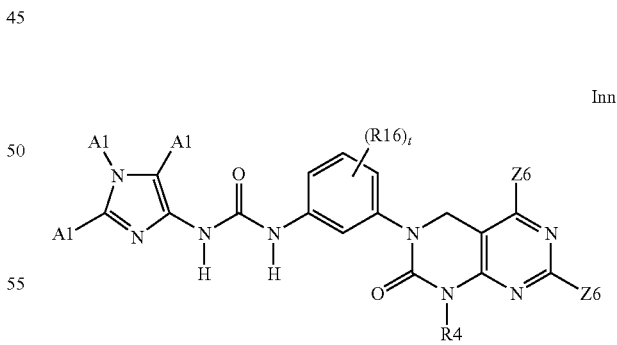

Inn wherein A1 is selected from the group consisting of hydrogen, Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, cyano, —CCH, or halogen.

1.15a Additional Compounds of Formula Inn which Exemplify More Preferred X2-E1 Moieties In an embodiment of section 1.15, preferred compounds have the structures of formula Ioo

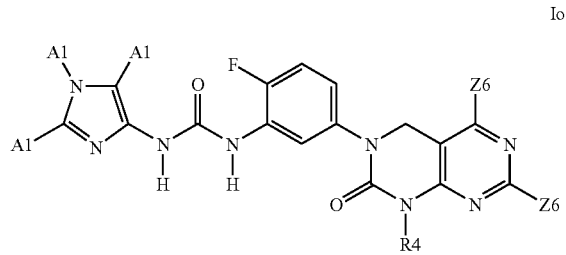

Ioo

1.15b Additional Compounds of Formula Inn which Exemplify More Preferred X2-E1 Moieties In another embodiment of section 1.15, preferred compounds have the structures of formula Ipp

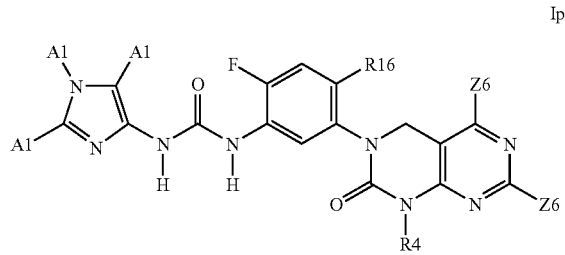

Ipp wherein R16 is C1-C6alkyl, cyano, —CCH, fluorine or chlorine.

1.16 Compounds of Formula Ia which Exemplify Additionally Preferred A Moieties In a different embodiment of section 1.1, additional preferred compounds have the structures of formula Iqq

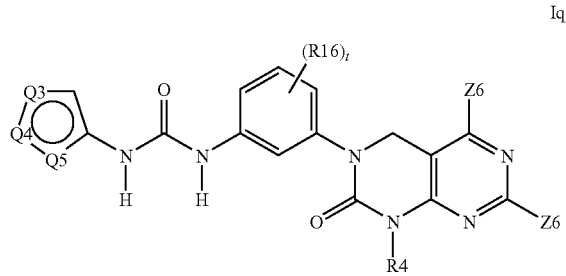

Iqq wherein Q3, Q4 and Q5 are selected from the group consisting of N-A1 and C-A1, and only one of Q3, Q4, or Q5 is N-A1;

and wherein A1 is selected from the group consisting of hydrogen, Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

1.16a Additional Compounds of Formula Iqq which Exemplify More Preferred X2-E1 Moieties In an embodiment of section 1.16, preferred compounds have the structures of formula Irr

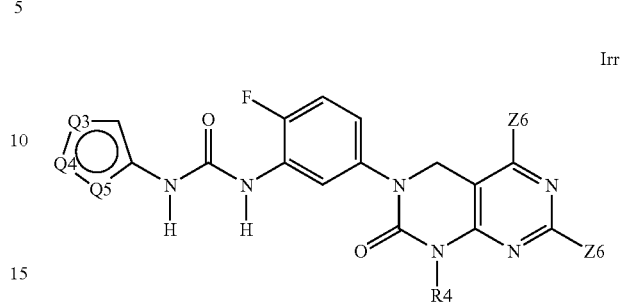

Irr

1.16b Additional Compounds of Formula Iqq which Exemplify More Preferred X2-E1 Moieties In another embodiment of section 1.16, preferred compounds have the structures of formula Iss

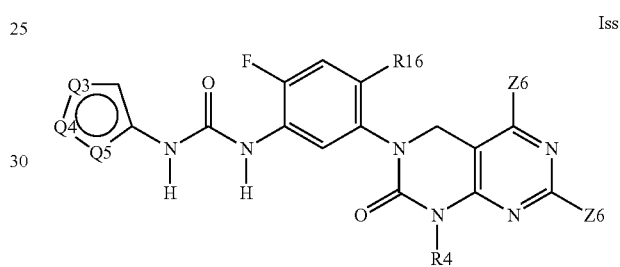

Iss wherein R16 is C1-C6alkyl, cyano, —CCH, fluorine or chlorine.

1.17 Methods

1.17a Methods of Protein Modulation

The invention includes methods of modulating kinase activity of RAF kinases and other kinases in the RAS-RAF-MEK-ERK-MAP kinase pathway including, but not limited to, A-Raf, B-Raf, and C-Raf. The kinases may be wildtype kinases, oncogenic forms thereof, aberrant fusion proteins thereof or polymorphs of any of the foregoing. The method comprises the step of contacting the kinase species with compounds of the invention and especially those set forth in sections 1.1-1.16. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

1.17b Treatment Methods

The methods of the invention, especially those of sections 1.1-1.16, also include treating individuals suffering from a condition selected from the group consisting of chronic myelogenous leukemia, acute lymphocytic leukemia, gastrointestinal stromal tumors, hypereosinophillic syndrome, glioblastomas, ovarian cancer, pancreatic cancer, prostate cancer, lung cancers, breast cancers, kidney cancers, cervical carcinomas, metastasis of primary solid tumor secondary sites, ocular diseases characterized by hyperproliferation leading to blindness including various retinopathies including diabetic retinopathy and age-related macular degeneration, rheumatoid arthritis, melanomas, colon cancer, thyroid cancer, a disease caused by a mutation in the RAS-RAF-MEK-ERK-MAP kinase pathway, human inflammation, rheumatoid spondylitis, ostero-arthritis, asthma, gouty arthritis, sepsis, septic shock, endotoxic shock, Gram-negative sepsis, toxic shock syndrome, adult respiratory distress syndrome, stroke, reperfusion injury, neural trauma, neural ischemia, psoriasis, restenosis, chronic obstructive pulmonary disease, bone resorptive diseases, graft-versus-host reaction, Chron's disease, ulcerative colitis, inflammatory bowel disease, pyresis, and combinations thereof.

1.18 Pharmaceutical Preparations

The compounds of the invention, especially those of sections 1.1-1.16, may form a part of a pharmaceutical composition by combining one or more such compounds with a pharmaceutically acceptable carrier. Additionally, the compositions may include an additive selected from the group consisting of adjuvants, excipients, diluents, and stabilizers.

2. Second Aspect of the Invention—Compounds, Methods, Preparations and Adducts

In the first aspect of the invention, compounds are of the formula IIa

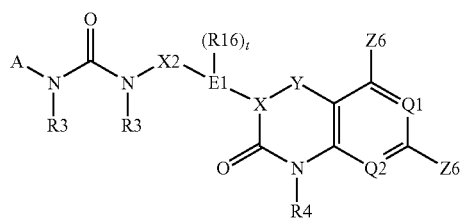

wherein X—Y in order is C=N or N—CH2;
wherein one of Q1 and Q2 is N and the other is CR3;
wherein E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;
wherein A is selected from the group consisting of phenyl, naphthyl, C3-C8carbocyclyl, indanyl, tetralinyl, indenyl, G1, G2, G3, G4 and —CHR4R8;
G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl;
G2 is a fused bicyclic heteroaryl taken from the group consisting of indolyl, indolinyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, pyrazolopyridinyl, imidazolonopyridinyl, thiazolopyridinyl, thiazolonopyridinyl, oxazolopyridinyl, oxazolonopyridinyl, isoxazolopyridinyl, isothiazolopyridinyl, triazolopyridinyl, imidazopyrimidinyl, pyrazolopyrimidinyl, imidazolonopyrimidinyl, thiazolopyrimidinyl, thiazolonopyrimidinyl, oxazolopyrimidinyl, oxazolonopyrimidinyl, isoxazolopyrimidinyl, isothiazolopyrimidinyl, triazolopyrimidinyl, dihydropurinonyl, pyrrolopyrimidinyl, purinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, and benzoxazepinyl;
G3 is a non-fused bicyclic heteroaryl taken from the group consisting of pyridylpyridiminyl pyrimidinylpyrimidinyl, oxazolylpyrimidinyl, thiazolylpyrimidinyl, imidazolylpyrimidinyl, isoxazolylpyrimidinyl, isothiazolylpyrimidinyl, pyrazolylpyrimidinyl, triazolylpyrimidinyl, oxadiazoylpyrimidinyl, thiadiazoylpyrimidinyl, morpholinylpyrimidinyl, dioxothiomorpholinylpyrimidinyl, and thiomorpholinylpyrimidinyl;
G4 is a heterocyclyl taken from the group consisting of oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl;
the A ring may be optionally substituted with one or more —X1-A1 moieties;
X1 is selected from the group consisting of —(CH$_2$)$_n$—(O)$_r$—(CH$_2$)$_n$—, —(CH$_2$), —(NR3)$_r$-(CH$_2$)$_n$—, —(CH$_2$)$_n$—(S)$_r$—(CH$_2$)$_n$—, —(CH$_2$)$_n$—(C=O)$_r$—(CH$_2$)$_n$—$_r$—(CH$_2$), —(C(=O)—NR3)$_r$-(CH$_2$)$_n$—, and —(CH$_2$), —(SO$_2$—NR3)$_r$-(CH$_2$)$_n$—, wherein any of the alkylenes may be straight or branched chain;
X2 is selected from the group consisting of C1-C6alkyl, branched C2-C6alkyl, and a direct bond wherein E1 is directly linked to the NR3 group of formula Ia;
A1 is selected from the group consisting of hydrogen, aryl, G1, G2, G3, G4, C1-C6 alkyl, branched C3-C8alkyl, R19 substituted C3-C8carbocyclyl, fluoroC1-C6alkyl wherein the alkyl is fully or partially fluorinated, halogen, cyano, hydroxyl, —N(R4)$_2$, —R5, —C(O)N(R4)$_2$, C(O)R5, C1-C6alkoxy, and fluoroC1-C6alkoxy wherein the alkyl group is fully or partially fluorinated;
When A and A1 have one or more substitutable sp2-hybridized carbon atom, each respective sp2 hybridized carbon atom may be optionally substituted with a Z1 or Z3 substituent;
when A and A1 have one or more substitutable sp3-hybridized carbon atom, each respective sp3 hybridized carbon atom may be optionally substituted with a Z2 or R3 substituent;
when A and A1 have one or more substitutable nitrogen atom, each respective nitrogen atom may be optionally substituted with a Z4 substituent;
each Z1 is independently and individually selected from the group consisting of hydrogen, hydroxyC1-C6alkyl, C1-C6alkoxy, C1-C6alkoxyC1-C6alkyl, (R4)$_2$NC1-C6alkyl, (R4)$_2$NC2-C6alkylN(R4)-(CH$_2$)$_n$, (R4)$_2$NC2-C6alkylO-(CH$_2$)$_n$, (R3)$_2$N—C(=O)—, (R4)$_2$N—C(=O)—, (R4)$_2$N—CO—C1-C6alkyl-, C1-C6alkoxycarbonyl-, -carboxyC1-C6alkyl, C1-C6alkoxycarbonylC1-C6alkyl, (R3)$_2$NSO$_2$—, —SOR3, (R4)$_2$NSO$_2$—, —SO$_2$R3, —SOR4, —C(=O)R6, —C(=NOH)R6, —C(=NOR3)R6, —(CH$_2$)$_n$N(R4)C(O)R8, —(CH$_2$)$_n$-G1, —(CH$_2$)$_n$-G4, phenoxy, —(CH$_2$), —O—(CH$_2$)$_n$-G1, —(CH$_2$)$_n$—O—(CH$_2$)$_n$-G4, —(CH$_2$), —NR3-(CH$_2$)$_n$-aryl, —(CH$_2$)$_n$—NR3-(CH$_2$)$_n$-G1, —(CH$_2$)$_n$—NR3-(CH$_2$)$_n$-G4, —S(O)$_2$R5, —N=S(O)R6R8, —S(O)(=NR3)R6, —(CH$_2$)$_n$NHC(O)NHS(O)$_2$R8, —(CH$_2$)$_n$NHS(O)$_2$NHC(O)R8, —C(O)NHS(O)$_2$R8, —S(O)$_2$NHC(O)R8, —(CH$_2$)$_n$NHC(O)(CH$_2$)$_n$R5, —(CH$_2$)$_n$NHS(O)$_2$(CH$_2$)$_n$R5, (CH$_2$)$_n$C(O)NH(CH$_2$)$_q$R5, —(CH$_2$)$_n$C(O)R5, —(CH$_2$)$_n$OC(O)R5, —(CH$_2$)$_n$S(O)$_2$NH(CH$_2$)$_q$R5, —CH(OH)(CH$_2$)$_p$R5, —CH(OH)CH(OH)R4, —(CH$_2$)$_n$N(R4)$_2$, —(CH$_2$)$_n$R5, —C(=NH)R5, —C(NH)N(R4)$_2$, —C(=NOR3)R5, —C(=NOR3)N(R4)$_2$, and —NHC(=NH)R8;

in the event that Z1 contains an alkyl or alkylene moiety, such moieties may be further substituted with one or more C1-C6alkyls;

each Z2 is independently and individually selected from the group consisting of hydrogen, aryl, C1-C6alkyl, C3-C8carbocyclyl, hydroxyl, hydroxyC1-C6alkyl-, cyano, (R3)$_2$N—, (R4)$_2$N—, (R4)$_2$NC1-C6alkyl-, (R4)$_2$NC2-C6alkylN(R4)-(CH$_2$)$_n$—, (R4)$_2$NC2-C6alkylO-(CH$_2$)$_n$—, (R3)$_2$N—C(=O)—, (R4)$_2$N—C(=O)—, (R4)$_2$N—CO—C1-C6alkyl-, carboxyl, carboxyC1-C6alkyl, C1-C6alkoxycarbonyl, C1-C6alkoxycarbonylC1-C6alkyl, (R3)$_2$NSO$_2$—, (R4)$_2$NSO$_2$—, —SO$_2$R5, —SO$_2$R8, —(CH$_2$)$_n$N(R4)C(O)R8, —C(O)R8, =O, =NOH, =N(OR6), —(CH$_2$)$_n$-G1, —(CH$_2$)$_n$-G4, —(CH$_2$), —O—(CH$_2$n-G1, —(CH$_2$)$_n$—O—(CH$_2$)$_n$-G4, —(CH$_2$), —NR3-(CH$_2$)$_n$-aryl, —(CH$_2$), —NR3-(CH$_2$)$_n$-G1, —(CH$_2$), —NR3-(CH$_2$)$_n$-G4, —(CH$_2$)$_n$NHC(O)NHS(O)$_2$R8, —(CH$_2$)$_n$NHS(O)$_2$NHC(O)R8, —C(O)NHS(O)$_2$R8, —(CH$_2$)NHC(O)(CH$_2$)$_n$R5, —(CH$_2$)$_n$NHS(O)$_2$R5, —(CH$_2$)$_n$C(O)NH(CH$_2$)$_q$R5, (CH$_2$)$_n$C(O)R5, —(CH$_2$)$_n$OC(O)R5, and —(CH$_2$)$_n$R5;

in the event that Z2 contains an alkyl or alkylene moiety, such moieties may be further substituted with one or more C1-C6alkyls;

each Z3 is independently and individually selected from the group consisting of H, C1-C6alkyl, branched C3-C7alkyl, C3-C8carbocyclyl, halogen, fluoroalkyl wherein the alkyl moiety can be partially or fully fluorinated, cyano, hydroxyl, methoxy, oxo, (R3)$_2$N—C(=O)—, (R4)$_2$N—C(=O)—, —N(R4-C(=O)R8, (R3)$_2$NSO$_2$—, (R4)$_2$NSO$_2$—, —N(R4)SO$_2$R5, —N(R4)SO$_2$R8, —(CH$_2$)$_n$—N(R3)$_2$, —(CH$_2$)$_n$—N(R4)$_2$, —O—(CH$_2$)$_q$—N(R4)$_2$, —O—(CH$_2$)$_q$—O-alkyl, —N(R3)-(CH$_2$)$_q$—O-alkyl, —N(R3)-(CH$_2$)$_q$—N(R4)$_2$, —O—(CH$_2$)$_q$—R5, —N(R3)-(CH$_2$)$_q$—R5, —C(=O)R5, —C(=O)R8, and nitro;

in the event that Z3 contains an alkyl or alkylene moiety, such moieties may be further substituted with one or more C1-C6alkyls;

each Z4 is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C1-C6allyl, carboxyC1-C6alkyl, C1-C6alkoxycarbonylC1-C6alkyl, —C2-C6alkylN(R4)C(O)R8, R8-C(=NR3)-, —SO$_2$R8, —COR8, —(CH$_2$)$_n$-G1, —(CH$_2$)-G4, —(CH$_2$)$_q$—O—(CH$_2$)$_n$-G1, —(CH$_2$)$_q$—O—(CH$_2$)$_n$-G4, —(CH$_2$)$_q$—NR3-(CH$_2$)$_n$-G1, —(CH$_2$)$_q$—NR3-(CH$_2$)$_n$-G4, —(CH$_2$)$_q$NHC(O)(CH$_2$)$_n$R5, (CH$_2$)$_q$C(O)NH(CH$_2$)$_q$R5, —(CH$_2$)$_q$C(O)R5, —(CH$_2$)$_q$OC(O)R5, —(CH$_2$)$_q$R5, (CH$_2$)$_q$NR4(CH$_2$)$_q$R5, and —(CH$_2$)$_q$—O—(CH$_2$)$_q$R5;

in the event that Z4 contains an alkyl or alkylene moiety, such moieties may be further substituted with one or more C1-C6alkyls;

each Z6 is independently and individually selected from the group consisting of H, C1-C6alkyl, branched C3-C7alkyl, hydroxyl, C1-C6alkoxy, —OR4, C1-C6alkylthio, (R3)$_2$N—, (R4)$_2$N—, —R5, —N(R3)COR8, —N(R4)COR8, —N(R3)SO$_2$R6-, —CON(R3)$_2$, —CON(R4)$_2$, —COR5, —SO$_2$N(R4)$_2$, halogen, fluoroC1-C6alkyl wherein the alkyl is fully or partially fluorinated, cyano, fluoroC1-C6alkoxy wherein the alkyl is fully or partially fluorinated, —O—(CH$_2$)$_q$—N(R4)$_2$, —N(R3)-(CH$_2$)$_q$—N(R4)$_2$, —O—(CH$_2$)$_q$—O-alkyl, —N(R3)-(CH$_2$)$_q$—O-alkyl, —O—(CH$_2$)$_q$—R5, —N(R3)-(CH$_2$)$_q$—R5, —NR3), —(CH$_2$)$_n$—R17, —(O)$_r$—R17, —(S)$_r$—R17, and —(CH$_2$)$_r$—R17;

in the event that Z6 contains an alkyl or alkylene moiety, such moieties may be further substituted with one or more C1-C6alkyls;

wherein each R3 is independently and individually selected from the group consisting of H, C1-C6alkyl, branched C3-C7alkyl, C3-C8carbocyclyl, and Z3-substituted phenyl;

each R4 is independently and individually selected from the group consisting of H, C1-C6alkyl, hydroxyC1-C6alkyl, dihydroxyC1-C6alkyl, C1-C6alkoxyC1-C6alkyl, branched C3-C7alkyl, branched hydroxyC1-C6alkyl, branched C1-C6alkoxyC1-C6alkyl, branched dihydroxyC1-C6alkyl, —(CH$_2$)$_p$—N(R7)$_2$, —(CH$_2$)$_p$R5, —(CH$_2$)$_p$—C(O)N(R7)$_2$, —(CH$_2$)$_n$C(O)R5, —(CH$_2$)$_n$—C(O)OR3, C3-C8carbocyclyl, hydroxyl substituted C3-C8carbocyclyl, alkoxy substituted C3-C8carbocyclyl, dihydroxy substituted C3-C8carbocyclyl, and —(CH$_2$)$_n$—R17;

each R5 is independently and individually selected from the group consisting of

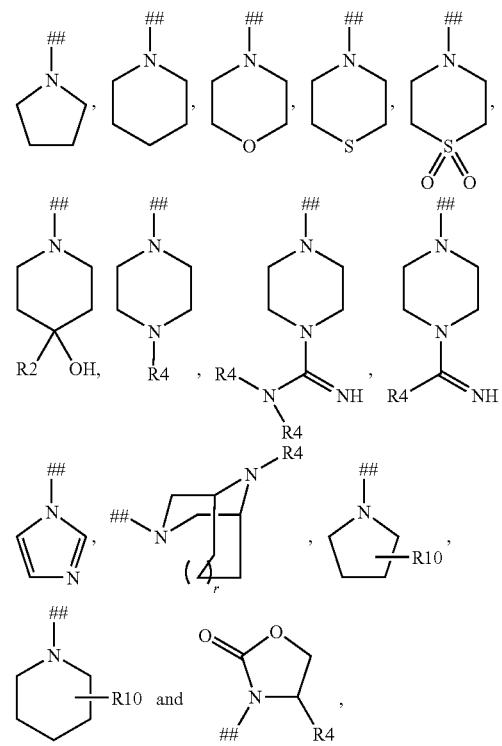

and wherein the symbol (##) is the point of attachment of the R5 moiety;

each R6 is independently and individually selected from the group consisting of C1-C6alkyl, branched C3-C7alkyl, C3-C8carbocyclyl, phenyl, G1, and G4;

each R7 is independently and individually selected from the group consisting of H, C1-C6alkyl, hydroxyC2-C6alkyl, dihydroxyC2-C6alkyl, C1-C6alkoxyC2-C6alkyl, branched C3-C7alkyl, branched hydroxyC2-C6 alkyl, branched C1-C6alkoxyC2-C6alkyl, branched dihydroxyC2-C6alkyl, —(CH$_2$)$_q$—R5, —(CH$_2$), —C(O)R5, —(CH$_2$), —C(O)OR3, C3-C8carbocyclyl, hydroxyl substituted C3-C8carbocyclyl, alkoxy substituted C3-C8carbocyclyl, dihydroxy substituted C3-C8carbocyclyl, and —(CH$_2$)$_n$—R17;

each R8 is independently and individually selected from the group consisting of C1-C6alkyl, branched C3-C7alkyl, fluoroalkyl wherein the alkyl moiety is partially or fully fluorinated, C3-C8carbocyclyl, Z3-substituted phenyl, Z3-substituted phenyl C1-C6alkyl, Z3-substituted G1, Z3-substituted G1-C1-C6alkyl, Z2-substituted G4, Z2-substituted G4-C1-C6alkyl, OH, C1-C6alkoxy, N(R3)$_2$, N(R4)$_2$, and R5;

each R10 is independently and individually selected from the group consisting of CO$_2$H, CO$_2$C1-C6alkyl, CO—N(R4)$_2$, OH, C1-C6alkoxy, and —N(R4)$_2$;

R16 is independently and individually selected from the group consisting of hydrogen, C1-C6alkyl, branched C3-C7alkyl, C3-C8carbocyclyl, halogen, fluoroalkyl wherein the alkyl moiety can be partially or fully fluorinated, cyano, hydroxyl, C1-C6alkoxy, C1-C6fluoroalkoxy wherein the alkyl moiety can be partially or fully fluorinated, —N(R3)$_2$, —N(R4)$_2$, C2-C3alkynyl, and nitro;

each R17 is taken from the group comprising phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, oxetanyl, azetadinyl, tetrahydrofuranyl, oxazolinyl, oxazolidinyl, pyranyl, thiopyranyl, tetrahydropyranyl, dioxalinyl, azepinyl, oxepinyl, diazepinyl, pyrrolidinyl, and piperidinyl;

wherein R17 can be further substituted with one or more Z2, Z3 or Z4 moieties;

R19 is H or C1-C6alkyl;

wherein two R3 or R4 moieties are independently and individually taken from the group consisting of C1-C6alkyl and branched C3-C6alkyl, hydroxyalkyl, and alkoxyalkyl and are attached to the same nitrogen atom, said moieties may cyclize to form a C3-C7 heterocyclyl ring;

and k is 1 or 2; n is 0-6; p is 1-4; q is 2-6; r is 0 or 1; t is 1-3.

2.1 Compounds of Formula IIa which Exemplify Preferred E1-X2 Moieties

In an embodiment of section 2, preferred compounds have the structures of formula IIb

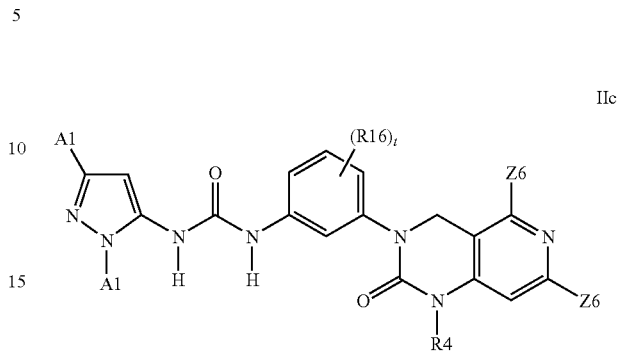

IIb 2.2 Compounds of Formula IIa which Exemplify Preferred A Moieties

In an embodiment of section 2.1, preferred compounds have the structures of formula IIc

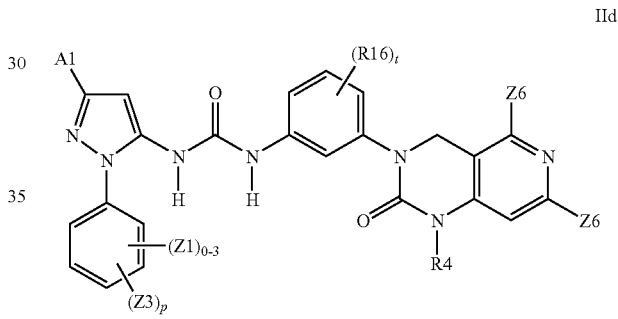

IIc 2.3 Compounds of Formula IIa which Exemplify Preferred A1 Moieties

In an embodiment of section 2.2, preferred compounds have the structures of formula IId

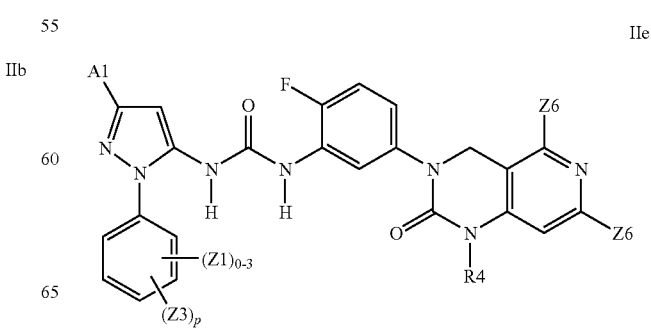

IId wherein A1 is selected from the group consisting of branched C3-C8alkyl, R19 substituted C3-C8carbocyclyl, C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

2.3a Compounds of Formula IId which Exemplify More Preferred X2-E1 Moieties

In an embodiment of section 2.3, preferred compounds have the structures of formula IIe IIe

2.3b Additional Compounds of Formula IId which Exemplify More Preferred X2-E1 Moieties In another embodiment of section 2.3, preferred compounds have the structures of formula IIf

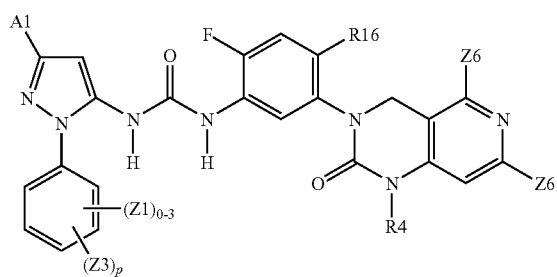

IIf wherein R16 is methyl, cyano, —CCH, fluorine or chlorine.

2.4 Compounds of Formula Ia which Exemplify Additional Preferred A1 Moieties In a different embodiment of section 2.2, additional preferred compounds have the structures of formula IIg

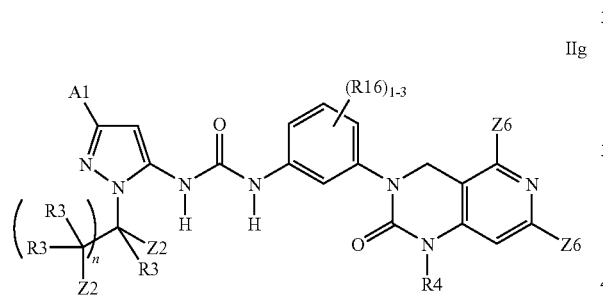

IIg wherein A1 is selected from the group consisting of branched C1-C8alkyl, R19 substituted C3-C8carbocyclyl, C1-C6alkyl, fluoroC1-C6alkyl wherein the alkyl is fully or partially fluorinated, Z3-substituted phenyl, and Z3-substituted G1;
and wherein R16 is C1-C6alkyl, cyano, —CCH, or halogen.

2.4a Additional Compounds of Formula IIg which Exemplify More Preferred X2-E1 Moieties In an embodiment of section 2.4, preferred compounds have the structures of formula IIh

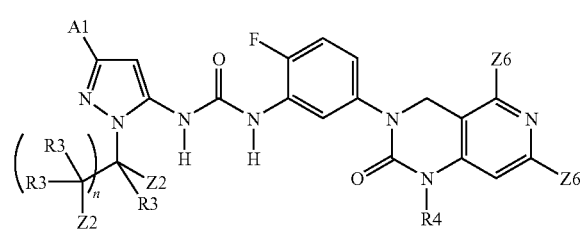

IIh

2.4b Additional Compounds of Formula IIg which Exemplify More Preferred X2-E1 Moieties In another embodiment of section 2.4, preferred compounds have the structures of formula IIi

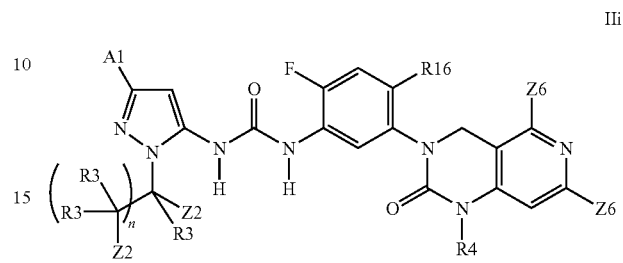

IIi wherein R16 is methyl, cyano, —CCH, fluorine or chlorine.

2.5 Compounds of Formula IIa which Exemplify Additionally Preferred A Moieties In a different embodiment of section 2.1, additional preferred compounds have the structures of formula IIj

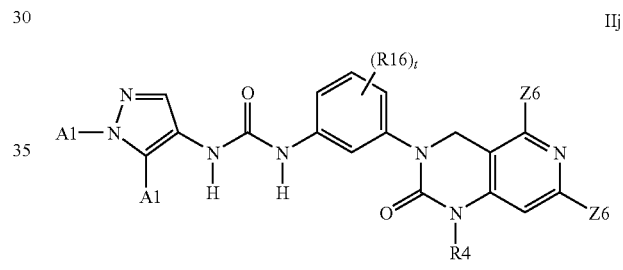

IIj wherein A1 is selected from the group consisting of branched Z2-substituted C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, cyano, —CCH, or halogen.

2.5a Additional Compounds of Formula IIj which Exemplify More Preferred X2-E1 Moieties In an embodiment of section 2.5, preferred compounds have the structures of formula IIk

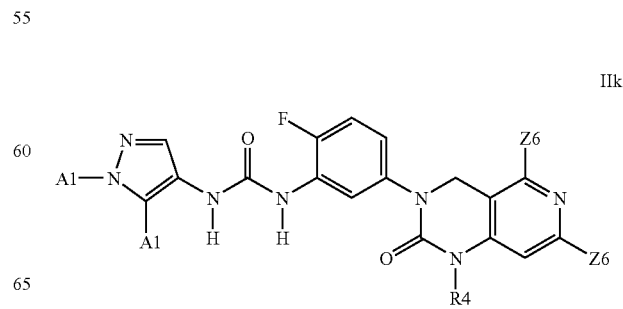

IIk 2.5b Additional Compounds of Formula IIj which Exemplify More Preferred X2-E1 Moieties In another embodiment of section 2.5, preferred compounds have the structures of formula Ill

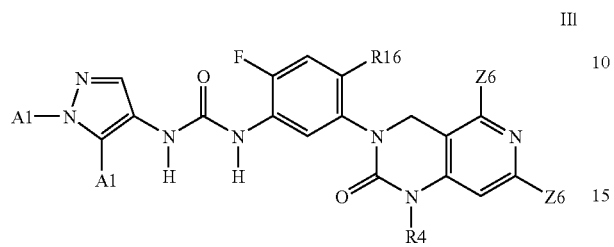

Ill wherein R16 is methyl, cyano, —CCH, fluorine or chlorine.

2.6 Compounds of Formula IIa which Exemplify Additionally Preferred A Moieties

In a different embodiment of section 2.1, additional preferred compounds have the structures of formula IIm

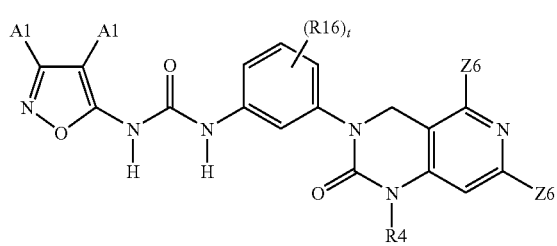

IIm wherein A1 is selected from the group consisting of hydrogen, Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

2.6a Additional Compounds of Formula IIm which Exemplify More Preferred X2-E1 Moieties In an embodiment of section 2.6, preferred compounds have the structures of formula IIn

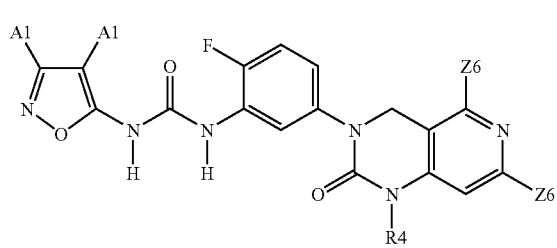

IIn 2.6b Additional Compounds of Formula IIm which Exemplify More Preferred X2-E1 Moieties In another embodiment of section 2.6, preferred compounds have the structures of formula IIo

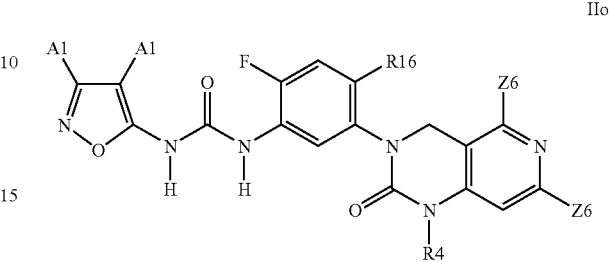

IIo wherein R16 is C1-C6alkyl, cyano, —CCH, fluorine or chlorine.

2.7 Compounds of Formula IIa which Exemplify Additionally Preferred A Moieties

In a different embodiment of section 2.1, additional preferred compounds have the structures of formula IIp

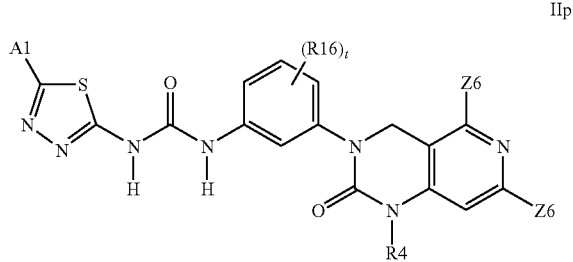

IIp wherein A1 is selected from the group consisting of Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

2.7a Additional Compounds of Formula IIp which Exemplify More Preferred X2-E1 Moieties In an embodiment of section 2.7, preferred compounds have the structures of formula IIq

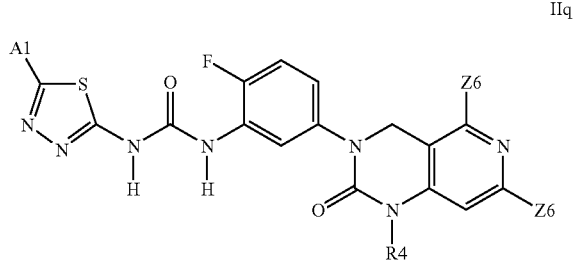

IIq

2.7b Additional Compounds of Formula IIp which Exemplify More Preferred X2-E1 Moieties In another embodiment of section 2.7, preferred compounds have the structures of formula IIr

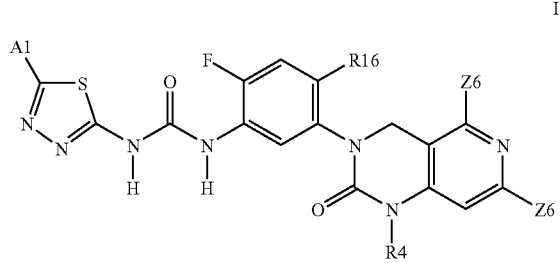

IIr and wherein R16 is methyl, cyano, —CCH, fluorine or chlorine.

2.8 Compounds of Formula IIa which Exemplify Additionally Preferred A Moieties In a different embodiment of section 2.1, additional preferred compounds have the structures of formula IIs

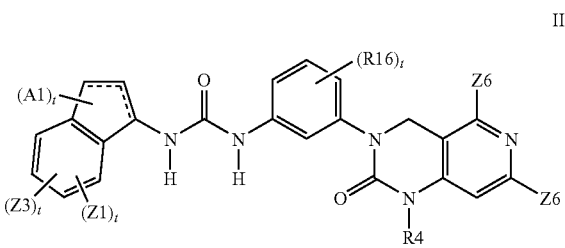

IIs wherein the hashed bond is a saturated or unsaturated bond;
and wherein A1 is selected from the group consisting of hydrogen, Z2-substituted branched C3-C8alkyl, R19 substituted C3-C8carbocyclyl, Z2-substituted C1-C6alkyl, halogen, fluoroC1-C6alkyl, cyano, C1-C6alkoxy, fluoroC1-C6alkoxy, fluoroC1-C6alkyl wherein the alkyl is fully or partially fluorinated, Z3-substituted phenyl, and Z3-substituted G1;
and wherein R16 is C1-C6alkyl, cyano, —CCH, or halogen.

2.8a Additional Compounds of Formula IIa which Exemplify More Preferred X2-E1 Moieties In an embodiment of section 2.8, preferred compounds have the structures of formula IIt IIt

2.8b Additional Compounds of Formula IIs which Exemplify More Preferred X2-E1 Moieties In another embodiment of section 2.8, preferred compounds have the structures of formula IIu

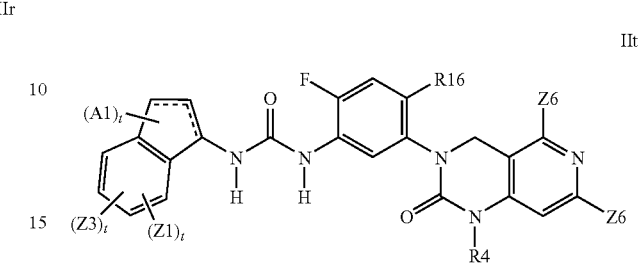

IIt and wherein R16 is C1-C6alkyl, cyano, —CCH, fluorine or chlorine.

2.9 Compounds of Formula IIa which Exemplify Additionally Preferred A Moieties In a different embodiment of section 2.1, additional preferred compounds have the structures of formula IIv IIv wherein the hashed bond is a saturated or unsaturated bond;
and wherein A1 is selected from the group consisting of hydrogen, Z2-substituted branched C3-C8alkyl, R19 substituted C3-C8carbocyclyl, Z2-substituted C1-C6alkyl, halogen, fluoroC1-C6alkyl, cyano, C1-C6alkoxy, fluoroC1-C6alkoxy, fluoroC1-C6alkyl wherein the alkyl is fully or partially fluorinated, Z3-substituted phenyl, and Z3-substituted G1;
and wherein R16 is C1-C6alkyl, cyano, —CCH, or halogen.

2.9a Additional Compounds of Formula IIv which Exemplify More Preferred X2-E1 Moieties In an embodiment of section 2.9, preferred compounds have the structures of formula IIw

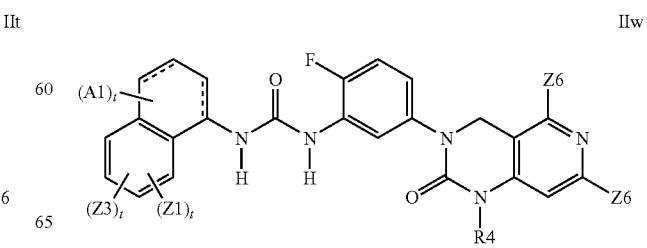

IIw

2.9b Additional Compounds of Formula IIv which Exemplify More Preferred X2-E1 Moieties In another embodiment of section 2.9, preferred compounds have the structures of formula IIx

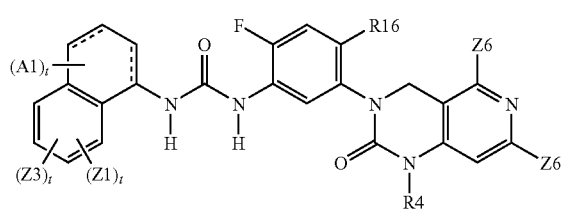

IIx and wherein R16 is C1-C6alkyl, cyano, —CCH, fluorine or chlorine.

2.10 Compounds of Formula IIa which Exemplify Additionally Preferred A Moieties In a different embodiment of section 2.1, additional preferred compounds have the structures of formula IIy

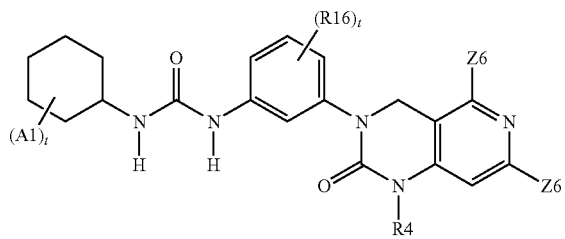

IIy wherein A1 is selected from the group consisting of Z2-substituted branched C3-C8alkyl, R19 substituted C3-C8carbocyclyl, Z2-substituted C1-C6alkyl, fluoroC1-C6alkyl wherein the alkyl is fuly or partially fluorinated, Z3-substituted phenyl, and Z3-substituted G1;

and wherein R16 is C1-C6alkyl, cyano, —CCH, or halogen.

2.10a Additional Compounds of Formula IIy which Exemplify More Preferred X2-E1 Moieties In an embodiment of section 2.10, preferred compounds have the structures of formula IIz

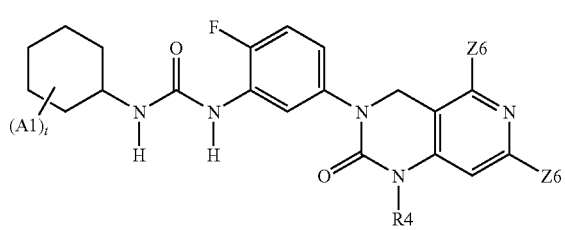

IIz

2.10b Additional Compounds of Formula IIy which Exemplify More Preferred X2-E1 Moieties In another embodiment of section 2.10, preferred compounds have the structures of formula IIaa

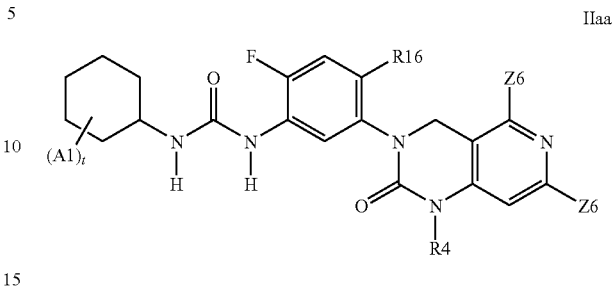

IIaa wherein R16 is methyl, cyano, —CCH, fluorine or chlorine.

2.11 Compounds of Formula IIa which Exemplify Additionally Preferred A Moieties In a different embodiment of section 2.1, additional preferred compounds have the structures of formula IIbb

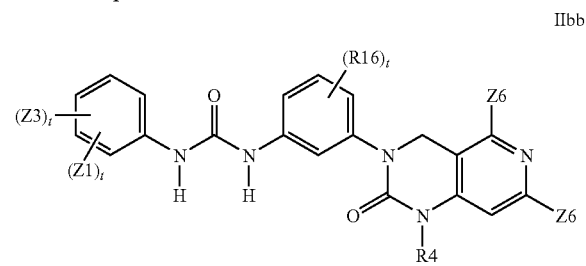

IIbb wherein R16 is C1-C6alkyl, cyano, —CCH, or halogen.

2.11a Additional Compounds of Formula IIbb which Exemplify More Preferred X2-E1 Moieties In an embodiment of section 2.11, preferred compounds have the structures of formula IIcc

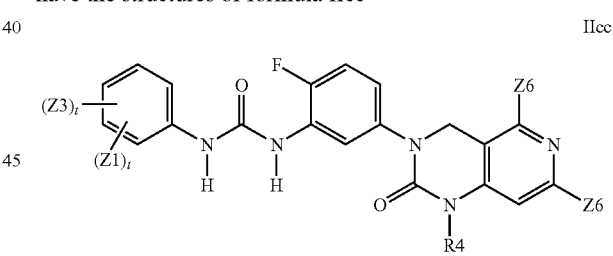

IIcc

2.11b Additional Compounds of Formula IIbb which Exemplify More Preferred X2-E1 Moieties In another embodiment of section 2.11, preferred compounds have the structures of formula IIdd

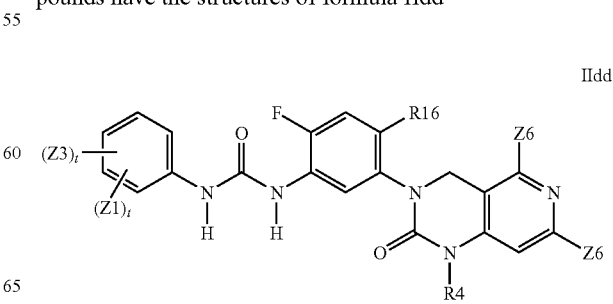

IIdd wherein R16 is C1-C6alkyl, cyano, —CCH, fluorine or chlorine.

2.12 Compounds of Formula IIa which Exemplify Additionally preferred A Moieties

In a different embodiment of section 2.1, additional preferred compounds have the structures of formula IIee

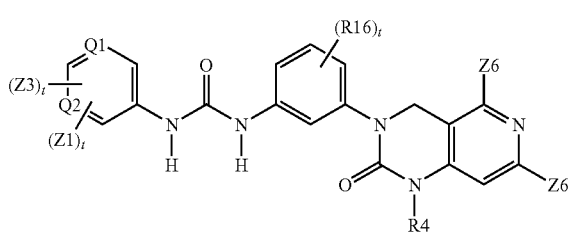

IIee wherein Q1 and Q2 individually and independently taken from the group consisting of N and CH;
and wherein R16 is C1-C6alkyl, cyano, —CCH, or halogen.

2.12a Additional Compounds of Formula IIee which Exemplify More Preferred X2-E1 Moieties In an embodiment of section 2.12 preferred compounds have the structures of formula IIff

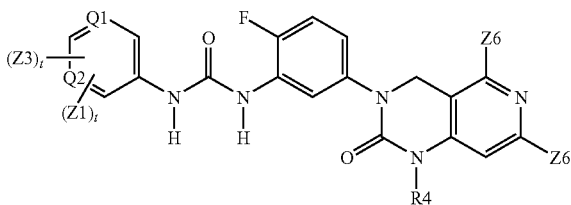

IIff 2.12b Additional Compounds of Formula Iee which Exemplify More Preferred X2-E1 Moieties In another embodiment of section 2.12, preferred compounds have the structures of formula IIgg

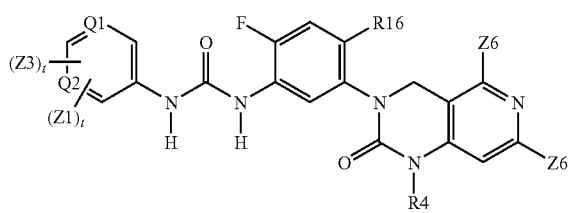

IIgg wherein R16 is C1-C6alkyl, cyano, —CCH, fluorine or chlorine.

2.13 Compounds of Formula IIa which Exemplify Additionally Preferred A Moieties

In a different embodiment of section 2.1, additional preferred compounds have the structures of formula IIhh

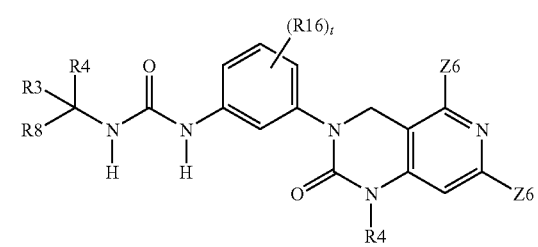

IIhh and wherein R16 is C1-C6alkyl, cyano, —CCH, or halogen.

2.13a Additional Compounds of Formula IIhh which Exemplify More Preferred X2-E1 Moieties In an embodiment of section 2.13, preferred compounds have the structures of formula IIii

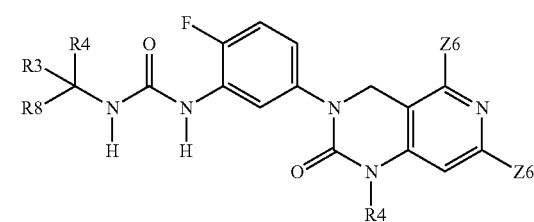

IIii 2.13b Additional Compounds of Formula IIhh which Exemplify More Preferred X2-E1 Moieties In another embodiment of section 2.13, preferred compounds have the structures of formula IIjj

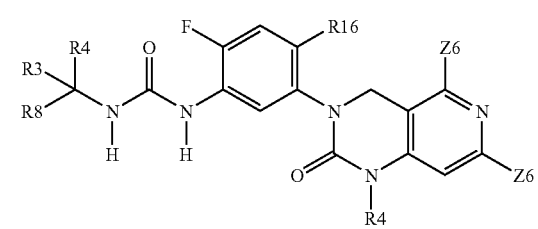

IIjj and wherein R16 is methyl, cyano, —CCH, fluorine or chlorine.

2.14 Compounds of Formula IIa which Exemplify Additionally Preferred A Moieties

In a different embodiment of section 2.1, additional preferred compounds have the structures of formula IIkk

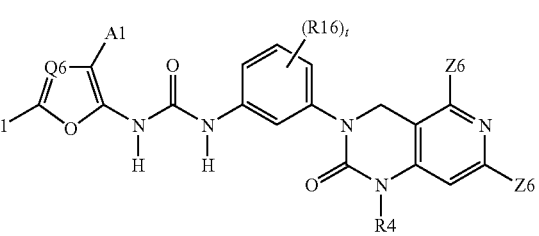

Ikk wherein Q6 is N or C-A1;
wherein A1 is selected from the group consisting of hydrogen, Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, cyano, —CCH, or halogen.

2.14a Additional Compounds of Formula IIkk which Exemplify More Preferred X2-E1 Moieties In an embodiment of section 2.14, preferred compounds have the structures of formula IIll

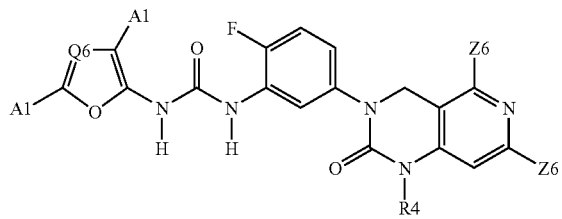

2.14b Additional Compounds of Formula IIkk which Exemplify More Preferred X2-E1 Moieties In another embodiment of section 2.14, preferred compounds have the structures of formula IImm

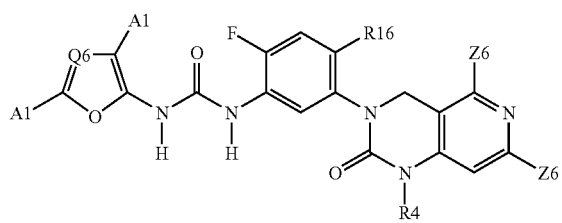

wherein R16 is C1-C6alkyl, cyano, —CCH, fluorine or chlorine.

2.15 Compounds of Formula IIa which Exemplify Additionally Preferred A Moieties

In a different embodiment of section 2.1, additional preferred compounds have the structures of formula Inn

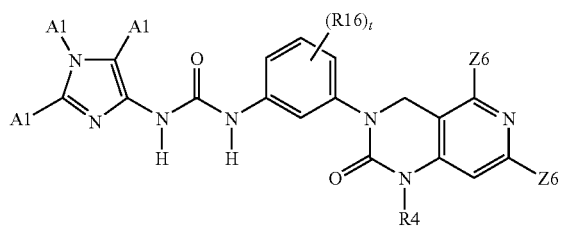

wherein A1 is selected from the group consisting of hydrogen, Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, cyano, —CCH, or halogen.

2.15a Additional Compounds of Formula IInn which Exemplify More Preferred X2-E1 Moieties In an embodiment of section 2.15, preferred compounds have the structures of formula Ioo

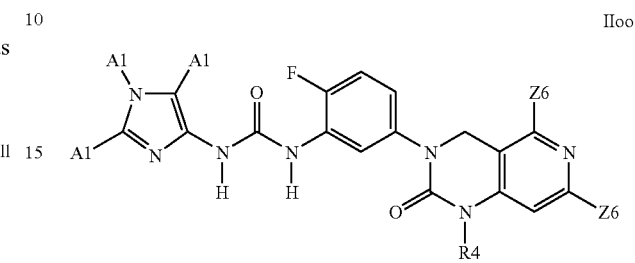

2.15b Additional Compounds of Formula IInn which Exemplify More Preferred X2-E1 Moieties In another embodiment of section 2.15, preferred compounds have the structures of formula IIpp

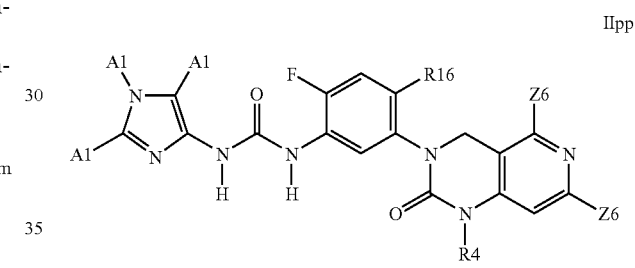

wherein R16 is C1-C6alkyl, cyano, —CCH, fluorine or chlorine.

2.16 Compounds of Formula IIa which Exemplify Additionally Preferred A Moieties

In a different embodiment of section 2.1, additional preferred compounds have the structures of formula IIqq

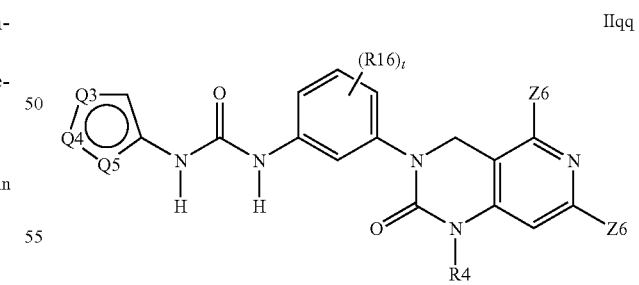

wherein Q3, Q4 and Q5 are selected from the group consisting of N-A1 and C-A1, and only one of Q3, Q4, or Q5 is N-A1;
and wherein A1 is selected from the group consisting of hydrogen, Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, cyano, —CCH, or halogen.

2.16a Additional Compounds of Formula IIqq which Exemplify More Preferred X2-E1 Moieties In an embodiment of section 2.16, preferred compounds have the structures of formula IIrr

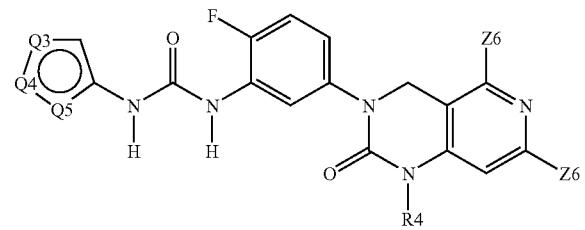

IIrr

2.16b Additional Compounds of Formula IIqq which Exemplify More Preferred X2-E1 Moieties In another embodiment of section 2.16, preferred compounds have the structures of formula IIss

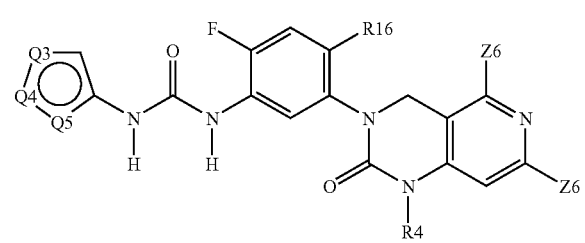

IIss wherein R16 is C1-C6alkyl, cyano, —CCH, fluorine or chlorine.

2.17 Methods

2.17a Methods of Protein Modulation

The invention includes methods of modulating kinase activity of RAF kinases and other kinases in the RAS-RAF-MEK-ERK-MAP kinase pathway including, but not limited to, A-Raf, B-Raf, and C-Raf. The kinases may be wildtype kinases, oncogenic forms thereof, aberrant fusion proteins thereof or polymorphs of any of the foregoing. The method comprises the step of contacting the kinase species with compounds of the invention and especially those set forth in sections 2.1-2.16. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

2.17b Treatment Methods

The methods of the invention, especially those of sections 2.1-2.16, also include treating individuals suffering from a condition selected from the group consisting of chronic myelogenous leukemia, acute lymphocytic leukemia, gastrointestinal stromal tumors, hypereosinophillic syndrome, glioblastomas, ovarian cancer, pancreatic cancer, prostate cancer, lung cancers, breast cancers, kidney cancers, cervical carcinomas, metastasis of primary solid tumor secondary sites, ocular diseases characterized by hyperproliferation leading to blindness including various retinopathies including diabetic retinopathy and age-related macular degeneration, rheumatoid arthritis, melanomas, colon cancer, thyroid cancer, a disease caused by a mutation in the RAS-RAF-MEK-ERK-MAP kinase pathway, human inflammation, rheumatoid spondylitis, ostero-arthritis, asthma, gouty arthritis, sepsis, septic shock, endotoxic shock, Gram-negative sepsis, toxic shock syndrome, adult respiratory distress syndrome, stroke, reperfusion injury, neural trauma, neural ischemia, psoriasis, restenosis, chronic obstructive pulmonary disease, bone resorptive diseases, graft-versus-host reaction, Chron's disease, ulcerative colitis, inflammatory bowel disease, pyresis, and combinations thereof,

2.18 Pharmaceutical Preparations

The compounds of the invention, especially those of sections 2.1-2.16, may form a part of a pharmaceutical composition by combining one or more such compounds with a pharmaceutically acceptable carrier. Additionally, the compositions may include an additive selected from the group consisting of adjuvants, excipients, diluents, and stabilizers.

3. Synthesis of Compounds of the Present Invention

The compounds of Formulae Ia and IIa are prepared by the general synthetic methods illustrated in the Schemes below and the accompanying examples.

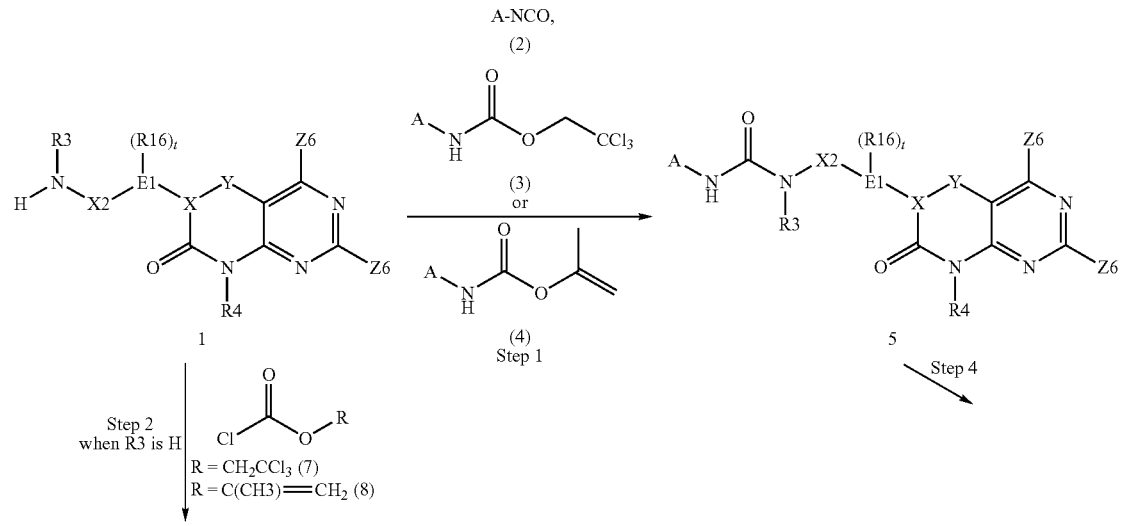

Scheme 1

-continued

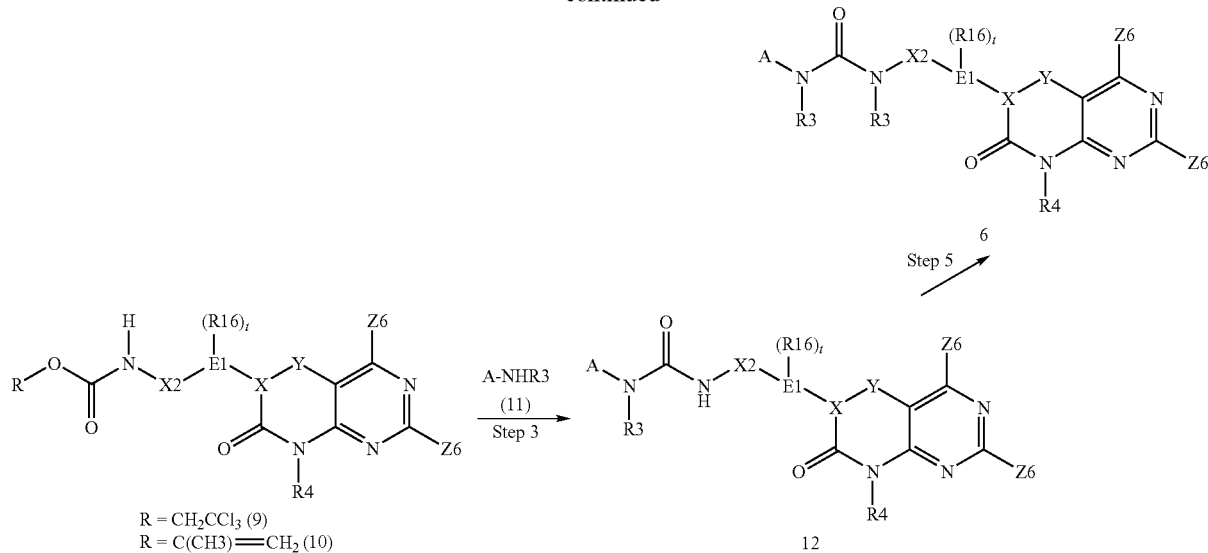

6

Step 5

12

The compounds of general formula Ia, wherein the variables are as defined above, can be prepared by general Scheme 1. Thus in step 1, reaction of amines of formula 1 with isocyanates of formula 2 provides ureas of formula 5, examples of formula Ia. It will be understood that the isocyanates 2 may be either introduced into the reaction directly or may be prepared in situ, for example, by the decomposition of acyl azides (Curtius rearrangement) in the presence of 1. It will be further understood by those skilled in the art that certain carbamates, for example trichloroethyl carbamates (3) and isopropenyl carbamates (4), also function as isocyanate equivalents and will find use in step 1.

Alternatively, when R3=H, amines of Formula 1 may be first converted to isocyanate equivalents 9 or 10 by reaction with trichloroethyl chloroformate (7) or isopropenyl chloroformate (8), respectively. Further reaction of carbamates 9 or 10 with amine 11 provides ureas of formula 12, a subset of Formula 1.

When R3 is not H, mono-R3-substituted ureas 5 and 12 may be converted to doubly-R3-substituted ureas as shown in Steps 4 and 5 of Scheme 1. Alkylation of the NH-ureas 5 or 12 with alkyl halides in the presence of a base, for example potassium carbonate, NaH, potassium t-butoxide or BEMP, in a suitable solvent such as DMF provides compounds of formula 6, wherein the newly introduced R3 is alkyl or cycloalkyl. Alternatively, exposure of ureas 5 or 12 to copper (II) acetate and phenylboronic acids [See: Chan et. al, *Tetrahedron Lett.* 2003, 44, 3863-3865; Chan et. al, *Tetrahedron Lett.* 1998, 39, 2933-2936; Chan, D. M. T. *Tetrahedron Lett.* 1996, 37, 9013-9016] provides the analogous compounds of formula 6 wherein the newly incorporated R3 is phenyl.

A modified route to compounds of general formula Ia (16) is shown below in Scheme 2. Thus, in step 1, compound 13 (equivalent to compound 5, 6 or 12 wherein one of the Z6 groups is thiomethyl) can be oxidized to a sulfoxide (14) or sulfone (15). Preferred reagents for such transformations include peroxybenzoic acids, oxone, oxaziridines, or other oxidants that will be recognized as standard oxidants of sulfur atoms by those skilled in the art. In practice, mixtures of 14 and 15 are generally as effective as either 14 or 15 alone. Purification of mixtures of 14 and 15 is not required prior to usage in step 2. In step 2, the sulfoxide 14/sulfone 15 can be converted to a Z6-substituted compound 16 wherein the new Z6 moiety is attached to the pyrimidine ring with a nitrogen atom linkage or an oxygen atom linkage by the contacting of 14/15 with an amine Z6-H (for example, NH(R4)$_2$) or a hydroxyl Z6-H (for example HOR4) respectively. Preferred solvents for such transformations include DMSO, DMF, THF, alcoholic solvents or neat HN(R4)$_2$ at temperatures ranging from 0° C. to 60° C.

Scheme 2

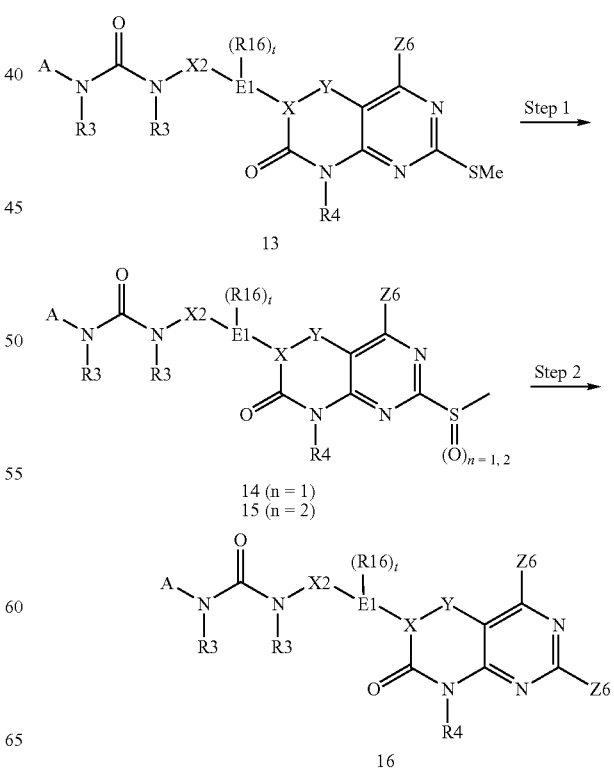

13

14 (n = 1)
15 (n = 2)

16

The synthesis of various amines of Formula 1 is further described in the following examples.

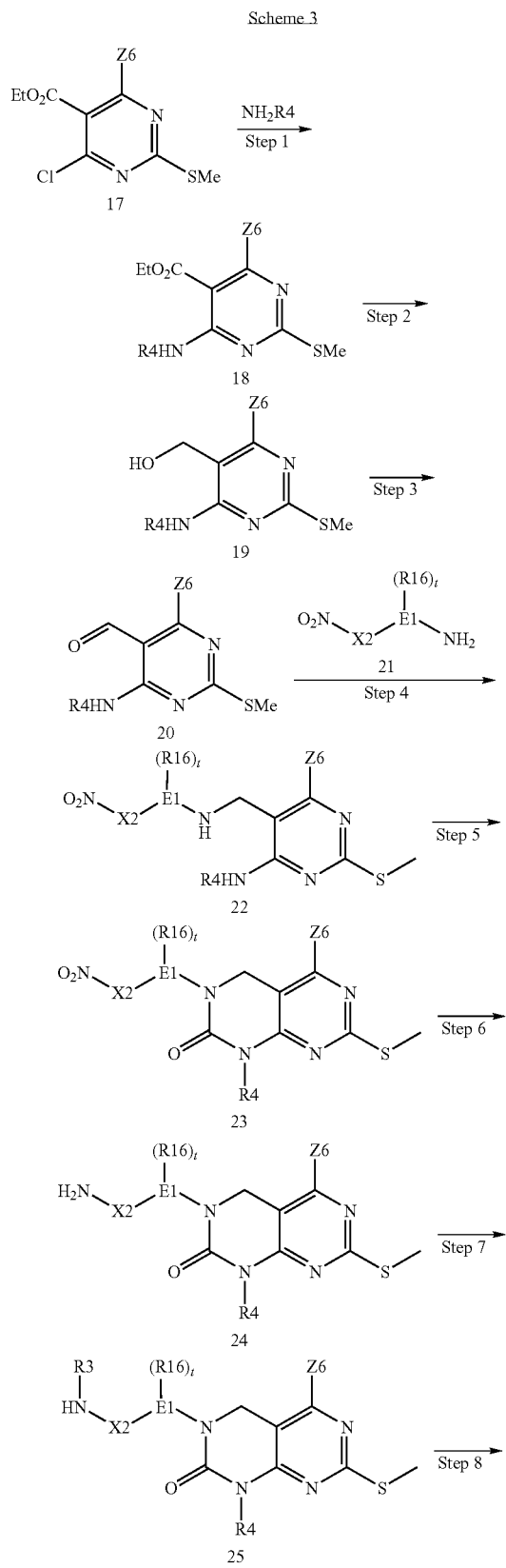

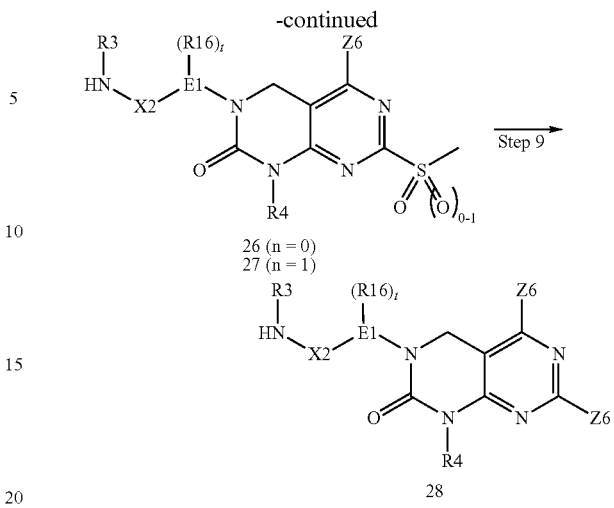

As indicated in Scheme 3, a suitable chloropyrimidine ester 17 is reacted with an R4-substituted amine (step 1) to provide compounds of formula 18. Preferred conditions for Scheme 3, step 1, include polar solvents such as DMF, THF, acetonitrile, dioxane, water or mixtures thereof in the presence of optionally added bases such as triethylamine at temperatures between 0° C. and 100° C. As shown in step 2, reduction of ester 18 provides alcohol 19. Preferred reagents for the transformation of step 2 include lithium aluminum hydride in THF at temperatures ranging from −78° C. to 50° C. As shown in step 3, aldehyde 20 can be prepared by oxidation of alcohol 19 with oxidants such as manganese dioxide.

In scheme 3 step 4, amino-aldehyde 20 can be converted into di-amine 22 by a reductive amination with amine 21. Step 4 may be accomplished in a one-pot procedure by in-situ generation of an imminium ion in the presence of a suitable reducing agent. Preferred conditions for this one-pot variant of step 4 include the combination of aldehyde 20, amine 21 and sodium triacetoxyborohydride in the presence of acetic acid or trifluoroacetic acid at a temperature between 0 and 100° C. Those skilled in the art will recognize that equivalent two-pot procedures exist for the transformation in step 4. For example, condensation of amine 21 and aldehyde 20 to form a discrete Schiff base (imine, not shown) that can be isolated and purified by standard methods if desired. Subsequent reduction of said imine with reducing agents such as lithium aluminumhydride then provides di-amines of formula 22.

In step 5, diamines 22 are reacted with phosgene or a phosgene equivalent to provide cyclic ureas 23. Suitable phosgene equivalents include diphosgene, triphosgene and carbonyldiimidazole. Preferred conditions for step 5 are contacting diamine 22 with diphosgene in the presence of a tertiary amine base such as triethylamine or diisopropylethylamine at a temperature between 0 and 100° C. Preferred solvents for step 5 include dioxane or toluene.

In Scheme 3 step 6, the nitro group of 23 is reduced to provide amine 24, an example of general amine 1. Preferred methods for step 6 include exposure of compounds of formula 23 to hydrogen gas in the presence of a suitable hydrogenation catalyst, for example Pd on carbon in a suitable solvent such as ethanol, ethyl acetate or THF. Other preferred methods for step 6 include reductions with powdered metal reagents, for example iron powder in the presence of aqueous HCl or zinc dust in the presence of ammonium chloride.

In Scheme 3, step 7, the amino moiety of 24 can be optionally "alkylated" to provide an R3-substituted amine 25, also an example of general amine 1. Those skilled in the art will recognize that a variety of standard synthetic methods exist for the transformation of step 7 including direct alkylation with a reagent of formula R3-X (where X is a leaving group such as a halide or tosylate), reductive amination with R3-containing aldehydes, or a two-step process in which the amine is first acylated to provide an R3-containing amide, which can be subsequently reduced to provide an R3-alkylated compound 25.

In step 8, the thiomethyl moiety of 25 can be oxidized to a sulfoxide 26 or sulfone 27. Preferred reagents for such transformations include peroxybenzoic acids, oxone, oxaziridines, or other oxidants that will be recognized as standard oxidants of sulfur atoms by those skilled in the art.

In an analogous manner to Scheme 2, sulfoxide 26/sulfone 27 can be converted to a Z6-substituted compound 28 (step 9) wherein the new Z6 moiety is attached to the pyrimidine ring with a nitrogen atom linkage or an oxygen atom linkage by the contacting of 26/27 with an amine Z6-H [for example, $NH(R4)_2$] or a hydroxyl Z6-H (for example HOR4) respectively. Preferred solvents for such transformations include DMF, THF, DMSO, alcoholic solvents or neat $NH(R4)_2$ at temperatures ranging from 0° C. to 200° C., optionally in the presence of a base such as potassium tert-butoxide, sodium hydride, hydroxide, or the like or, alternatively, in the presence of a strong acid such as hydrochloric acid. Those skilled in the art will recognize that in certain instances, compounds of formula 28 can be prepared directly from compounds of formula 25 using the conditions of step 9.

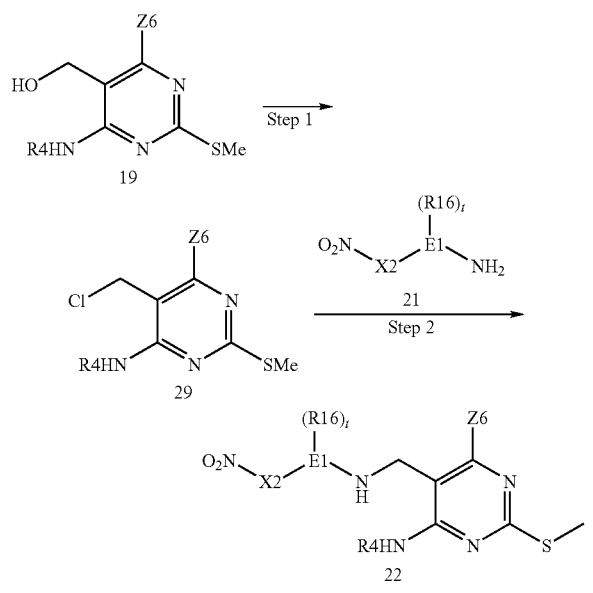

An alternate synthetic route to compounds of Formula 22 is shown in Scheme 4. Thus, alcohol 19 can be converted to chloride 29 by the action of thionyl chloride or phosphorus oxychloride ($POCl_3$). Reaction of chloride 29 with amine 21 provides diamine 22. Preferred conditions for the Scheme 4 step 2 transformation include contacting chloride 29 with amine 21 in the presence of diisopropylethylamine and optionally in die presence of sodium iodide. Preferred solvents for step 2 include acetonitrile and dioxane at temperatures between 0 and 80° C.

Those skilled in the art will recognize that the nitro moiety of amine 21 in schemes 3 and 4 represents an amine surrogate and hence the nitro amine 21 may be replaced in schemes 3 and 4 with amine 30, below, wherein the group "P" in formula 30 represents an amine protecting group, such as tert-butyl carbamate (Boc), benzyl carbamate (Cbz), acetamide or the like. It will be understood by those skilled in the art that when intermediate 30 is substituted in place of amine 21 in Scheme 3, the protecting group P of formula 30 can be removed by appropriate deprotection conditions (for example, acidic removal for a Boc or hydrogenation for a Cbz) to provide compounds leading to the production of intermediate 25. It will be further understood by those skilled in the art that the moiety R3-N—P—X2 in formula 30 might also represent an amino-X2 surrogate such as a cyano that can be converted to an aminomethyl group in an analogous manner by reduction under suitable conditions.

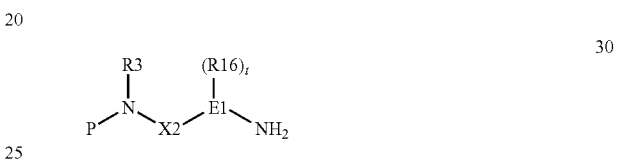

Non-commercially available pyrimidines 17 can be readily prepared from known intermediate 31 [See Seto, et al *Biorg, Med, Chem. Lett.* 2005, 15, 1485]. (Scheme 5) Thus, lithiation of 31 with LDA followed by $CO_2$ quench provides acid 32. Conversion of acid 32 to ester 33 provides a scaffold to introduce Z6 groups of the invention. When the Z6 moiety is attached to the pyrimidine ring through a Z6 nitrogen atom, a Z6 oxygen atom or a Z6 sulfur atom, compounds of formula 17 can be prepared by contacting the amine Z6-H, the alcohol Z6-H or the thiol Z6-H with compound 33, either neat (Z6-H as solvent) or in a suitable solvent such as DMF, DMSO or an alcoholic solvent at temperatures ranging from −78° C. to 200° C. in the presence of suitable base such as triethylamine, potassium carbonate, or potassium tert-butoxide. When the Z6 moiety is attached to the pyrimidine through a Z6 carbon atom, preferred methods include contacting compound 33 with a species of formula Z6-M in the presence of a palladium catalyst, wherein M is a species that participates in transition-metal catalyzed cross-coupling reactions. Examples of suitable M groups include but are not limited to, boronic acids and boronic esters, zinc, copper, tin, silicon, magnesium, lithium, and aluminum.

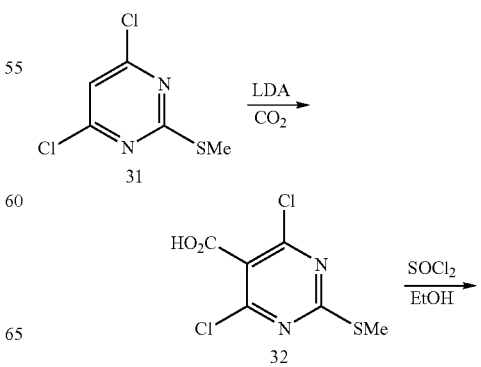

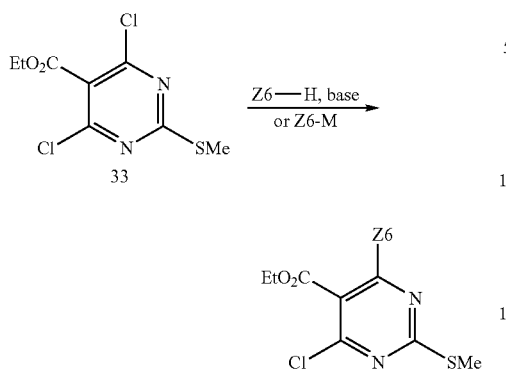

Some amines of general formula 1 can also be prepared as shown in Scheme 6. Thus, reaction of R4-substituted amines with 5-bromo-2,6-dichloropyrimidine (34, commercially available) provides bromo amine 35. In step 2, treatment of bromides 35 with tributylvinyltin in the presence of a palladium catalyst provides 36. In step 3, oxidative cleavage of the olefin moiety provides aldehydes of formula 37. Application of steps 4-7 of Scheme 3 converts aldehyde 37 to amine 38. In Scheme 6 step 8, chloride 38 can be converted to Z6-substituted 39 by several methods, depending on the nature of Z6. When the Z6 moiety is attached to the pyridopyrimidine ring through a Z6 nitrogen atom, preferred methods include heating 38 with an excess of the amine Z6-H either neat or in a solvent such as DMF, DMSO or an alcoholic solvent at temperatures ranging from room temp to 200° C. For the case of aryl and heteroaryl amines Z6-H, additional preferred methods include the heating of compounds 38 with an excess of the amine Z6-H and an acid catalyst (for example, TsOH, HCl, HOAc or the like) in a suitable solvent such as DMF, DMSO or an alcoholic solvent. Additional preferred methods for aryl and heteroarylamines Z6-H include heating with 38 in the presence of a transition metal catalyst such as a palladium catalyst in a suitable solvent like 1,4-dioxane or DMF. When the Z6 moiety is attached to the pyridopyrimidine through a Z6 oxygen or sulfur atom, preferred methods include heating 38 with alcohol or thiol Z6-H in the presence of a strong base (for example, NaH or potassium tert-butoxide) either neat using Z6-H as the solvent, or in a polar solvent such as DMF or DMSO at temperatures ranging from room temp to 200° C. When the Z6 moiety is attached to the pyridopyrimidine through a Z6 carbon atom, preferred methods include contacting 38 with a species of formula Z6-M in the presence of a palladium catalyst, wherein M is a species that participates in transition-metal catalyzed cross-coupling reactions. Examples of suitable M groups include but are not limited to, boronic acids and boronic esters, zinc, trialkyltin, silicon, magnesium, lithium, and aluminum. In the instance that Z6 is hydrogen, preferred methods include exposure of 38 to hydrogen gas in the presence of a suitable hydrogenation catalyst, for example Raney Nickel® or Pd on carbon in a suitable solvent such as ethanol, ethyl acetate or THF.

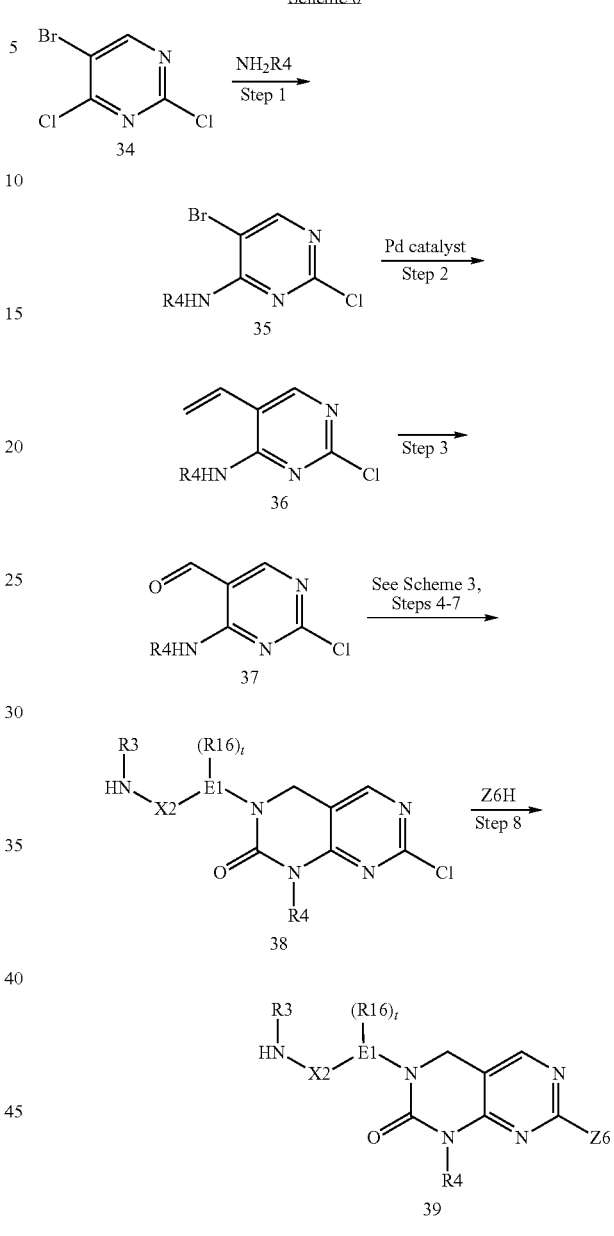

Some compounds of Formula IIa can be prepared by the methods in Scheme 7. By analogy to Scheme 1, amines 40 or 41 (wherein all variables are as described above) are reacted with isocyanate (2) or isocyanate surrogate such as 3, 4 or an acyl azide via a Curtius rearrangement (not shown) to provide ureas 42 and 43 respectively, examples of general Formula IIa. In the instances where R3=H, amines of Formula 40 and 41 may be first converted to isocyanate equivalents 44-47 by reaction with trichloroethyl chloroformate (7) or isopropenyl chloroformate (8). Further reaction of carbamates 44-47 with amine 11 provides ureas of formula 48 and 49, examples of Formula IIa. When R3 is not H, mono-R3-substituted ureas 42, 43, 48, or 49 may be converted to doubly-R3-substituted ureas 50 or 51 as shown in Steps 4 and 5 of Scheme 7 by the methods described above in Scheme 1.

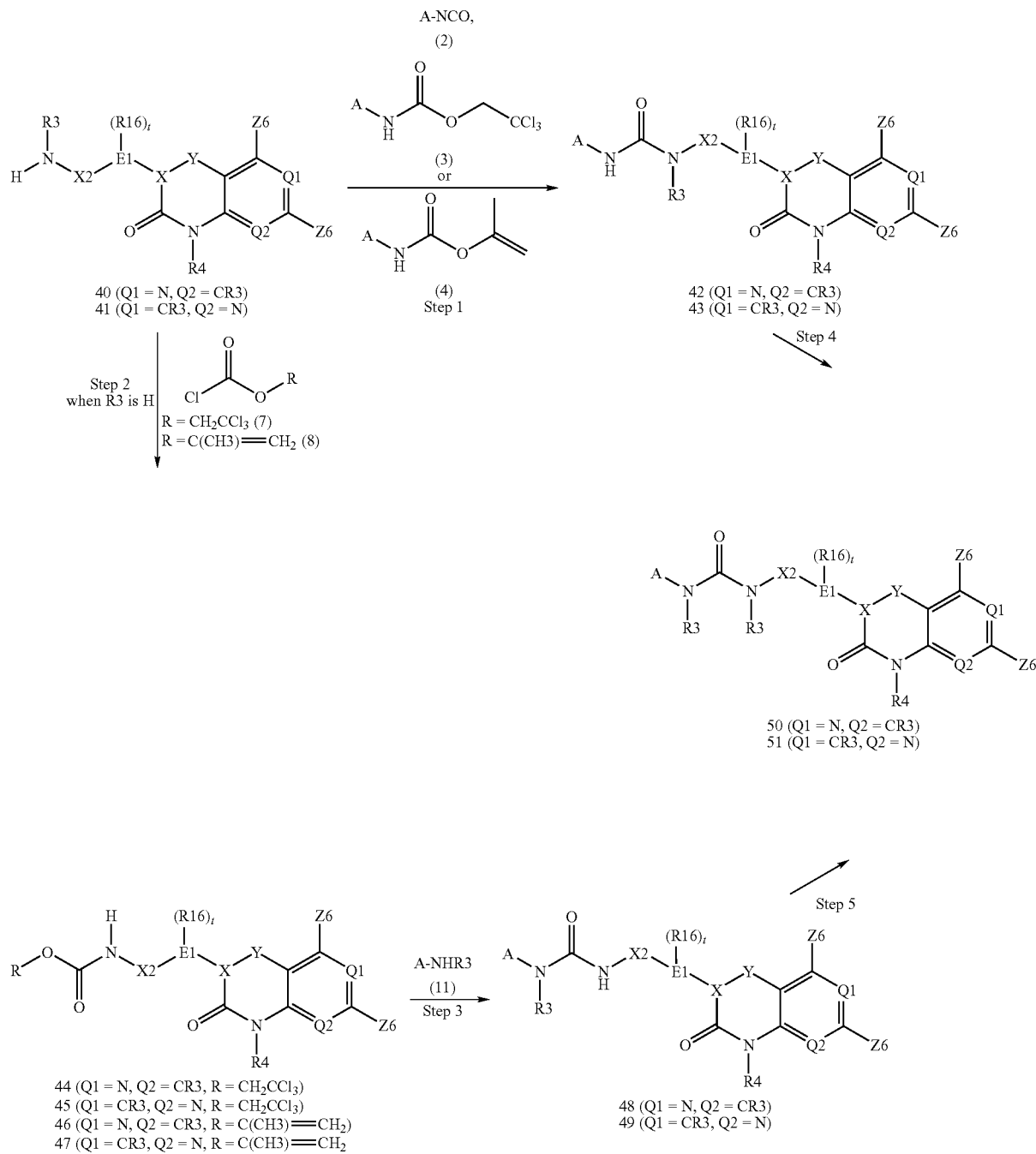

Scheme 7

Amines of general formulae 40 and 41 are available by the following schemes and accompanying experimental examples. Scheme 8 details the preparation of general amine 60. By analogy to Scheme 3, a Z6-substituted dichloronicotinic acid ethyl ester 52 is reacted with an R4-substituted amine (Scheme 8, step 1) to provide compounds of formula 53. Preferred conditions for Scheme 8, step 1, include polar solvents such as DMF, THF, acetonitrile, dioxane, water or mixtures thereof in the presence of optionally added bases such as triethylamine at temperatures between 0° C. and 100° C. As shown in step 2, reduction of ester 53 provides alcohol 54. Preferred reagents for the transformation of step 2 include lithium aluminum hydride in THF at temperatures ranging from −78° C. to 50° C. As shown in step 3, aldehyde 55 can be prepared by oxidation of alcohol 54 with oxidants such as manganese dioxide.

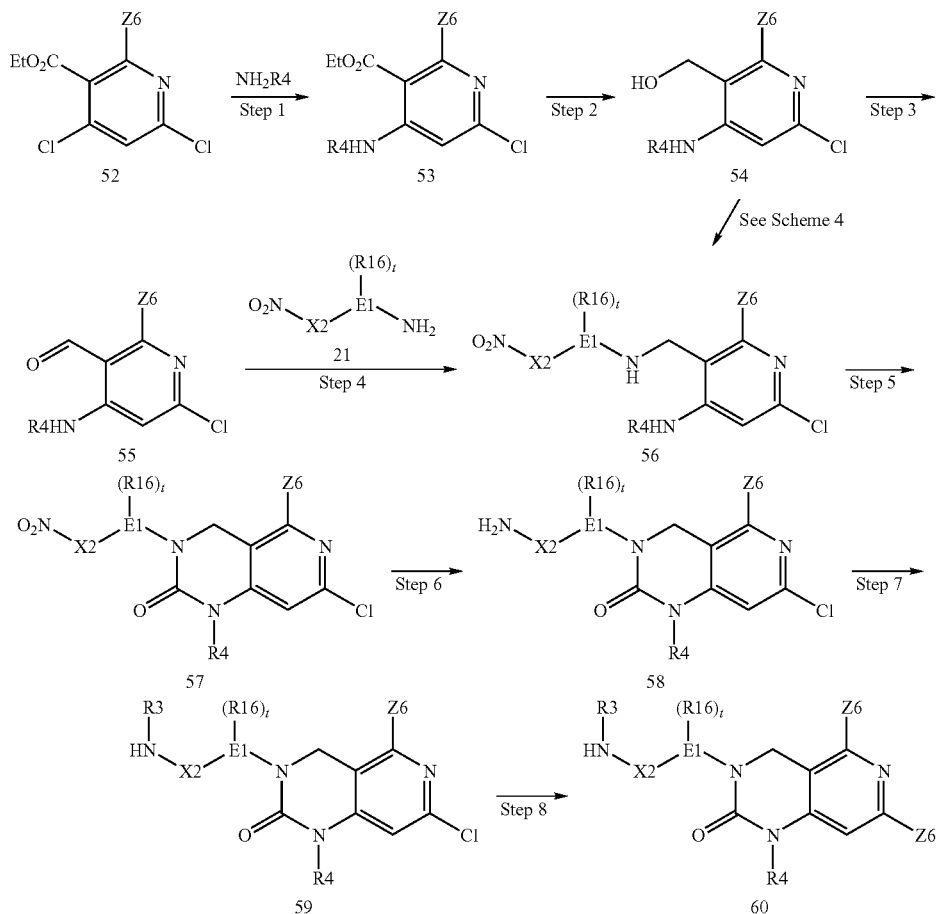

Scheme 8

In Scheme 8 step 4, amino-aldehyde 55 can be converted into di-amine 56 by a reductive amination with amine 21. Step 4 may be accomplished in a one-pot procedure by in-situ generation of an imminium ion in the presence of a suitable reducing agent. Preferred conditions for this one-pot variant of step 4 include the combination of aldehyde 55, amine 21 and sodium triacetoxyborohydride in the presence of acetic acid or trifluoroacetic acid at a temperature between 0 and 100° C. Alternately, step 4 can be a two-pot procedure in which amine 21 and aldehyde 55 are first condensed to form a discrete Schiff base (imine, not shown) that can be isolated and purified by standard methods if desired. Subsequent reduction of said imine with reducing agents such as lithium aluminumhydride then provides di-amines of formula 56. More preferably, 56 can also be prepared from alcohol 54 via the corresponding chloride (not shown) according to the procedure described above for Scheme 4.

In step 5, diamines 56 are reacted with phosgene or a phosgene equivalent to provide cyclic ureas 57. Suitable phosgene equivalents include diphosgene, triphosgene and carbonyldiimidazole. Preferred conditions for step 5 are contacting diamine 56 with diphosgene in the presence of a tertiary amine base such as triethylamine or diisopropylethylamine at a temperature between 0 and 100° C. Preferred solvents for step 5 include dioxane or toluene.

In Scheme 8 step 6, the nitro group of 57 is reduced to provide amine 58. Preferred methods for step 6 include exposure of compounds of formula 57 to powdered metal reagents, for example iron powder in the presence of aqueous HCl or zinc dust in the presence of ammonium chloride. In step 7, the amino moiety of 58 can be optionally "alkylated" to provide an R3-substituted amine 59. Those skilled in the art will recognize that a variety of standard synthetic methods exist for the transformation of step 7 including direct alkylation with a reagent of formula R3-X (where X is a leaving group such as a halide or tosylate), reductive amination with R3-containing aldehydes, or two-step processes in which the with the amine is first acylated to provide an R3-containing amide, which can be subsequently reduced to provide an R3-alkylated compound 59.

Compounds of formula 59 can be converted to compounds of formula 60, an example of general formula 40, by replacement of the chloride moiety of 59 with a Z6 moiety (step 8). There are several methods through which this can be accomplished, depending on the nature of the Z6-H. When the Z6 moiety is attached to the pyridine ring through a Z6 nitrogen atom, preferred methods include heating compounds of formula 59 with an excess of the amine Z6-H either neat or in a solvent such as DMF, DMSO or an alcoholic solvent at temperatures ranging from room temp to 200° C. For the case of aryl and heteroaryl amines Z6-H, additional preferred methods include the heating of compound 59 with an excess of the amine Z6-H and an acid catalyst (for example, TsOH, HCl, HOAc or the like) in a suitable solvent such as DMF, DMSO or an alcoholic solvent. Additional preferred methods for aryl and heteroarylamines Z6-H include heating with compound 59 in the presence of a transition metal catalyst such as a palladium catalyst in a suitable solvent like 1,4-dioxane or DMF. When the Z6 moiety is attached to the pyridine through a Z6 carbon atom, preferred methods include contacting compound 59 with a species of formula Z6-M in the presence of a palladium catalyst, wherein M is a species that participates in transition-metal catalyzed cross-coupling reactions. Examples of suitable M groups include but are not limited to, boronic acids and boronic esters, zinc, trialkyltin, silicon, magnesium, lithium, and aluminum. In the instance that Z6 is hydrogen, preferred methods include exposure of compounds of formula 59 to hydrogen gas in the presence of a suitable hydrogenation catalyst, for example Pd on carbon in a suitable solvent such as ethanol, ethyl acetate or THF.

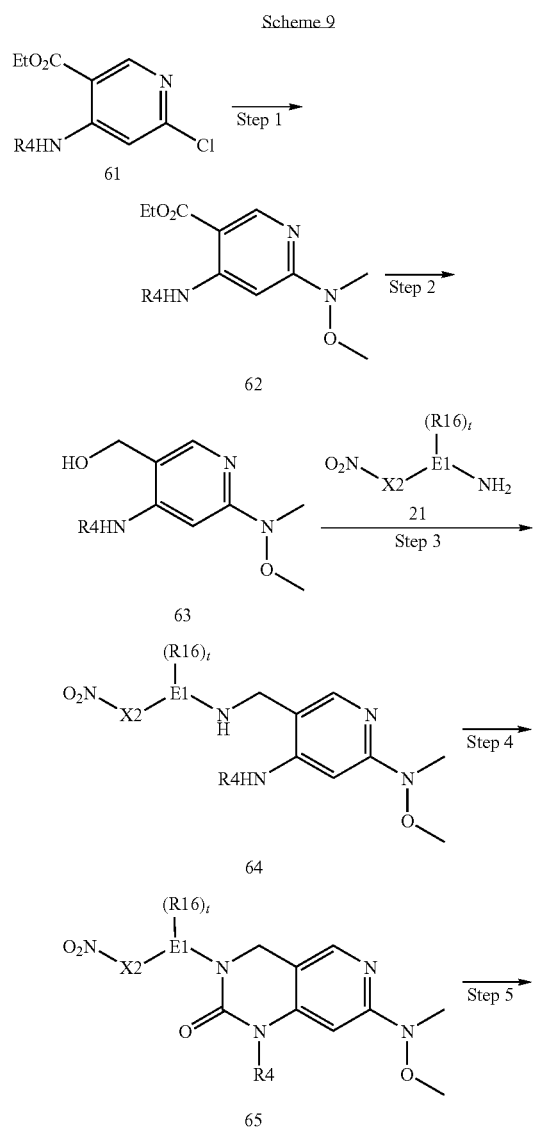

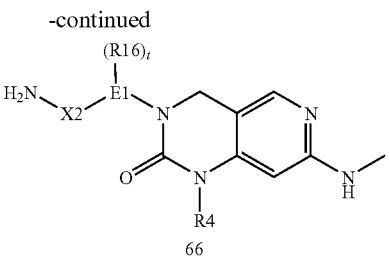

A preferred method for preparing amines of general Formula 40 in which the pyridine ring Z6 substituent is aminomethyl is illustrated in Scheme 9 with the preparation of general amine 66. Thus, chloropyridine 61 (prepared from ethyl 2,4-dichloronicotinate by analogy to Scheme 8, step 1) undergoes reaction with N,O-dimethylhydroxylamine HCl to provide aminopyridine ester 62 (step 1). The ester 62 can be reduced to alcohol 63 as described above. In step 3, alcohol 63 is converted to diamine 64 following the protocols described in Scheme 4 above. Treatment of 64 with diphosgene as described above provides the cyclic urea 65. Concomitant reduction of the nitro group and cleavage of the methoxyamine N—O bond in Scheme 9 step 5, provides 66, an example of general amine 40. Preferred conditions for step 5 include exposing 65 to hydrogen gas in the presence of a suitable hydrogenation catalyst, for example Pd on carbon, in a suitable solvent such as methanol, ethanol, ethyl acetate or THF at a pressure of 1-100 psi and a temperature of 15-80° C.

Amines of general formula 41 can be prepared as shown in Scheme 10. Starting with 3-bromo-2,6-dichloropyridine (67, available by the procedure of Pierrat et al. *J. Comb. Chem.* 2005, 7, 879-886), reaction of R4-substituted amines provides bromo amine 68. In step 2, treatment of bromide 68 with tributylvinyltin in the presence of a palladium catalyst provides 69, and then by analogy to Scheme 6, amine 71 can be prepared as an example of general amine 41.

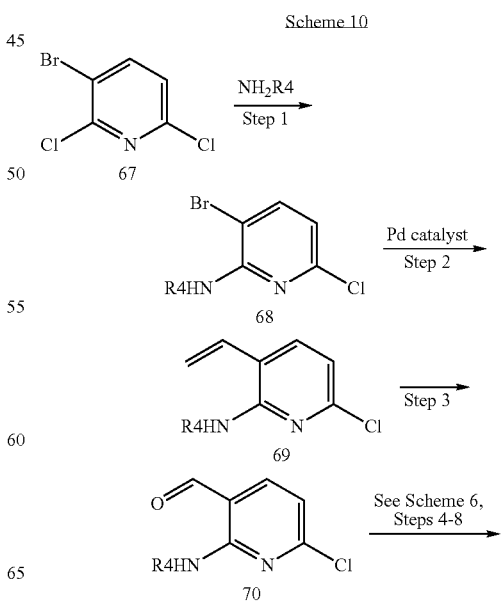

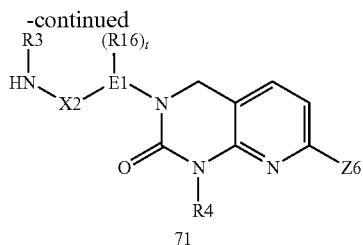

71

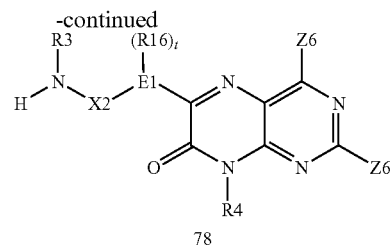

78

Amines of formula 1 wherein X—Y is C═N can be prepared as outlined in Scheme 11. Thus, in step 1, selective displacement of one of the chlorine atoms in dichloro-nitropyrimidines 72 (Z6=H, Z6=methyl, Z6=carboxyethyl are commercially available) can be accomplished by treatment with R4-substituted amines in an appropriate solvent such as THF at a temperature between −78° C. and room temp to provide compounds 73. In step 2, replacement of the remaining chlorine atom with a Z6 moiety can be accomplished by the method discussed above in Scheme 6 step 8 to provide compound 74. Reduction of the nitro group provides a diamine of formula 75 (step 3). Condensation of compounds 75 with alpha-ketoesters of formula 76 in step 4 provides compounds of formula 77. In step 5, the optional protecting group P is removed to provide compounds 78, an example of amine 1.

By analogy to Scheme 11, examples of amines 40 and 41 wherein X—Y is C═N can be prepared as shown in Scheme 12. In step 1, reaction of dichloro-nitropyridines 79 (Z6=H: See *Recueil des Travaux Chimiques des Pays-Bas,* 1976, 95, 127-129) and 80 (Z6=H: commercially available) with R4-substituted amines in an appropriate solvent such as THF provides compounds 81 and 82 respectively. In step 2, replacement of the remaining chlorine atom with a Z6 moiety can be accomplished by the method discussed above in Scheme 6 step 8 to provide compounds 83-84. By analogy to Scheme 11, steps 3-5, nitroamines 83 and 84 can be converted to 85 and 86, examples of amines 40 and 41 respectively.

Scheme 11

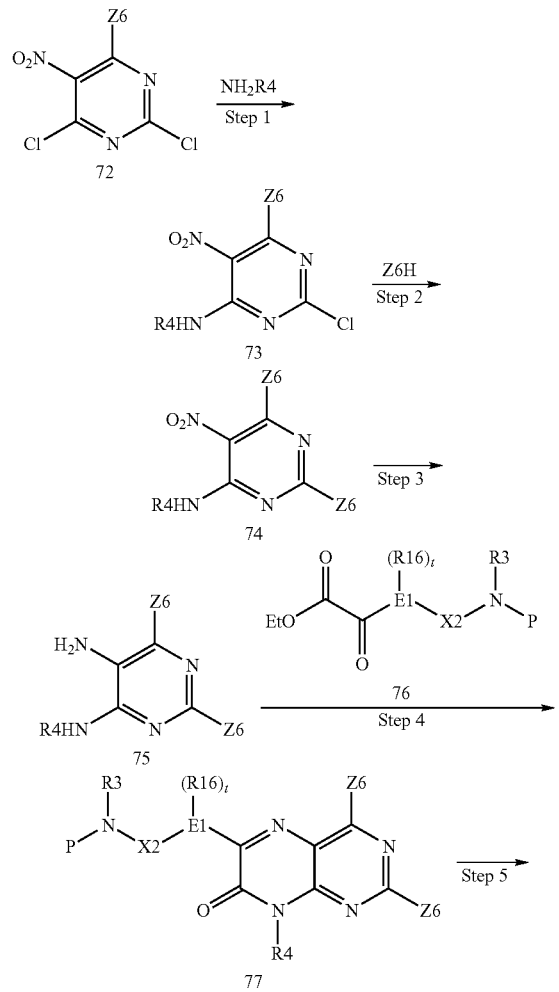

Scheme 12

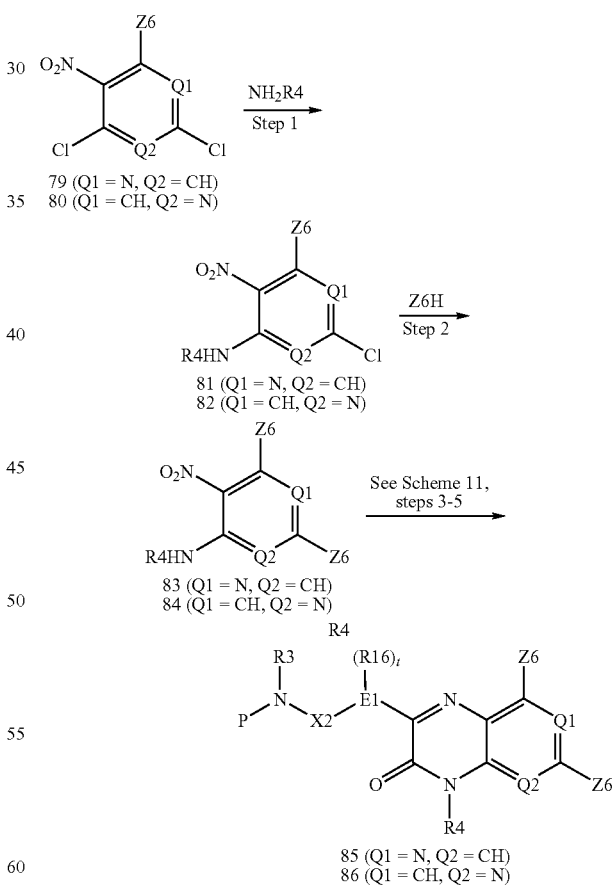

General method A: To a solution of the starting pyrazole amine (1 eq) in EtOAc were added 2,2,2-trichloroethylchloroformate (1.1 eq) and saturated NaHCO₃ (2-3 eq) at 0° C. After stirring for 3 h at RT, the layers were separated and the aqueous layer extracted with EtOAc. The combined organic extracts were washed with brine, dried (Na$_2$SO$_4$) and concentrated in vacuo to yield the crude TROC carbamate of the pyrazole amine. To the carbamate (1 eq) in DMSO were added diisopropylethylamine (2 eq), the appropriate amine (2 eq) and the mixture was stirred at 60° C. for 16 h or until all the starting carbamate was consumed. Water was added to the mixture and the product was extracted with EtOAc (2×25 mL). The combined organic extracts were washed with brine solution, dried (Na$_2$SO$_4$) and concentrated in vacuo to yield crude product, which was purified by column chromatography to yield the target compound.

General method B: To a suspension of the amine (usually 0.67 mmol) in EtOAc (2 mL) was added aqueous 1N NaOH. The reaction mixture was cooled to 0° C. and treated with isopropenyl chloroformate (0.1 mL, 0.94 mmol) over 30 sec. The reaction mixture was stirred 15 min at 0° C. and 1 h at RT. The reaction was poured into THF-EtOAc (1:1; 40 mL) and washed with H$_2$O (2×10 mL) and brine (2×10 mL). The organics were dried (Na$_2$SO$_4$), concentrated in vacuo and the residue purified via column chromatography to provide the target (prop-1-en-2-yl)carbamate. To the carbamate (usually 0.26 mmol) was added the appropriate amine (usually 0.26 mmol) in THF (2 mL) and 1-methylpyrrolidine (Catalytic amount) at 60° C. for 18 h. The mixture was diluted with CH$_2$Cl$_2$ (2 mL) and hexane (0.5 mL) solution, and stirred for 10 min. The resultant solid was filtered and dried and the resulting solid converted to the amine hydrochloride salt by treatment with 0.1 N HCl solution and lyophilization.

General Method C: To a stirring solution of amine (2 mmol, 1.00 eq) and pyridine (4 mmol, 2.00 eq) in CH$_2$Cl$_2$ (18 ml) at RT was added Troc-Cl (1.87 mmol, 1.05 eq). After 4 hours the reaction was washed with 3M HCl (1×), satd. NaHCO$_3$ (1×), dried (Na$_2$SO$_4$), filtered and evaporated to afford the target 2,2,2-trichloroethyl carbamate. The material was used as is in the next reaction.

The 2,2,2-trichloroethyl carbamate (0.7 mmol, 1.00 eq), the appropriate (0.7 mmol, 1.00 eq) and iPr$_2$NEt (1.54 mmol, 2.20 eq) were combined in DMSO (3 ml) and stirred with heating at 70° C. After 18 h, the completed reaction was diluted with brine (30 ml) and extracted with EtOAc (3×). The combined organics were washed with brine (2×), dried (MgSO$_4$), filtered and evaporated to give the crude product which was purified via flash column chromatography.

General Method D: To a stirring solution of carboxylic acid (0.50 mmol, 1.00 eq) and DPPA (0.75 mmol, 1.50 eq) in 1,4-dioxane (5.0 ml) at RT was added Et$_3$N (1.5 mmol, 3.00 eq). After stirring for 30 min at RT, the appropriate amine (0.76 mmol, 1.50 eq) was added and the mixture was heated at 100° C. After 2 h, the completed reaction was cooled to RT, diluted with brine and extracted with EtOAc (2×). The combined organics were washed with 3M HCl (1×), satd. NaHCO$_3$ (2×), and brine (1×), dried (MgSO$_4$), filtered and evaporated to give the crude product which was purified by flash column chromatography to afford the target urea.

General Method E: To a solution of aryl sulfone and/or aryl sulfoxide (0.4 mmol) in THF was added the appropriate amine (2 mmol, 5 eq) and the reaction was stirred for 2 h at RT. The mixture was diluted with EtOAc (3 mL) and resultant solid filtered, washed and dried to provide the desired product aryl amine.

General Method F: To a stirring suspension of isocyanate (0.51 mmol, 1.00 eq) and pyridine (0.0418 ml, 0.51 mmol, 1.00 eq) in CH$_2$Cl$_2$ (5 ml) at RT was added the appropriate amine (0.51 mmol, 1.00 eq). A thick suspension gradually formed. After 3.5 h, the solids were collected by filtration, rinsed well with CH$_2$Cl$_2$ and dried on the filter to afford the desired urea.

General Method G: To a solution of amine (11 mmol) in THF (100 mL) was added LiHMDS (22 mmol) at −78° C. under Ar. After 20 min, prop-1-en-2-yl chloroformate (11 mmol) was added and the reaction was stirred for 30 min. The mixture was quenched with 2N HCl (15 mL) at −78° C. and warmed to RT. It was diluted with brine (50 mL) and EtOAc (50 mL), the organic layer was separated and washed with brine, dried (Na$_2$SO$_4$) and concentrated in vacuo. Purification by silica gel chromatography or recrystallization provided the appropriate prop-1-en-2-yl carbamate.

To the carbamate (usually 0.26 mmol) was added the appropriate amine (usually 0.26 mmol) in THF (2 mL) and 1-methylpyrrolidine (Catalytic amount) at 60° C. for 18 h. The mixture was diluted with CH$_2$Cl$_2$ (2 mL) and hexane (0.5 mL) solution, and stirred for 10 min. The resultant solid was filtered and dried and the resulting solid converted to the amine hydrochloride salt by treatment with 0.1 N HCl solution and lyophilization.

EXAMPLE A1

Acetic acid (10 mL, 174 mmol) was added to a mixture of Example C2 (10 g, 54.6 mmol) and 4-fluoro-3-nitroaniline (8.5 g, 54.6 mmol) in water (350 mL) and the mixture was stirred at RT overnight. The solid was collected by filtration and washed with MeOH (2×20 mL) to give 5-((4-fluoro-3-nitrophenylimino)methyl)-N-methyl-2-(methylthio)pyrimidin-4-amine (8.0 g, 46% yield) as a yellow solid. $^1$H NMR (300 MHz, DMSO-d$_6$): δ 9.39 (m, 1 H), 8.71 (s, 1 H), 8.33 (s, 1 H), 8.18 (m, 1 H), 7.80 (m, 1 H), 7.61 (t, J=6.9 Hz, 1 H), 3.05 (d, J=3.6 Hz, 3 H), 2.48 (s, 3 H); MS (ESI) m/z: 322.2 (M+H$^+$).

To a suspension of LiAlH$_4$ (1.3 g, 34 mmol) in anhydrous THF at 0° C. was added the above 5-((4-fluoro-3-nitrophenylimino)methyl)-N-methyl-2-(methylthio)pyrimidin-4-amine portionwise over 20 min. After the addition was complete, the mixture was stirred at 0° C. for 30 min. Aqueous 10% NaOH (2 mL) was added and the resultant precipitate was removed by filtration. The filtrate was concentrated under reduced pressure to give 5-((4-fluoro-3-nitrophenylamino)methyl)-N-methyl-2-(methylthio)pyrimidin-4-amine (6.0 g, 56% yield) as a brown solid. $^1$H NMR (300 MHz, DMSO-d$_6$): δ 7.84 (s, 1 H), 7.28 (dd, J=6.6, 8.4 Hz, 1 H), 7.17 (m, 1 H), 7.03 (m, 1 H), 6.42 (t, J=3.9 Hz, 1 H), 4.00 (d, J=3.9 Hz, 2 H), 2.82 (d, J=4.8 Hz, 3 H), 2.39 (s, 3 H); MS (ESI) m/z: 324.1 (M+H$^+$).

To a solution of diphosgene (3.5 g, 17.7 mmol) in dioxane (350 mL) at 0° C. was slowly added a solution comprised of 5-((4-fluoro-3-nitrophenylamino)methyl)-N-methyl-2-(methylthio)pyrimidin-4-amine (5.2 g, 16.1 mmol) and Et$_3$N (4.5 mL, 32.1 mmol) in dioxane (250 mL). The resultant reaction mixture was stirred at RT overnight. The solvent was removed in vacuo and the residue was partitioned between EtOAc and H$_2$O. The combined organics were dried (Na$_2$SO$_4$) and concentrated to give crude product, which was washed with cold MeOH (5 mL) to give 3-(4-fluoro-3-nitrophenyl)-1-methyl-7-(methylthio)-3,4-dihydropyrimido[4,5-d]pyrimidin-2(1H)-one (5.0 g, 89% yield) as a brown solid. $^1$H NMR (300 MHz, DMSO-d$_6$): δ 8.26 (s, 1 H), 8.20 (m, 1 H), 7.82 (m, 1 H), 7.64 (dd, J=6.9, 8.4 Hz, 1 H), 4.82 (s, 2 H), 3.29 (s, 3 H), 2.50 (s, 3 H); MS (ESI) m/z: 350.3 (M+H$^+$).

To a solution of 3-(4-fluoro-3-nitrophenyl)-1-methyl-7-(methylthio)-3,4-dihydropyrimido[4,5-d]pyrimidin-2(1H)-one (3.0 g, 8.6 mmol) in MeOH (30 mL) was added 10% Pd/C (1.2 g, 1.1 mmol). The resultant mixture was stirred overnight under H$_2$ (30 psi). The mixture was filtered, concentrated in vacuo and purified by silica gel column chromatography to give 3-(3-amino-4-fluorophenyl)-1-methyl-7-(methylthio)-3,4-dihydropyrimido[4,5-d]pyrimidin-2(1H)-one (1.8 g, 66% yield) as a brown solid. $^1$H NMR (300 MHz, DMSO-d$_6$): δ 8.21 (s, 1 H), 6.99 (dd, J=6.6, 8.4 Hz, 1 H), 6.70 (dd, J=1.8, 6.0 Hz, 1 H), 6.47 (m, 1 H), 5.21 (br s, 2 H), 4.65 (s, 2 H), 3.26 (s, 3 H), 2.50 (s, 3 H); MS (ESI) m/z: 320.0 (M+H$^+$).

EXAMPLE A2

To a solution of Example A1 (400 mg, 1.3 mmol) in CH$_2$Cl$_2$ (5 mL) was added 3-chloroperoxybenzoic acid (mCPBA) (430 mg, 2.5 mmol) in one portion. After stirring for 2 h, the reaction mixture was quenched with aq NaHCO$_3$ and aq NaHSO$_3$. The organic layer was separated and was washed with brine, dried Na$_2$SO$_4$) and concentrated in vacuo. The crude product was dissolved in DMSO (2 mL) and was treated with a solution of ammonia in dioxane (2 M, 30 ml, 60 mmol). The mixture stirred overnight at RT. The reaction was concentrated under reduced pressure and the residue was purified by silica gel chromatography to provide 7-amino-3-(3-amino-4-fluorophenyl)-1-methyl-3,4-dihydropyrimido[4,5-d]pyrimidin-2(1H)-one (276 mg, 77% yield) as a yellow solid. $^1$H NMR (300 MHz, DMSO-d$_6$): δ 7.88 (s, 1 H), 6.96 (dd, J=8.4, 6.6 Hz, 1 H), 6.68 (dd, J=6.3, 2.1 Hz, 1 H), 6.52 (br s, 2 H), 6.44 (m, 1 H), 5.18 (s, 2 H), 4.48 (s, 2 H), 3.19 (s, 3 H); MS (ESI) m/z: 289.2. (M+H$^+$).

EXAMPLE A3

Example A1 (1.0 g, 3.1 mmol), mCPBA (1.1 g, 6.3 mmol) and methylamine were combined by the procedure of Example A2 to provide 3-(3-amino-4-fluorophenyl)-1-methyl-7-(methylamino)-3,4-dihydropyrimido[4,5-d]pyrimidin-2(1H)-one (370 mg, 39% yield) as a yellow solid. $^1$H NMR (400 MHz, DMSO-d$_6$): δ 7.93 (s, 1 H), 6.99-6.94 (m, 2 H), 6.69 (d, J=8.4 Hz, 1 H), 6.44 (m, 1 H), 5.18 (s, 2 H), 4.50 (s, 2 H), 3.23 (s, 3 H), 2.78 (d, J=4.0 Hz, 3 H); MS (ESI) m/z: (M+H$^+$) 303.2

EXAMPLE A4

POCl$_3$ (5.86 g, 38.6 mmol) was added dropwise to a solution of Example C3 (3.8 g, 19.3 mmol) in THF (25 ml) at 0° C. The resulting mixture was allowed to warm to 25° C. for 4 h. The solvent was removed under reduced pressure to give crude 5-(chloromethyl)-N2-methoxy-N2,N4-dimethylpyridine-2,4-diamine HCl (3.5 g, 84% yield), which was used in the next step without further purification.

A mixture of the above 5-(chloromethyl)-N2-methoxy-N2,N4-dimethylpyridine-2,4-diamine HCl (3.5 g, 16.3 mmol) and 4-fluoro-3-nitroaniline (41.5 mL, 0.3 mol) in pyridine (150 mL) was stirred at 50° C. for 8 h. The reaction mixture was concentrated in vacuo to afford a crude product which was washed with H$_2$O and dried to give 5-((4-fluoro-3-nitrophenylamino)methyl)-N2-methoxy-N2,N4-dimethylpyridine-2,4-diamine (3.3 g, 60% yield). $^1$H NMR (400 MHz, DMSO-d$_6$): δ 7.83 (m, 1 H), 7.62 (s, 1 H), 7.30 (t, J=9.2 Hz, 1 H), 7.20 (m, 1 H), 6.98 (m, 1 H), 6.81 (s, 1 H), 5.98 (s, 1 H), 4.14 (s, 2 H), 3.69 (s, 3 H), 3.30 (s, 3H), 2.89 (d, J=4.8 Hz, 3 H); MS (ESI) m/z: 336.2 (M+H$^+$)

To a solution of diphosgene (1.15 mL, 9.5 mmol) in anhydrous dioxane (100 mL) was added a mixture of 5-((4-fluoro-3-nitrophenylamino)methyl)-N2-methoxy-N2,N4-dimethylpyridine-2,4-diamine (3.0 g, 9.0 mmol) and Et$_3$N (2.5 mL, 18.0 mmol) in dioxane (200 mL) at 10° C. After addition, the resulting mixture was stirred at 30° C. for 10 h. H$_2$O was added to quench the above reaction and the mixture was neutralized to pH 7 with saturated Na$_2$CO$_3$ solution. The dioxane was removed under reduced pressure and the remaining aqueous solution was extracted with EtOAc (3×50 mL). The combined organics were washed with brine, dried over MgSO$_4$ and concentrated to give 3-(4-fluoro-3-nitrophenyl)-7-(methoxy(methyl)amino)-1-methyl-3,4-dihydropyrido[4,3-d]pyrimidin-2(1H)-one (2.1 g, 65% yield), which was used in the next step without further purification. $^1$H NMR (300 MHz, DMSO-d$_6$): δ 8.15 (m, 1 H), 7.97 (s, 1 H), 7.80 (m, 1 H), 7.62 (t, J=9.3 Hz, 1 H), 6.58 (s, 1 H), 4.80 (s, 2 H), 3.72 (s, 3 H), 3.27 (s, 3 H), 3.15 (s, 3 H); MS (ESI) m/z: 362.2 (M+H$^+$).

A solution 3-(4-fluoro-3-nitrophenyl)-7-(methoxy(methyl)amino)-1-methyl-3,4-dihydropyrido[4,3-d]pyrimidin-2(1H)-one (2 g, 5.5 mmol) in methanol (30 mL) was stirred with 10% Pd/C (1.0 g, 0.94 mmol) under hydrogen (45 psi) at 45° C. for 24 h. The complete reaction mixture was filtered, and the filtrate was concentrated in vacuo. The residue was washed with ethyl ether and dried in vacuo to provide 3-(3-amino-4-fluorophenyl)-1-methyl-7-(methylamino)-3,4-dihydropyrido[4,3-d]pyrimidin-2(1H)-one (1.1 g, 66% yield). $^1$H NMR (400 MHz, DMSO-d$_6$): δ 7.70 (s, 1 H), 6.94 (t, J=9.6 Hz, 1 H), 6.66 (d, J=6.8 Hz, 1 H), 6.40 (m, 2H), 5.92 (s, 1 H), 5.17 (s, 2 H), 4.50 (s, 2 H), 3.13 (s, 3 H), 2.73 (d, J=4.0 Hz, 3 H), MS (ESI) m/z: 302.1 (M+H$^+$).

EXAMPLE A5 n-Butyllithium (1.6 M in hexane, 109 mL, 0.175 mol) was added dropwise to a −78° C. solution of 1-bromo-4-fluoro-2-methylbenzene (30 g, 0.16 mol) in THF (500 mL) under N$_2$. After complete addition, the reaction mixture was stirred for 1 h at −78° C. The bright yellow solution was quickly cannulated to another flask containing a pre-cooled (−78° C.) solution of diethyl oxalate (27.8 g, 0.19 mol) in THF (400 mL). After stirring for another 30 min at −78° C., the reaction mixture was quenched by the addition of saturated NH$_4$Cl solution (800 mL). The aqueous layer was extracted with EtOAc (3×400 mL) and the combined organics were dried (Na$_2$SO$_4$), concentrated in vacuo and purified via silica gel chromatography to provide ethyl 2-(4-fluoro-2-methylphenyl)-2-oxoacetate (22.0 g, yield, 66% yield). $^1$H NMR (400 MHz, CDCl$_3$): δ 7.73 (dd, J=9.2, 5.6 Hz, 1 H), 7.02-6.96 (m, 2 H), 4.40 (m, 2 H), 2.60 (s, 3 H), 1.29 (t, J=6.8 Hz, 3 H). MS (ESI) m/z: 233.0 [M+Na]$^+$ HNO$_3$ (6.92 g, 71.4 mmol) was added dropwise to a suspension of ethyl 2-(4-fluoro-2-methylphenyl)-2-oxoacetate (15 g, 71.4 mmol) in conc. H$_2$SO$_4$ (50 mL) at ° C. After complete addition the resulting mixture was stirred at 0° C. for 30 min. The mixture was poured into ice water, and extracted with EtOAc. The organic extract was washed with brine, dried (MgSO$_4$) and concentrated in vacuo to give ethyl 2-(4-fluoro-2-methyl-5-nitrophenyl)-2-oxoacetate (15 g, 83% yield), which was used in the next step without further purification. $^1$H NMR (400 MHz, CDCl$_3$): δ 8.53 (d, J=7.2 Hz, 1 H), 7.24 (d, J=7.2 Hz, 1 H), 4.47 (q, J=7.2 Hz, 2 H), 2.67 (s, 3 H), 1.43 (t, J=7.2 Hz, 3 H).

A mixture of ethyl 2-(4-fluoro-2-methyl-5-nitrophenyl)-2-oxoacetate (15 g, 59 mmol) and Fe (46 g, 828 mmol) in AcOH (200 mL) was stirred at RT overnight. The solid was removed by filtration, and the solvent was removed under reduced pressure. The residue was partitioned with water and EtOAc. The organic layer was washed with brine, dried (MgSO$_4$), and concentrated in vacuo to give ethyl 2-(5-amino-4-fluoro-2-methylphenyl)-2-oxoacetate (9.0 g, 70% yield), which was used in the next step without further purification. $^1$H NMR (400 MHz, CDCl$_3$): δ 7.16 (d, J=6.9 Hz, 1 H), 6.91 (d, J=8.7 Hz, 1 H), 4.41 (q, J=7.2 Hz, 2 H), 2.50 (s, 3 H), 1.40 (t, J=7.2 Hz, 3 H).

Acetyl chloride (3.12 g, 40 mmol) was added to a 0° C. solution of ethyl 2-(5-amino-4-fluoro-2-methylphenyl)-2-oxoacetate (9 g, 40 mmol) and Et$_3$N (8.1 g, 80 mmol) in CH$_2$Cl$_2$ (80 mL). The resulting mixture was stirred at RT for 3 h. The solvent was removed under reduced pressure to give ethyl 2-(5-acetamido-4-fluoro-2-methylphenyl)-2-oxoacetate (10.7 g, 100% yield), which was used in the next step without further purification. $^1$H NMR (300 MHz, CDCl$_3$): δ 8.71 (d, J=6.0 Hz, 1 H), 7.37 (brs, 1 H), 6.95 (d, J=8.7 Hz, 1 H), 4.39 (q, J=7.2 Hz, 2 H), 2.50 (s, 3H), 2.10 (s, 3 H), 1.40 (t, J=7.2 Hz, 3 H).

A mixture of ethyl 2-(5-acetamido-4-fluoro-2-methylphenyl)-2-oxoacetate (5 g, 19 mmol), Example D3 (5.7 g, 38 mmol) and AcOH (2 mL) in EtOH (100 mL) was charged in steel bomb and heated at 100° C. for 48 h. The solvent was removed under reduced pressure and the residue was purified by column chromatography to give N-(2-fluoro-4-methyl-5-(8-methyl-2-(methylamino)-7-oxo-7,8-dihydropteridin-6-yl)phenyl)acetamide (1.5 g, 23% yield). $^1$H NMR (400 MHz, DMSO-d$_6$): δ 9.71 (br s, 1 H), 8.66 (s, 1 H), 8.00 (s, 1 H), 7.87 (m, 1 H), 7.16 (d, J=11.2 Hz, 1 H), 3.58 (s, 3 H), 2.93 (s, 3 H), 2.18 (s, 3 H), 2.06 (s, 3 H); MS (ESI) m/z: 357.2 [M+H]$^-$.

A solution of N-(2-fluoro-4-methyl-5-(8-methyl-2-(methylamino)-7-oxo-7,8-dihydropteridin-6-yl)phenyl)acetamide (1.5 g, 4.2 mmol) and conc. HCl (1 mL) in MeOH (20 mL) was heated at reflux overnight. The solvent was removed under reduced pressure. Water was added, and the mixture basified to pH=8. The resulting precipitate was collected by filtration and dried to give 6-(5-amino-4-fluoro-2-methylphenyl)-8-methyl-2-methylamino)pteridin-7(8H)-one (1.0 g, 78% yield). $^1$H NMR (400 MHz, DMSO-d$_6$): δ 8.70 (s, 0.3 H), 8.62 (s, 0.7 H) ☐7.96 (m, 0.7 H) ☐7.85 (m, 0.3 H) ☐6.88 (d, J=12.4 Hz, 1 H), 6.78 (d, J=9.2 Hz, 1 H), 4.98 (s, 2 H), 3.56 (s, 2 H), 3.48 (s, 1 H) ☐2.91 (d, J=4 Hz, 3 H), 2.03 (s, 3 H). MS (ESI) m/z: 315.2 [M+H]$^+$.

EXAMPLE A6

Sodium triacetoxy borohydride (2.70 g, 12.8 mmol) was added to a solution of Example C5 (2.10 g, 10.6 mmol), 4-fluoro-3-nitroaniline (1.66 g, 10.6 mmol) and TFA (2.43 g, 21.3 mmol) in EtOAc (50 mL). After stirring for 30 min. the reaction mixture was diluted with water (50 mL), and 2N NaOH was added to adjust the pH to alkaline. The organic phase was separated, washed with brine, dried (MgSO$_4$) and concentrated to give yellow orange solid. The solid was slurried in MTBE, collected by filtration, washed and dried in vacuo to give N-ethyl-5-(4-(fluoro-3-nitrophenylamino(methyl)-2-(methylthio)pyrimidin-4-amine (2.2 g, 61% yield) as a bright yellow solid.

To a suspension of N-ethyl-5-((4-fluoro-3-nitrophenylamino)methyl)-2-(methylthio)pyrimidin-4-amine (2.20 g, 6.5 mmol) in CH$_2$Cl$_2$ (25 mL) was added Et$_3$N (2.7 mL, 20 mmol) followed by phosgene (20% solution in toluene, 4.3 mL, 7.8 mmol). The reaction mixture was stirred for 2 h at RT and then diluted with water. The organic layer was separated and washed with brine, dried (MgSO$_4$) and concentrated to provide an orange yellow solid, which on stirring in ethyl acetate followed by filtration provided 1-ethyl-3-(4-fluoro-3-nitrophenyl)-7-(methylthio)-3,4-dihydropyrimido[4,5-d]pyrimidin-2(1H)-one as a light yellow solid.

To a solution of 1-ethyl-3-(4-fluoro-3-nitrophenyl)-7-(methylthio)-3,4-dihydropyrimido[4,5-d]pyrimidin-2(1H)-one (2.4 g, 6.5 mmol) in ethyl acetate and methanol (1:1, 40 mL) was added Pd/C (230 mg) and the mixture was hydrogenated (55 psi) in a Parr shaker for 2 days. The reaction mixture was filtered and the filter cake was washed with methanol. The combined filtrates were concentrated in vacuo. The residue was dissolved in THF and the solid was filtered. The filtrate was concentrated and purified by silica gel column chromatography to obtain 3-(3-amino-4-fluorophenyl)-1-ethyl-7-(methylthio)-3,4-dihydropyrimido[4,5-d]pyrimidin-2(1H)-one (0.65 g, 30% yield). $^1$H-NMR (400 MHz, DMSO-d$_6$): δ 8.20 (s, 1 H), 6.97 (m, 1 H), 6.70 (dd, J=8.0, 2.4 Hz, 1 H), 6.46 (m, 1 H), 5.21 (s, 2 H), 4.64 (s, 2 H), 3.94 (q, J=6.8 Hz, 2 H), 2.48 (s, 3 H), 1.15 (t, J=6.8 Hz, 3 H); MS (ESI) m/z: 334.1 (M+H$^+$).

EXAMPLE A7

Using a procedure analogous to Example A2, Example A6 (0.65 g, 1.9 mmol) was treated with mCPBA (70% wt, 0.58 g, 2.3 mmol) and then N-methylamine (2.0M in THF, 3.9 mL, 7.8 mmol) to afford 3-(3-amino-4-fluorophenyl)-1-ethyl-7-(methylamino)-3,4-dihydropyrimido[4,5-d]pyrimidin-2 (1H)-one (1.79 g, 94% yield). $^1$H NMR (400 MHz, DMSO-d$_6$, major tautomer): δ 8.00 (s, 1 H), 7.04 (m, 2 H), 6.76 (dd, J=8.4, 2.8 Hz, 1 H), 6.52 (m, 1 H), 5.27 (s, 2 H), 4.57 (s, 2 H), 3.99 (q, J=6.4 Hz, 2H), 2.84 (d, J=4.8 Hz, 3 H), 1.22 (t, J=6.4 Hz, 3 H); MS (ESI) m/z: 317.0 (M+H$^+$).

EXAMPLE A8

To a solution of Example A1 (700 mg, 2.2 mmol) in THF (10 mL) was added Raney-Ni (50% wt slurry in water, 1.0 g) and then the reaction mixture was stirred under 1 atm of H$_2$ at 60° C. for 5 h. The mixture was filtered through diatomite and the cake was washed with THF. The combined filtrate was concentrated to give 3-(3-amino-4-fluoro-phenyl)-1-methyl-3,4-dihydro-1H-pyrimido[4,5-d]pyrimidin-2-one (460 mg, 76% yield) as a yellow solid. $^1$H NMR (300 MHz, DMSO-d$_6$): δ 8.77 (s, 1 H), 8.39 (s, 1 H), 6.99 (dd, J=11.4, 8.7 Hz, 1 H), 6.72 (d, J=8.1 Hz, 1 H), 6.49 (m, 1 H), 5.24 (br s, 2 H), 4.73 (s, 2 H), 3.28 (s, 3 H). MS (ESI) m/z: 274.2 (M+H$^+$).

EXAMPLE A9

Using a procedure analogous to Example A10, Example C6 (7 g, 33 mmol) and 4-fluoro-3-nitrophenylamine (4.7 g, 30 mmol) were converted to 3-(3-amino-4-fluorophenyl)-1-isopropyl-7-(methylthio)-3,4-dihydropyrimido[4,5-d]pyrimidin-2(1H)-one (2 g). $^1$H NMR (400 MHz, DMSO-d$_6$): δ 8.23 (s, 1 H), 6.97 (m, 1 H), 6.69 (dd, J=8.4, 2.4 Hz, 1 H), 6.44 (m, 1 H), 5.22 (s, 2 H), 4.94 (m, 1 H), 4.59 (s, 2 H), 2.49 (s, 3 H), 1.45 (d, J=6.8 Hz, 6 H); MS (ESI) m/z: 348.1 [M+H]$^+$.

EXAMPLE A10

To a solution of Example C1 (10 g, 56 mmol) in anhydrous THF (120 mL) was added thionyl chloride (10.4 mL, 140 mmol) slowly at 0° C. The resulting mixture was stirred at 80° C. for 4 hours. The solvent was removed under reduced pressure to give 5-(chloromethyl)-N-methyl-2-(methylthio)pyrimidin-4-amine (11.5 g, >100% yield), which was used directly in the next step.

To a solution of 5-(chloromethyl)-N-methyl-2-(methylthio)pyrimidin-4-amine (11.5 g) and Example D1 (9.6 g, 56 mmol) in anhydrous CH$_3$CN (160 mL) was added NaI (1.7 g, 11 mmol) and diisopropylethylamine (14.6 g, 112 mmol), then the mixture was stirred at 60° C. overnight. After removing the solvent, the residue was purified by column chromatography to give 5-((4-fluoro-2-methyl-5-nitrophenylamino) methyl)-N-methyl-2-(methylthio)pyrimidin-4-amine (7 g, 37% yield). $^1$H NMR (400 MHz, DMSO-d$_6$): δ 7.83 (s, 1 H), 7.22 (d, J=12 Hz, 1H), 7.08 (m, 1 H), 6.98 (d, J=8 Hz, 1 H), 5.79 (s, 1 H), 4.09 (d, J=8 Hz, 2 H), 2.85 (d, J=4 Hz, 3 H), 2.37 (s, 3 H), 2.17 (s, 3 H); MS (ESI) m/z: 337.9 [M+H]$^+$.

To a solution of diphosgene (0.85 mL, 7.2 mmol) in anhydrous dioxane (20 mL) was added a solution of 5-((4-fluoro-2-methyl-5-nitrophenylamino)methyl)-N-methyl-2-(methylthio)pyrimidin-4-amine (2.2 g, 6.5 mmol) and Et$_3$N (1.32 g, 13 mmol) in anhydrous dioxane (50 ml) at 0° C. After the addition, the resulting mixture was stirred at 50° C. overnight. Water was added and the mixture was neutralized with saturated Na$_2$CO$_3$ solution to pH 8. The dioxane was removed in vacuo, and the aqueous layer was extracted with EtOAc (3×60 mL). The combined organics were washed with brine, dried (Na$_2$SO$_4$) and concentrated. The residue was washed with ether and dried in vacuo to afford 3-(4-fluoro-2-methyl-5-nitrophenyl)-1-methyl-7-(methylthio)-3,4-dihydropyrimido [4,5-d]pyrimidin-2(1H)-one (2 g, 84%). $^1$H NMR (400 MHz, CDCl$_3$): δ 8.04 (s, 1 H), 7.97 (d, J=8 Hz, 1 H), 7.18 (d, J=12 Hz, 1 H), 4.73 (d, J=14.8 Hz, 1 H), 4.42 (d, J=14.8 Hz, 1 H), 3.40 (s, 3 H), 2.52 (s, 3 H), 2.25 (s, 3 H); MS (ESI) m/z: 364.1 [M+H]$^+$.

3-(4-fluoro-2-methyl-5-nitrophenyl)-1-methyl-7-(methylthio)-3,4-dihydropyrimido[4,5-d]pyrimidin-2(1H)-one (3 g, 8.26 mmol) was added to a solution of HCl (1.6 g, 16.5 mmol) in EtOH (50 ml) followed by iron power (4.6 g, 80 mmol), and the resulting mixture was stirred at 50° C. for 6 hours. The mixture was filtered and the filtrate was neutralized with saturated Na$_2$CO$_3$ solution to pH 8 and the mixture was extracted with EtOAc (3×150 mL). The combined extracts were washed with brine, dried Na$_2$SO$_4$) and evaporated to give 3-(5-amino-4-fluoro-2-methylphenyl)-1-methyl-7-(methylthio)-3,4-dihydropyrimido[4,5-d]pyrimidin-2 (1H)-one (1.9 g, 67% yield). $^1$H NMR (400 MHz, DMSO-d$_6$): δ 8.19 (s, 1 H), 6.89 (d, J=12.4 Hz, 1H), 6.65 (d, J=8.8 Hz, 1 H), 5.01 (s, 2 H), 4.62 (d, J=14.8 Hz, 1 H), 4.44 (d, J=14.8 Hz, 1 H), 3.24 (s, 3 H), 2.48 (s, 3 H), 1.92 (s, 3 H); MS (ESI) m/z: 334.1 [M+H]$^+$.

EXAMPLE A11

Using the procedure of Example A9, steps 2-4, Example D1 (3.68 g, 22 mmol) and 5-(chloromethyl)-N-isopropyl-2-(methylthio)pyrimidin-4-amine (5 g, 22 mmol) were combined to afford 3-(5-amino-4-fluoro-2-methylphenyl)-1-isopropyl-7-(methylthio)-3,4-dihydropyrimido[4,5-d] pyrimidin-2(1H)-one (1 g, 12% yield over 3 steps). $^1$H NMR (400 MHz, DMSO-d$_6$): δ 8.23 (s, 1 H), 6.90 (d, J=12.0 Hz, 1 H), 6.67 (d, J=8.8 Hz, 1 H), 5.04 (s, 2 H), 4.97 (m, 1 H), 4.60 (d, J=14.4 Hz, 1 H), 4.40 (d, J=14.4 Hz, 1 H), 2.50 (s, 3 H), 1.93 (s, 3 H), 1.46 (d, J=6.8 Hz, 6 H); MS (ESI) m/z: 362.1 [M+H]$^-$.

EXAMPLE A12

A solution of 3-amino-5-nitrobenzonitrile (3.59 g, 22 mmol) in CH$_3$CN (10 mL) was added dropwise to a mixture of 5-(chloromethyl)-N-isopropyl-2-(methylthio)pyrimidin-4-amine from Example A9 (5 g, 22 mmol), sodium iodide (0.33 g, 2.2 mmol), and diisopropylethylamine (2 mL, 12 mmol) in CH$_3$CN (100 mL) at 0° C. The resultant reaction mixture was stirred at RT overnight. The solvent was evaporated and the residue was diluted with water, and extracted with EtOAc. The combined organics were washed with brine, dried (MgSO$_4$), concentrated and purified by silica gel chromatography to afford 3-((4-(isopropylamino)-2-(methylthio) pyrimidin-5-yl)methylamino)-5-nitrobenzonitrile (2.2 g, 28% yield). $^1$H NMR (400 MHz, DMSO-d$_6$): δ 7.87 (s, 1 H), 7.74 (s, 1 H), 7.56 (s, 1 H), 7.32 (s, 1H), 7.08 (m, 1 H), 6.63 (d, J=7.6 Hz, 1 H), 4.30 (m, 1 H), 4.15 (s, 2 H), 2.50 (s, 3 H), 1.17-1.15 (d, J=6.4 Hz, 6 H); MS (ESI) m/z: 359.2[M+H]$^+$.

Diphosgene (5 mL, 41 mmol), 3-((4-(isopropylamino)-2-(methylthio)pyrimidin-5-yl)methylamino)-5-nitrobenzonitrile (2.2 g, 6.15 mmol) and Et$_3$N (2.5 mL) were combined by the procedure of Example A4 step 3 to give 3-(1-isopropyl-7-(methylthio)-2-oxo-1,2-dihydropyrimido[4,5-d]pyrimidin-3(4H)-yl)-5-nitrobenzonitrile (1.2 g, 51% yield), which was used in the next step without further purification.

3-(1-Isopropyl-7-(methylthio)-2-oxo-1,2-dihydropyrimido[4,5-d]pyrimidin-3(4H)-yl)-5-nitrobenzonitrile (1.2 g, 3.13 mmol), iron powder (1.75 g, 31 mmol) and conc HCl (0.5 ml, 6 mmol) were combined in methanol (100 mL) by the procedure of Example A10, step 4, to provide 3-amino-5-(1-isopropyl-7-(methylthio)-2-oxo-1,2-dihydropyrimido[4,5-d]pyrimidin-3(4H)-yl)benzonitrile (280 mg, 25% yield). $^1$H NMR (400 MHz, DMSO-d$_6$): δ 8.27 (s, 1 H), 6.89 (m, 1 H), 6.86 (d, J=2.0 Hz, 1 H), 6.76 (t, J=2.0 Hz, 1 H), 5.73 (d, J=2.8 Hz, 2 H), 4.98 (m, 1 H), 4.68 (s, 2 H), 2.51 (s, 3 H), 1.48 (d, J=6.8 Hz, 6 H); MS (ESI) m/z: 355.1 [M+H]$^+$.

EXAMPLE A13

Using the procedure of Example A10, Example C4 (6.0 g, 30.2 mmol) and Example D1 (3.9 g, 23 mmol) were converted to 3-(5-amino-4-fluoro-2-methyl-phenyl)-1-ethyl-7-(methylthio)-3,4-dihydropyrimido[4,5-d]pyrimidin-2(1H)-one (2.5 g, 31% yield over 4 steps). $^1$H NMR (400 MHz, DMSO-d$_6$): δ 8.28 (s, 1 H), 6.98 (d, J=12.0 Hz, 1 H), 6.75 (d, J=8.4 Hz, 1H), 5.11 (s, 2 H), 4.72 (d, J=14.4 Hz, 1 H), 4.53 (d, J=14.4 Hz, 1 H), 4.03 (m, 2 H), 2.57 (s, 3H), 2.01 (s, 3 H), 1.22 (t, J=6.8 Hz, 3 H); MS (ESI) m/z: 348.2 [M+H]$^+$.

EXAMPLE A14

Using the procedure of Example A15 steps 2-4, 5-(chloromethyl)-N-ethyl-2-(methylthio)pyrimidin-4-amine from Example A13 (2.4 g, 10.5 mmol) and Example D2 (2.0 g, 10.5 mmol) were combined to afford 3-(5-amino-2-chloro-4-fluorophenyl)-1-ethyl-7-(methylthio)-3,4-dihydropyrimido[4,5-d]pyrimidin-2(1H)-one (0.9 g, 26% yield over 3 steps). $^1$H NMR (400 MHz, DMSO-d$_6$): δ 8.26 (s, 1 H), 7.31 (d, J=10.8 Hz, 1 H), 6.87 (d, J=9.2 Hz, 1H), 5.51 (s, 2 H), 4.68 (d, J=14.4 Hz, 1 H), 4.54 (d, J=14.4 Hz, 1 H), 3.98 (m, 2 H), 2.52 (s, 3H), 1.18 (t, J=6.8 Hz, 3 H); MS (ESI) m/z: 367.9 [M+H]$^+$.

EXAMPLE A15

To a solution of Example C1 (2 g, 11 mmol) in anhydrous THF (120 mL) was added thionyl chloride (1.74 mL, 23 mmol) slowly at 0° C. The resulting mixture was stirred at 80° C. for 4 hours. The solvent was removed under reduced pressure to give 5-(chloromethyl)-N-methyl-2-(methylthio)pyrimidin-4-amine (2.1 g) which was used directly in the next step.

To a solution of 5-(chloromethyl)-N-methyl-2-(methylthio)pyrimidin-4-amine (2.1 g) and Example D2 (2 g, 11 mmol) in anhydrous CH$_3$CN (50 mL) was added NaI (0.32 g, 2.2 mmol) and diisopropylethylamine (2.8 g, 22 mmol). The resultant mixture was stirred at 60° C. overnight. After the solvent was removed, the residue was washed with EtOAc (3×100 mL) and purified by column chromatography to give 5-((2-chloro-4-fluoro-5-nitrophenylamino)methyl)-N-methyl-2-(methylthio)pyrimidin-4-amine (1.2 g, 30% yield). $^1$H NMR (400 MHz, DMSO-d$_6$): δ 7.86 (s, 1 H), 7.70 (d, J=12 Hz, 1 H), 7.23 (d, J=8 Hz, 1 H), 7.16 (m, 1 H), 6.33 (t, J=8 Hz, 1 H), 4.17 (d, J=8 Hz, 2 H), 2.81 (d, J=8 Hz, 3 H), 2.37 (s, 3H); MS (ESI) m/z: 357.9 [M+H]$^+$.

To a solution of diphosgene (2.1 mL, 6.8 mmol) in anhydrous dioxane (30 mL) was added a solution of 5-((2-chloro-4-fluoro-5-nitrophenylamino)methyl)-N-methyl-2-(methylthio)pyrimidin-4-amine (2.2 g, 6.2 mmol) and Et$_3$N (1.32 g, 13 mmol) in anhydrous dioxane (30 mL) at 0° C. After complete addition, the resulting mixture was stirred at 50° C. overnight. Water was added and the mixture was basified with saturated Na$_2$CO$_3$ solution. The mixture was concentrated in vacuo and the residue was extracted with EtOAc (3×100 mL). The combined organic layers were washed with brine, dried (Na$_2$SO$_4$) and concentrated in vacuo. The residual solid was washed with ether and dried to afford 3-(2-chloro-4-fluoro-5-nitrophenyl)-1-methyl-7-(methylthio)-3,4-dihydropyrimido[4,5-d]pyrimidin-2(1H)-one (1.4 g, 59%). $^1$H NMR (400 MHz, DMSO-d$_6$): δ 8.53 (d, J=8 Hz, 1 H), 8.26 (s, 1 H), 8.08 (d, J=12 Hz, 1 H), 4.82 (d, J=16 Hz, 1 H), 4.57 (d, J=16 Hz, 1 H), 3.29 (s, 3 H), 2.50 (s, 3 H); MS (ESI) m/z: 384.1 [M+H]$^+$.

To a solution of 3-(2-chloro-4-fluoro-5-nitrophenyl)-1-methyl-7-(methylthio)-3,4-dihydropyrimido[4,5-d]pyrimidin-2(1H)-one (1.4 g, 3.7 mmol) in EtOH (30 mL) was added conc. HCl (0.75 g, 9 mmol), followed by active iron power (2 g, 36 mmol). The reaction was stirred at 50° C. for 6 hours. The reaction was filtered and the filtrate was diluted with water and treated with saturated aq Na$_2$CO$_3$ solution until pH 8. The aqueous mixture was extracted with EtOAc (3×80 mL). The combined extracts were dried (Na$_2$SO$_4$) and concentrated in vacuo to give 3-(5-amino-2-chloro-4-fluorophenyl)-1-methyl-7-(methylthio)-3,4-dihydropyrimido[4,5-d]pyrimidin-2(1H)-one (1.08 g, 84% yield). $^1$H NMR (400 MHz, DMSO-d$_6$): δ 8.25 (s, 1 H), 7.30 (d, J=11.2 Hz, 1 H), 6.84 (d, J=8.8 Hz, 1 H), 5.50 (s, 2 H), 4.66 (d, J=14.6 Hz, 1 H), 4.53 (d, J=14.6 Hz, 1 H), 3.27 (s, 3 H), 2.51 (s, 3 H); MS (ESI) m/z: 354.3 [M+H]$^+$.

EXAMPLE A16

Thionyl chloride (3.7 mL, 51 mmol) was added dropwise to a 0° C. solution of Example C3 (4 g, 20.3 mmol) in anhydrous THF (20 mL). The resultant mixture was stirred at 25° C. for 4 h. The solvent was removed under reduced pressure to give 5-(chloromethyl)-N2-methoxy-N2,N4-dimethylpyridine-2,4-diamine (3.9 g, 89% yield), which was used in the next step without further purification.

Using a procedure analogous to Example A4 steps 2-4, 5-(Chloromethyl)-N2-methoxy-N2,N4-dimethylpyridine-2,4-diamine (3.9 g, 18 mmol) and Example D1 (3.08 g, 18.1 mmol) were combined to give 3-(5-amino-4-fluoro-2-methylphenyl)-1-methyl-7-(methylamino)-3,4-dihydropyrido[4,3-d]pyrimidin-2(1H)-one (1.5 g, 29% yield over 3 steps). $^1$H NMR (400 MHz, DMSO-d$_6$): δ 7.72 (s, 1 H), 6.90 (d, J=12.0 Hz, 1 H), 6.65 (d, J=8.4 Hz, 1 H), 6.41 (m, 1 H), 5.95 (s, 1 H), 5.02 (s, 2 H), 4.52 (d, J=13.6 Hz, 1 H), 4.33 (d, J=13.6 Hz, 1 H), 3.17 (s, 3 H), 2.77 (d, J=4.8 Hz, 3 H), 1.94 (s, 3 H); MS (ESI) m/z: 316.2[M+H]$^+$.

EXAMPLE A17

Thionyl chloride (5.86 g, 23.8 mmol) was added dropwise to a 0° C. solution of Example C7 (2.9 g, 11.9 mmol) in anhydrous THF (30 mL). The resulting mixture was stirred at 25° C. for 4 h. The solvent was removed under reduced pressure to give 5-(chloromethyl)-N4-isopropyl-N2-methoxy-N2-methylpyridine-2,4-diamine (2.7 g, 87% yield), which was used in the next step without further purification.

A mixture of 5-(chloromethyl)-N4-isopropyl-N2-methoxy-N2-methylpyridine-2,4-diamine (2.7 g, 11.1 mmol) and Example D1 (1.9 g, 11.1 mol) in pyridine (60 mL) was stirred at 50° C. for 8 h. The pyridine was removed under reduced pressure and the residue was purified by silica gel chromatography to give 5-((4-fluoro-2-methyl-5-nitrophenylamino)methyl)-N4-isopropyl-N2-methoxy-N2-methylpyridine-2,4-diamine (3.0 g, 71.6% yield). $^1$H NMR (400 MHz, DMSO-d$_6$): δ 7.84 (s, 1 H), 7.32 (d, J=12.4 Hz, 1 H), 7.16 (d, J=6.4 Hz, 1 H), 6.22 (s, 1H), 6.00 (t, J=5.2 Hz, 2 H), 4.28 (d, J=5.2 Hz, 2 H), 3.82 (m, 1 H), 3.72 (s, 3 H), 3.17 (s, 3 H), 2.27 (s, 3 H), 1.27 (d, J=6.4 Hz, 6 H).

Using the procedure of Example A4 step 3, diphosgene (1.3 g, 6.4 mmol), 5-((4-fluoro-2-methyl-5-nitrophenylamino)methyl)-N4-isopropyl-N2-methoxy-N2-methylpyridine-2,4-diamine (2.0 g, 5.3 mmol) and Et$_3$N (2.2 g, 21.2 mmol) were reacted in dioxane to give 3-(4-fluoro-2-methyl-5-nitrophenyl)-1-isopropyl-7-(methoxy(methyl)amino)-3,4-dihydropyrido[4,3-d]pyrimidin-2(1H)-one (1.5 g, 70% yield). $^1$H NMR (400 MHz, DMSO-d$_6$): δ 8.18 (d, J=7.2 Hz, 1 H), 7.94 (s, 1 H), 7.55 (d, J=12.4 Hz, 1 H), 6.68 (s, 1 H), 4.77 (d, J=13.6 Hz, 1 H), 4.45-4.37 (m, 2 H), 3.71 (s, 3 H), 3.13 (s, 3 H), 2.14 (s, 3 H), 1.46 (t, J=6.4 Hz, 6H).

Using the procedure of Example A4 step 4, a mixture of 3-(4-fluoro-2-methyl-5-nitrophenyl)-1-isopropyl-7-(methoxy(methyl-3-amino)-3,4-dihydropyrido[4,3-d]pyrimidin-2(1H)-one (1.5 g, 3.7 mmol) and Pd/C (0.7 g) was hydrogenated (45 psi) in methanol (60 mL) at 45° C. to afford 3-(5-amino-4-fluoro-2-methylphenyl)-1-isopropyl-7-(methylamino)-3,4-dihydropyrido[4,3-d]pyrimidin-2(1H)-one (0.83 g, 65.0% yield). $^1$H NMR (400 MHz, DMSO-d$_6$): δ 7.72 (s, 1 H), 6.87 (d, J=12.4 Hz, 1 H), 6.61 (d, J=8.8 Hz, 1 H), 6.35 (m, 1 H), 6.13 (s, 1H), 4.98 (s, 2 H), 4.41-4.20 (m, 3 H), 2.76 (d, J=4.8 Hz, 3 H), 1.90 (s, 3 H), 1.45 (t, J=6.4 Hz, 6 H); MS (ESI) m/z: 344.2. [M+H]$^-$.

EXAMPLE A18

2-Chloro-4-fluoro-5-nitro-phenylamine (1.4 g, 7.4 mmol) was added to a solution of 5-(chloromethyl)-N2-methoxy-N2,N4-dimethylpyridine-2,4-diamine from example A16 (1.6 g, 7.4 mmol) in pyridine (30 mL) and the mixture was stirred at 50° C. for 8 hours. The reaction mixture was concentrated under reduced pressure and the solid residue was thoroughly washed with water to give 5-((2-chloro-4-fluoro-5-nitrophenylamino)methyl)-N2-methoxy-N2,N4-dimethylpyridine-2,4-diamine (1.5 g, 56% yield). $^1$H NMR (400 MHz, DMSO-d$_6$): δ 8.01 (s, 1H), 7.76 (d, J=8.4 Hz, 1 H), 7.71 (s, 1 H), 7.34 (d, J=8 Hz, 1 H), 6.56 (m, 1 H), 5.98 (s, 1 H), 4.36 (d, J=4 Hz, 2 H), 3.71 (s, 3 H), 3.31 (s, 3 H), 2.91-2.92 (d, J=4 Hz, 3 H); MS (ESI) m/z: 369.9 [M+H]$^+$.

Diphosgene (0.6 ml, 4.8 mmol), 5-((2-chloro-4-fluoro-5-nitrophenylamino)methyl)-N2-methoxy-N2,N4-dimethylpyridine-2,4-diamine (1.7 g, 4.6 mmol) and Et$_3$N (0.93 g, 9.2 mmol) were combined by the procedure of Example A4, step 3 to afford 3-(2-chloro-4-fluoro-5-nitrophenyl)-7-(methoxy(methyl)amino)-1-methyl-3,4-dihydropyrido[4,3-d]pyrimidin-2(1H)-one (1.5 g, 83% yield). $^1$H NMR (400 MHz, DMSO-d$_6$): δ 8.59 (d, J=8 Hz, 1 H), 8.15 (d, J=8 Hz, 1 H), 8.04 (s, 1 H), 6-66 (s, 1 H), 4.94 (d, J=14 Hz, 1 H), 4.61 (d, J=14 Hz, 1 H), 3.84 (s, 3 H), 3.35 (s, 3 H), 3.25 (s, 3 H); MS (ESI) m/z: 396.1 [M+H]$^+$.

3-(2-chloro-4-fluoro-5-nitrophenyl)-7-(methoxy(methyl) amino)-1-methyl-3,4-dihydro pyrido[4,3-d]pyrimidin-2

(1H)-one (1 g, 2.5 mmol), Pd/C (0.3 g) were combined in MeOH (30 mL) and hydrogenated (45 psi) at 50° C. for 4 days. The catalyst was removed by filtration and the filtrate was concentrated in vacuo. The residual solid was washed with ethyl acetate and dried in vacuo to give 3-(5-amino-2-chloro-4-fluorophenyl)-1-methyl-7-(methylamino)-3,4-dihydropyrido[4,3-d]pyrimidin-2(1H)-one (0.6 g, 71% yield). $^1$H-NMR (400 MHz, DMSO-d$_6$): δ 7.71 (s, 1 H), 7.26 (d, J=10.8 Hz, 1 H), 6.78 (d, J=8.8 Hz, 1 H), 6.41 (m, 1 H), 5.94 (s, 1 H), 5.43 (s, 2 H), 4.50 (d, J=13.6 Hz, 1 H), 4.40 (d, J=13.6 Hz, 1 H), 3.16 (s, 3 H), 2.76 (d, J=5.2 Hz, 3 H); MS (ESI) m/z: 336.2 [M+H]$^+$.

EXAMPLE A19

Thionyl chloride (3.5 mL, 0.048 mol) was added dropwise to a solution of Example C8 (5 g, 0.024 mol) in dry THF (50 mL) at 0° C. The resulting mixture was stirred at RT for 4 hours and concentrated in vacuo to give 5-(chloromethyl)-N4-ethyl-N2-methoxy-N2-methylpyridine-2,4-diamine (5.4 g, 98% yield), which was used in the next step without further purification.

5-(Chloromethyl)-N4-ethyl-N2-methoxy-N2-methylpyridine-2,4-diamine (5.4 g, 0.024 mol) and Example D1 (4 g, 0.024 mol) were combined according to Example A4 step 2 to provide 5-((2-chloro-4-fluoro-5-nitrophenylamino)methyl)-N4-ethyl-N2-methoxy-N2-methylpyridine-2,4-diamine (6 g, 70%). $^1$H NMR (400 MHz, DMSO-d$_6$): δ 7.66 (s, 1 H), 7.25 (d, J=12 Hz, 1 H), 7.05 (d, J=6.4 Hz, 1 H), 6.04 (s, 1 H), 5.96 (m, 1 H), 4.24 (d, J=8 Hz, 2H), 3.67 (s, 3 H), 3.32 (q, J=1 Hz, 2 H), 3.23 (s, 3 H), 2.18 (s, 3 H) 1.16 (t, J=8 Hz, 3 H); MS (ESI) m/z: 384.0 [M+H]$^+$.

Diphosgene (2.4 mL, 19 mmol), 5-((2-chloro-4-fluoro-5-nitrophenylamino)methyl)-N4-ethyl-N2-methoxy-N2-methylpyridine-2,4-diamine (6 g, 16 mmol) and Et$_3$N (4.6 mL, 32 mmol) were combined by the procedure of Example A4 step 3 to provide 1-ethyl-3-(4-fluoro-2-methyl-5-nitro-phenyl)-7-(methoxy(methyl)amino)-3,4-dihydropyrido[4,3-d]pyrimidin-2(1H)-one (4.5 g, 70% yield). $^1$H NMR (400 MHz, DMSO-d$_6$): δ 8.27 (d, J=8 Hz, 1 H), 7.94 (s, 1 H), 7.58 (d, J=12 Hz, 1 H), 6.58 (s, 1 H), 4.89 (d, J=16 Hz, 1 H), 4.48 (d, J=16 Hz, 1 H), 3.84-3.92 (m, 2H), 3.73 (s, 3 H), 3.16 (s, 3 H), 2.20 (s, 1 H), 1.19 (t, J=8 Hz, 3 H); MS (ESI) m/z: 390.2 [M+H]$^+$.

1-Ethyl-3-(4-fluoro-2-methyl-5-nitrophenyl)-7-(methoxy(methyl)amino)-3,4-dihydropyrido[4,3-d]pyrimidin-2(1H)-one (3.2 g, 8.2 mmol) and Pd/C (0.3 g) were combined in MeOH (60 ml) and subjected to hydrogen (45 psi) at 50° C. overnight. The reaction mixture was filtered, concentrated in vacuo and purified by column chromatography to give 3-(5-amino-4-fluoro-2-methylphenyl)-1-ethyl-7-(methylamino)-3,4-dihydropyrido[4,3-d]pyrimidin-2(1H)-one (2.1 g, 78% yield). $^1$H NMR (400 MHz, DMSO-d$_6$): δ 7.71 (s, 1 H), 6.88 (d, J=12.0 Hz, 1 H), 6.64 (d, J=8.4 Hz, 1 H), 6.38 (m, 1 H), 5.99 (s, 1 H), 5.01 (s, 2 H), 4.51 (d, J=13.6 Hz, 1 H), 4.29 (d, J=13.6 Hz, 1 H), 3.76 (m, 2 H), 2.75 (d, J=4.8 Hz, 3 H), 1.91 (s, 3 H), 1.14 (t, J=7.2 Hz, 3 H); MS (ESI) m/z: 330.2 [M+H]$^+$.

EXAMPLE A20

A mixture of 5-(chloromethyl)-N4-ethyl-N2-methoxy-N2-methylpyridine-2,4-diamine from Example A19 (3.2 g, 14.7 mmol) and Example D2 (2.6 g, 14.7 mol) were combined using the procedure of Example A8 steps 2-4 to provide 3-(5-amino-2-chloro-4-fluorophenyl)-1-ethyl-7-(methylamino)-3,4-dihydropyrido[4,3-d]pyrimidin-2(1H)-one (2 g). $^1$H NMR (400 MHz, DMSO-d$_6$): δ 7.72 (s, 1 H), 7.24 (d, J=10.8 Hz, 1 H), 6.81 (d, J=9.2 Hz, 1H), 6.44 (bs, 1 H), 6.02 (s, 1 H), 5.42 (s, 2 H), 4.50 (d, J=13.2 Hz, 1 H), 4.38 (d, J=13.2 Hz, 1H), 3.77 (m, 2 H), 2.76 (d, J=4.8 Hz, 3 H), 1.15 (t, J=7.2 Hz, 3 H); MS (ESI) m/z: 350.2[M+H]$^+$.

EXAMPLE A21

Example A10 (0.500 g, 1.50 mmol), mCPBA (70% 0.444 g, 1.80 mmol), and methylamine (2 M in THF, 3.75 mL) were combined by the procedure of Example A2 to provide 3-(5-amino-4-fluoro-2-methylphenyl)-1-methyl-7-(methylamino)-3,4-dihydropyrimido[4,5-d]pyrimidin-2(1H)-one (0.363 g, 77% yield). $^1$H NMR (400 MHz, DMSO-d$_6$), δ 7.92 (s, 1H), 7.00 (s, 1H), 6.90 (d, J=11.2 Hz, 1H), 6.64 (d, J=8.4 Hz, 1H), 5.03 (s, 2H), 4.48 (d, J=13.2 Hz, 1H), 4.30 (d, J=13.2 Hz, 1H), 3.22 (s, 3H), 2.78 (s, 3H), 1.94 (s, 3H); MS (ESI) m/z: 317.3 [M+H]$^+$.

EXAMPLE A22

Using a procedure analogous to Example A2, Example A9 (0.85 g, 2.447 mmol), mCPBA (0.464 g, 2.69 mmol) and 2M methylamine in THF (6 mL) were combined and purified by silica gel chromatography to afford 3-(3-amino-4-fluorophenyl)-1-isopropyl-7-(methylamino)-3,4-dihydropyrimido[4,5-d]pyrimidin-2(1H)-one as white solid (0.56 g, 69% yield). $^1$H NMR (400 MHz, DMSO-d$_6$): δ 7.93 (s, 1H), 6.96 (dd, J=11.6 Hz, 8.8 Hz, 1H), 6.68 (dd, J=8.0 Hz, 2.4 Hz, 1H), 6.44-6.40 (m, 1H), 5.12 (s, 2H), 4.99-4.92 (m, 1H), 4.44 (s, 2H), 2.77 (d, J=4.8 Hz, 3H), 1.45 (d, J=6.8 Hz, 6H); MS (ESI) m/z: 331.2 (M+H$^+$).

EXAMPLE A23

Using a procedure analogous to example A2, Example A11 (0.50 g, 1.38 mmol), mCPBA (0.41 g, 1.66 mmol) and methyl amine (2 M in THF, 2.8 mL, 5.6 mmol) were combined to provide 3-(5-amino-4-fluoro-2-methylphenyl)-1-isopropyl-7-(methylamino)-3,4-dihydropyrimido[4,5-d]pyrimidin-2 (1H)-one (240 mg, 50% yield). MS (ESI) m/z: 345.0 (M+H$^+$).

EXAMPLE A24

To a 0° C. solution of ethyl 6-chloro-4-(methylamino)nicotinate (4 g, 18.7 mmol, from Example C3) in THF (40 mL) was added LiAlH$_4$ (1.4 g, 37.4 mmol) portionwise under a N$_2$ atmosphere. After stirring for 20 min, the reaction was quenched by cautious addition of water followed by aqueous solution of 2 N NaOH. The suspension was filtered and the filtrate was concentrated to afford (6-chloro-4-(methylamino)pyridin-3-yl)methanol (2.9 g, 90.6% yield), which was used in next step without purification. $^1$HNMR (400 MHz, DMSO-d$_6$): δ 7.96 (s, 1 H), 6.63 (s, 1 H), 6.46 (s, 1 H), 5.04 (s, 1 H), 4.39 (m, 2 H), 2.81-2.68 (m, 3 H).

A mixture of (6-chloro-4-(methylamino)pyridin-3-yl) methanol (2.9 g, 16.7 mmol) and MnO$_2$ (11.7 g, 133.6 mmol) in anhydrous DCM (25 mL) was stirred at 30° C. for 6 h. The reaction mixture was cooled to RT, filtered and concentrated in vacuo to give 6-chloro-4-(methylamino)nicotinaldehyde (2.5 g, 87% yield). $^1$H NMR (400 MHz, DMSO-d$_6$): δ 9.83 (s, 1H), 8.52 (br s, 1 H), 8.40 (s, 1 H), 6.75 (s, 1 H), 2.87 (d, J=5.8 Hz, 3 H); MS (ESI) m/z: 171.0 [M+H]$^+$.

To a solution of 6-chloro-4-(methylamino)nicotinaldehyde (1.00 g, 5.88 in mmol) and Example D1 (1.00 g, 5.88 mmol) in glacial acetic acid (7.5 mL) was added sodium triacetoxy borohydride (2.49 g, 11.7 mmol). The mixture was stirred overnight at RT. Another portion of sodium triacetoxy borohydride (1.30 g, 6.11 mmol) was added and the mixture was stirred another 24 h. The reaction was diluted with ice water and basified (pH ~7-8) with NaOH. The yellow precipitate was collected by filtration, washed with $H_2O$ and dried under vacuum to give crude 2-chloro-5-((4-fluoro-2-methyl-5-nitrophenylamino)methyl)-N-methylpyridin-4-amine (2.04 g, 107% yield), which was used without further purification. MS (ESI) m/z: 325.0 [M+H]$^+$.

To suspension 2-chloro-5-((4-fluoro-2-methyl-5-nitrophenylamino)methyl)-N-methylpyridin-4-amine (2.04 g, 6.28 mmol) in dioxane (30 mL) was added $Et_3N$ (3.50 mL, 25 mmol) and phosgene (20% solution in toluene, 6.90 mL, 12.6 mmol). The reaction mixture was stirred at RT for 2.5 h. Water 30 mL was added and the mixture was extracted with EtOAc (2×70 mL). The combined organics were washed with brine (15 mL), dried ($MgSO_4$) and concentrated in vacuo. The residue was stirred with EtOAC for 15 min and the precipitate was collected by filtration and dried in vacuo to give 7-chloro-3-(4-fluoro-2-methyl-5-nitrophenyl)-1-methyl-3,4-dihydropyrido[4,3-d]pyrimidin-2(1H)-one (0.785 g, 36% yield). $^1$H NMR (400 MHz, DMSO-$d_6$): δ 8.31 (s, 1H), 8.11 (s, 1H), 7.61 (s, 1H), 7.15 (s, 1H), 4.94 (s, 1H), 4.61 (s, 1H), 3.26 (s, 3H), 2.22 (s, 3H); MS (ESI) m/z: 351.0 [M+H$^+$].

Zn Dust (0.575 g, 8.80 mmol) was added to a suspension of 7-chloro-3-(4-fluoro-2-methyl-5-nitrophenyl)-1-methyl-3,4-dihydropyrido[4,3-d]pyrimidin-2(1H)-one (0.309 g, 0.880 mmol) and $NH_4Cl$ (0.471 g, 8.80 mmol in MeOH/THF (1:1, 16 mL) and the mixture was stirred 1.5 h at RT. The mixture was filtered through Celite, rinsing forward with MeOH and the filtrates were concentrated, diluted with brine and extracted with THF (2×). The combined organics layers were washed with brine, dried (MgSO4), and concentrated to afford 3-(5-amino-4-fluoro-2-methylphenyl)-7-chloro-1-methyl-3,4-dihydropyrido[4,3-d]pyrimidin-2(1H)-one (0.260 g, 92% yield). MS (ESI) m/z: 321.0 [M+H$^+$].

EXAMPLE A25

Example A24 (0.260 g, 0.811 mmol) and N',N'-dimethylethane-1,2-diamine (9.25 mL) were combined and heated to 175° C. for 2 days. The excess solvent was removed under reduced pressure. And the residue was partitioned with saturated aq $NaHCO_3$ (15 mL) and EtOAc (2×35 mL). The combined organics were washed with brine (15 mL), dried (MgSO4) and concentrated. The light yellow residue was dissolved in minimal amount of EtOAc. Hexane was added and the mixture was stirred for 15 min. The precipitate was collected by filtration, washed with hexane and dried under vacuum to obtain 3-(5-amino-4-fluoro-2-methylphenyl)-7-(2-(dimethylamino)ethylamino)-1-methyl-3,4-dihydropyrido[4,3-d]pyrimidin-2(1H)-one (0.153 g, 51% yield). $^1$H NMR (400 MHz, DMSO-$d_6$): δ 7.68 (s, 1 H), 6.88 (d, J=12.0 Hz, 1 H), 6.62 (d, J=8.8 Hz, 1 H), 6.25 (t, J=5.4 Hz, 1 H), 6.03 (s, 1 H), 5.00 (s, 2 H), 4.49 (d, J=13.6 Hz, 1H), 4.30 (d, J=13.6 Hz, 1 H), 3.29 (m, 2 H), 3.13 (s, 3 H), 2.38 (t, J=6.4 Hz, 2 H), 2.16 (s, 6H), 1.91 (s, 3 H).

EXAMPLE A26

5-(Chloromethyl)-N4-ethyl-N2-methoxy-N2-methylpyridine-2,4-diamine (4.3 g, 18.7 mmol, from Example A19) and 4-fluoro-3-nitro-phenylamine (3 g, 19 mmol) were combined in pyridine (50 ml) by the method of Example A4 to provide N4-ethyl-5-((4-fluoro-3-nitrophenylamino)methyl)-N2-methoxy-N2-methylpyridine-2,4-diamine (5.6 g, 85% yield). $^1$H NMR (400 MHz, DMSO-$d_6$): δ 7.65 (s, 1 H), 7.63 (s, 1 H), 7.34-7.29 (m, 1 H), 7.23-7.21 (m, 1H), 7.02-7.6.98 (m, 1 H), 6.84 (s, 1 H), 6.06 (s, 1 H), 4.18 (d, J=3.2 Hz, 2 H), 3.71 (s, 3 H), 3.31 (s, 3 H), 3.32 (q, J=7.2 Hz, 2 H), 1.18 (t, J=7.2 Hz, 3 H); MS (ESI) m/z: 350.1 [M+H]$^+$.

Diphosgene (2.4 mL, 20 mmol), N4-ethyl-5-((4-fluoro-3-nitrophenylamino)methyl)-N2-methoxy-N2-methylpyridine-2,4-diamine (5.6 g, 16 mmol) and $Et_3N$ (4.3 g, 40 mmol) were combined by the procedure of Example A4 to provide 1-ethyl-3-(4-fluoro-3-nitrophenyl)-7-(methoxy(methyl)amino)-3,4-dihydropyrido[4,3-d]pyrimidin-2(1H)-one (4.8 g, 80% yield). $^1$H NMR (400 MHz, DMSO-$d_6$): δ 8.14 (m, 1 H), 7.96 (s, 1 H), 7.79 (m, 1 H), 7.61 (m, 1 H), 6.57 (s, 1 H), 4.78 (s, 2 H), 3.88 (d, J=7.2 Hz, 2 H), 3.71 (s, 3 H), 3.15 (s, 3 H), 1.20 (t, J=7.2 Hz, 3H); MS (ESI) m/z: 376.2 [M+H]$^+$.

1-Ethyl-3-(4-fluoro-3-nitrophenyl)-7-(methoxy(methyl)amino)-3,4-dihydropyrido[4,3-d]pyrimidin-2(1H)-one (4.6 g, 12 mmol), Pd/C (0.5 g) and hydrogen (45 psi) were reacted in MeOH (100 mL) at 50° C. overnight to give 3-(3-amino-4-fluorophenyl)-1-ethyl-7-(methylamino)-3,4-dihydropyrido[4,3-d]pyrimidin-2(1H)-one (3.2 g, 84%). $^1$H-NMR (400 MHz, DMSO-$d_6$): δ 7.70 (s, 1 H), 6.94 (dd, J=11.2, 8.8 Hz, 1 H), 6.67 (dd, J=8.0, 2.4 Hz, 1 H), 6.42 (m, 1 H), 6.33 (m, 1 H), 5.98 (s, 1 H), 5.14 (s, 2 H), 4.48 (s, 2 H), 3.74 (q, J=7.2 Hz, 2 H), 2.73 (d, J=5.2 Hz, 3 H), 1.15 (t, J=7.2 Hz, 3 H); MS (ESI) m/z: 316.2 [M+H]$^+$.

EXAMPLE A27

To a solution of Example A10 (0.500 g, 1.50 mmol) in $CH_2Cl_2$ (10 mL) was added mCPBA (0.444 g, 1.20 eq) in a portion wise manner. After stirring for 1 h, N',N'-dimethyl-ethane-1,2-diamine (0.661 g, 7.5 mmol) was added and the reaction mixture was stirred overnight. Water was added and the solution was stirred for 1 h. The aqueous was extracted with $CH_2Cl_2$ (2×) and the combined organics were washed with saturated $NaHCO_3$, 3N NaOH, and brine. The organics were dried ($MgSO_4$) and concentrated to provide 3-(5-amino-4-fluoro-2-methylphenyl)-7-(2-(dimethylamino)ethylamino)-1-methyl-3,4-dihydropyrimido[4,5-d]pyrimidin-2(1H)-one (0.358 g, 64%). $^1$H NMR (400 MHz, DMSO-$d_6$): δ 7.91 (s, 1H), 6.92-6.88 (m, 2H), 6.64 (d, J=8.8 Hz, 1H), 5.03 (s, 2H), 4.48 (d, J=14.0 Hz, 1H), 4.30 (d, J=14.0 Hz, 1H), 4.33 (m, 2H), 3.22 (s, 3H), 2.38 (t, J=6.8 Hz, 2H), 2.16 (s, 6H), 1.94 (s, 3H).

EXAMPLE A28

Using a procedure analogous to Example A17, 5-(chloromethyl)-N4-isopropyl-N2-methoxy-N2-methylpyridine-2,4-diamine (3.3 g, 13.6 mmol, see Example A17) and 4-fluoro-5-nitroaniline (2.1 g, 13.6 mol) were combined to provide 3-(3-amino-4-fluorophenyl)-1-isopropyl-7-(methylamino)-3,4-dihydropyrido[4,3-d]pyrimidin-2(1H)-one (2.1 g, 47% yield over 3 steps). $^1$H NMR (400 MHz, DMSO-$d_6$): δ 7.81 (s, 1 H), 7.02 (dd, J=11.2, 8.8 Hz, 1 H), 6.74 (dd, J=8.0, 2.4 Hz, 1 H), 6.48-6.43 (m, 2 H), 6.22 (s, 1 H), 5.24 (s, 2 H), 4.49 (s, 2 H), 4.39 (m, 1 H), 2.82 (d, J=4.8 Hz, 3 H), 1.52 (d, J=6.8 Hz, 6 H); MS (ESI) m/z: 330.2. [M+H]$^+$.

EXAMPLE A29

A solution of ethyl 4,6-dichloronicotinate (10 g, 45.7 mmol) in tert-butylamine (100 mL) was stirred at 50° C. for 10 h. The solvent was removed under reduced pressure and the residue was suspended in $H_2O$ and extracted with EtOAc (3×100 mL). The organics were washed with brine, dried ($MgSO_4$), concentrated in vacuo and purified by silica gel chromatography to provide ethyl 4-(tert-butylamino)-6-chloronicotinate (7 g, 60% yield). ¹HNMR (400 MHz, DMSO-d₆): δ 8.53 (s, 1 H), 8.39 (s, 1 H), 6.80 (s, 1 H), 4.25 (d, J=7.2 Hz, 2H), 1.37 (s, 9 H), 1.27 (t, J=7.2 Hz, 3 H).

LiAlH₄ ((2.1 g, 54.7 mmol) was added portion wise to a 0° C. solution of ethyl 4-(tert-butylamino)-6-chloronicotinate (7 g, 27.3 mmol) in THF (100 mL). After 20 min, the reaction was quenched by the addition of water (2.1 mL), followed by 2 N aq NaOH (2 N, 2.1 ml. The resulting suspension was filtered and the filtrate was concentrated to afford (4-tert-butylamino-6-chloro-pyridin-3-yl)-methanol (5.0 g, 86.2% yield), which was used in next step without purification. ¹H NMR (400 MHz, DMSO-d₆): δ 7.73 (s, 1 H), 6.61 (s, 1 H), 5.87 (s, 1 H), 5.43 (t, J=5.2 Hz, 1 H), 4.38 (d, J=5.2 Hz, 2 H), 1.35 (s, 9 H).

A mixture of (4-tert-butylamino-6-chloro-pyridin-3-yl)-methanol (5.0 g, 23.4 mmol) and MnO₂ (14.3 g, 163.6 mmol) in anhydrous CH₂Cl₂ (100 mL) was stirred at RT for 10 h. The reaction was filtered and the filtrate was concentrated to give 4-(tert-butylamino)-6-chloronicotinaldehyde (4.0 g, 87.0% yield), which was used in the next step without further purification. ¹H NMR (400 MHz, DMSO-d₆): δ 9.83 (s, 1 H), 8.90 (s, 1 H), 8.44 (s, 1 H), 6.86 (s, 1 H), 1.40 (s, 9 H).

A mixture of 4-(tert-butylamino)-6-chloronicotinaldehyde (4.0 g, 18.9 mmol), 4-fluoro-3-nitroaniline (2.9 g, 18.9 mmol) and NaBH(OAc)₃ (7.1 g, 37.8 mmol) in CH₃COOH (80 mL) was heated to 80° C. for 10 h. The reaction was concentrated under reduced pressure to give a sticky solid, which was suspended in ice water. The mixture was neutralized (pH 7) with 2N aqueous NaOH solution and was extracted with EtOAc. The extracts were washed with brine, dried Na₂SO₄) and concentrated in vacuo. Purification of the residue by chromatography provided N-tert-butyl-2-chloro-5-((4-fluoro-3-nitrophenylamino)methyl)pyridin-4-amine (4.3 g, 65% yield). ¹H NMR (400 MHz, DMSO-d₆): δ 7.87 (s, 1 H), 7.32 (m, 1 H), 7.27 (m, 1 H), 7.04 (m, 1 H), 6.68 (s, 1 H), 6.52 (m, 1 H), 5.46 (s, 1 H), 4.17 (d, J=4.8 Hz, 2 H), 1.36 (s, 9 H).

NaH (1.5 g, 36.6 mmol) was added portion wise to a solution of N-tert-butyl-2-chloro-5-((4-fluoro-3-nitrophenylamino)methyl)pyridin-4-amine (4.3 g, 12.2 mmol) in anhydrous dioxane (400 mL) at 0° C. and the resulting mixture was stirred at RT for 10 min. A solution of triphosgene (3.6 g, 12.2 mmol) in dioxane (30 mL) was added to the above mixture at 0° C. After the addition, the mixture was heated at 100° C. for 10 h. The cooled reaction was quenched with water and the pH was adjusted to pH>7 with saturated NaHCO₃ solution. The dioxane was removed under reduced pressure and the residue was partitioned between water and EtOAc (3×50 mL). The combined organic layers were washed with brine, dried (Na₂SO₄) and concentrated in vacuo. Purification by silica gel chromatography provided 1-tert-butyl-7-chloro-3-(4-fluoro-3-nitrophenyl)-3,4-dihydropyrido[4,3-d]pyrimidin-2(1H)-one (3.5 g, 76% yield). ¹H NMR (400 MHz, DMSO-d₆): δ 8.21 (s, 1 H), 8.07 (m, 1 H), 7.71 (m, 1 H), 7.57 (m, 1 H), 7.32 (s, 1 H), 4.70 (s, 2 H) 1.57 (s, 9 H).

Iron powder was added (5.2 g, 93 mmol) in portions to a solution of 1-tert-butyl-7-chloro-3-(4-fluoro-3-nitrophenyl)-3,4-dihydropyrido[4,3-d]pyrimidin-2(1H)-one (3.5 g, 9.3 mmol) and conc. HCl (0.35 mL, 4.2 mmol) in 10/1 EtOH/H₂O (11 mL). The resulting mixture was stirred at 40° C. for 30 min. The reaction mixture was filtered and the filter cake was washed with EtOH. The ethanolic filtrate was concentrated and the residue was partitioned between EtOAc and H₂O. The aqueous layer was extracted with EtOAc (3×80 mL). The combined organics were washed with brine, dried (Na₂SO₄), concentrated in vacuo and purified by chromatography on silica gel to afford 3-(3-amino-4-fluorophenyl)-1-tert-butyl-7-chloro-3,4-dihydropyrido[4,3-d]pyrimidin-2 (1H)-one (2.0 g, 62% yield). ¹HNMR (400 MHz, DMSO-d₆): δ 8.20 (s, 1 H), 7.26 (s, 1 H), 6.92 (m, 1 H), 6.62 (m, 1 H), 6.34 (m, 1 H), 5.17 (s, 2 H), 4.50 (s, 2H), 1.55 (s, 9 H).

3-(3-Amino-4-fluorophenyl)-1-tert-butyl-7-chloro-3,4-dihydro-1H-pyrido[4,3-d]pyrimidin-2-one (2.0 g, 5.7 mmol), CuI (200 mg, 1.05 mmol) and methylamine (200 mL) were combined in a steel bomb and heated to 180° C. for 48 h. The reaction vessel was cooled to −78° C., unsealed, and warmed to RT. The reaction was partitioned between EtOAc and H₂O, and the aqueous layer was extracted with EtOAc. The combined organics were washed with brine (2×100 mL), dried (Na₂SO₄), concentrated and purified by neutral aluminum oxide column chromatography to provide 3-(3-amino-4-fluorophenyl)-1-tert-butyl-7-(methylamino)-3,4-dihydropyrido[4,3-d]pyrimidin-2(1H)-one (900 mg, 46% yield). ¹H NMR (400 MHz, DMSO-d₆): δ 7.76 (s, 1 H), 6.91 (dd, J=11.1, 8.7 Hz, 1 H), 6.61 (dd, J=8.1, 2.4 Hz, 1 H), 6.35-6.32 (m, 3 H), 5.14 (s, 2 H), 4.29 (s, 2 H), 2.74 (d, J=4.8 Hz, 3 H), 1.55 (s, 9 H); MS (ESI) m/z: 344.0 [M+H]⁺.

EXAMPLE A30

By analogy to Example A24, 6-chloro-4-(methylamino) nicotinaldehyde (from Example A24), 4-fluoro-3-nitroaniline and sodium triacetoxy borohydride are combined in glacial acetic acid to give crude 2-chloro-5-((4-fluoro-3-nitrophenylamino)methyl)-N-methylpyridin-4-amine, which is reacted with diphosgene by the procedure of Example A75 to give 7-chloro-3-(4-fluoro-3-nitrophenyl)-1-methyl-3,4-dihydropyrido[4,3-d]pyrimidin-2(1H)-one. Zn Dust is reacted with a suspension of 7-chloro-3-(4-fluoro-3-nitrophenyl)-1-methyl-3,4-dihydropyrido[4,3-d]pyrimidin-2(1H)-one and NH₄Cl in MeOH/THF (1:1) to provide 3-(3-amino-4-fluorophenyl)-7-chloro-1-methyl-3,4-dihydropyrido[4,3-d]pyrimidin-2(1H)-one. By analogy to Example A25, 4-methoxybenzylamine and 3-(3-amino-4-fluorophenyl)-7-chloro-1-methyl-3,4-dihydropyrido[4,3-d]pyrimidin-2(1H)-one are combined and heated to 180° C. to provide 7-(4-methoxybenzylamino)-3-(3-amino-4-fluorophenyl)-1-methyl-3,4-dihydropyrido[4,3-d]pyrimidin-2(1H)-one, which is further reacted with trifluoroacetic acid to provide 7-amino-3-(3-amino-4-fluorophenyl)-1-methyl-3,4-dihydropyrido[4,3-d]pyrimidin-2(1H)-one.

EXAMPLE A31

S2-Amino-6-(5-amino-4-fluoro-2-methylphenyl)-8-methylpteridin-7(8H)-one can be prepared by the procedure of Example A5 by substituting N4-methylpyrimidine-2,4,5-triamine sulfate (O'Brien, et. al. *J. Med. Chem.* (1966), 9, p 121-6) for Example D3.

EXAMPLE A32

A mixture of 5-(chloromethyl)-N4-ethyl-N2-methoxy-N2-methylpyridine-2,4-diamine (3.2 g, 14.7 mmol, from Example A9) and Example D2 (2.6 g, 14.7 mol) were combined using the procedure of Example A4 to provide 5-((2-chloro-4-fluoro-5-nitrophenylamino)methyl)-N4-ethyl-N2-methoxy-N2-methylpyridine-2,4-diamine (4.3 g, 76% yield), which was used in the next step without further purification.

Diphosgene (3.1 g, 15.66 mmol), 5-((2-chloro-4-fluoro-5-nitrophenylamino)methyl)-N4-ethyl-N2-methoxy-N2-methylpyridine-2,4-diamine (4.3 g, 13.1 mmol) and Et₃N (7 g, 65.2 mmol) were combined by the procedure of Example A4 to give 3-(2-chloro-4-fluoro-5-nitrophenyl)-1-ethyl-7-(methoxy(methyl)amino)-3,4-dihydropyrido[4,3-d]pyrimidin-2(1H)-one (2.7 g, 60% yield). $^1$H NMR (400 MHz, DMSO-d$_6$): δ 8.55 (d, J=7.6 Hz, 1 H), 8.09 (d, J=11.2 Hz, 1 H), 8.00 (s, 1 H), 6.63 (s, 1 H), 4.91 (d, J=13.6 Hz, 1 H), 4.55 (d, J=13.6 Hz, 1 H), 3.93 (m, 2 H), 3.77 (s, 3 H), 3.20 (s, 3 H), 1.23 (t, J=7.2 Hz, 3 H); MS (ESI) m/z: 410.2 [M+H]$^+$.

3-(2-Chloro-4-fluoro-5-nitrophenyl)-1-ethyl-7-(methoxy (methyl)amino)-3,4-dihydropyrido[4,3-d]pyrimidin-2(1H)-one (2.7 g, 6.6 mmol), Pd/C (1.4 g) and hydrogen (30 psi) were combined at 45° C. by the procedure of Example A4 to provide 3-(5-amino-2-chloro-4-fluorophenyl)-1-ethyl-7-(methylamino)-3,4-dihydropyrido[4,3-d]pyrimidin-2(1H)-one (2 g, 87.0% yield). $^1$H NMR (400 MHz, DMSO-d$_6$): δ 7.72 (s, 1 H), 7.24 (d, J=10.8 Hz, 1 H), 6.81 (d, J=9.2 Hz, 1 H), 6.44 (bs, 1 H), 6.02 (s, 1 H), 5.42 (s, 2 H), 4.50 (d, J=13.2 Hz, 1 H), 4.38 (d, J=13.2 Hz, 1 H), 3.77 (m, 2 H), 2.76 (d, J=4.8 Hz, 3 H), 1.15 (t, J=7.2 Hz, 3 H); MS (ESI) m/z: 350.2[M+H]$^+$.

EXAMPLE B1

Phenyl hydrazine and 4,4-dimethyl-3-oxopentanenitrile were combined according to literature procedures to yield 3-tert-butyl-1-phenyl-1H-pyrazol-5-amine. See WO 2006/071940.

EXAMPLE B2

To a solution of quinolin-6-ylamine (5 g, 35 mmol) in conc. HCl (12 mL) was added dropwise an aqueous solution (4 mL) of NaNO$_2$ (2.42 g, 35 mmol) at 0° C. The resulting mixture was stirred for 1 h and then treated dropwise with a solution of SnCl$_2$.2H$_2$O (15.8 g, 70 mmol) in conc. HCl (15 mL) at 0° C. The reaction mixture was stirred for 2 h at RT. The precipitate was collected and washed with EtOH and Et$_2$O to yield 1-(quinolin-6-yl)hydrazine hydrochloride (4.3 g, 77% yield) as a yellow powder, which was used for the next reaction without further purification.

A mixture of 1-(quinolin-6-yl)hydrazine hydrochloride (4.0 g, 20.5 mmol) and 4,4-dimethyl-3-oxo-pentanenitrile (3.6 g, 30 mol) in EtOH (50 mL) and conc. HCl (5 mL) was heated at reflux overnight. After removal of the solvent, the residue was purified by column chromatography to yield 3-t-butyl-1-(quinolin-6-yl)-1H-pyrazol-5-amine (2.8 g, 51% yield). $^1$H NMR (300 MHz, DMSO-d$_6$): δ 8.84 (d, J=4.2 Hz, 1H), 8.37 (d, J=7.5 Hz, 1H), 8.09 (s, 1H), 8.04 (s, 2H), 7.52 (m, 1H), 5.46 (s, 1H), 5.40 (brs, 2H), 1.29 (s, 9H).

EXAMPLE B3

3-t-butylisoxazol-5-amine was prepared according to the method disclosed in WO 99/32111, 0.250.

EXAMPLE B4

4,4,4-Trifluoro-3-oxo-butyronitrile and phenylhydrazine were combined by the procedure of Example B11 to provide 1-phenyl-3-(trifluoromethyl)-1H-pyrazol-5-amine.
$^1$H-NMR (400 MHz, DMSO-d$_6$) δ 7.59-7.50 (m, 4 H), 7.42 (m, 1 H), 5.78 (s, 1 H), 5.73 (br s, 2 H).

EXAMPLE B5

Methyl hydrazine and 4,4-dimethyl-3-oxopentanenitrile were combined according to literature procedures to yield 3-tert-butyl-1-methyl-1H-pyrazol-5-amine. See WO 2006/071940.

EXAMPLE B6

A mixture of 1,1,3,3-tetramethoxypropane (37 g, 226 mmol), tert-butyl-hydrazine hydrochloride (28 g, 226 mmol) and conc HCl (60 mL, 720 mmol) in EtOH (300 mL) was heated at reflux overnight. The mixture was poured into water and the resulting mixture was extracted with ether. The combined organics were washed with brine, dried (MgSO$_4$) and concentrated in vacuo to give 1-tert-butyl-1H-pyrazole (25 g, 89% yield). $^1$H NMR (400 MHz, DMSO-d$_6$): δ7.73 (s, 1 H), 7.38 (s, 1 H), 6.17 (s, 1 H), 1.47 (s, 9 H); MS (ESI) m/z: 125.1 [M+H]$^+$.

HNO$_3$ (11.7 g, 185 mmol)was added dropwise to a mixture of 1-tert-butyl-1H-pyrazole (23 g, 185 mmol) in conc. H$_2$SO$_4$ (30 mL) at 0° C. The resulting mixture was stirred at 0° C. for 30 min and was poured onto crashed ice. The aqueous mixture was extracted with EtOAc. The combined organics were washed with brine, dried (MgSO$_4$) and concentrated in vacuo to give 1-tert-butyl-4-nitro-1H-pyrazole (20 g, 64% yield). $^1$H NMR (400 MHz, DMSO-d$_6$): δ8.85 (s, 1H), 8.23 (s, 1 H), 1.52 (s, 9 H).

EXAMPLE B7

To a suspension of Na$_2$CO$_3$ (36 g, 339 mmol) in CH$_2$Cl$_2$ (300 mL) was added 1-t-butyl-1H-pyrazole from Example B19 (21 g, 170 mmol) and Br$_2$ (9 mL), and the resulting mixture was stirred at RT overnight. The solid was removed by filtration and the filter cake was washed with CH$_2$Cl$_2$. The filtrates were washed with water and brine, dried (MgSO$_4$), and concentrated to give crude 4-bromo-1-t-butyl-1H-pyrazole (29 g, 85%), used without further purification. $^1$H NMR (300 MHz, CDCl$_3$): δ 7.49 (s, 1 H), 7.45 (s, 1 H), 1.53 (s, 9 H); MS (ESI) m/z: 203 [M+H]$^+$.

To a −78° C. solution of 4-bromo-1-t-butyl-1H-pyrazole (15 g, 74.3 mmol) in anhydrous THF (100 mL) was added n-BuLi (2.5 M in hexane, 53 mL, 132 mmol) under N$_2$, and the resulting mixture was stirred at −78° C. for 30 min. Excess dry ice was added at −78° C., and the mixture was warmed slowly to RT and stirred overnight. The reaction was concentrated in vacuo, water was added and the pH was adjusted to pH 3 by the addition of 2N aq HCl. The aqueous solution was extracted with EtOAc. The extracts were washed with brine, dried (MgSO$_4$) and concentrated in vacuo. The residue was recrystallized (EtOAc-pet. ether) to give 1-t-butyl-1H-pyrazole-4-carboxylic acid (8.0 g, 67% yield). $^1$H NMR (300 MHz, CDCl$_3$): δ 8.10 (s, 1 H), 8.03 (s, 1 H), 1.64 (s, 9 H); MS (ESI) m/z: 168.9 [M+H]$^+$.

EXAMPLE B8

In ethanol (10 mL) was placed the tert-butylhydrazine hydrochloride (1.35 g, 10.8 mmol) and ethyl 2-((dimethylaminomethylene)-3-oxobutanoate (2.00 g, 10.8 mmol). The mixture warmed to reflux and stirred for 2 hrs, cooled to RT and stirred overnight. The mixture was evaporated at reduced pressure to give an oil which was dissolved in ether (25 mL) and washed successively with water (25 mL), saturated sodium bicarbonate (25 mL) and brine (25 mL), dried (Na$_2$SO$_4$ and evaporated at reduced pressure to give an oil. The oil was purified by chromatography (Biotage S1-25 column, 10-40% ethyl acetate/Hex 750 mL) to give ethyl 1-tert-butyl-5-methyl-1H-pyrazole-4-carboxylate (1.48 g, 65% yield) as an oil. MS (ESI) m/z: 211.0 (M+H$^+$).

In a mixture of ethanol:water:dioxane (1:1:1, 21 mL) was placed ethyl 1-tert-butyl-5-methyl-1H-pyrazole-4-carboxylate (1.48 g, 7.04 mmol) and lithium hydroxide hydrate (886 mg, 21.12 mmol). The reaction was stirred at 40° C. for 3 hrs and then at RT overnight. The reaction was diluted with water (25 μL) and ether (25 mL). The ether layer was discarded and the aqueous phase made acidic (pH~=4) with 1N HCl. The acidic phase was then extracted with ethyl acetate (2×25 mL) and the combined ethyl acetate layers were washed with brine, dried ($Na_2SO_4$), evaporated at reduced pressure to give 1-tert-butyl-5-methyl-1H-pyrazole-4-carboxylic acid as a white solid (1.12 g, 87% yield). $^1$H NMR (300 MHz, DMSO-$d_6$): δ 1.56 (s, 9 H), 2.67 (s, 3 H), 7.65 (s, 1 H), 12.13 (s, 1 H); MS (ESI) m/z: 183.0 (M+H$^+$).

EXAMPLE 19

To a suspension of KCN (1.90 g, 29.1 mmol) in MeOH (35 mL) was added dropwisely 3-bromo-1,1,1-trifluoropropan-2-one oxine (5.00 g, 24.3 mmol) in MeOH (72 mL) at RT. The reaction mixture was stirred at RT for 3 hours. The solution was evaporated and then the residue was dissolved in EtOAc and stirred at RT. The solid was filtered (KBr) and the filtrate was evaporated to obtain the crude product. The crude product was purified by silica gel column chromatography (Biotage: 25M, 10% to 60% EtOAc/hexane: 550 mL). Pure fractions were combined and evaporated to obtain 3-(trifluoromethyl)isoxazol-5-amine (1.38 g, 37% yield). MS (ESI) m/z: 153.0 (M+H$^+$).

EXAMPLE B10

In ethanol (40 mL) was placed t-butylcarbamidine hydrochloride (3.71 g, 27.2 mmol). This was treated with 21% sodium ethoxide in ethanol (8.80 g, 27.2 mmol) and stirred at RT for 15 min. To this was added the diethyl ethoxymethylenemalonate (5.87 g, 27.2 mmol) and the reaction mixture was stirred overnight at RT. The reaction mixture was refluxed for 1 hour and then cooled to RT. The solution was evaporated and the residue was dissolved in water (100 mL) and the pH adjusted to 3-4 (wet litmus) with acetic acid. The mixture formed a precipitate. The solid collected by filtration, washed with water (50 mL) and dried under vacuum to obtain ethyl 2-tert-butyl-4-hydroxypyrimidine-5-carboxylate (2.18 g, 36% yield). $^1$H NMR (400 MHz, DMSO-$d_6$): δ 12.6 (brs, 1H), 8.44 (s, 1H), 4.20 (q, J=7.2 Hz, 2H), 1.25 (s, 9H), 1.23 (t, J=7.2 Hz, 3H); MS (ESI) m/z: 225.0 (M+H$^+$).

In cold (~0° C.) $POCl_3$ (20 mL) was dropped triethylamine (0.55 mL) with stirring. To this was added in parts of ethyl 2-tert-butyl-4-hydroxypyrimidine-5-carboxylate (2.18 g, 9.72 mmol). The mixture then warmed to 40° C. and stirred under Argon for 1 hour. The mixture was evaporated until free of $POCl_3$, diluted with $CHCl_3$ (100 mL) and poured carefully into ice (300 mL). The solution was stirred at RT to melt. The organic phase was separated, washed with sodium bicarbonate (100 mL), water (100 mL) and dried ($Na_2SO_4$). The solvents evaporated to give ethyl 2-tert-butyl-4-chloropyrimidine-5-carboxylate (2.0 g, 85% yield). $^1$H NMR (400 MHz, DMSO-$d_6$): δ 9.12 (s, 1H), 4.34 (q, J=6.8 Hz, 2H), 1.33 (s, 9H), 1.27 (t, J=6.8 Hz, 3H); MS (ESI) m/z: 243.0 (M+H$^+$).

To a stirring suspension of ethyl 4-(4-(tert-butoxycarbonyl)piperazin-1-yl)-2-tert-butylpyrimidine-5-carboxylate (0.49 g, 1.24 mmol) in 1:1:1 THF/EtOH/$H_2O$ (9 ml) at RT was added LiOH.$H_2O$ (120 mg, 4.94 mmol) and the mixture was stirred overnight at RT. The reaction mixture was checked by LC-MS and the completed reaction was concentrated to an aqueous residue, acidified (pH 3-4) with 3M HCl and the solution was extracted with EtOAc (3×). The combined organics were washed with brine (1×), dried (MgSO4), filtered and concentration. The crude was dissolved in isopropanol and the solid (LiCl and NaCl) was filtered and washed with isopropanol. The filtrate was concentrated to obtain the desired product 4-(4-(tert-butoxycarbonyl)piperazin-1-yl)-2-tert-butylpyrimidine-5-carboxylic acid (0.36 g, 80% yield). MS (ESI) m/z: 365.0 (M+H$^+$).

EXAMPLE B11

A solution of ethyl trifluoroacetate (14.2 g, 0.1 mol) and anhydrous acetonitrile (5.0 g, 0.12 mol) in THF (100 mL) was added dropwise to a suspension of NaH (60%, 6.0 g, 0.15 mol) in THF (100 mL) at 80° C. The resulting mixture was heated to reflux overnight, and then cooled to RT. The reaction mixture was concentrated in vacuo and the residue was diluted with EtOAc and 10% aq HCL. The organic layer was washed with water and brine, dried (MgSO$_4$) and concentrated in vacuo to yield crude 4,4,4-trifluoro-3-oxo-butyronitrile (15 g), which was used without further purification.

A solution of methylhydrazine (5.0 g, 60 mmol) and 4,4,4-trifluoro-3-oxo-butyronitrile (9.8 g, 71 mmol) in EtOH (50 mL) was treated with conc. HCl (5 mL) and the resultant mixture was heated to reflux overnight. The solvent was removed in vacuo and the crude product was dissolved in EtOAc washed with saturated aq. $Na_2CO_3$ solution until the washings were pH 8. The organics were concentrated and purified by pre-HPLC to provide 2-methyl-5-trifluoromethyl-2H-pyrazol-3-ylamine (2.07 g, 21% yield). $^1$HNMR (300 MHz, DMSO-$d_6$), δ 5.57 (s, 1 H), 5.54 (br s, 2 H), 3.55 (s, 3 H); MS (ESI) m/z: 166.1 (M+H$^+$).

EXAMPLE B12

To a stirring solution of ethyl 2-(5-amino-1-phenyl-1H-pyrazol-3-yl)-2-methylpropanoate (DP-2440, 0.240 g, 0.86 mmol) in dry THF (8.0 mL) at RT was added LiAlH$_4$ (1.0 M in THF, 2.6 mL, 2.6 mmol) and the resulting mixture was stirred at RT for 1 h. The reaction was carefully quenched by the addition of $H_2O$ (0.10 mL), 3M NaOH (0.10 mL) and $H_2O$ (0.20 mL), and the mixture was stirred at RT overnight. The suspension was filtered through Celite and rinsed with EtOAc (20 mL). The filtrate was dried (MgSO$_4$) and concentrated to afford 2-(5-amino-1-phenyl-1H-pyrazol-3-yl)-2-methylpropan-1-ol (0.208, 105% yield) as a yellow oil. MS (ESI) m/z: 232.2 (M+H$^+$).

To a solution of above 2-(5-amino-1-phenyl-1H-pyrazol-3-yl)-2-methylpropan-1-ol (0.208 g, 0.85 mmol) in DMF (2.0 mL) was added imidazole (0.32 g, 4.7 mmol) and TBSCl (0.39 g, 2.6 mmol). The resulting mixture was stirred at RT for 5 h. Solvent was removed under reduced pressure. The residue was diluted with $H_2O$ (10 mL) and extracted with EtOAc (2×20 mL). The combined organic layers were dried (MgSO$_4$) and concentrated. The crude product was purified by chromatography to afford 3-(1-(tert-butyldimethylsilyloxy)-2-methylpropan-2-yl)-1-phenyl-1H-pyrazol-5-amine (0.125 g, 42% yield) as a light yellow oil. MS (ESI) m/z: 346.3 (M+H$^+$).

EXAMPLE B13

Using a procedure analogous to Example B13, ethyl 2-(5-amino-1-methyl-1H-pyrazol-3-yl)-2-methylpropanoate (DP-2525) was converted to 3-(1-(tert-butyldimethylsilyloxy)-2-methylpropan-2-yl)-1-methyl-1H-pyrazol-5-amine in 42% yield. $^1$H NMR (400 MHz, CDCl$_3$): δ 5.59 (s, 1H), 3.69 (s, 3H), 3.55 (s, 2H), 1.26 (s, 6H), 0.89 (s, 9H), 0.00 (s, 6H); MS (ESI) m/z: 284.2 (M+H$^+$).

EXAMPLE C1

A solution of ethyl 4-chloro-2-(methylthio)pyrimidine-5-carboxylate (42 g, 181 mmol) in EtOH (400 mL) was treated with a solution of methylamine (12.3 g, 397 mmol) in EtOH (100 mL) at 0° C. and the mixture was stirred for 3 h. The mixture was concentrated and then partitioned between $H_2O$ (200 mL) and $CH_2Cl_2$ (500 mL). The organic layer was washed with brine, dried ($Na_2SO_4$) and concentrated in vacuo to give ethyl 4-(methylamino)-2-(methylthio)pyrimidine-5-carboxylate as a white solid (36.0 g, 88% yield). $^1$H NMR (300 MHz, $CDCl_3$), 8.59 (s, 1 H), 8.18 (br s, 1 H), 4.31 (q, J=7.2 Hz, 2 H), 3.05 (d, J=4.8 Hz, 3 H), 2.52 (s, 3 H), 1.34 (t, J=7.2 Hz, 3 H); MS (ESI) m/z: 228.1 (M+H$^+$).

To a solution of ethyl 4-(methylamino)-2-(methylthio)pyrimidine-5-carboxylate (30 g, 132 mmol) in THF (300 mL) was added LiAlH$_4$ (7.5 g, 198 mmol). The reaction mixture was stirred for 1 h at RT. The reaction was carefully quenched with 10 mL water, 7 mL of 10% aq NaOH. The mixture was stirred for 1 h, filtered and the filtrate was concentrated to give (4-(methylamino)-2-(methylthio)pyrimidin-5-yl)methanol (22.0 g, 90% yield). $^1$H NMR (300 MHz, DMSO-d$_6$): 7.79 (s, 1 H), 6.79 (m, 1 H), 5.04 (t, J=5.4 Hz, 1 H), 4.27 (d, J=5.4 Hz, 2H), 2.83 (d, J=4.8 Hz, 3 H), 2.40 (s, 3 H). MS (ESI) m/z: 186.1 (M+H$^+$).

EXAMPLE C2

A mixture of Example C1 (22.0 g, 119 mmol) and MnO$_2$ (44 g, 506 mmol) in CHCl$_3$ (300 mL) was stirred at RT for 3 h. The reaction was filtered and the filtrate was concentrated to give 4-(methylamino)-2-(methylthio)pyrimidine-5-carbaldehyde as a pale solid (20 g, 92% yield). $^1$H NMR (400 MHz, DMSO-d$_6$): 9.71 (s, 1 H), 8.60 (br s, 1 H), 8.49 (s, 1 H), 2.96 (d, J=4.8 Hz, 3 H), 2.48 (s, 3 H) MS (ESI) m/z: 184.0 (M+H$^+$).

EXAMPLE C3

To a solution of ethyl 4,6-dichloronicotinate (5 g, 22.8 mmol) in CH$_3$CN (30 mL) was added dropwise aqueous methylamine (65%, 5.2 g, 45.6 mmol) at 0° C. The resulting mixture was stirred at RT for 8 h. The organic solution was removed under reduced pressure to give the crude product, which was suspended in H$_2$O and extracted with EtOAc (3×20 mL). The combined extracts were washed with brine, dried (MgSO$_4$) and concentrated to give ethyl 6-chloro-4-(methylamino)nicotinate (4 g, 82% yield), which was used in the next step without further purification. $^1$HNMR (300 MHz, DMSO-d$_6$): δ 8.48 (s, 1 H), 8.04 (d, J=4.5 Hz, 1 H), 6.71 (s, 1 H), 4.27 (q, J=6.9 Hz, 2 H), 2.85 (d, J=5.1 Hz, 3 H), 1.29 (t, J=6.9 Hz, 3 H).

A mixture of ethyl 6-chloro-4-(methylamino)nicotinate (8 g, 37.4 mmol) and O,N-dimethylhydroxylamine hydrochloride (91 g, 0.94 mol) in dioxane (10 mL) was heated to 180° C. for 6 h. The reaction mixture was cooled to RT, and saturated aq Na$_2$CO$_3$ solution was added until pH 7. The aqueous solution was extracted with EtOAc (3×100 mL). The combined organics were washed with brine, dried (MgSO$_4$) and concentrated in vacuo to give ethyl 6-(methoxy(methyl)amino)-4-(methylamino)nicotinate (6.6 g, 74% yield), which was used in the next step without further purification. $^1$HNMR (400 MHz, DMSO-d$_6$): δ 8.44 (s, 1 H), 7.82 (m, 1H), 6.05 (s, 1 H), 4.20 (q, J=7.2 Hz, 2 H), 3.67 (s, 3 H), 3.17 (s, 3 H), 2.82 (d, J=5.2 Hz, 3 H), 1.25 (t, J=7.2 Hz, 3 H), MS (ESI) m/z: 240.1 (M+H$^+$)

To a solution of ethyl 6-(methoxy(methyl)amino)-4-(methylamino)nicotinate (6 g, 25 mmol) in THF (60 mL) at 0° C. was added LiAlH$_4$ (1.9 g, 50.2 mmol) in portions under N$_2$ atmosphere. After 20 min, the reaction was quenched by addition of water followed by aqueous 2N NaOH. The resultant suspension was filtered and the filtrate was concentrated in vacuo to afford (6-(methoxy(methyl)amino)-4-(methylamino)pyridin-3-yl)methanol (3.8 g, 77.6% yield), which was used without further purification. $^1$H NMR (400 MHz, DMSO-d$_6$): δ 7.61 (s, 1 H), 6.08 (s, 1 H), 5.86 (m, 1 H), 4.88 (t, J=5.2 Hz, 1 H), 4.30 (d, J=5.2 Hz, 2 H), 3.64 (s, 3 H), 3.04 (s, 3 H), 2.73 (d, J=4.8 Hz, 3 H); MS (ESI) m/z: 198.2 (M+H$^+$).

EXAMPLE C4

To a 0° C. solution of ethyl 4-chloro-2-(methylthio)pyrimidine-5-carboxylate (19 g, 82 mmol) in CH$_3$CN (100 mL) was added a solution of aqueous ethylamine (70%, 8.1 g, 126 mmol). The resulting mixture was stirred at RT for 8 h. The organic solution was removed under reduced pressure, and the residue was partitioned between EtOAc and H$_2$O. The aqueous layer was extracted with ethyl acetate (3×30 mL) and the combined organics were washed with brine, dried (MgSO$_4$) and concentrated to give ethyl 4-(ethylamino)-2-(methylthio)pyrimidine-5-carboxylate (19.5 g, 99.1% yield). $^1$H NMR (400 MHz, DMSO-d$_6$): δ 8.49 (s, 1 H), 8.26 (t, J=4.8 Hz, 1 H), 4.23 (q, J=7.2 Hz, 2 H), 3.48 (q, J=7.2 Hz, 2 H), 2.44 (s, 3 H), 1.26 (t, J=7.2 Hz, 3 H), 1.13 (t, J=7.2 Hz, 3 H).

To a solution of ethyl 4-(ethylamino)-2-(methylthio)pyrimidine-5-carboxylate (19.5 g, 81.9 mmol) in anhydrous THF (100 mL) was added LiAlH$_4$ (12.3 g, 327.6 mmol) in portions at 0° C. under N$_2$ atmosphere. After stirring for 30 min, the reaction was quenched with water and then 2N aqueous NaOH as added. The suspension was filtered and the filtrate was concentrated to afford (4-(ethylamino)-2-(methylthio)pyrimidin-5-yl)methanol (15 g, 92.0% yield). $^1$H NMR (400 MHz, DMSO-d$_6$): δ 7.78 (s, 1 H), 6.74 (t, J=4.8 Hz, 1 H), 5.05 (t, J=5.2 Hz, 1 H), 4.26 (d, J=5.2 Hz, 2 H), 3.36 (m, 2 H), 2.37 (s, 3 H) 1.10 (m, 3 H).

EXAMPLE C5

Activated MnO$_2$ (52 g, 0.6 mol) was added to a solution of (4-(ethylamino)-2-(methylthio)pyrimidin-5-yl)methanol (15 g, 0.075 mol) in CH$_2$CL$_2$ (300 mL) and the reaction mixture was stirred overnight at RT. The reaction solution was filtered and the filtrate was concentrated to give 4-(ethylamino)-2-(methylthio)pyrimidine-5-carbaldehyde (14 g, 93% yield). $^1$H NMR (300 MHz, DMSO-d$_6$): δ 9.71 (s, 1 H), 8.67 (br s, 1 H), 8.49 (s, 1 H), 3.51 (m, 2 H), 2.48 (s, 3 H), 1.17 (t, J=7.2 Hz, 3 H).

EXAMPLE C6

A solution of isopropylamine in water (7.6 g, 0.13 mol) was added dropwise to a solution of ethyl 4-chloro-2-(methylthio)pyrimidine-5-carboxylate (15 g, 64.7 mmol) in CH$_3$CN (100 mL) at 0° C. The resulting mixture was stirred at RT for 8 h. The reaction was concentrated under reduced pressure and the residue was partitioned between water and EtOAc. The aqueous layer was extracted with EtOAc (3×50 mL) and the combined organics were washed with brine, dried (MgSO$_4$) and concentrated to give ethyl 4-(isopropylamino)-2-(methylthio)pyrimidine-5-carboxylate (16.4 g, 99% yield). $^1$H NMR (400 MHz, DMSO-d$_6$): δ 8.51 (s, 1 H), 8.05 (d, J=7.6 Hz, 1 H), 4.31-4.22 (m, 3 H), 2.46 (s, 3 H), 1.27 (t, J=7.2 Hz, 3H), 1.20 (d, J=6.4 Hz, 6 H).

To a solution of ethyl 4-(isopropylamino)-2-(methylthio) pyrimidine-5-carboxylate (16.4 g, 64.4 mmol) in anhydrous THF (100 mL) was added LiAlH$_4$ (6.1 g, 0.16 mol) in portions at 0° C. under N$_2$ atmosphere. The reaction mixture was stirred an additional 30 min at RT and was quenched by the addition of water (6 mL) followed by aqueous 2 N NaOH (6 mL). The suspension was filtered and the filtrate was concentrated to give (4-(isopropylamino)-2-(methylthio)pyrimidin-5-yl)methanol (13.5 g, 98% yield), which was used without further purification. $^1$H NMR (400 MHz, DMSO-d$_6$): δ 7.79 (s, 1 H), 6.37 (d, J=7.6 Hz, 1 H), 5.10 (t, J=5.6 Hz, 1 H), 4.28-4.20 (m, 3 H), 2.38 (s, 3 H), 1.13 (d, J=6.4 Hz, 6 H).

EXAMPLE C7

To a solution of ethyl 4,6-dichloronicotinate (5 g, 23 mmol) in CH$_3$CN (100 mL) was added dropwise a solution of isopropylamine in water (60%, 4.5 g, 46 mmol) at 0° C. The resulting mixture was stirred at RT for 8 h. The organic solution was removed under reduced pressure and the residue was partitioned between water and EtOAc. The aqueous layer was extracted with EtOAc (3×30 mL). The combined organics were washed with brine, dried (MgSO$_4$) and concentrated to give ethyl 6-chloro-4-(isopropylamino) nicotinate (5 g, 90% yield). $^1$H NMR (300 MHz, DMSO-d$_6$): δ 8.51 (s, 1 H), 7.97 (m, 1 H), 6.82 (s, 1 H), 4.27 (q, J=7.2 Hz, 2 H), 3.85 (m, 1 H), 1.31 (t, J=7.2 Hz, 3 H), 1.15 (d, J=6.3 Hz, 6 H).

A mixture of ethyl 6-chloro-4-(isopropylamino)nicotinate (3.0 g, 12.4 mmol), O,N-dimethylhydroxylamine hydrochloride (35.0 g, 0.35 mol) in dioxane (10 mL) was heated at 180° C. for 6 h. After cooling to RT, the reaction mixture was neutralized with saturated Na$_2$CO$_3$ solution to pH 7-8. The aqueous mixture was concentrated under reduced pressure and was extracted with EtOAc (3×100 mL). The combined organics were washed with brine, dried (MgSO$_4$) and concentrated to give ethyl 4-(isopropylamino)-6-(methoxy(methyl)amino)nicotinate (3.2 g, 97% yield). $^1$H NMR (400 MHz, DMSO-d$_6$): δ 8.48 (s, 1 H), 7.82 (d, J=7.2 Hz, 1 H), 6.10 (s, 1 H), 4.22 (q, J=7.2 Hz, 2 H), 3.77 (m, 4H), 3.18 (s, 3 H), 1.27 (t, J=7.2 Hz, 3 H), 1.20 (d, J=6.4 Hz, 6 H).

LiAlH$_4$ (0.9 g, 24.0 mmol) was added in portions to a solution of ethyl 4-(isopropylamino)-6-(methoxy(methyl)amino)nicotinate (3.2 g, 12.0 mmol) in THF (60 mL) at 0° C. and the resultant reaction mixture was stirred at RT for 30 min. The reaction was quenched by the addition of water (1 mL) and aqueous 2N NaOH (1 mL). The resulting precipitates were removed by filtration and the filtrate was concentrated to afford (4-(isopropylamino)-6-(methoxy(methyl)amino)pyridine-3-yl)methanol (2.9 g, >100% yield), which was used without further purification. $^1$HNMR (400 MHz, DMSO-d$_6$): δ 7.62 (s, 1 H), 6.16 (s, 1 H), 5.44 (d, J=7.2 Hz, 1 H), 5.02 (bs, 1 H), 4.33 (s, 2 H), 3.69-3.61 (m, 4 H), 3.06 (s, 3 H), 1.18 (d, J=6.4 Hz, 6 H).

EXAMPLE C8

Using a procedure analogous to Example C7, ethyl 4,6-dichloronicotinate (20 g, 0.09 mol) and ethylamine (15.3 g, 0.22 mol) were combined to provide (4-(ethylamino)-6-(methoxy(methyl)amino)pyridin-3-yl)methanol (16 g, 87% yield). $^1$H NMR (400 MHz, DMSO-d$_6$): δ 7.60 (s, 1 H), 6.12 (s, 1 H), 5.64 (m, 1 H), 4.92 (m, 1 H), 4.31 (d, J=5.2 Hz, 2 H), 3.63 (s, 3 H), 3.12 (q, J=7.2 Hz, 2 H), 3.04 (s, 3 H), 1.16 (t, J=7.2 Hz, 3 H); MS (ESI) m/z: 211.9 [M+H]$^+$.

EXAMPLE D1

Concentrated nitric acid (17 g, 0.18 mol) was added dropwise to a stirred solution of 4-fluoro-2-methylaniline (20 g, 0.16 mol) in conc H$_2$SO$_4$ (300 mL) at −10° C. The mixture was stirred at −10° C. for 10 min., and the reaction mixture was poured into ice water. The resultant solid was collected by filtration and partitioned between EtOAc and aq Na$_2$CO$_3$ solution (pH 8). The organic solution was washed with brine, dried (MgSO$_4$) and concentrated to give 4-fluoro-2-methyl-5-nitroaniline (20 g, 74% yield). $^1$H NMR (400 MHz, DMSO-d$_6$): δ 7.27 (d, J=6.8 Hz, 1 H), 7.14 (d, J=12.4 Hz, 1 H) 5.37 (s, 2 H), 2.10 (s, 3 H).

EXAMPLE D2

Concentrated nitric acid (8.8 g, 91 mmol) was added drop wise over 30 min to a stirred solution of 2-chloro-4-fluorophenylamine (12 g, 82.3 mmol) in conc H$_2$SO$_4$ acid (100 mL) at −10° C. The mixture was stirred at that temperature for 10 min. Then the reaction mixture was poured into cooled EtOAc, and ice water was added. The organic layer was separated and washed with brine and saturated NaHCO$_3$ solution, dried (MgSO4) and concentrated in vacuo. Recrystallization (ethyl ether) provided 2-chloro-4-fluoro-5-nitroaniline (5.0 g, 32% yield). $^1$H NMR (400 MHz, DMSO-d$_6$): δ7.59 (d, J=11.2 Hz, 1 H), 7.48 (d, J=7.2 Hz, 1 H), 5.84 (s, 2 H).

EXAMPLE D3

To a solution of 2,4-dichloro-5-nitropyrimidine (8 g, 41 mmol) in EtOH was added dropwise a solution of methyl amine in EtOH (65%, 7.8 g, 0.164 mmol) at −78° C., then the mixture was warmed to RT and stirred overnight. The precipitate was collected by filtration, and the yellow solid was recrystallized (DMSO) to afford N2,N4-dimethyl-5-nitropyrimidine-2,4-diamine (6.5 g, 86% yield). $^1$H NMR (400 MHz, DMSO-d$_6$): δ 8.98 (s, 0.3 H), 8.90 (s, 0.7H), 8.72 (m, J=3.9 Hz, 0.7 H), 8.52 (s, br, 0.3 H), 8.14 (m, 0.7 H), 7.97 (m, 0.3 H), 2.98 (d, J=4.8 Hz, 2.1 H), 2.90 (d, J=3.9 Hz, 0.9 H), 2.85 (d, J=3.9 Hz, 3 H).

To a solution of N2,N4-dimethyl-5-nitropyrimidine-2,4-diamine (4 g, 21.8 mmol) in EtOH was added 10% Pd/C (0.5 g) and 1 N aq HCl solution (10 mL, 10 mmol). The mixture was hydrogenated (30 psi) for 2 h. The reaction mixture was filtered and the filtrate was concentrated to give N2,N4-dimethylpyrimidine-2,4,5-triamine HCl (4 g, 97% yield). $^1$H NMR (400 MHz, CD$_3$OD): δ 9.00 (s, 1 H), 3.45 (s, 3 H), 3.35 (s, 3 H).

EXAMPLE 1

To a solution of Example B1 (10.00 g, 46.4 mmol, 1.00 eq) and pyridine (7.58 ml, 92.9 mmol, 2.00 eq) in CH$_2$Cl$_2$ (225 ml) at 0° C. was added isopropenyl chloroformate (5.33 ml, 4.8.8 mol, 1.05 eq). After 45 min at 0° C., the completed reaction was washed with 3M HCl (2×), satd. NaHCO$_3$ (1×), and brine (1×), dried (MgSO$_4$), filtered and evaporated to afford crude product (14.9 g) as an oil that solidified on the pump. The crude material obtained was upgraded by triturating in warm (60° C.) hexanes (70 ml) for 20-30 min until a powdery precipitate was obtained. After cooling to RT, the solids were collected by filtration, rinsing forward with hexanes. The cake was washed with more hexanes and then dried on the filter to afford prop-1-en-2-yl 3-t-butyl-1-phenyl-1H-pyrazol-5-ylcarbamate (10.79 g, 78% yield) as a tan powder which was used as is in the next reaction. MS (ESI) m/z: 300.3 (M+H$^+$).

Prop-1-en-2-yl 3-t-butyl-1-phenyl-1H-pyrazol-5-ylcarbamate (0.100 g, 0.334 mmol, 1.00 eq), Example A2 (0.0963 g, 0.334 mmol, 1.00 eq) and 1-methylpyrrolidine (0.00174 ml, 0.0167 mmol, 0.05 eq) were combined in THF (3.5 ml) and stirred with heating at 70° C. overnight. The completed reaction was cooled to RT and concentrated to a solid residue. This was treated with CH$_2$Cl$_2$ to give a suspension which was thoroughly chilled in ice. The solids were collected by filtration, rinsed well with ice-cold CH$_2$Cl$_2$ and dried on the filter to afford 1-(5-(7-amino-1-methyl-2-oxo-1,2-dihydropyrimido[4,5-d]pyrimidin-3(4H)-yl)-2-fluorophenyl)-3-(3-t-butyl-1-phenyl-1H-pyrazol-5-yl)urea (0.1336 g, 76% yield) as a pale yellow solid. This was suspended in MeCN, treated with certified 0.1N HCl (2.52 ml, 1.0 eq) frozen and lyophilized to afford the HCl salt (0.1641 g) as a pale yellow solid. $^1$H NMR (400 MHz, DMSO-d$_6$): δ 9.14 (brs, 1H), 8.99 (brs, 1H), 8.22-8.20 (m, 1H), 8.04 (s, 1H), 7.58-7.51 (m, 4H), 7.47-7.42 (m, 1H), 7.34-7.29 (m, 1H), 7.04-7.01 (m, 1H), 6.40 (s, 1H), 4.66 (s, 2H), 3.31 (s, 3H), 1.27 (s, 9H); MS (ESI) m/z; 530.2 (M+H$^+$).

EXAMPLE 2

Using general method A, the TROC carbamate of Example B5 (0.100 g, 0.344 mmol, 1.00 eq) and Example A2 (0.0877 g, 0.304 mmol, 1.00 eq) were combined to afford 1-(5-(7-amino-1-methyl-2-oxo-1,2-dihydropyrimido[4,5-d]pyrimidin-3(4H)-yl)-2-fluorophenyl)-3-(3-t-butyl-1-methyl-1H-pyrazol-5-yl)urea (44.4 mg, 31% yield) as a white solid which was converted to the HCl salt (48.0 mg). $^1$H NMR (400 MHz, DMSO-d$_6$): δ 9.24 (s, 1H), 9.07 (brs, 1H), 8.31 (dd, 1H, J=2.8 and 7.2 Hz), 8.04 (s, 1H), 7.34 (dd, 1H, J=8.80 and 10.8 Hz), 7.03 (ddd, 1H, J=2.8, 4.40 and 8.80 Hz), 6.10 (s, 1H), 4.67 (brs, 2H), 3.64 (s, 3H), 3.31 (s, 3H), 1.20 (s, 9H); MS (ESI) m/z: 468.2 (M+H$^+$).

EXAMPLE 3

Using general method G, 1-phenyl-3-(trifluoromethyl)-1H-pyrazol-5-amine (2.51 g, 11 mmol) and Example A3 (0.17 g, 0055 mmol) were combined to afford 1-(2-fluoro-5-(1-methyl-7-(methylamino)-2-oxo-1,2-dihydropyrimido[4,5-d]pyrimidin-3(4H)-yl)phenyl)-3-(1-phenyl-3-(trifluoromethyl)-1H-pyrazol-5-yl)urea as an off-white solid (0.145 g, 48%, yield). $^1$H NMR (400 MHz, DMSO-d$_6$): δ 9.15 (s, 1H), 9.11 (d, J=2.0 Hz, 1H), 8.05 (dd, J=7.2 Hz, 2.8 Hz, 1H), 7.91 (s, 1H), 7.58-7.52 (m, 5H), 7.21 (dd, J=10.8 Hz, 8.8 Hz, 1H), 6.98-6.94 (m, 2H), 6.83 (s, 1H), 4.52 (s, 2H), 3.19 (s, 3H), 2.73 (d, J=4.4 Hz, 3H); MS (ESI) m/z: 556.3 (M+H$^+$).

EXAMPLE 4

Using general method B, prop-1-en-2-yl 3-tert-butylphenylcarbamate (0.070 g, 0.30 mmol) and Example A3 (0.0907 g, 0.30 mmol) were combined to afford 1-(3-tert-butylphenyl)-3-(2-fluoro-5-(1-methyl-7-(methylamino)-2-oxo-1,2-dihydropyrimido[4,5-d]pyrimidin-3(4H)-yl)phenyl)urea (0.030 g, 21% yield) as a white solid. $^1$H NMR (400 MHz, DMSO-d$_6$), δ 9.09 (s, 1H), 8.59 (s, 1H), 8.18 (dd, J=7.6, 2.4 Hz, 1H), 7.98 (s, 1H), 7.47 (s, 1H), 7.31-7.21 (m, 3H), 7.05-6.98 (m, 3H), 4.60 (s, 1H), 3.27 (s, 3H), 2.81 (d, J=4.4 Hz, 3H), 1.27 (s, 9H); MS (ESI) m/z: 478.3 (M+H$^+$).

EXAMPLE 5

Using general method C, the carbamate of Example B2 (100 mg, 0.23 mmol) and Example A2 (65 mg, 0.23 mmol) were combined to provide 1-(5-(7-amino-1-methyl-2-oxo-1,2-dihydropyrimido[4,5-d]pyrimidin-3(4H)-yl)-2-fluorophenyl)-3-(3-tert-butyl-1-(quinolin-6-yl)-1H-pyrazol-5-yl)urea (76 mg, 58% yield). $^1$H NMR (400 MHz, DMSO-d$_6$): δ 9.02 (s, 1 H), 8.99 (m, 1 H), 8.95 (dd, J=4.2, 1.5 Hz, 1 H), 8.48 (m, 1 H), 8.17-8.10 (m, 3 H), 7.92 (dd, J=9.0, 2.4 Hz, 1 H), 7.91 (s, 1 H), 7.60 (dd, J=8.4, 4.3 Hz, 1 H), 7.23 (dd, J=11.0, 8.6 Hz, 1 H), 6.97 (m, 1 H), 6.55 (s, 2 H), 6.46 (s, 1 H), 4.54 (s, 2 H), 3.29 (s, 3 H), 1.28 (s, 9 H); MS (ESI) m/z: 581.3 (M+H$^+$).

EXAMPLE 6

Using general method C, the TROC carbamate of Example B3 (0.100 g, 0.317 mmol) and Example A3 (0.0958 g, 0.317 mmol) were combined and purified by reverse phase chromatography (5-42% MeCN (w/0.1% TFA)/H$_2$O (w/0.1% TFA)) to afford 1-(3-t-butylisoxazol-5-yl)-3-(2-fluoro-5-(1-methyl-7-(methylamino)-2-oxo-1,2-dihydropyrimido[4,5-d]pyrimidin-3(4H)-yl)phenyl)urea (62.7 mg, 42% yield) following lyophilization. $^1$H NMR (400 MHz, DMSO-d$_6$): δ 10.41 (s, 1H), 8.87 (brs, 1H), 8.14 (dd, J=2.8 and 7.2 Hz, 1H), 8.03 (s, 1H), 7.33 (dd, J=8.8 and 10.8 Hz, 1H), 7.07 (ddd, J=2.8, 4.0, and 8.4 Hz, 1H), 6.04 (s, 1H), 4.65 (s, 2H), 3.31 (brs, 3H), 2.90 (brs, 3H), 1.23 (s, 9H); MS (ESI) m/z: 469.2 (M+H$^+$).

EXAMPLE 7

Using general method B, the carbamate of Example B4 (0.15 g, 0.48 mmol) and Example A7 (0.15 g, 0.48 mmol) were combined to afford 1-(5-(1-ethyl-7-(methylamino)-2-oxo-1,2-dihydropyrimido[4,5-d]pyrimidin-3(4H)-yl)-2-fluorophenyl)-3-(1-phenyl-3-(trifluoromethyl)-1H-pyrazol-5-yl)urea (0.17 g, 62% yield). $^1$H NMR (400 MHz, DMSO-d$_6$): δ 9.20 (s, 1H), 9.15 (brs, 1H), 8.09 (dd, J=2.8, and 7.6 Hz, 1H), 7.95 (s, 1H), 7.5-7.7 (m, 5H), 7.26 (dd, J=8.8, and 10.8 Hz, 1H), 6.8-7.05 9m, 2H), 6.87 (s, 1H), 4.55 (s, 3H), 3.94 (q, J=6.8 Hz, 2H), 2.77 (d, J=4.8 Hz, 3H), 1.16 (t, J=6.8 Hz, 3H); MS (ESI) m/z: 570.2 (M+H$^+$).

EXAMPLE 8

Using general method A, the TROC carbamate of Example B3 (0.35 g, 1.1 mmol) and Example A6 (0.37 g, 1.1 mmol) were combined to afford 1-(3-tert-butylisoxazol-5-yl)-3-(5-(1-ethyl-7-(methylthio)-2-oxo-1,2-dihydropyrimido[4,5-d]pyrimidin-3(4H)-yl)-2 -fluorophenyl)urea (0.17 g, 31% yield). MS (ESI) m/z: 500.3 (M+H$^+$).

Using a procedure analogous to Example A2, 1-(3-tert-butylisoxazol-5-yl)-3-(5 -(1-ethyl-7-(methylthio)-2-oxo-1,2-dihydropyrimido[4,5-d]pyrimidin-3(4H)-yl)-2 -fluorophenyl)urea (0.080 g, 0.16 mmol) was treated with mCPBA (70% wt, 0.10 g, 0.41 mmol) and then N-methylamine (2.0M in THF, 0.68 mL, 1.4 mmol) to afford 3-(3-amino-4 -fluorophenyl)-1-ethyl-7-(methylamino)-3,4-dihydropyrimido[4,5-d]pyrimidin-2(1H)-one (0.14 g, 85% yield). $^1$H NMR (400 MHz, DMSO-d$_6$): δ 10.4 (s, 1H), 8.80 (d, J=2.4 Hz, 1H), 8.09 (dd, J=2.8, and 7.6 Hz, 1H), 7.96 (s, 1H), 7.29 (dd, J=8.8, and 10.8 Hz, 1H), 7.06 (m, 1H), 7.00 (m, 1H), 6.05 (s, 1H), 4.57 (s, 3H), 3.95 (q, J =4.0 Hz, 2H), 2.78 (d, J=4.8 Hz, 3H), 1.23 (s, 9H), 1.17 (t, J=4.0 Hz, 3H); MS (ESI) m/z: 483.3 (M+H$^+$).

EXAMPLE 9

Using general method B, the carbamate of 5-t-butylisoxazol-3-amine (58 mg, 0.26 mmol) and Example A5 (0.080 g, 0.26 mmol) were combined to provide 1-(5-tert-butylisoxazol-3-yl)-3-(2-fluoro-4-methyl-5-(8-methyl-2-(methylamino)-7-oxo-7,8-dihydropteridin-6-yl)phenyl)urea (41 mg, 34% yield). $^1$H NMR (400 MHz, DMSO-d$_6$): δ 8.74 and 8.57 (s, 1 H), 8.10 (d, J=8.4 Hz, 1 H), 8.00 (br m, 1 H), 7.24-7.12 (m, 2 H), 6.44 (s, 1 H), 3.57 and 3.50 (s, 3H), 2.92 (br s, 3 H), 2.28 (s, 3 H), 1.26 (s, 9 H); MS (ESI) m/z: 481.2 (M+H$^+$).

EXAMPLE 10

Using general method A, the TROC carbamate of B4 (0.21 g, 0.52 mmol) and Example A21 (0.2 g, 0.47 mmol) were combined to provide 1-(2-fluoro-4-methyl-5-(1-methyl-7-(methylamino)-2-oxo-1,2-dihydropyrimido[4,5-d]pyrimidin-3(4H)-yl)phenyl)-3-(1-phenyl-3-(trifluoromethyl)-1H-pyrazol-5-yl)urea (140 mg, 52% yield). $^1$H NMR (400 MHz, DMSO-d$_6$) δ9.13 (brs, 2H), 8.03 (d, J=9 Hz, 1H), 7.93 (s, 1H), 7.64-7.51 (m, 5H), 7.18 (d, J=12 Hz, 1H), 7.01 (m, 1H), 6.85 (s, 1H), 4.52 (d, J=14 Hz, 1H), 4.34 (d, J=14 Hz, 1H), 3.23 (brs, 3H), 2.78 (d, J=5 Hz, 3H), 2.05 (s, 3H); MS (ESI, m/z: 570.2, M+H$^+$).

EXAMPLE 11

Using general method A, the TROC carbamate of Example B3 (0.3 g, 0.95 mmol) and Example A10 (0.3 g, 0.9 mmol) were combined to provide 1-(3-tert-butylisoxazol-5-yl)-3-(2-fluoro-4-methyl-5-(1-methyl-7-(methylthio)-2-oxo-1,2-dihydropyrimido[4,5-d]pyrimidin-3(4H)-yl)phenyl)urea (220 mg, 46% yield). $^1$H NMR (400 MHz, DMSO-d$_6$): δ10.32 (brs, 1H), 8.74 (brs, 1H), 8.22 (s, 1H), 8.04 (d, J=8 Hz, 1H), 7.24 (d, J=12 Hz, 1H), 6.03 (s, 1H), 4.70 (d, J=15 Hz, 1H), 4.52 (d, J=15 Hz, 1H), 3.27 (s, 3H), 2.50 (s, 3H), 2.06 (s, 3H), 1.21 (s, 9H); MS (ESI) m/z: 500.3 (M+H$^+$).

Using a procedure analogous to Example A2, 1-(3-tert-butylisoxazol-5-yl)-3-(2-fluoro-4-methyl-5-(1-methyl-7-(methylthio)-2-oxo-1,2-dihydropyrimido[4,5-d]pyrimidin-3(4H)-yl)phenyl)urea (0.58 g, 1.2 mmol) and methylamine (1 ml, 3 mmol, 3.0M in THF) were combined to provide 1-(3-tert-butylisoxazol-5-yl)-3-(2-fluoro-4-methyl-5-(1-methyl-7-(methylamino)-2-oxo-1,2-dihydropyrimido[4,5-d]pyrimidin-3(4H)-yl)phenyl)urea (0.995 g, 95% yield). $^1$H NMR (400 MHz, DMSO-d$_6$): δ 10.31 (brs, 1H), 8.73 (s, 1H), 8.00 (d, J=9 Hz, 1H), 7.94 (brs, 1H), 7.23 (d, J=12 Hz, 1H), 7.02 (m, 1H), 6.04 (s, 1H), 4.55 (d, J=14 Hz, 1H), 4.35 (d, J=14 Hz, 1H), 3.24 (brs, 3H), 2.79 (d, J=5 Hz, 3H), 2.08 (s, 3H), 1.22 (s, 9H); MS (ESI) m/z: 483.3 (M+H$^+$).

EXAMPLE 12

Using general method A, the TROC carbamate of Example B5 (0.16 g, 0.47 mmol) and Example A21 (0.15 g, 0.47 mmol) were combined to provide 1-(3-tert-butyl-1-methyl-1H-pyrazol-5-yl)-3-(2-fluoro-4-methyl-5-(1-methyl-7-(methylamino)-2-oxo-1,2-dihydropyrimido[4,5-d]pyrimidin-3(4H)-yl)phenyl)urea (190 mg, 81% yield). $^1$H NMR (400 MHz, DMSO-d$_6$): δ 8.86 (brs, 2H), 8.05 (d, J=9 Hz, 1H), 7.93 (s, 1H), 7.19 (d, J=12 Hz, 1H), 7.01 (m, 1H), 6.06 (s, 1H), 4.54 (d, J=14 Hz, 1H), 4.35 (d, J=14 Hz, 1H), 3.59 (s, 3H), 3.23 (brs, 3H), 2.78 (d, J=5 Hz, 3H), 2.05 (s, 3H), 1.17 (s, 9H); MS (ESI, m/z: 496.3, M+H$^+$).

EXAMPLE 13

Using general method C, the TROC carbamate of Example B3 (0.3 g, 0.95 mmol) and Example A10 (0.3 g, 0.9 mmol) were combined to provide 1-(3-tert-butylisoxazol-5-yl)-3-(2-fluoro-4-methyl-5-(1-methyl-7-(methylthio)-2-oxo-1,2-dihydropyrimido[4,5-d]pyrimidin-3(4H)-yl)phenyl)urea (0.22 g, 46% yield) $^1$H NMR (400 MHz, DMSO-d$_6$): δ 10.32 (brs, 1H), 8.74 (brs, 1H), 8.22 (s, 1H), 8.04 (d, J=8 Hz, 1H), 7.24 (d, J=12 Hz, 1H), 6.03 (s, 1H), 4.70 (d, J=15 Hz, 1H), 4.52 (d, J=15 Hz, 1H), 3.27 (s, 3H), 2.50 (s, 3H), 2.06 (s, 3H), 1.21 (s, 9H); MS (ESI) m/z: 500.3 (M+H$^+$).

Using a procedure analogous to Example A2, oxidation of the sulfide with mCPBA followed by reaction with excess N,N-dimethylethylamine provided 1-(3-tert-butylisoxazol-5-yl)-3-(5-(7-(2-(dimethylamino)ethylamino)-1-methyl-2-oxo-1,2-dihydropyrimido[4,5-d]pyrimidin-3(4H)-yl)-2-fluoro-4-methyl)phenyl)urea which was converted to methane sulfonic acid salt (52% yield) $^1$H NMR (400 MHz, DMSO-d$_6$): δ10.35 (brs, 1H), 8.57 (brs, 1H), 8.02 (d, J=9 Hz, 1H), 8.0 (s, 1H), 7.3 (m, 1H), 7.25 (d, J=12 Hz, 1H), 6.03 (s, 1H), 4.60 (d, J=14 Hz, 1H), 4.40 (d, J=14 Hz, 1H), 3.60 (m, 2H), 3.20 (m, 2H), 2.80 (s, 6H), 2.32 (s, 3H), 2.03 (s, 3H), 1.21 (s, 9H); MS (ESI) m/z: 498.0 (M+H$^+$).

EXAMPLE 14

Using general method G, the carbamate of 5-t-butylisoxazol-3-amine (0.050 g, 0.223 mmol) and Example A21 (0.078 g, 0.245 mmol) were combined to afford 1-(5-tert-butylisoxazol-3-yl)-3-(2-fluoro-4-methyl-5-(1-methyl-7-(methylamino)-2-oxo-1,2-dihydropyrimido[4,5-d]pyrimidin-3 (4H)-yl)phenyl)urea (0.042 g, 39% yield) as a white solid. $^1$H NMR (400 MHz, DMSO-d$_6$): δ 9.82 (s, 1H), 8.80 (s, 1H), 8.03 (d, J=7.6 Hz, 1H), 7.94 (s, 1H), 7.23 (d, J=12.0 Hz, 1H), 7.02 (m, 1H), 6.46 (s, 1H), 4.55 (d, J=13.6 Hz, 1H), 4.36 (d, J=13.6 Hz, 1H), 3.24 (s, 3H), 2.79 (d, J=4.0 Hz, 3H), 2.07 (s, 3H), 1.26 (s, 9H); MS (ESI) m/z: 483.3 (M+H$^+$).

EXAMPLE 15

Using general method F, 3-(trifluoromethyl)phenylisocyanate (41 mg, 0.22 mmol) and Example A21 (70 mg, 0.22 mmol) in the presence of pyridine (36 µL, 0.44 mmol) were combined to afford 1-(2-fluoro-4-methyl-5-(1-methyl-7-(methylamino)-2-oxo-1,2-dihydropyrimido[4,5-d]pyrimidin-3(4H)-yl)phenyl)-3-(3-(trifluoromethyl)phenyl)urea (59 mg, 53% yield). $^1$H NMR (400 MHz, DMSO-d$_6$): δ 9.38 (s, 1H), 8.65 (d, J=2.0 Hz, 1H), 8.04 (m, 2H), 7.94 (brs, 1H), 7.48 (m, 2H), 7.31 (m, 1H), 7.21 (d, J=12.4 Hz, 1H), 7.01 (q, J=4.8 Hz, 1H), 4.58 (d, J=14.0 Hz, 1H), 4.35 (d, J=14.0 Hz, 1H), 3.24 (brs, 3H), 2.79 (d, J=4.8 Hz, 3H), 2.07 (s, 3H); MS (ESI) m/z: 504.0 (M+H$^+$).

EXAMPLE 16

Using general method B, the carbamate of 5-t-butylisoxazol-3-amine (50 mg, 0.22 mmol) and Example A23 (77 mg, 0.22 mmol) were combined to afford 1-(5-tert-butylisoxazol-3-yl)-3-(2-fluoro-5-(1-isopropyl-7-(methylamino)-2-oxo-1,2-dihydropyrimido[4,5-d]pyrimidin-3(4H)-yl)-4-methylphenyl)urea (0.067 g, 59% yield). $^1$H NMR (400 MHz, DMSO-d$_6$): δ 9.82 (s, 1H), 8.80 (brs, 1H), 8.01 (d, J=7.6 Hz, 1H), 7.94 (brs, 1H), 7.21 (d, J=12.0 Hz, 1H), 6.99 (m, 1H), 6.47 (s, 1H), 4.99 (m, 1H), 4.52 (d, J=14.0 Hz, 1H), 4.28 (d, J=14.0 Hz, 1H), 2.78 (d, J=4.8 Hz, 3H), 2.04 (s, 3H), 1.46 (d, J=6.4 Hz, 6H), 1.27 (s, 9H); MS (ESI) m/z: 511.2 (M+H$^+$).

EXAMPLE 17

Using general method C, the TROC carbamate of Example B3 (0.165 g, 0.523 mmol) and Example A23 (0.120 g, 0.348 mmol) were combined to afford 1-(3-tert-butylisoxazol-5-yl)-3-(2-fluoro-5-(1-isopropyl-7-(methylamino)-2-oxo-1,2-dihydropyrimido[4,5-d]pyrimidin-3(4H)-yl)-4-methylphenyl)urea (0.022 g, 12% yield) as a white solid. $^1$H NMR (400 MHz, DMSO-$d_6$): δ 10.32 (s, 1H), 8.74 (s, 1H), 7.98 (d, J=8.0 Hz, 1H), 7.94 (s, 1H), 7.22 (d, J=12.0 Hz, 1H), 7.00 (m, 1H), 6.05 (s, 1H), 5.00 (m, 1H), 4.52 (d, J=13.6 Hz, 1H), 4.28 (d, J=13.6 Hz, 1H), 2.78 (d, J=4.8 Hz, 3H), 2.05 (s, 3H), 1.46 (d, J=6.4 Hz, 6H), 1.23 (s, 9H); MS (ESI) m/z: 511.2 (M+H$^+$).

EXAMPLE 18

Using general method B, the carbamate of 5-t-butylisoxazol-3-amine (50 mg, 0.22 mmol) and Example A22 (74 mg, 0.22 mmol) were combined to afford 1-(5-tert-butylisoxazol-3-yl)-3-(2-fluoro-5-(1-isopropyl-7-(methylamino)-2-oxo-1,2-dihydropyrimido[4,5-d]pyrimidin-3(4H)-yl)phenyl)urea (0.033 g, 30% yield). $^1$H NMR (400 MHz, DMSO-$d_6$): δ 9.86 (s, 1H), 8.86 (brs, 1H), 8.08 (dd, J=2.8, and 7.2 Hz, 1H), 7.96 (brs, 1H), 7.27 (dd, J=8.8, and 10.84 Hz, 1H), 7.00 (m, 2H), 4.97 (m, 1H), 4.51 (s, 2H), 2.78 (d, J=4.8 Hz, 1H), 1.47 (d, J=6.4 Hz, 6H), 1.27 (s, 9H); MS (ESI) m/z: 497.2 (M+H$^+$).

EXAMPLE 19

Using general method D, Example B7 (0.041 g, 0.24 mol) and Example A17 (0.084 g, 0.24 mmol) in presence of triethylamine (0.1 g, 0.97 mmol) and DPPA (0.2 g, 0.73 mmol) were combined to afford 1-(1-tert-butyl-1H-pyrazol-4-yl)-3-(2-fluoro-5-(1-isopropyl-7-(methylamino)-2-oxo-1,2-dihydropyrimido[4,5-d]pyrimidin-3(4H)-yl)-4-methylphenyl)urea as a white solid (0.037 g, 30% yield). $^1$H NMR (400 MHz, DMSO-$d_6$): δ 8.67 (s, 1H), 8.48 (d, J=2.0 Hz, 1H), 8.04 (d, J=8.0 Hz, 1H), 7.94 (s, 1H), 7.81 (m, 1H), 7.38 (s, 1H), 7.16 (d, J=12.0 Hz, 1H), 6.98-6.97 (m, 1H), 5.02-4.95 (m, 1H), 4.51 (d, J=13.6 Hz, 1H), 4.28 (d, J=13.6 Hz, 1H), 2.78 (d, J=4.4 Hz, 3H), 2.02 (s, 3H), 1.47-1.44 (m, 15H); MS (ESI) m/z: 510.2 (M+H$^+$).

EXAMPLE 20

Using general method D, Example B7 (0.051 g, 0.3 mmol) and Example A22 (0.1 g, 0.3 mmol) in presence of triethylamine (0.12 g, 1.2 mmol) and diphenylphospharyl azide (0.25 g, 0.9 mmol) were combined to afford 1-(1-tert-butyl-1H-pyrazol-4-yl)-3-(2-fluoro-5-(1-isopropyl-7-(methylamino)-2-oxo-1,2-dihydropyrimido[4,5-d]pyrimidin-3(4H)-yl)phenyl)urea as a white solid (0.045 g, 30% yield). $^1$H NMR (400 MHz, DMSO-$d_6$): δ 8.72 (s, 1H), 8.56 (s, 1H), 8.11 (dd, J=7.6 Hz, 2.4 Hz, 1H), 7.96 (s, 1H), 7.81 (s, 1H), 7.39 (s, 1H), 7.23 (dd, J=11.2 Hz, 8.8 Hz, 1H), 6.99-6.96 (m, 1H), 6.94-6.89 (m, 1H), 5.00-4.93 (m, 1H), 4.49 (s, 2H), 2.77 (d, J=4.4 Hz, 3H), 1.46-1.44 (m, 1H); MS (ESI) m/z: 496.3 (M+H$^+$).

EXAMPLE 21

Using general method B, the carbamate of Example B5 (50 mg, 0.21 mmol) and Example A7 (67 mg, 0.21 mmol) were combined to afford 1-(3-tert-butyl-1-methyl-1H-pyrazol-5-yl)-3-(5-(1-ethyl-7-(methylamino)-2-oxo-1,2-dihydropyrimido[4,5-d]pyrimidin-3(4H)-yl)-2-fluorophenyl)urea (0.060 g, 58% yield). $^1$H NMR (400 MHz, DMSO-$d_6$): δ 8.95 (s, 1H), 8.88 (d, J=2.0 Hz, 1H), 8.13 (dd, J=3.2, and 7.6 Hz, 1H), 7.96 (s, 1H), 7.28 (dd, J=8.8, and 11.2 Hz, 1H), 7.00 (m, 2H), 6.08 (s, 1H), 4.56 (s, 2H), 3.93 (q, J=4.8 Hz, 2H), 3.60 (s, 3H), 2.78 (d, J=4.8 Hz, 3H), 1.18 (s, 9H), 1.15 (t, J=4.8 Hz, 3H), 1.27 (s, 9H); MS (ESI) m/z: 496.3 (M+H$^+$).

EXAMPLE 22

Using general method B, the carbamate of Example B4 (70 mg, 0.22 mmol) and Example A4 (68 mg, 0.22 mmol) were combined to afford 1-(2-fluoro-5-(1-methyl-7-(methylamino)-2-oxo-1,2-dihydropyrido[4,3-d]pyrimidin-3(4H)-yl)phenyl)-3-(1-phenyl-3-(trifluoromethyl)-1H-pyrazol-5-yl)urea (0.066 g, 53% yield). $^1$H NMR (400 MHz, DMSO-$d_6$): δ 9.20 (s, 1H), 9.14 (brs, 1H), 8.08 (dd, J=2.8, and 7.2 Hz, 1H), 7.74 (s, 1H), 7.62 (m, 5H), 7.24 (d, J=8.8, and 10.8 Hz, 1H), 6.97 (m, 1H), 6.87 (s, 1H), 6.42 (q, J=4.8 Hz, 1H), 5.95 (s, 1H), 4.57 (s, 2H), 3.15 (s, 3H), 2.75 (d, J=4.8 Hz, 3H); MS (ESI) m/z: 555.2 (M+H$^+$).

EXAMPLE 23

Using a modified general method C, the TROC carbamate of Example B6 (128 mg, 0.40 mmol) and Example A4 (118 mg, 0.39 mmol) in DMF (1 mL) was treated with iPr$_2$NEt (0.070 mL, 0.40 mmol). The reaction mixture was heated to 100° C. for 4 days. The reaction was concentrated in vacuo and purified by chromatography on reverse phase silica gel to provide 1-(1-tert-butyl-1H-pyrazol-4-yl)-3-(2-fluoro-5-(1-methyl-7-(methylamino)-2-oxo-1,2-dihydropyrido[4,3-d]pyrimidin-3(4H)-yl)phenyl)urea (54 mg, 28% yield). $^1$H NMR (400 MHz, DMSO-$d_6$): δ 8.72 (s, 1H), 8.53 (d, J=2.2 Hz, 1H), 8.13 (dd, J=7.3, 2.5 Hz, 1H), 7.80 (s, 1H), 7.74 (s, 1H), 7.38 (s, 1H), 7.22 (dd, J=11.3, 8.8 Hz, 1H), 6.90 (ddd, J=8.8, 4.3, 2.8 Hz, 1H), 6.41 (q, J=4.8 Hz, 1H), 5.95 (s, 1H), 4.57 (s, 2H), 3.17 (s, 3H), 2.75 (d, J=5.0 Hz, 3H), 1.46 (s, 9H); MS (ESI) m/z: 467.3 (M+H$^+$).

EXAMPLE 24

Using general method B, the carbamate of Example B5 (0.050 g, 0.211 mmol) and Example A16 (0.066 g, 0.211 mmol) were combined to afford 1-(3-tert-butyl-1-methyl-1H-pyrazol-5-yl)-3-(2-fluoro-4-methyl-5-(1-methyl-7-(methylamino)-2-oxo-1,2-dihydropyrido[4,3-d]pyrimidin-3(4H)-yl)phenyl)urea (0.061 g, 59% yield) as a white solid. $^1$H NMR (400 MHz, DMSO-$d_6$): δ 8.89 (s, 1H), 8.80 (d, J=1.2 Hz, 1H), 8.02 (d, J=8.0 Hz, 1H), 7.72 (s, 1H), 7.19 (d, J=12.0 Hz, 1H), 6.41 (m, 1H), 6.07 (s, 1H), 5.95 (s, 1H), 4.56 (d, J=13.6 Hz, 1H), 4.36 (d, J=14.0 Hz, 1H), 3.59 (s, 3H), 3.16 (s, 3H), 2.75 (d, J=4.8 Hz, 3H), 2.04 (s, 3H), 1.18 (s, 9H); MS (ESI) m/z: 495.2 (M+H$^+$).

EXAMPLE 25

Using general method C, the TROC carbamate of example B3 (0.080 g, 0.254 mmol) and Example A16 (80 mg, 0.254 mmol) were combined to afford 1-(3-tert-butylisoxazol-5-yl)-3-(2-fluoro-4-methyl-5-(1-methyl-7-(methylamino)-2-oxo-1,2-dihydropyrido[4,3-d]pyrimidin-3(4H)-yl)phenyl)urea. This was treated with methanesulfonic acid to afford 1-(3-tert-butylisoxazol-5-yl)-3-(2-fluoro-4-methyl-5-(1-methyl-7-(methylamino)-2-oxo-1,2-dihydropyrido[4,3-d]pyrimidin-3(4H)-yl)phenyl)urea mesylate salt (58 mg, 40% yield). $^1$H NMR (400 MHz, DMSO-$d_6$): δ 10.3 (s, 1H), 8.78 (brs, 1H), 8.13 (brs, 1H), 8.03 (d, J=7.6 Hz, 1H), 7.77 (s, 1H), 7.25 (d, J=11.6 Hz, 1H), 6.26 (s, 1H), 6.03 (s, 1H), 4.66 (d, J=14.8 Hz, 1H), 4.49 (d, J=14.8 Hz, 1H), 3.25 (s, 3H), 2.90 (d, J=4.8 Hz, 3H), 2.31 (s, 3H), 2.07 (s, 3H), 1.23 (s, 9H); MS (ESI) m/z: 482.2 (M+H$^+$).

EXAMPLE 26

Using general method B, the carbamate of 5-t-butylisoxazol-3-amine (70 mg, 0.31 mmol) and Example A16 (98 mg, 0.31 mmol) were combined to afford 1-(5-tert-butylisoxazol-3-yl)-3-(2-fluoro-4-methyl-5-(1-methyl-7-(methylamino)-2-oxo-1,2-dihydropyrido[4,3-d]pyrimidin-3(4H)-yl)phenyl)urea. This was treated with methanesulfonic acid to afford 1-(5-tert-butylisoxazol-3-yl)-3-(2-fluoro-4-methyl-5-(1-methyl-7-(methylamino)-2-oxo-1,2-dihydropyrido[4,3-d]pyrimidin-3(4H)-yl)phenyl)urea mesylate salt (38 mg, 20% yield). $^1$H NMR (400 MHz, DMSO-$d_6$): δ 9.84 (s, 1H), 8.84 (brs, 1H), 8.34 (brs, 1H), 8.07 (d, J=8.0 Hz, 1H), 7.77 (s, 1H), 7.25 (d, J=12.4 Hz, 1H), 6.45 (s, 1H), 6.29 (s, 1H), 4.68 (d, J=15.2 Hz, 1H), 4.50 (d, J=15.2 Hz, 1H), 3.26 (s, 3H), 2.92 (d, J=4.8 Hz, 3H), 2.29 (s, 3H), 2.07 (s, 3H), 1.27 (s, 9H); MS (ESI) m/z: 482.2 (M+H$^+$).

EXAMPLE 27

Using general method D, Example B7 (0.051 g, 0.3 mmol) and Example A16 (0.096 g, 0.3 mmol) in presence of triethylamine (0.092 g, 0.91 mmol) and diphenylphospharyl azide (0.16 g, 0.6 mmol) were combined to afford 1-(1-tert-butyl-1H-pyrazol-4-yl)-3-(2-fluoro-4-methyl-5-(1-methyl-7-(methylamino)-2-oxo-1,2-dihydropyrido[4,3-d]pyrimidin-3(4H)-yl)phenyl)urea as a white solid (37 mg. 25% yield). $^1$H NMR (400 MHz, DMSO-$d_6$): δ 8.67 (s, 1H), 8.47 (s, 1H), 8.03 (d, J=8.0 Hz, 1H), 7.80 (s, 1H), 7.71 (s, 1H), 7.38 (s, 1H), 7.15 (d, J=12.0 Hz, 1H), 6.43-6.40 (m, 1H), 5.94 (s, 1H), 4.55 (d, J=13.6 Hz, 1H), 4.37 (d, J=13.6 Hz, 1H), 3.16 (s, 3H), 2.75 (d, J=4.8 Hz, 3H), 2.03 (s, 3H), 1.46 (s, 9H), 1.20 (t, J=6.8 Hz, 3H); MS (ESI) m/z: 481.2 (M+H$^+$).

EXAMPLE 28

Using general method C, the TROC carbamate of Example B3 (50 mg, 0.16 mmol) and Example A18 (50 mg, 0.15 mmol) were combined to provide 1-(3-tert-butylisoxazol-5-yl)-3-(4-chloro-2-fluoro-5-(1-methyl-7-(methylamino)-2-oxo-1,2-dihydropyrido[4,3-d]pyrimidin-3(4H)-yl)phenyl)urea (33 mg, 41% yield). $^1$H NMR (400 MHz, DMSO-$d_6$): δ 10.39 (s, 1H), 8.92 (s, 1H), 8.21 (d, J=8.0 Hz, 1H), 7.73 (s, 1H), 7.65 (d, J=10.8 Hz, 1H), 6.44 (q, J=4.7 Hz, 1H), 6.60 (s, 1H), 5.97 (s, 1H), 4.57 (d, J=13.6 Hz, 1H), 4.43 (d, J=13.5 Hz, 1H), 3.17 (s, 3H), 2.76 (d, J=4.7 Hz, 3H), 1.22 (s, 9H); MS (ESI) m/z: 502.0, 504.0 (M+H$^+$).

EXAMPLE 29

Using general method B, the carbamate of 5-t-butylisoxazol-3-amine (60 mg, 0.27 mmol) and Example A17 (92 mg, 0.27 mmol) were combined to afford 1-(5-tert-butylisoxazol-3-yl)-3-(2-fluoro-5-(1-isopropyl-7-(methylamino)-2-oxo-1,2-dihydropyrido[4,3-d]pyrimidin-3(4H)-yl)-4-methylphenyl)urea (0.041 g, 30% yield). $^1$H NMR (400 MHz, DMSO-$d_6$): δ 9.81 (s, 1H), 8.78 (brs, 1H), 7.98 (d, J=7.6 Hz, 1H), 7.73 (s, 1H), 7.18 (d, J=12.0 Hz, 1H), 6.48 (s, 1H), 6.39 (q, J=4.8 Hz, 1H), 6.16 (s, 1H), 4.47 (q, J=13.6 Hz, 1H), 4.32 (m, 1H), 4.27 (d, J=13.6 Hz, 1H), 2.75 (d, J=4.8 Hz, 3H), 2.01 (s, 1H), 1.45 (m, 6H), 1.27 (s, 9H); MS (ESI) m/z: 510.2 (M+H$^+$).

EXAMPLE 20

Using general method C, the TROC carbamate of Example B3 (0.076 g, 0.242 mmol) and Example A17 (0.076 g, 0.22 mmol) were combined to afford 1-(3-tert-butylisoxazol-5-yl)-3-(2-fluoro-5-(1-isopropyl-7-(methylamino)-2-oxo-1,2-dihydropyrido[4,3-d]pyrimidin-3(4H)-yl)-4-methylphenyl)urea (0.025 g, 22% yield) as a white solid. $^1$H NMR (400 MHz, DMSO-$d_6$): δ 10.32 (s, 1H), 8.73 (s, 1H), 7.95 (d, J=7.2 Hz, 1H), 7.73 (s, 1H), 7.19 (d, J=12.0 Hz, 1H), 6.40 (m, 1H), 6.16 (s, 1H), 6.06 (s, 1H), 4.47 (d, J=13.2 Hz, 1H), 4.33-4.25 (m, 2H), 2.75 (d, J=4.8 Hz, 3H), 1.99 (s, 3H), 1.45 (t, J=4.8 Hz, 6H), 1.23 (s, 9H); MS (ESI) m/z: 510.2 (M+H$^+$).

EXAMPLE 31

Using general method D, Example B7 (0.051 g, 0.3 mmol) and Example A17 (0.104 g, 0.3 mmol) in presence of triethylamine (0.092 g, 0.91 mmol) and DPPA (0.25 g, 0.9 mmol) were combined to afford 1-(1-tert-butyl-1H-pyrazol-4-yl)-3-(2-fluoro-5-(1-isopropyl-7-(methylamino)-2-oxo-1,2-dihydropyrido[4,3-d]pyrimidin-3(4H)-yl)-4-methylphenyl)urea as a white solid (42 mg. 27% yield). $^1$H NMR (400 MHz, DMSO-$d_6$): δ 8.67 (s, 1H), 8.47 (s, 1H), 8.03 (d, J=7.6 Hz, 1H), 7.81 (s, 1H), 7.73 (s, 1H), 7.38 (s, 1H), 7.13 (d, J=12.0 Hz, 1H), 6.42-6.39 (m, 1H), 6.15 (s, 1H), 4.47 (d, J=13.6 Hz, 1H), 4.34-4.24 (m, 2H), 2.75 (d, J=4.8 Hz, 3H), 1.99 (s, 3H), 1.46-1.45 (m, 15H); MS (ESI) m/z: 509.2 (M+H$^+$).

EXAMPLE 32

Using general method F, Example A18 (88 mg, 0.29 mmol) and 1-isocyanato-3-(trifluoromethyl)benzene (63 mg, 0.34 mmol) were combined and purified by chromatography on reverse phase silica gel to provide 1-(4-chloro-2-fluoro-5-(1-methyl-7-(methylamino)-2-oxo-1,2-dihydropyrido[4,3-d]pyrimidin-3(4H)-yl)phenyl)-3-(3-(trifluoromethyl)phenyl)urea (12 mg, 13% yield). $^1$H NMR (400 MHz, DMSO-$d_6$): δ 9.46 (s, 1H), 8.86 (s, 1H), 8.27 (d, J=8.1 Hz, 1H), 8.05 (s, 1H), 7.73 (s, 1H), 7.63 (d, J=10.8 Hz, 1H), 7.54-7.47 (m, 2H), 7.34 (d, J=6.8 Hz, 1H), 6.53 (m, 1H), 5.98 (s, 1H), 4.61 (d, J=13.8 Hz, 1H), 4.44 (d, J=13.8 Hz, 1H), 3.18 (s, 3H), 2.77 (d, J=4.7 Hz, 3H); MS (EST) m/z: 523.0, 525.0 (M+H$^+$).

EXAMPLE 33

Using general method C, the TROC carbamate of Example 133 (0.158 g, 0.501 mmol) and Example A22 (0.110 g, 0.334 mmol) were combined to afford 1-(3-tert-butylisoxazol-5-yl)-3-(2-fluoro-5-(1-isopropyl-7-(methylamino)-2-oxo-1,2-dihydropyrimido[4,5-d]pyrimidin-3(4H)-yl)phenyl)urea (0.056 g, 34% yield was as a white solid. $^1$H NMR (400 MHz, DMSO-$d_6$): δ 10.36 (s, 1H), 8.80 (d, J=2.4 Hz, 1H), 8.06 (dd, J=7.2, 2.4 Hz, 1H), 7.96 (s, 1H), 7.29 (m, 1H), 7.05-6.98 (m, 2H), 6.06 (s, 1H), 4.97 (m, 1H), 4.51 (s, 2H), 2.78 (d, J=4.4 Hz, 3H), 1.47 (t, J=6.4 Hz, 6H), 1.23 (s, 9H); MS (ESI) m/z: 497.2 (M+H$^+$).

EXAMPLE 34

Using general method C, the TROC carbamate of 3-isopropyl-1-phenyl-1H-pyrazol-5-amine (0.061 g, 0.16 mmol) and Example A18 (0.054 g, 0.16 mmol) were combined to afford 1-(4-chloro-2-fluoro-5-(1-methyl-7-(methylamino)-2-oxo-1,2-dihydropyrido[4,3-d]pyrimidin-3(4H)-yl)phenyl)-3-(3-isopropyl-1-phenyl-1H-pyrazol-5-yl)urea as a white solid (24 mg, 26% yield). $^1$H NMR (400 MHz, DMSO-$d_6$): δ 9.16 (s, 1H), 8.93 (s, 1H), 8.25 (d, J=8.0 Hz, 1H), 7.72 (s, 1H), 7.60 (d, J=10.8 Hz, 1H), 7.55-7.48 (m, 3H), 7.44-7.40 (m, 1H), 6.46-6.42 (m, 1H), 6.34 (s, 1H), 5.96 (s, 1H), 4.56 (d, J=14.0 Hz, 1H), 4.43 (d, J=14.0 Hz, 1H), 3.17 (s, 3H), 2.89-

2.82 (m, 1H), 2.74 (d, J=4.8 Hz, 3H), 1.20 (d, J=6.8 Hz, 6H); MS (ESI) m/z: 564.0 (M+H$^+$).

EXAMPLE 35

Using general method B, the carbamate of Example B6 (0.096 g, 0.43 mmol) and Example A25 (0.080 g, 0.215 mmol) were combined to afford 1-(1-tert-butyl-1H-pyrazol-4-yl)-3-(5-(7-(2-(dimethylamino)ethylamino)-1-methyl-2-oxo-1,2-dihydropyrido[4,3-d]pyrimidin-3(4H)-yl)-2-fluoro-4-methylphenyl)urea (0.020 g, 17% yield) as a white solid. It was converted to corresponding bismethylate salt by reacting with MsOH (2.0 eq.). $^1$H NMR (400 MHz, DMSO-d$_6$): δ 9.50 (s, 1H), 8.72 (s, 1H), 8.55 (s, 1H), 8.81 (d, J=7.6 Hz, 1H), 7.85 (s, 1H), 7.78 (s, 1H), 7.41 (s, 1H), 7.20 (d, J=12.0 Hz, 1H), 6.33 (s, 1H), 4.70 (d, J=14.4 Hz, 1H), 4.52 (d, J=14.4 Hz, 1H), 3.72 (m, 2H), 3.34-3.28 (m, 5H), 2.85 (s, 6H), 2.32 (s, 6H), 2.05 (s, 3H), 1.47 (s, 9H); MS (ESI) m/z: 538.3 (M+H$^+$).

EXAMPLE 36

Using general method C, the TROC carbamate of Example B3 (0.080 g, 0.254 mmol) and Example A19 (89 mg, 0.254 mmol) were combined to afford 1-(3-tert-butylisoxazol-5-yl)-3-(5-(1-ethyl-7-(methylamino)-2-oxo-1,2-dihydropyrido[4,3-d]pyrimidin-3(4H)-yl)-2-fluoro-4-methylphenyl)urea (0.040 g, 32% yield). $^1$H NMR (400 MHz, DMSO-d$_6$): δ 10.3 (s, 1H), 8.72 (s, 1H), 7.98 (d, J=7.6 Hz, 1H), 7.72 (s, 1H), 7.21 (d, J=12.0 Hz, 1H), 6.39 (q, J=4.4 Hz, 1H), 6.05 (s, 1H), 6.01 (s, 1H), 4.58 (d, J=13.6 Hz, 1H), 4.34 (d, J=13.6 Hz, 1H), 3.77 (m, 2H), 2.76 (d, J=4.4 Hz, 3H), 2.04 (s, 3H), 1.23 (s, 9H), 1.16 (t, J=6.8 Hz, 3H); MS (ESI) m/z: 496.3 (M+H$^+$).

EXAMPLE 37

Using general method C, the TROC carbamate of Example B3 (0.080 g, 0.254 mmol) and Example A20 (89 mg, 0.254 mmol) were combined to afford 1-(3-tert-butylisoxazol-5-yl)-3-(4-chloro-5-(1-ethyl-7-(methylamino)-2-oxo-1,2-dihydropyrido[4,3-d]pyrimidin-3(4H)-yl)-2-fluorophenyl) urea (0.030 g, 23% yield). $^1$H NMR (400 MHz, DMSO-d$_6$): δ 10.4 (s, 1H), 8.91 (s, 1H), 8.22 (d, J=8.0 Hz, 1H), 7.73 (s, 1H), 7.64 (d, J=10.8 Hz, 1H), 6.41 (q, J=4.8 Hz, 1H), 6.06 (s, 1H), 6.03 (s, 1H), 4.58 (d, J=13.2 Hz, 1H), 4.41 (d, J=13.2 Hz, 1H), 3.78 (m, 2H), 2.76 (d, J=4.8 Hz, 3H), 1.23 (s, 9H), 1.16 (t, J=6.8 Hz, 3H); MS (ESI) m/z: 516.0 (M+H$^+$).

EXAMPLE 38

Using general method F, 1-isocyanato-3-(trifluoromethyl) benzene (0.170 g, 0.911 mmol) and Example A19 (0.250 g, 0.759 mmol) were combined to provide 1-(5-(1-ethyl-7-(methylamino)-2-oxo-1,2-dihydropyrido[4,3-d]pyrimidin-3 (4H)-yl)-2-fluoro-4-methylphenyl)-3-(3-(trifluoromethyl) phenyl)urea which was converted to the mesylate salt (0.130 g, 33.2% yield). $^1$H NMR (400 MHz, DMSO-d$_6$): δ9.49 (s, 1H), 8.76 (brs, 1H), 8.36 (brs, 1H), 8.09 (m, 2H), 7.78 (s, 1H), 7.49 (m, 2H), 7.31 (m, 1H), 7.21 (d, J=12.5 Hz, 1H), 6.38 (s, 1H), 4.74 (d, J=15 Hz, 1H), 4.48 (d, J=15 Hz, 1H), 3.87 (m, 2H), 2.92 (d, J=6 Hz, 3H), 2.32 (s, 3H), 2.05 (s, 3H), 1.21 (t, J=6 Hz, 3H); MS (ESI) m/z: 517.0 (M+H$^+$).

EXAMPLE 39

Using general method B, the carbamate of Example B1 (0.500 g, 1.670 mmol) and Example A10 (0.557 g, 1.670 mmol) was combined to furnish 1-(3-tert-butyl-1-phenyl-1H-pyrazol-5-yl)-3-(2-fluoro-4-methyl-5-(1-methyl-7-(methylthio)-2-oxo-1,2-dihydropyrimido[4,5-d]pyrimidin-3(4H)-yl)phenyl)urea (0.64 g, 66.7% yield). $^1$H NMR (400 MHz, DMSO-d$_6$): δ 9.01 (s, 1H), 8.89 (s, 1H), 8.23 (s, 1H), 8.09 (d, J=8 Hz, 1H), 7.52 (m, 4H), 7.41 (m, 1H), 7.19 (d, J=12 Hz, 1H), 6.37 (s, 1H), 4.70 (d, J=15 Hz, 1H), 4.52 (d, J=15 Hz, 1H), 3.28 (s, 3H), 2.51 (s, 3H), 2.06 (s, 3H), 1.24 (s, 9H); MS (ESI) in m/z: 575.2 (M+H$^+$).

Using a procedure analogous to Example A2, the sulfide was oxidized with mCPBA to the sulfone and then treated with methylamine to provide 1-(3-tert-butyl-1-phenyl-1H-pyrazol-5-yl)-3-(2-fluoro-4-methyl-5-(1-methyl-7-(methylamino)-2-oxo-1,2-dihydropyrimido[4,5-d]pyrimidin-3 (4H)-yl)phenyl)urea (0.163 g, 66% yield). $^1$H NMR (400 MHz, DMSO-d$_6$): δ 8.98 (s, 1H), 8.85 (brs, 1H), 8.05 (d, J=8.0 Hz, 1H), 7.94 (s, 1H), 7.52 (m, 3H), 7.42 (m, 1H), 7.18 (d, J=12 Hz, 1H), 7.02 (m, 1H), 6.38 (s, 1H), 4.53 (d, J=14 Hz, 1H), 4.33 (d, J=14 Hz, 1H), 3.25 (brs, 3H), 2.78 (d, J=5 Hz, 3H), 2.04 (s, 3H), 1.25 (s, 9H); MS (ESI) m/z: 558.3 (M+H$^+$).

EXAMPLE 40

Using general method C, the TROC carbamate of Example 132 (0.400 g, 0.906 mmol) and Example A10 (0.302 g, 0.906 mmol) were combined to provide 1-(3-tert-butyl-1-(quinolin-6-yl)-1H-pyrazol-5-yl)-3-(2-fluoro-4-methyl-5-(1-methyl-7-(methylthio)-2-oxo-1,2-dihydropyrimido[4,5-d]pyrimidin-3(4H)-yl)phenyl)urea (0.49 g, 86% yield). $^1$HNMR (400 MHz, DMSO-d$_6$): δ9.03 (s, 1H), 8.96 (m, 2H), 8.48 (brd, J=9 Hz, 1H), 8.23 (s, 1H), 8.18 (s, 1H), 8.15 (m, 1H), 8.09 (d, J=8 Hz, 1H), 7.93 (dd, J=9, 2.5 Hz, 1H), 7.60 (dd, J=9, 5 Hz, 1H), 7.18 (d, J=12 Hz, 1H), 6.45 (s, 1H), 4.70 (d, J=15 Hz, 1H), 4.52 (d, J=15 Hz, 1H), 3.28 (s, 3H), 2.51 (s, 3H), 2.06 (s, 3H), 1.28 (s, 9H); MS (ESI) m/z: 626.3.3 (M+H$^+$).

Using a procedure analogous to Example A2, the sulfide was oxidized with mCPBA to the sulfone and then treated with methylamine to provide 1-(3-tert-butyl-1-(quinolin-6-yl)-1H-pyrazol-5-yl)-3-(2-fluoro-4-methyl-5-(1-methyl-7-(methylamino)-2-oxo-1,2-dihydropyrimido[4,5-d]pyrimidin-3(4H)-yl)phenyl)urea. $^1$H NMR (400 MHz, DMSO-d$_6$): δ 8.95 (m, 2H), 8.48 (m, 1H); 8.15 (m, 1H), 8.04 (d, J=8 Hz, 1H), 7.92 (m, 2H), 7.60 (dd, J=8, Hz, 1H), 7.17 (d, J=12 Hz, 1H), 7.02 (m, 1H), 6.46 (s, 1H), 4.53 (d, J=14 Hz, 1H), 4.33 (d, J=14 Hz, 1H), 3.25 brs, 3H), 2.78 (d, J=5 Hz, 3H), 2.04 (s, 3H), 1.28 (s, 9H); MS (ESI) m/z 609.2 (M+H$^+$).

EXAMPLE 41

Using general method F, 1-chloro-4-isocyanato-2-(trifluoromethyl)benzene (0.191 g, 0.861 mmol) and Example A1 (0.250 g, 0.783 mmol) were combined to provide 1-(4-chloro-3-(trifluoromethyl)phenyl)-3-(2-fluoro-5-(1-methyl-7-(methylthio)-2-oxo-1,2-dihydropyrimido[4,5-d]pyrimidin-3(4H)-yl)phenyl)urea 10.29 g, 69% yield). $^1$H NMR (400 MHz, DMSO-d$_6$): δ 9.53 (s, 1H), 8.77 (brs, 1H), 8.26 (s, 1H)), 8.13 (m, 2H), 7.61 (d, J=9 Hz, 1H), 7.55 (dd, J=9, 2.5 Hz, 1H), 7.30 (dd, J=12, 9 Hz, 1H), 7.04 (m, 1H), 4.74 (s, 2H), 3.28 (s, 3H), 2.51 (s, 3H); MS (ESI) m/z: 541.0 (M+H$^+$)

Using a procedure analogous to Example A2, 1-(4-chloro-3-(trifluoromethyl)phenyl)-3-(2-fluoro-5-(1-methyl-7-(methylthio)-2-oxo-1,2-dihydropyrimido[4,5-d]pyrimidin-3 (4H)-yl)phenyl)urea was oxidized with mCPBA to the sulfone and then treated with methylamine to provide 1-(4-chloro-3-(trifluoromethyl)phenyl)-3-(2-fluoro-5-(1-methyl-7-(methylamino)-2-oxo-1,2-dihydropyrimido[4,5-d]pyrimidin-3(4H)-yl)phenyl)urea (0.045 g, 16% yield). $^1$H NMR (400 MHz, DMSO-d$_6$: δ 9.55 (s, 1H), 8.77 (s, 1H), 8.12 (d, J=2.5 Hz, 1H)), 8.09 (dd, J=8, 2.5 Hz, 1H), 7.96 (brs, 1H), 7.59 (m, 2H), 7.28 (dd, J=12.9 Hz, 1H), 7.01 (m, 2H), 5.74 (s, 1H), 4.58 (s, 2H), 3.28 (brs, 3H), 2.78 (d, J=5 Hz, 3H); MS (ESI) m/z: 524.0 (M+H$^+$)

EXAMPLE 42

Using general method F, 1-chloro-4-isocyanato-2-(trifluoromethyl)benzene (0.159 g, 0.720 mmol) and Example A9 (0.250 g, 0.720 mmol) were combined to provide 1-(4-chloro-3-(trifluoromethyl)phenyl)-3-(2-fluoro-5-(1-isopropyl-7-(methylthio)-2-oxo-1,2-dihydropyrimido[4,5-d]pyrimidin-3(4H)-yl)phenyl)urea (0.37 g, 90% yield). $^1$H NMR (400 MHz, DMSO-d$_6$): δ 9.53 (s, 1H), 8.77 (brs, 1H)), 8.26 (s, 1H)), 8.11 (d, J=2.5 Hz, 1H), 8.09 (dd, J=9, 2.5 Hz, 1H), 7.61 (d, J=9 Hz, 1H), 7.56 (dd, J=9, 2.5 Hz, 1H), 7.29 (dd, J=12, 9 Hz, 1H), 7.03 (m, 1H), 4.97 (m, 1H), 4.68 (s, 2H), 2.51 (s, 3H), 1.47 d, J=6 Hz, 6H); MS (ESI) m/z: 569.0 (M+H$^+$).

Using a procedure analogous to Example A2, oxidation with MCPBA to sulfone followed by reaction with methylamine provided 1-(4-chloro-3-(trifluoromethyl)-3-(2-fluoro-5-(1-isopropyl-7-(methylamino)-2-oxo-1,2-dihydropyrimido[4,5-d]pyrimidin-3(4H)-yl)phenyl)urea (0.265 g, 74% yield). $^1$H NMR (400 MHz, DMSO-d$_6$) δ 8.12 (s, 1H), 8.03 (dd, J=8, 2.5 Hz, 1H), 7.96 (brs, 1H), 7.58 (brs, 1H), 7.25 (dd, J=12.9 Hz, 1H), 6.97 (m, 2H), 4.98 (m, 1H), 4.52 (s, 2H), 2.78 (brs 3H), 1.47 (d, J=6 Hz, 6H); MS (ESI) m/z: 552.2 (M+H$^+$).

EXAMPLE 43

Using general method B, the carbamate of 3-isopropyl-1-phenyl-1H-pyrazol-5-amine (0.244 g, 0.861 mmol) and Example A1 (0.250 g, 0.783 mmol) were combined to provide 1-(2-fluoro-5-(1-methyl-7-(methylthio)-2-oxo-1,2-dihydropyrimido[4,5-d]pyrimidin-3(4H)-yl)phenyl)-3-(3-isopropyl-1-phenyl-1H-pyrazol-5-yl)urea. $^1$H NMR (400 MHz, DMSO-d$_6$): δ 9.06 (brs, 1H), 8.92 (s, 1H), 8.25 s, 1H), 8.16 (dd, J=8, 2.5 Hz, 1H)), 7.51 (m, 3H), 7.42 (m, 2H), 7.27 (dd, J=11, 8 Hz, 1H), 7.00 (m, 1H), 6.33 (s, 1H), 4.72 (s, 2H), 3.28 (s, 3H), 2.86 (m, 1H), 2.52 (s, 3H), 1.20 (d, J=6 Hz, 6H); MS (ESI) m/z: 547.0 (M+H$^+$).

Using a procedure analogous to Example A2, the sulfide was oxidized with mCPBA to the sulfone and treated with methylamine to provide 1-(2-fluoro-5-(1-methyl-7-(methylamino)-2-oxo-1,2-dihydropyrimido[4,5-d]pyrimidin-3(4H)-yl)phenyl)-3-(3-isopropyl-1-phenyl-1H-pyrazol-5-yl)urea (74% yield). $^1$H NMR (400 MHz, DMSO-d$_6$): δ 9.05 (s, 1H), 8.13 (dd, J=8, 2.5 Hz, 1H), 7.96 (brs, 1H), 7.52 (m, 4H), 7.42 (m, 1H), 7.25 (dd, J=12.9 Hz, 1H), 7.00 (m, 2H), 6.34 (s, 1H), 4.56 (s, 2H), 3.25 (brs, 3H), 2.86 (m, 1H), 2.78 (d, J=5 Hz, 3H), 1.20 (d, J=6 Hz, 6H); MS (EST) m/z: 530.2 (M+H$^+$).

EXAMPLE 44

Using general method B, the carbamate of Example B6 (0.375 g, 1.696 mmol) and Example A15 (0.400 g, 1.131 mmol) were combined to provide 1-(1-tert-butyl-1H-pyrazol-4-yl)-3-(4-chloro-2-fluoro-5-(1-methyl-7-(methylthio)-2-oxo-1,2-dihydropyrimido[4,5-d]pyrimidin-3(4H)-yl)phenyl)urea (0.32 g, 55% yield). $^1$H NMR (400 MHz, DMSO-d$_6$): δ 8.77 (brs, 1H), 8.73 (brs, 1H)), 8.36 (d, J=9 Hz, 1H)), 8.25 (s, 1H), 7.81 (s, 1H), 7.62 (s, 1H), 7.40 (s, 1H), 4.72 (d, J=14 Hz, 1H), 4.56 (d, J=14 Hz, 1H), 3.31 (s, 3H), 2.52 (s, 3H), 1.46 (s, 9H); MS (ESI) m/z: 519.2 (M+H$^+$).

Using a procedure analogous to Example A2, the sulfide was oxidized with mCPBA to the sulfone and then treated with methylamine to provide 1-(1-tert-butyl-1H-pyrazol-4-yl)-3-(4-chloro-2-fluoro-5-(1-methyl-7-(methylamino)-2-oxo-1,2-dihydropyrimido[4,5-d]pyrimidin-3(4H)-yl)phenyl)urea (0.448 mmol, 73% yield). $^1$H NMR (400 MHz, DMSO-d$_6$): δ 8.76 (s, 1H), 8.72 (brs, 1H), 8.32 (d, J=8.5 Hz, 1H), 7.96 (brs, 1H), 7.82 (s, 1H), 7.60 (d, J=11 Hz, 1H), 7.41 (s, 1H), 7.04 m, 1H), 6.34 s, 1H), 4.56 (d, J=14 Hz, 1H), 4.41 (d, J=14 Hz, 1H), 3.25 (brs, 3H), 2.78 (d, J=5 Hz, 3H), 1.47 (m, 9H); MS (ESI) m/z: 502.2 (M+H).

EXAMPLE 45

Using general method F, 1-isocyanato-3-(trifluoromethyl)benzene (0.122 g, 0.652 mmol) and Example A14 (0.2 g, 0.544 mmol) were combined to provide to provide 1-(4-chloro-5-(1-ethyl-7-(methylthio)-2-oxo-1,2-dihydropyrimido[4,5-d]pyrimidin-3(4H)-yl)-2-fluorophenyl)-3-(3-(trifluoromethyl)phenyl)urea (0.2 g, 66% yield). $^1$H NMR (400 MHz, DMSO-d$_6$): δ 9.46 (s, 1H), 8.88 brs, 1H)), 8.36 (d, J=9 Hz, 1H), 8.25 (s, 1H), 8.09 (s, 1H), 7.66 (d, J=11 Hz, 1H), 7.50 (m, 2H), 7.33 (m, 1H), 4.78 (d, J=14 Hz, 1H), 4.54 (d, J=14 Hz, 1H), 3.97 (m, 2H), 2.52 (s, 3H), 1.66 (d, J=6 Hz, 3H); MS (ESI) m/z: 555.0 (M+H$^+$).

Using a procedure analogous to Example A2, the sulfide was oxidized with mCPBA to the sulfone and then treated with methylamine to provide 1-(4-chloro-5-(1-ethyl-7-(methylamino)-2-oxo-1,2-dihydropyrimido[4,5-d]pyrimidin-3(4H)-yl)-2-fluorophenyl)-3-(3-(trifluoromethyl)phenyl)urea (0.279 mmol, 88% yield). $^1$H NMR (400 MHz, DMSO-d$_6$): δ 9.51 (s, 1H), 8.32 (d, J=8.0 Hz, 1H), 8.06 (s, 1H), 7.96 (brs, 1H), 7.87 (s, 1H), 7.64 (d, J=11 Hz, 1H), 7.50 (m, 2H), 7.33 (m, 1H), 7.02 (m, 1H), 4.60 (d, J=14 Hz, 1H), 4.40 (d, J=14 Hz, 1H), 3.95 (m, 2H), 2.78 (d, J=5 Hz, 3H), 1.15 (t, 3H); MS (ESI) m/z: 538.3 (M+H$^+$).

EXAMPLE 46

Using general method D, Example B8 (80 mg, 0.437 mmol), triethylamine (51 mg, 0.502 mmol), Example A17 (150 mg, 0.437 mmol) and DPPA (138 mg, 0.502 mmol) were combined to afford 1-(1-tert-butyl-5-methyl-1H-pyrazol-4-yl)-3-(2-fluoro-5-(1-isopropyl-7-(methylamino)-2-oxo-1,2-dihydropyrido[4,3-d]pyrimidin-3(4H)-yl)-4-methylphenyl)urea (35 mg, 15% yield). $^1$H NMR (300 MHz, DMSO-d$_6$): δ 1.44 (t, 6H), 1.52 (s, 9H), 1.99 (s, 3H), 2.29 (s, 3H), 2.76 (m, 3H), 4.31 (hep, 1H), 4.39 (d of d, 2H), 6.18 (s, 1H), 6.60 (br. s, 1H), 7.14 (d, 1H), 7.42 (s, 1H), 7.73 (s, 1H), 8.02 (d, 1H), 8.13 (s, 1H), 8.52 (br. s, 1H); MS (ESI) m/z: 523.2 (M+H$^+$).

EXAMPLE 47

Using general method B, the carbamate of Example B9 (0.078 g, 0.332 mmol) and Example A21 (0.070 g, 0.221 mmol) were combined to afford 1-(2-fluoro-4-methyl-5-(1-methyl-7-(methylamino)-2-oxo-1,2-dihydropyrimido[4,5-d]pyrimidin-3(4H)-yl)phenyl)-3-(3-(trifluoromethyl)isoxazol-5-yl)urea (0.064 g, 59%) as light yellow solid. $^1$H NMR (400 MHz, DMSO-d$_6$): δ 11.00 (s, 1H), 8.88 (d, J=1.2 Hz, 1H), 7.94-7.92 (m, 2H), 7.26 (d, J=11.6 Hz, 1H), 7.02 (m, 1H), 6.48 (s, 1H), 4.56 (d, J=14.0 Hz, 1H), 4.36 (d, J=14.0 Hz, 1H), 3.24 (s, 3H), 2.79 (d, J=4.8 Hz, 3H), 2.08 (s, 3H); MS (ESI) m/z: 495.0 (M+H$^+$).

EXAMPLE 48

Using general method B, Example B9 (0.066 g, 0.281 mmol) and Example A27 (0.070 g, 0.187 mmol) were combined to afford 1-(5-(7-(2-(dimethylamino)ethylamino)-1-methyl-2-oxo-1,2-dihydropyrimido[4,5-d]pyrimidin-3(4H)-yl)-2-fluoro-4-methylphenyl)-3-(3-(trifluoromethyl)isoxazol-5-yl)urea (0.039 g, 38%) as a light yellow solid. It was converted to corresponding mesylate salt by reacting with MsOH (1.0 eq.). $^1$H NMR (400 MHz, DMSO-d$_6$): δ 8.97 (s, 1H), 8.00 (s, 1H), 7.93 (d, J=7.6 Hz, 1H), 7.29-7.25 (m, 2H), 6.47 (s, 1H), 4.60 (d, J=14.0 Hz, 1H), 4.40 (d, J=14.0 Hz, 1H), 3.56 (m, 2H), 3.26 (s, 3H), 3.15 (m, 2H), 2.74 (s, 6H), 2.31 (s, 3H), 2.09 (s, 3H); MS (ESI) m/z: 552.2 (M+H$^+$).

EXAMPLE 49

Using general method B, the carbamate of Example B5 (60 mg, 0.25 mmol) and Example A26 (80 mg, 0.25 mmol) were combined to afford 1-(3-tert-butyl-1-methyl-1H-pyrazol-5-yl)-3-(5-(1-ethyl-7-(methylamino)-2-oxo-1,2-dihydropyrido[4,3-d]pyrimidin-3(4H)-yl)-2-fluorophenyl)urea (43 mg, 34% yield). $^1$H NMR (400 MHz, DMSO-d$_6$): δ 8.94 (s, 1H), 8.86 (brs, 1H), 8.10 (dd, J=2.4, and 7.2 Hz, 1H), 7.74 (s, 1H), 7.26 (dd, J=8.8, and 11.2 Hz, 1H), 6.96 (m, 1H), 6.41 (q, J=4.8 Hz, 1H), 6.08 (s, 1H), 6.02 (s, 1H), 4.56 (s, 2H), 3.78 (q, J=7.2 Hz, 2H), 3.60 (s, 3H), 2.75 (q, J=4.8 Hz, 2H), 1.18 (s, 9H), 1.17 (t, J=7.2 Hz, 3H); MS (ESI) m/z: 495.2 (M+H$^+$).

EXAMPLE 50

Using general method C, the TROC carbamate of Example B3 (80 mg, 0.25 mmol) and Example A26 (80 mg, 0.25 mmol) were combined to afford 1-(3-tert-butylisoxazol-5-yl)-3-(5-(1-ethyl-7-(methylamino)-2-oxo-1,2-dihydropyrido[4,3-d]pyrimidin-3(4H)-yl)-2-fluorophenyl)urea (31 mg, 25% yield). $^1$H NMR (400 MHz, DMSO-d$_6$): δ 10.4 (s, 1H), 8.79 (brs, 1H), 8.06 (dd, J=2.8, and 7.2 Hz, 1H), 7.75 (s, 1H), 7.27 (dd, J=8.8, and 10.8 Hz, 1H), 7.02 (m, 1H), 6.40 (q, J=4.4 Hz, 1H), 6.06 (s, 1H), 6.02 (s, 1H), 4.57 (s, 2H), 3.78 (q, J=7.2 Hz, 2H), 2.75 (q, J=4.4 Hz, 2H), 1.23 (s, 9H), 1.18 (t, J=7.2 Hz, 3H); MS (ESI) m/z: 482.2 (M+H$^+$).

EXAMPLE 51

Using general method D, Example B7 (0.051 g, 0.3 mmol) and Example A26 (0.096 g, 0.3 mmol) in presence of triethylamine (0.09 g, 0.9 mmol) and DPPA (0.125 g, 0.45 mmol) were combined to afford 1-(1-tert-butyl-1H-pyrazol-4-yl)-3-(5-(1-ethyl-7-(methylamino)-2-oxo-1,2-dihydropyrido[4,3-d]pyrimidin-3(4H)-yl)-2-fluorophenyl)urea as a white solid (0.028 g, 19% yield). $^1$H NMR (400 MHz, DMSO-d$_6$): δ 8.73 (s, 1H), 8.55 (s, 1H), 8.13 (dd, J=7.6 Hz, 2.8 Hz, 1H), 7.82 (s, 1H), 7.76 (s, 1H), 7.41 (s, 1H), 7.23 (dd, J=11.2 Hz, 10.8 Hz, 1H), 6.96-6.92 (m, 1H), 6.41-6.38 (m, 1H), 6.03 (s, 1H), 4.57 (s, 2H), 3.82-3.77 (m, 2H), 2.77 (d, J=4.4 Hz, 3H), 1.49 (s, 9H), 1.19 (t, J=6.8 Hz, 3H); MS (ESI) m/z: 481.2 (M+H$^+$).

EXAMPLE 52

Using general method B, Example B9 (0.066 g, 0.281 mmol) and Example A25 (0.070 g, 0.187 mmol) were combined to afford 1-(5-(7-(2-(dimethylamino)ethylamino)-1-methyl-2-oxo-1,2-dihydropyrido[4,3-d]pyrimidin-3(4H)-yl)-2-fluoro-4-methylphenyl)-3-(3-(trifluoromethyl)isoxazol-5-yl)urea (0.0304 g, 29%) as a white solid. It was converted to corresponding mesylate salt by reacting with MsOH (1.0 eq.). $^1$H NMR (400 MHz, DMSO-d$_6$): δ 11.08 (s, 1H), 8.99 (s, 1H), 7.95 (d, J=7.6 Hz, 1H), 7.83 (s, 1H), 7.28 (d, J=12.0 Hz, 1H), 6.46 (s, 1H), 6.23 (s, 1H), 4.67 (d, J=14.4 Hz, 1H), 4.47 (d, J=14.4 Hz, 1H), 3.66 (m, 2H), 3.28-3.23 (m, 5H), 2.84 (s, 6H), 2.33 (s, 3H), 2.07 (s, 3H); MS (ESI) m/z: 551.2 (M+H$^+$).

EXAMPLE 53

Using general method B, prop-1-en-2-yl 5-tert-butyl-1,3,4-thiadiazol-2-ylcarbamate (55.9 mg, 0.232 mmol) and Example A3 (70 mg, 0.232 mmol) were combined and purified directly by reverse phase chromatography (MeCN (w/0.1% TFA)/H$_2$O (w/0.1% TFA)) to afford 1-(5-tert-butyl-1,3,4-thiadiazol-2-yl)-3-(2-fluoro-5-(1-methyl-7-(methylamino)-2-oxo-1,2-dihydropyrimido[4,5-d]pyrimidin-3(4H)-yl)phenyl)urea (37 mg, 33% yield) as an off-white solid. $^1$H NMR (400 MHz, DMSO-d$_6$): δ 9.04 (brs, 1H), 8.14-8.12 (m, 1H), 8.03 (s, 1H), 7.38-7.33 (m, 1H), 7.11-7.07 (m, 1H), 4.66 (s, 2H), 3.31 (brs, 3H), 2.90 (brs, 3H), 1.37 (s, 9H); MS (ESI) m/z: 486.0 (M+H$^+$).

EXAMPLE 54

Using general method F, 1-isocyanatonaphthalene (0.05 g, 0.3 mmol) and example A19 (0.1 g, 0.3 mmol) were combined to afford 1-(5-(1-ethyl-7-(methylamino)-2-oxo-1,2-dihydropyrido[4,3-d]pyrimidin-3(4H)-yl)-2-fluoro-4-methylphenyl)-3-(naphthalen-1-yl)urea as a white solid (0.032 g, 21% yield). $^1$H NMR (400 MHz, DMSO-d$_6$): δ 9.19 (s, 1H), 9.12 (s, 1H), 8.19 (t, J=8.0 Hz, 2H), 8.08 (d, J=7.6 Hz, 1H), 7.98 (d, J=8.0 Hz, 1H), 7.78 (s, 1H), 7.69-7.58 (m, 3H), 7.50 (t, J=8.0 Hz, 1H), 7.27 (d, J=12.0 Hz, 1H), 6.47-6.44 (m, 1H), 6.06 (s, 1H), 4.66 (d, J=14.0 Hz, 1H), 4.42 (d, J=14.0 Hz, 1H), 3.87-3.78 (m, 2H), 2.81 (d, J=4.8 Hz, 3H), 2.10 (s, 3H), 1.21 (t, J=6.8 Hz, 3H); MS (ESI) m/z: 499.2 (M+H$^+$).

EXAMPLE 55

Using general method F, 1-isocyanatonaphthalene (0.05 g, 0.31 mmol) and Example A26 (0.1 g, 0.31 mmol) were combined to afford 1-(5-(1-ethyl-7-(methylamino)-2-oxo-1,2-dihydropyrido[4,3-d]pyrimidin-3(4H)-yl)-2-fluorophenyl)-3-(naphthalen-1-yl)urea as a white solid (0.061 g, 40% yield). $^1$H NMR (400 MHz, DMSO-d$_6$): δ 9.24 (s, 1H), 9.19 (s, 1H), 8.26 (dd, J=7.2 Hz, 2.8 Hz, 1H), 8.21 (d, J=8.4 Hz, 1H), 8.08 (dd, J=11.6 Hz, 0.8 Hz, 1H), 7.99 (d, J=7.6 Hz, 1H), 7.81 (s, 1H), 7.71-7.58 (m, 4H), 7.52 (t, J=8.0 Hz, 1H), 7.05-7.01 (m, 1H), 6.46 (q, J=4.8 Hz, 1H), 6.08 (s, 1H), 4.64 (s, 2H), 3.84 (q, J=6.8 Hz, 2H), 2.81 (d, J=4.8 Hz, 3H), 1.24 (t, J=6.8 Hz, 3H); MS (ESI) m/z: 485.0 (M+H$^+$).

EXAMPLE 56

Using general method F, 1-isocyanatonaphthalene (0.05 g, 0.3 mmol) and Example A32 (0.105 g, 0.3 mmol) were combined to afford 1-(4-chloro-5-(1-ethyl-7-(methylamino)-2-oxo-1,2-dihydropyrido[4,3-d]pyrimidin-3(4H)-yl)-2-fluorophenyl)-3-(naphthalen-1-yl)urea as a white solid (0.059 g, 38% yield). $^1$H NMR (400 MHz, DMSO-d$_6$): δ 9.33 (brs, 2H), 8.41 (d, J=8.0 Hz, 1H), 8.20 (d, J=8.0 Hz, 1H), 8.06 (d, J=6.8 Hz, 1H), 7.98 (d, J=7.6 Hz, 1H), 7.78 (s, 1H), 7.71-7.58 (m, 4H), 7.51 (t, J=8.0 Hz, 1H), 6.46 (q, J=4.8 Hz, 1H), 6.08 (s, 1H), 4.65 (d, J=13.6 Hz, 1H), 4.48 (d, J=13.6 Hz, 1H), 3.84-3.80 (m, 2H), 2.81 (d, J=4.8 Hz, 3H), 1.21 (t, J=6.8 Hz, 3H); MS (ESI m/z: 519.0 (M+H$^+$).

EXAMPLE 57

Using general method D, Example B10 (70 mg, 0.19 mmol) and Example A3 (58 mg, 0.19 mmol) in presence of DPPA (55 μL, 0.21 mmol) and Et₃N (30 μL, 0.21 mmol) were combined to afford tert-butyl 4-(2-tert-butyl-5-(3-(2-fluoro-5-(1-methyl-7-(methylamino)-2-oxo-1,2-dihydropyrido[4,5-d]pyrimidin-3(4H)-yl)phenyl)ureido)pyrimidin-4-yl)piperazine-1-carboxylate (32 mg, 25% yield) which was treated with HCl (4.0 M, in dioxane) to afford 1-(2-tert-butyl-4-(piperazin-1-yl)pyrimidin-5-yl)-3-(2-fluoro-5-(1-methyl-7-(methylamino)-2-oxo-1,2-dihydropyrimido[4,5-d]pyrimidin-3(4H)-yl)phenyl)urea HCl salt (24 mg, 88% yield). $^1$H NMR (400 MHz, DMSO-d₆, major isomer): δ 9.60 (brs, 1H), 9.54 (brs, 2H), 8.62 (s, 1H), 8.54 (brs, 1H), 8.21 (dd, J=2.4, and 7.2 Hz, 1H), 8.18 (s, 1H), 7.41 (dd, J=9.2, and 10.8 Hz, 1H), 7.13 (m, 1H), 4.76 (s, 2H), 4.07 (brm, 4H), 3.46 (brs, 3H), 3.35 (brm, 4H), 3.03 (brs, 3H), 1.45 (s, 9H); MS (EST) m/z: 564.3 (M+H⁺).

EXAMPLE 58

Using general method F, 1-isocyanato-3-(trifluoromethyl)benzene (0.05 g, 0.267 mmol) and Example A28 (0.088 g, 0.267 mmol) were combined to provide 1-(2-fluoro-5-(1-isopropyl-7-(methylamino)-2-oxo-1,2-dihydropyrido[4,3-d]pyrimidin-3(4H)-yl)phenyl)-3-(3-(trifluoromethyl)phenyl)urea (0.11 g, 80%). $^1$H NMR (400 MHz, DMSO-d₆): δ 9.48 (s, 1H), 8.76 (s, 1H), 8.09 (m, 2H), 7.82 (s, 1H), 7.56 (m, 2H), 7.38 (m, 1H), 7.29 (m, 1H), 7.0 (m, 1H), 6.42 (m, 1H), 6.22 (s, 1H), 4.55 (s, 2H), 4.37 (m, 1H), 2.81 (d, J=5 Hz, 3H), 1.52 (d, J=6 Hz, 6H); MS (ESI) m/z: 517.0 (M+H⁺).

EXAMPLE 59

Using general method F, 1-chloro-4-isocyanato-2-(trifluoromethyl)benzene (70 mg, 0.32 mmol) and Example A4 (95 mg, 0.32 mmol) were combined to afford 1-(4-chloro-3-(trifluoromethyl)phenyl)-3-(2-fluoro-5-(1-methyl-7-(methylamino)-2-oxo-1,2-dihydropyrido[4,3-d]pyrimidin-3(4H)-yl)phenyl)urea (91 mg, 64% yield). $^1$H NMR (400 MHz, DMSO-d₆): δ 9.58 (s, 1H), 8.80 (s, 1H), 8.18 (d, J=2.0 Hz, 1H), 8.13 (dd, J=2.8, and 7.6 Hz, 1H), 7.81 (s, 1H), 7.68 (d, J=8.4 Hz, 1H), 7.63 (dd, J=2.4, and 8.4 Hz, 1H), 7.33 (dd, J=8.8, and 10.8 Hz, 1H), 7.06 (m, 1H), 6.48 (q, J=4.8 Hz, 1H), 6.03 (s, 1H), 4.66 (s, 2H), 3.25 (s, 3H), 2.82 (d, J=4.8 Hz, 3H); MS (ESI) m/z: 523.0 (M+H⁺).

EXAMPLE 60

To a stirring suspension of Example A26 (100 mg, 0.317 mmol) in CH₂Cl₂ (3.036 ml), thoroughly cooled to 0° C., was rapidly added 20% COCl₂ in PhMe (0.184 ml, 0.349 mmol). After 10 min at 0° C., the reaction was then treated with Et₃N (0.133 ml, 0.951 mmol). After another 10 min at 0° C., cyclohexylamine (0.040 ml, 0.349 mmol) was added and the reaction was stirred for 72 h at RT. The crude reaction mixture was purified directly by flash column chromatography (100% CH₂Cl₂ to 30% THF/CH₂Cl₂). The still impure product was re-purified by reverse phase chromatography (MeCN (w/0.1% TFA)/H₂O (w/0.1% TFA)) to afford a white solid. The TFA salt thus obtained was dissolved in THF and converted to the free base with MP-Carbonate resin to afford 1-cyclohexyl-3-(5-(1-ethyl-7-(methylamino)-2-oxo-1,2-dihydropyrido[4,3-d]pyrimidin-3(4H)-yl)-2-fluorophenyl)urea (15 mg, 12% yield) as a white solid. $^1$H NMR (400 MHz, DMSO-d₆): δ 9.23 (brs, 1H), 8.05 (s, 1H), 7.02-6.97 (m, 1H), 6.86 (s, 1H), 6.73-6.68 (m, 2H), 6.49-6.46 (m, 1H), 4.68 (s, 2H), 3.89 (q, J=6.8 Hz, 2H), 3.57 (m, 1H), 1.83-1.77 (m, 2H), 1.64-1.60 (m, 2H), 1.55-1.47 (m, 1H), 1.34-1.17 (m, 8H); MS (ESI) m/z: 441.2 (M+H⁺).

EXAMPLE 61

Using general method B, the carbamate of 5-t-butylisoxazol-3-amine (58 mg, 0.26 mmol) and Example A5 (0.080 g, 0.26 mmol) were combined to provide 1-(5-tert-butylisoxazol-3-yl)-3-(2-fluoro-4-methyl-5-(8-methyl-2-(methylamino)-7-oxo-7,8-dihydropteridin-6-yl)phenyl)urea (41 mg, 34% yield). $^1$H NMR (400 MHz, DMSO-d₆): δ 8.74 and 8.57 (s, 1H), 8.10 (d, J=8.4 Hz, 1H), 8.00 (br m, 1H), 7.24-7.12 (m, 2H), 6.44 (s, 1H), 3.57 and 3.50 (s, 3H), 2.92 (br s, 3H), 2.28 (s, 3H), 1.26 (s, 9H); MS (ESI) m/z: 481.2 (M+H⁺).

EXAMPLE 62

Using general method F, 1-chloro-4-isocyanato-2-(trifluoromethyl)benzene (70 mg, 0.32 mmol) and Example A4 (95 mg, 0.32 mmol) in presence of pyridine (51 μL, 0.63 mmol) were combined to afford 1-(4-chloro-3-(trifluoromethyl)phenyl)-3-(2-fluoro-5-(1-methyl-7-(methylamino)-2-oxo-1,2-dihydropyrido[4,3-d]pyrimidin-3(4H)-yl)phenyl)urea (93 mg, 56% yield), $^1$H NMR (400 MHz, DMSO-d₆): δ 9.58 (s, 1H), 8.80 (s, 1H), 8.18 (d, J=2.0 Hz, 1H), 8.13 (dd, J=2.8, and 7.6 Hz, 1H), 7.81 (s, 1H), 7.68 (d, J=8.4 Hz, 1H), 7.63 (dd, J=2.4, and 8.4 Hz, 1H), 7.33 (dd, J=8.8, and 10.8 Hz, 1H), 7.06 (m, 1H), 6.48 (q, J=4.8 Hz, 1H), 6.03 (s, 1H), 4.66 (s, 2H), 3.25 (s, 3H), 2.82 (d, J=4.8 Hz, 3H); MS (ESI) m/z: 523.0 (M+H⁺).

EXAMPLE 63

Using General Method F, Example A28 (100 mg, 0.304 mmol), cyclohexyl isocyanate (0.078 mL, 0.611 mmol) and pyridine (0.493 mL, 0.611 mmol) were reacted to afford 1-cyclohexyl-3-(2-fluoro-5-(1-isopropyl-7-(methylamino)-2-oxo-1,2-dihydropyrido[4,3-d]pyrimidin-3(4H)-yl)phenyl)urea (30 mg, 22% yield) as a white solid. $^1$H NMR (400 MHz, DMSO-d₆): δ 8.27 (d, J=2.8, 1H), 8.11 (dd, J=2.8 and 7.6 Hz, 1H), 7.79 (s, 1H), 7.19 (dd, J=8.8 and 11.2 Hz, 1H), 6.86 (s, 1H), 6.85-6.81 (m, 1), 6.66-6.64 (m, 1H), 6.38 (brs, 1H), 4.55 (s, 2H), 4.39 (septet, J=6.8 Hz, 1H), 3.47-3.39 (m, 1H), 2.85 (d, J=4.4 Hz, 3H), 1.79-1.75 (m, 2H), 1.66-1.58 (m, 2H), 1.52-1.46 (m, 1H), 1.46 (d, J=6.8 Hz, 6H), 1.31-1.07 (m, 5H); MS (ESI) m/z: 455.3 (M+H⁺).

EXAMPLE 64

Using General Method F, Example A4 (100 mg, 0.332 mmol) and cyclohexyl isocyanate (0.085 ml, 0.664 mmol) were reacted to afford 1-cyclohexyl-3-(2-fluoro-5-(1-methyl-7-(methylamino)-2-oxo-1,2-dihydropyrido[4,3-d]pyrimidin-3(4H)-yl)phenyl)urea (18 mg, 13% yield) as a white solid. $^1$H NMR (400 MHz, DMSO-d₆): δ 8.22 (d, J=1.6 Hz, 1H), 8.08 (dd, J=2.0 and 6.8 Hz, 1H), 7.70 (s, 1H), 7.14 (dd, J=8.8 and 11.2 Hz, 1H), 6.82-6.78 (m, 2H), 6.60-6.58 (m, 1H), 6.02 (brs, 1H), 4.54 (s, 2H), 3.38 (brm, 1H), 3.14 (s, 3H), 2.76 (d, J=4.4 Hz, 3H), 1.74-1.67 (m, 2H), 1.63-1.56 (m, 2H), 1.47-1.42 (m, 1H), 1.27-1.08 (m, 5H); MS (ESI) m/z: 427.2 (M+H⁺).

EXAMPLE 65

Using general method A, the TROC carbamate of Example B3 (75 mg, 0.238 mmol) and Example A29 (80 mg, 0.233 mmol) were combined to provide 1-(5-(1-tert-butyl-7-(methylamino)-2-oxo-1,2-dihydropyrido[4,3-d]pyrimidin-3(4H)-yl-2-fluorophenyl)-3-(3-tert-butylisoxazol-5-yl)urea (50 mg, 41% yield). $^1$H NMR (400 MHz, DMSO-d₆): δ 10.35

(s, 1H), 8.77 (s, 1H), 8.00 (dd, J=7.6, 2.4 Hz, 1H), 7.79 (s, 1H), 7.25 (m, 1H), 6.94 (m, 1H), 6.40 (m, 1H), 6.35 (s, 1H), 6.07 (s, 1H), 4.38 (s, 2H), 2.75 (d, J=4.8 Hz, 1H), 1.57 (s, 9H), 1.23 (s, 9H); MS (ESI) m/z: 510.2 (M+H$^+$).

EXAMPLE 66

Using general method F, 1-isocyanato-3-(trifluoromethyl)benzene (0.050 g, 0.267 mmol) was reacted with Example A20 (0.093 g, 0.267 mmol) in methylene chloride to provide 1-(4-chloro-5-(1-ethyl-7-(methylamino)-2-oxo-1,2-dihydropyrido[4,3-d]pyrimidin-3(4H)-yl)-2-fluorophenyl)-3-(3-(trifluoromethyl)phenyl)urea, (0.022 g, 15% yield). $^1$H NMR (400 MHz, DMSO-d$_6$) δ 11.85 (s, 1H), 8.27 (s, 1H), 8.12 (s, 1H), 7.86 (d, J=7.5 Hz, 1H), 7.60 (t, J=8.5 Hz, 1H), 7.43 (d, J=8 Hz, 1H), 7.37 (d, J=11 Hz, 1H), 6.94 (m, 2H), 5.58 (s, 2H), 4.82 (d, J=14 Hz, 1H), 4.68 (d, J=14 Hz, 1H), 4.00 (q, J=6 Hz, 2H), 3.51 (s, 3H), 1.24 (t, J=6 Hz, 3H); MS (ESI) m/z: 537.0 (M+H$^+$).

EXAMPLE 67

Using general method F, 1-isocyanato-3-(trifluoromethyl)benzene (0.05 g, 0.267 mmol) was reacted with Example A20 (0.093 g, 0.266 mmol) in methyl t-butyl ether (2 ml) for 2 hours to provide 1-(4-chloro-5-(1-ethyl-7-(methylamino)-2-oxo-1,2-dihydropyrido[4,3-d]pyrimidin-3(4H)-yl)-2-fluorophenyl)-3-(3-(trifluoromethyl)phenyl)urea (0.025 g, 17% yield). $^1$H NMR (400 MHz, DMSO-d$_6$): δ 9.46 (s, 1H), 8.56 (s, 1H), 8.26 (d, J=8 Hz, 1H), 8.04 (s, 1H), 7.72 (s, 1H), 7.61 (d, J=10.5 Hz, 1H), 7.49 (m, 2H), 7.32 (m, 1H), 6.40 (m, 1H), 6.02 (s, 1H), 4.61 (d, J=14 Hz, 1H), 4.40 (d, J=14 Hz, 1H), 3.77 (m, 2H), 2.75 (d, J=5 Hz, 3H), 1.15 (t, J=6 Hz, 3H); MS (ESI) m/z: 537.0 (M+H$^+$).

EXAMPLE 68

Using general method D, 2,3-difluorobenzoic acid (0.068 g, 0.430 mmol) and Example A20 (0.100 g, 0.287 mmol) were stirred at RT for one hour followed by heating at 80° C. for one more hour in dioxane (5 ml) to provide 1-(4-chloro-5-(1-ethyl-7-(methylamino)-2-oxo-1,2-dihydropyrido[4,3-d]pyrimidin-3(4H)-yl)-2-fluorophenyl)-3-(2,3-difluorophenyl)urea (0.015 g, 10% yield). $^1$H NMR (400 MHz, DMSO-d$_6$): δ 9.26 (brs, 1H), 8.31 (d, J=9 Hz, 1H), 7.96 (m, 1H), 7.74 (s, 1H), 7.65 (d, J=11 Hz, 1H), 7.17-7.0 (m, 2H), 6.47 (brs, 1H), 6.04 (s, 1H), 4.61 (d, J=13 Hz, 1H), 4.43 (d, J=13 Hz, 1H), 3.81 (m, 2H), 2.76 (d, J=5 Hz, 3H), 1.17 (t, J=6 Hz, 3H); MS (ESI) m/z: 505.0 (M+H$^+$).

EXAMPLE 69

Using general method A, Example B1 and Example A3 are combined to yield 1-(3-tert-butyl-1-phenyl-1,4-pyrazol-5-yl)-3-(2-fluoro-5-(1-methyl-7-(methylamino)-2-oxo-1,2-dihydropyrimido[4,5-d]pyrimidin-3(4H)-yl)phenyl)urea.

EXAMPLE 70

Using general method A and the same procedure as for Example A2, Example B5 and Example A3 are combined to yield 1-(3-tert-butyl-1-methyl-1H-pyrazol-5-yl)-3-(2-fluoro-5-(1-methyl-7-(methylamino)-2-oxo-1,2-dihydropyrimido[4,5-d]pyrimidin-3(4H)-yl)phenyl)urea.

EXAMPLE 71

Using general method A, Example B1 and Example A30 are combined to yield 1-(5-(7-amino-1-methyl-2-oxo-1,2-dihydropyrido[4,3-d]pyrimidin-3(4H)-yl)-2-fluorophenyl)-3-(3-tert-butyl-1-phenyl-1H-pyrazol-5-yl)urea.

EXAMPLE 72

Using general method A, Example B5 and Example A30 are combined to yield 1-(5-(7-amino-1-methyl-2-oxo-1,2-dihydropyrido[4,3-d]pyrimidin-3(4H)-yl)-2-fluorophenyl)-3-(3-tert-butyl-1-methyl-1H-pyrazol-5-yl)urea.

EXAMPLE 73

Using general method A, Example 11 and Example A4 are combined to yield 1-(3-tert-butyl-1-phenyl-1H-pyrazol-5-yl)-3-(2-fluoro-5-(1-methyl-7-(methylamino)-2-oxo-1,2-dihydropyrido[4,3-d]pyrimidin-3(4H)-yl)phenyl)urea.

EXAMPLE 74

Using general method A, Example B5 and Example A4 are combined to yield 1-(3-tert-butyl-1-methyl-1H-pyrazol-5-yl)-3-(2-fluoro-5-(1-methyl-7-(methylamino)-2-oxo-1,2-dihydropyrido[4,3-d]pyrimidin-3(4H)-yl)phenyl)urea.

EXAMPLE 75

Using general method A, Example B1 and Example A31 are combined to yield 1-(6-(5-amino-4-fluoro-2-methylphenyl)-8-methyl-7-oxo-7,8-dihydropteridin-2-yl)-3-(3-tert-butyl-1-phenyl-1H-pyrazol-5-yl)urea.

EXAMPLE 76

Using general method A, Example B5 and Example A31 are combined to yield 1-(5-(2-amino-8-methyl-7-oxo-7,8-dihydropteridin-6-yl)-2-fluoro-4-methylphenyl)-3-(3-tert-butyl-1-methyl-1H-pyrazol-5-yl)urea.

EXAMPLE 77

Using general method A, Example B1 and Example A5 are combined to yield 1-(3-tert-butyl-1-phenyl-1H-pyrazol-5-yl)-3-(2-fluoro-4-methyl-5-(8-methyl-2-(methylamino)-7-oxo-7,8-dihydropteridin-6-yl)phenyl)urea.

EXAMPLE 78

Using general method A, Example A30 and Example B1 are combined to yield 1-(5-(7-amino-1-methyl-2-oxo-1,2-dihydropyrido[4,3-d]pyrimidin-3(4H)-yl)-2-fluorophenyl)-3-(3-tert-butyl-1-phenyl-1H-pyrazol-5-yl)urea.

EXAMPLE 79

Using general method A, Example B1 and Example A4 are combined to yield 1-(3-tert-butyl-1-phenyl-1H-pyrazol-5-yl)-3-(2-fluoro-5-(1-methyl-7-(methylamino)-2-oxo-1,2-dihydropyrido[4,3-d]pyrimidin-3(4H)-yl)phenyl)urea is synthesized.

The following examples are prepared by the methods described in Schemes 1-12, General Methods A-G, the above Examples and the methods described in WO 2006/071940.

| Ex | |
|---|---|
| 80 | 1-(3-tert-butyl-4-methylisoxazol-5-yl)-3-(2-fluoro-4-methyl-5-(1-methyl-7-(methylamino)-2-oxo-1,2-dihydropyrido[4,3-d]pyrimidin-3(4H)-yl)phenyl)urea |
| 81 | 1-(3-tert-butyl-4-methylisoxazol-5-yl)-3-(2-fluoro-4-methyl-5-(1-methyl-7-(methylamino)-2-oxo-1,2-dihydropyrimido[4,5-d]pyrimidin-3(4H)-yl)phenyl)urea |
| 82 | 1-(3-tert-butyl-4-methylisoxazol-5-yl)-3-(4-chloro-2-fluoro-5-(1-methyl-7-(methylamino)-2-oxo-1,2-dihydropyrido[4,3-d]pyrimidin-3(4H)-yl)phenyl)urea |
| 83 | 1-(3-tert-butyl-4-methylisoxazol-5-yl)-3-(4-chloro-2-fluoro-5-(1-methyl-7-(methylamino)-2-oxo-1,2-dihydropyrimido[4,5-d]pyrimidin-3(4H)-yl)phenyl)urea |
| 84 | 1-(3-tert-butyl-4-methylisoxazol-5-yl)-3-(2,4-difluoro-5-(1-methyl-7-(methylamino)-2-oxo-1,2-dihydropyrido[4,3-d]pyrimidin-3(4H)-yl)phenyl)urea |
| 85 | 1-(3-tert-butyl-4-methylisoxazol-5-yl)-3-(2,4-difluoro-5-(1-methyl-7-(methylamino)-2-oxo-1,2-dihydropyrimido[4,5-d]pyrimidin-3(4H)-yl)phenyl)urea |
| 86 | 1-(3-tert-butyl-4-fluoroisoxazol-5-yl)-3-(2-fluoro-4-methyl-5-(1-methyl-7-(methylamino)-2-oxo-1,2-dihydropyrido[4,3-d]pyrimidin-3(4H)-yl)phenyl)urea |
| 87 | 1-(3-tert-butyl-4-fluoroisoxazol-5-yl)-3-(2-fluoro-4-methyl-5-(1-methyl-7-(methylamino)-2-oxo-1,2-dihydropyrimido[4,5-d]pyrimidin-3(4H)-yl)phenyl)urea |
| 88 | 1-(3-tert-butyl-4-chloroisoxazol-5-yl)-3-(2-fluoro-4-methyl-5-(1-methyl-7-(methylamino)-2-oxo-1,2-dihydropyrido[4,3-d]pyrimidin-3(4H)-yl)phenyl)urea |
| 89 | 1-(3-tert-butyl-4-chloroisoxazol-5-yl)-3-(2-fluoro-4-methyl-5-(1-methyl-7-(methylamino)-2-oxo-1,2-dihydropyrimido[4,5-d]pyrimidin-3(4H)-yl)phenyl)urea |
| 90 | 1-(3-tert-butyl-4-fluoroisoxazol-5-yl)-3-(5-(1-ethyl-7-(methylamino)-2-oxo-1,2-dihydropyrido[4,3-d]pyrimidin-3(4H)-yl)-2-fluorophenyl)urea |
| 91 | 1-(3-tert-butyl-4-chloroisoxazol-5-yl)-3-(5-(1-ethyl-7-(methylamino)-2-oxo-1,2-dihydropyrido[4,3-d]pyrimidin-3(4H)-yl)-2-fluorophenyl)urea |
| 92 | 1-(1-tert-butyl-1H-imidazol-4-yl)-3-(2-fluoro-4-methyl-5-(1-methyl-7-(methylamino)-2-oxo-1,2-dihydropyrimido[4,5-d]pyrimidin-3(4H)-yl)phenyl)urea |
| 93 | 1-(1-tert-butyl-1H-imidazol-4-yl)-3-(2-fluoro-4-methyl-5-(1-methyl-7-(methylamino)-2-oxo-1,2-dihydropyrido[4,3-d]pyrimidin-3(4H)-yl)phenyl)urea |
| 94 | 1-(1-tert-butyl-1H-imidazol-4-yl)-3-(4-chloro-2-fluoro-5-(1-methyl-7-(methylamino)-2-oxo-1,2-dihydropyrimido[4,5-d]pyrimidin-3(4H)-yl)phenyl)urea |
| 95 | 1-(1-tert-butyl-1H-imidazol-4-yl)-3-(4-chloro-2-fluoro-5-(1-methyl-7-(methylamino)-2-oxo-1,2-dihydropyrido[4,3-d]pyrimidin-3(4H)-yl)phenyl)urea |
| 96 | 1-(1-tert-butyl-1H-imidazol-4-yl)-3-(5-(1-ethyl-7-(methylamino)-2-oxo-1,2-dihydropyrimido[4,5-d]pyrimidin-3(4H)-yl)-2-fluorophenyl)urea |
| 97 | 1-(1-tert-butyl-1H-imidazol-4-yl)-3-(5-(1-ethyl-7-(methylamino)-2-oxo-1,2-dihydropyrido[4,3-d]pyrimidin-3(4H)-yl)-2-fluorophenyl)urea |
| 98 | 1-(1-tert-butyl-5-methyl-1H-imidazol-4-yl)-3-(2-fluoro-4-methyl-5-(1-methyl-7-(methylamino)-2-oxo-1,2-dihydropyrimido[4,5-d]pyrimidin-3(4H)-yl)phenyl)urea |
| 99 | 1-(1-tert-butyl-5-methyl-1H-imidazol-4-yl)-3-(2-fluoro-4-methyl-5-(1-methyl-7-(methylamino)-2-oxo-1,2-dihydropyrido[4,3-d]pyrimidin-3(4H)-yl)phenyl)urea |
| 100 | 1-(1-tert-butyl-5-methyl-1H-imidazol-4-yl)-3-(4-chloro-2-fluoro-5-(1-methyl-7-(methylamino)-2-oxo-1,2-dihydropyrimido[4,5-d]pyrimidin-3(4H)-yl)phenyl)urea |
| 101 | 1-(1-tert-butyl-5-methyl-1H-imidazol-4-yl)-3-(4-chloro-2-fluoro-5-(1-methyl-7-(methylamino)-2-oxo-1,2-dihydropyrido[4,3-d]pyrimidin-3(4H)-yl)phenyl)urea |
| 102 | 1-(1-tert-butyl-2-methyl-1H-imidazol-4-yl)-3-(2-fluoro-4-methyl-5-(1-methyl-7-(methylamino)-2-oxo-1,2-dihydropyrimido[4,5-d]pyrimidin-3(4H)-yl)phenyl)urea |
| 103 | 1-(1-tert-butyl-2-methyl-1H-imidazol-4-yl)-3-(2-fluoro-4-methyl-5-(1-methyl-7-(methylamino)-2-oxo-1,2-dihydropyrido[4,3-d]pyrimidin-3(4H)-yl)phenyl)urea |
| 104 | 1-(2-fluoro-5-(1-methyl-7-(methylamino)-2-oxo-1,2-dihydropyrido[4,3-d]pyrimidin-3(4H)-yl)phenyl)-3-(5-(trifluoromethyl)pyridin-3-yl)urea |
| 105 | 1-(5-(1-ethyl-7-(methylamino)-2-oxo-1,2-dihydropyrido[4,3-d]pyrimidin-3(4H)-yl)-2-fluorophenyl)-3-(5-(trifluoromethyl)pyridin-3-yl)urea |
| 106 | 1-(5-(1-ethyl-7-(methylamino)-2-oxo-1,2-dihydropyrimido[4,5-d]pyrimidin-3(4H)-yl)-2-fluorophenyl)-3-(5-(trifluoromethyl)pyridin-3-yl)urea |
| 107 | 1-(2-fluoro-4-methyl-5-(1-methyl-7-(methylamino)-2-oxo-1,2-dihydropyrido[4,3-d]pyrimidin-3(4H)-yl)phenyl)-3-(5-(trifluoromethyl)pyridin-3-yl)urea |
| 108 | 1-(2-fluoro-4-methyl-5-(1-methyl-7-(methylamino)-2-oxo-1,2-dihydropyrimido[4,5-d]pyrimidin-3(4H)-yl)phenyl)-3-(5-(trifluoromethyl)pyridin-3-yl)urea |
| 109 | 1-(4-chloro-2-fluoro-5-(1-methyl-7-(methylamino)-2-oxo-1,2-dihydropyrimido[4,5-d]pyrimidin-3(4H)-yl)phenyl)-3-(5-(trifluoromethyl)pyridin-3-yl)urea |
| 110 | 1-(4-chloro-2-fluoro-5-(1-methyl-7-(methylamino)-2-oxo-1,2-dihydropyrido[4,3-d]pyrimidin-3(4H)-yl)phenyl)-3-(5-(trifluoromethyl)pyridin-3-yl)urea |
| 111 | 1-(2-fluoro-5-(1-(2-hydroxyethyl)-7-(methylamino)-2-oxo-1,2-dihydropyrido[4,3-d]pyrimidin-3(4H)-yl)-4-methylphenyl)-3-(3-(trifluoromethyl)phenyl)urea |
| 112 | 1-(5-(1-ethyl-7-(methylamino)-2-oxo-1,2-dihydropyrido[4,3-d]pyrimidin-3(4H)-yl)-2-fluorophenyl)-3-(2-fluoro-5-(trifluoromethyl)phenyl)urea |
| 113 | 1-(5-(1-ethyl-7-(methylamino)-2-oxo-1,2-dihydropyrimido[4,5-d]pyrimidin-3(4H)-yl)-2-fluorophenyl)-3-(2-fluoro-5-(trifluoromethyl)phenyl)urea |
| 114 | 1-(2-fluoro-4-methyl-5-(1-methyl-7-(methylamino)-2-oxo-1,2-dihydropyrido[4,3-d]pyrimidin-3(4H)-yl)phenyl)-3-(2-fluoro-5-(trifluoromethyl)phenyl)urea |
| 115 | 1-(5-tert-butyl-1,3,4-thiadiazol-2-yl)-3-(2-fluoro-4-methyl-5-(1-methyl-7-(methylamino)-2-oxo-1,2-dihydropyrimido[4,5-d]pyrimidin-3(4H)-yl)phenyl)urea |
| 116 | 1-(4-tert-butylthiophen-2-yl)-3-(2-fluoro-4-methyl-5-(1-methyl-7-(methylamino)-2-oxo-1,2-dihydropyrido[4,3-d]pyrimidin-3(4H)-yl)phenyl)urea |
| 117 | 1-(4-tert-butyl-3-methylthiophen-2-yl)-3-(2-fluoro-4-methyl-5-(1-methyl-7-(methylamino)-2-oxo-1,2-dihydropyrido[4,3-d]pyrimidin-3(4H)-yl)phenyl)urea |

-continued

| Ex | |
|---|---|
| 118 | 1-(4-tert-butyl-3-chlorothiophen-2-yl)-3-(2-fluoro-4-methyl-5-(1-methyl-7-(methylamino)-2-oxo-1,2-dihydropyrido[4,3-d]pyrimidin-3(4H)-yl)phenyl)urea |
| 119 | 1-(4-tert-butyl-3-fluorothiophen-2-yl)-3-(2-fluoro-4-methyl-5-(1-methyl-7-(methylamino)-2-oxo-1,2-dihydropyrido[4,3-d]pyrimidin-3(4H)-yl)phenyl)urea |
| 120 | 1-(1-tert-butyl-5-methyl-1H-pyrazol-4-yl)-3-(2-fluoro-4-methyl-5-(1-methyl-7-(methylamino)-2-oxo-1,2-dihydropyrido[4,3-d]pyrimidin-3(4H)-yl)phenyl)urea |
| 121 | 1-(1-tert-butyl-5-methyl-1H-pyrazol-4-yl)-3-(4-chloro-2-fluoro-5-(1-methyl-7-(methylamino)-2-oxo-1,2-dihydropyrido[4,3-d]pyrimidin-3(4H)-yl)phenyl)urea |
| 122 | 1-(5-(7-amino-1-methyl-2-oxo-1,2-dihydropyrimido[4,5-d]pyrimidin-3(4H)-yl)-2-fluoro-4-methylphenyl)-3-(3-tert-butylisoxazol-5-yl)urea |
| 123 | 1-(5-(7-amino-1-ethyl-2-oxo-1,2-dihydropyrimido[4,5-d]pyrimidin-3(4H)-yl)-2-fluorophenyl)-3-(3-tert-butylisoxazol-5-yl)urea |
| 124 | 1-(3-tert-butylisoxazol-5-yl)-3-(2-fluoro-5-(1-methyl-7-(methylamino)-2-oxo-1,2-dihydropyrido[4,3-d]pyrimidin-3(4H)-yl)phenyl)urea |
| 125 | 1-(3-tert-butylisoxazol-5-yl)-3-(5-(1-cyclopentyl-7-(methylamino)-2-oxo-1,2-dihydropyrido[4,3-d]pyrimidin-3(4H)-yl)-2-fluorophenyl)urea |
| 126 | 1-(3-tert-butylisoxazol-5-yl)-3-(2-fluoro-5-(1-(2-hydroxyethyl)-7-(methylamino)-2-oxo-1,2-dihydropyrido[4,3-d]pyrimidin-3(4H)-yl)-4-methylphenyl)urea |
| 127 | 1-(3-tert-butylisoxazol-5-yl)-3-(2-fluoro-5-(1-(2-hydroxyethyl)-7-(methylamino)-2-oxo-1,2-dihydropyrido[4,3-d]pyrimidin-3(4H)-yl)phenyl)urea |
| 128 | 1-(3-tert-butylisoxazol-5-yl)-3-(2-fluoro-5-(1-(2-hydroxyethyl)-7-(methylamino)-2-oxo-1,2-dihydropyrimido[4,5-d]pyrimidin-3(4H)-yl)phenyl)urea |
| 129 | 1-(3-tert-butylisoxazol-5-yl)-3-(4-chloro-5-(1-ethyl-7-(methylamino)-2-oxo-1,2-dihydropyrimido[4,5-d]pyrimidin-3(4H)-yl)-2-fluorophenyl)urea |
| 130 | 1-(3-tert-butylisoxazol-5-yl)-3-(5-(1-ethyl-7-(methylamino)-2-oxo-1,2-dihydropyrimido[4,5-d]pyrimidin-3(4H)-yl)-2,4-difluorophenyl)urea |
| 131 | 1-(3-tert-butylisoxazol-5-yl)-3-(4-chloro-5-(1-ethyl-7-(methylamino)-2-oxo-1,2-dihydropyrido[4,3-d]pyrimidin-3(4H)-yl)-2-fluorophenyl)urea |
| 132 | 1-(3-tert-butylisoxazol-5-yl)-3-(5-(1-ethyl-7-(methylamino)-2-oxo-1,2-dihydropyrido[4,3-d]pyrimidin-3(4H)-yl)-2,4-difluorophenyl)urea |
| 133 | 1-(3-tert-butylisoxazol-5-yl)-3-(5-(1-cyclopentyl-7-(methylamino)-2-oxo-1,2-dihydropyrimido[4,5-d]pyrimidin-3(4H)-yl)-2-fluorophenyl)urea |
| 134 | 1-(3-tert-butylisoxazol-5-yl)-3-(5-(1-cyclopentyl-7-(methylamino)-2-oxo-1,2-dihydropyrido[4,3-d]pyrimidin-3(4H)-yl)-2-fluorophenyl)urea |
| 135 | 1-(3-tert-butylisoxazol-5-yl)-3-(2,4-difluoro-5-(7-(methylamino)-2-oxo-1-phenyl-1,2-dihydropyrimido[4,5-d]pyrimidin-3(4H)-yl)phenyl)urea |
| 136 | 1-(3-tert-butylisoxazol-5-yl)-3-(2,4-difluoro-5-(7-(methylamino)-2-oxo-1-phenyl-1,2-dihydropyrido[4,3-d]pyrimidin-3(4H)-yl)phenyl)urea |
| 137 | 1-(5-(1-ethyl-7-(methylamino)-2-oxo-1,2-dihydropyrimido[4,5-d]pyrimidin-3(4H)-yl)-2-fluorophenyl)-3-(3-isopropylisoxazol-5-yl)urea |
| 138 | 1-(5-(1-ethyl-7-(methylamino)-2-oxo-1,2-dihydropyrido[4,3-d]pyrimidin-3(4H)-yl)-2-fluorophenyl)-3-(3-isopropylisoxazol-5-yl)urea |
| 139 | 1-(5-(1-ethyl-7-(methylamino)-2-oxo-1,2-dihydropyrimido[4,5-d]pyrimidin-3(4H)-yl)-2-fluoro-4-methylphenyl)-3-(3-isopropylisoxazol-5-yl)urea |
| 140 | 1-(5-(1-ethyl-7-(methylamino)-2-oxo-1,2-dihydropyrido[4,3-d]pyrimidin-3(4H)-yl)-2-fluoro-4-methylphenyl)-3-(3-isopropylisoxazol-5-yl)urea |
| 141 | 1-(4-chloro-5-(1-ethyl-7-(methylamino)-2-oxo-1,2-dihydropyrimido[4,5-d]pyrimidin-3(4H)-yl)-2-fluorophenyl)-3-(3-isopropylisoxazol-5-yl)urea |
| 142 | 1-(4-chloro-5-(1-ethyl-7-(methylamino)-2-oxo-1,2-dihydropyrido[4,3-d]pyrimidin-3(4H)-yl)-2-fluorophenyl)-3-(3-isopropylisoxazol-5-yl)urea |
| 143 | 1-(1-tert-butyl-2-methyl-1H-pyrrol-3-yl)-3-(2-fluoro-4-methyl-5-(1-methyl-7-(methylamino)-2-oxo-1,2-dihydropyrido[4,3-d]pyrimidin-3(4H)-yl)phenyl)urea |
| 144 | 1-(1-tert-butyl-2-methyl-1H-pyrrol-3-yl)-3-(4-chloro-2-fluoro-5-(1-methyl-7-(methylamino)-2-oxo-1,2-dihydropyrido[4,3-d]pyrimidin-3(4H)-yl)phenyl)urea |
| 145 | 1-(4-tert-butylfuran-2-yl)-3-(2-fluoro-4-methyl-5-(1-methyl-7-(methylamino)-2-oxo-1,2-dihydropyrido[4,3-d]pyrimidin-3(4H)-yl)phenyl)urea |
| 146 | 1-(2-tert-butyloxazol-5-yl)-3-(2-fluoro-4-methyl-5-(1-methyl-7-(methylamino)-2-oxo-1,2-dihydropyrido[4,3-d]pyrimidin-3(4H)-yl)phenyl)urea |
| 147 | 1-cyclohexyl-3-(5-(1-ethyl-7-(methylamino)-2-oxo-1,2-dihydropyrido[4,3-d]pyrimidin-3(4H)-yl)-2-fluoro-4-methylphenyl)urea |
| 148 | 1-(2-fluoro-4-methyl-5-(1-methyl-7-(methylamino)-2-oxo-1,2-dihydropyrido[4,3-d]pyrimidin-3(4H)-yl)phenyl)-3-((1R,2R)-2-methylcyclohexyl)urea |
| 149 | 1-(5-(1-ethyl-7-(methylamino)-2-oxo-1,2-dihydropyrimido[4,5-d]pyrimidin-3(4H)-yl)-2-fluorophenyl)-3-((1S,2S)-2-methylcyclohexyl)urea |
| 150 | 1-cyclohexyl-3-(5-(1-cyclopentyl-7-(methylamino)-2-oxo-1,2-dihydropyrido[4,3-d]pyrimidin-3(4H)-yl)-2-fluorophenyl)urea |
| 151 | 1-(bicyclo[2.2.1]heptan-2-yl)-3-(2-fluoro-4-methyl-5-(1-methyl-7-(methylamino)-2-oxo-1,2-dihydropyrimido[4,5-d]pyrimidin-3(4H)-yl)phenyl)urea |
| 152 | 1-(bicyclo[2.2.1]hept-5-en-2-yl)-3-(2-fluoro-4-methyl-5-(1-methyl-7-(methylamino)-2-oxo-1,2-dihydropyrimido[4,5-d]pyrimidin-3(4H)-yl)phenyl)urea |
| 153 | 1-cyclopropyl-3-(2-fluoro-4-methyl-5-(1-methyl-7-(methylamino)-2-oxo-1,2-dihydropyrido[4,3-d]pyrimidin-3(4H)-yl)phenyl)urea |
| 154 | 1-(2-fluoro-4-methyl-5-(1-methyl-7-(methylamino)-2-oxo-1,2-dihydropyrido[4,3-d]pyrimidin-3(4H)-yl)phenyl)-3-isopropylurea |
| 155 | 1-(2-fluoro-4-methyl-5-(1-methyl-7-(methylamino)-2-oxo-1,2-dihydropyrido[4,3-d]pyrimidin-3(4H)-yl)phenyl)-3-(1-(pyridin-3-yl)ethyl)urea |

-continued

| Ex | |
|---|---|
| 156 | (R)-1-(2-fluoro-4-methyl-5-(1-methyl-7-(methylamino)-2-oxo-1,2-dihydropyrido[4,3-d]pyrimidin-3(4H)-yl)phenyl)-3-(1-phenylethyl)urea |
| 157 | (S)-1-(2-fluoro-4-methyl-5-(1-methyl-7-(methylamino)-2-oxo-1,2-dihydropyrido[4,3-d]pyrimidin-3(4H)-yl)phenyl)-3-(1-phenylethyl)urea |
| 158 | 1-(1-tert-butyl-1H-pyrazol-4-yl)-3-(2-fluoro-5-(1-(1-hydroxy-2-methylpropan-2-yl)-7-(methylamino)-2-oxo-1,2-dihydropyrido[4,3-d]pyrimidin-3(4H)-yl)phenyl)urea |
| 159 | 1-cyclohexyl-3-(2-fluoro-5-(1-(1-hydroxy-2-methylpropan-2-yl)-7-(methylamino)-2-oxo-1,2-dihydropyrido[4,3-d]pyrimidin-3(4H)-yl)phenyl)urea |
| 160 | 1-(3-tert-butylisoxazol-5-yl)-3-(2-fluoro-5-(1-(1-hydroxy-2-methylpropan-2-yl)-7-(methylamino)-2-oxo-1,2-dihydropyrido[4,3-d]pyrimidin-3(4H)-yl)phenyl)urea |
| 161 | 1-(1-tert-butyl-1H-pyrazol-4-yl)-3-(2-fluoro-5-(1-(1-hydroxy-2-methylpropan-2-yl)-7-(methylamino)-2-oxo-1,2-dihydropyrido[4,3-d]pyrimidin-3(4H)-yl)-4-methylphenyl)urea |
| 162 | 1-cyclohexyl-3-(2-fluoro-5-(1-(1-hydroxy-2-methylpropan-2-yl)-7-(methylamino)-2-oxo-1,2-dihydropyrido[4,3-d]pyrimidin-3(4H)-yl)-4-methylphenyl)urea |
| 163 | 1-(3-tert-butylisoxazol-5-yl)-3-(2-fluoro-5-(1-(1-hydroxy-2-methylpropan-2-yl)-7-(methylamino)-2-oxo-1,2-dihydropyrido[4,3-d]pyrimidin-3(4H)-yl)-4-methylphenyl)urea |
| 164 | 1-(3-tert-butylisoxazol-5-yl)-3-(2-fluoro-5-(7-(methylamino)-2-oxo-1-(tetrahydrofuran-3-yl)-1,2-dihydropyrido[4,3-d]pyrimidin-3(4H)-yl)phenyl)urea |
| 165 | 1-(3-tert-butylisoxazol-5-yl)-3-(2-fluoro-5-(7-(methylamino)-2-oxo-1-(pyrrolidin-3-yl)-1,2-dihydropyrimido[4,5-d]pyrimidin-3(4H)-yl)phenyl)urea |
| 166 | 1-(1-tert-butyl-1H-pyrazol-4-yl)-3-(2-fluoro-5-(7-(methylamino)-2-oxo-1-(piperidin-4-yl)-1,2-dihydropyrimido[4,5-d]pyrimidin-3(4H)-yl)phenyl)urea |
| 167 | 1-(1-tert-butyl-1H-pyrazol-4-yl)-3-(2-fluoro-5-(7-(methylamino)-2-oxo-1-(tetrahydrofuran-3-yl)-1,2-dihydropyrimido[4,5-d]pyrimidin-3(4H)-yl)phenyl)urea |
| 168 | 1-(1-tert-butyl-1H-pyrazol-4-yl)-3-(2-fluoro-5-(7-(methylamino)-2-oxo-1-(tetrahydro-2H-pyran-4-yl)-1,2-dihydropyrimido[4,5-d]pyrimidin-3(4H)-yl)phenyl)urea |
| 169 | 1-(3-tert-butylisoxazol-5-yl)-3-(2-fluoro-5-(1-(3-hydroxycyclopentyl)-7-(methylamino)-2-oxo-1,2-dihydropyrido[4,3-d]pyrimidin-3(4H)-yl)phenyl)urea |
| 170 | 1-(3-tert-butylisoxazol-5-yl)-3-(2-fluoro-5-(1-(3-fluorophenyl)-7-(methylamino)-2-oxo-1,2-dihydropyrido[4,3-d]pyrimidin-3(4H)-yl)phenyl)urea |
| 171 | 1-(2-fluoro-5-(1-(3-fluorophenyl)-7-(methylamino)-2-oxo-1,2-dihydropyrimido[4,5-d]pyrimidin-3(4H)-yl)phenyl)-3-(3-isopropylisoxazol-5-yl)urea |
| 172 | 1-(3-tert-butylisoxazol-5-yl)-3-(5-(7-(1,3-dimethyl-1H-pyrazol-5-ylamino)-1-methyl-2-oxo-1,2-dihydropyrimido[4,5-d]pyrimidin-3(4H)-yl)-2-fluorophenyl)urea |
| 173 | 1-(3-(7-(1,3-dimethyl-1H-pyrazol-5-ylamino)-1-methyl-2-oxo-1,2-dihydropyrimido[4,5-d]pyrimidin-3(4H)-yl)-4-methylphenyl)-3-(3-(trifluoromethyl)phenyl)urea |
| 174 | 1-(3-tert-butylisoxazol-5-yl)-3-(5-(1-ethyl-7-(methylamino)-2-oxo-1,2-dihydropyrimido[4,5-d]pyrimidin-3(4H)-yl)-2-fluoro-4-methylphenyl)urea |

B-Raf(V600E) Kinase Assay: The activity of B-Raf (V600E) kinase was determined by following the formation of ADP from the reaction through coupling with the pyruvate kinase/lactate dehydrogenase system (e.g., Schindler, et al. Science (2000) 289, 1938-1942). In this assay, die oxidation of NADH (thus the decrease at $A_{340nm}$) was continuously monitored spectrophotometrically. The reaction mixture (100 µl) contained B-Raf(V600E) kinase (2.1 nM nominal concentration), unphosphorylated, full-length MEK1 (45 nM), $MgCl_2$ (13 mM), pyruvate kinase (3.5 units), lactate dehydrogenase (5.5 units), phosphoenolpyruvate (1 µM), and NADH (0.28 mM), in 60 mM Tris buffer, containing 0.13% octylglucoside and 3.5% DMSO concentration at pH 7.5. The test compounds were incubated with the reaction mixture at 30° C. for 2 h or 4 h. The reaction was initiated by adding ATP (0.2 mM, final concentration). The absorption at 340 nm was continuously monitored for 3 h at 30° C. on a Polarstar Optima plate reader (BMG). The reaction rate was calculated using the 1.5 h to 2.5 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

```
B-Raf(V600E) protein sequence used for screening:
                                         (SEQ. ID NO. 1)
EDRNRMKTLGRRDSSDDWEIFDGQITVGQRIGSGSFGTVYKGKWEGDVAV

KMLNVTAPTPQQLQAFKNEVGVLRKTRHVNILLFMGYSTKPQLAIVTQWC

EGSSLYHHLHIIETKFEMTKLIDIARQTAQGMDYLHAKSIIHRDLKSNNI

FLHEDLTVKIGDFGLATEKSRWSGSHQFEQLSGSILWMAPEVIRMQDKNP

YSFQSDVYAFGIVLYELMTGQLFYSNINNRDQIIFMVGRGYLSPDLSKVR

SNCPKAMKRLMAECLKKKRDERPLFPQILASIELLARSLPKIHR

MEK1 protein sequence used for screening:
                                         (SEQ. ID NO. 2)
MELKDDDFEKISELGAGNGGVVFKVSHKPSGLVMARKLIHLEIKPAIRNQ

IIRELQVLHECNSPYIVGFYGAFYSDGEISICMEHMDGGSLDQVLKKAGR

IPEQILGKVSIAVIKGLTYLREKHKIMHRDVKPSNILVNSRGEIKLCDFG

VSGQLIDSMANSFVGTRSYMSPERLQGTHYSVQSDIWSMGLSLVEMAVGR

YPIPPPDAKELELMFGCQVEGDAAETPPRPRTPGRPLSSYGMDSRPPMAI

FELLDYIVNEPPPKLPSGVFSLEFQDFVNKCLIKNPAERADLKQLMVHAF

IKRSDAEEVDFAGWLCSTIGLNQPSTPTHAAGV
```

C-Raf Kinase Assay: The activity of C-Raf kinase was determined by following the formation of ADP from the reaction through coupling with the pyruvate kinase/lactate dehydrogenase system (e.g., Schindler, et al. Science (2000) 289, 1938-1942). In this assay, the oxidation of NADH (thus the decrease at $A_{340nm}$) was continuously monitored spectrophotometrically. The reaction mixture (100 µl) contained C-Raf kinase (0.28 nM nominal concentration, available from Upstate, catalogue #14-352), unphosphorylated, full-length MEK1 (27 nM), $MgCl_2$ (13 mM), pyruvate kinase (3.5 units), lactate dehydrogenase (5.5 units), phosphoenolpyruvate (1 mM), and NADH (0.28 mM), in 60 mM Tris buffer, containing 0.13% octyl-glucoside and 3.5% DMSO concentration at pH 7.5. The test compounds were incubated with the reaction mixture at 30° C. for 2 h or 4 h. The reaction was initiated by adding ATP (0.2 mM, final concentration). The absorption at 340 nm was continuously monitored for 3 h at 30° C. on a Polarstar Optima plate reader (BMG). The reaction rate was calculated using the 1.0 h to 2.0 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

In general, compounds 1-68 disclosed herein exhibited >50% inhibition activity at 0.2-2 uM concentration against V600E BRaf and CRaf kinases utilizing the above assay conditions.

Cell Culture: A-375 cells were obtained from American Type Culture Collection (Rockville, Md.). Briefly, cells were grown in Dulbecco's Modified Eagle Medium with 4.5 g/L glucose, 6 mM L-glutamine, and 10% certified fetal bovine serum (Invitrogen, Carlsbad, Calif.) at 37 degrees Celsius, 5% CO2, 95% humidity. Cells were allowed to expand until reaching 80% confluency at which point they were subcultured or harvested for assay use.

Cell Proliferation Assay: A serial dilution of test compound was dispensed into a 96 well black clear bottom plate (Corning, Corning, N.Y.). Five thousand cells (A375) were then added to each well in growth medium. Plates were incubated for 72 hours at 37 degrees Celsius, 5% CO2, 95% humidity. At the end of the incubation period Cell Titer Blue (Promega, Madison, Wis.) was added to each well and an additional 4.5 hour incubation at 37 degrees Celsius, 5% CO2, 95% humidity was performed. Plates were then read on a BMG Fluostar Optima (BMG, Durham, N.C.) using an excitation of 544 nM and an emission of 612 nM. Data was analyzed using Prism software (Graphpad, San Diego, Calif.) to calculate $IC_{50}$ values.

In general, compounds 1-68 disclosed herein exhibited >50% inhibition of proliferation at 1-10 uM concentration against A375 cells utilizing the above assay conditions.

All references mentioned or referred to herein are incorporated by reference into this disclosure.

The invention claimed is:

1. Compounds of the formula Ia′

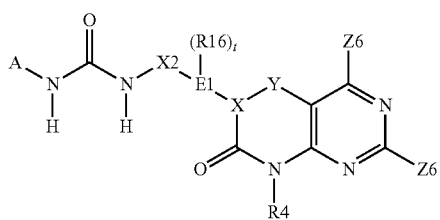

wherein X—Y in order is N—CH2;

X2 is a direct bond;

E1 is phenyl;

A is selected from the group consisting of phenyl, naphthyl, C3-C8carbocyclyl, bicycloheptanyl, bicycloheptenyl, and G1;

G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl;

the A ring may be optionally substituted with one or more —X1-A1 moieties;

X1 is selected from the group consisting of —(CH$_2$)$_n$—(O)$_r$—(CH$_2$)$_n$—, —(CH$_2$)$_n$—(NR3)$_r$—(CH$_2$)$_n$—, —(CH$_2$)$_n$—(S)$_r$—(CH$_2$)$_n$—, —(CH$_2$)$_n$—(C=O)$_r$—CH$_2$)$_n$—, —(CH$_2$)$_n$—(C(=O)—NR3)$_r$—(CH$_2$)$_n$—, and —(CH$_2$)$_n$—(SO$_2$—NR3)$_r$—(CH$_2$)$_n$—, wherein any of the alkylenes may be straight or branched chain;

A1 is selected from the group consisting of hydrogen, aryl, G1, C1-C6 alkyl, branched C3-C8alkyl, R19 substituted C3-C8carbocyclyl, fluoroC1-C6alkyl wherein the alkyl is fully or partially fluorinated, halogen, cyano, hydroxyl, —N(R4)$_2$, —R5, —C(O)N(R4)$_2$, C(O)R5, C1-C6alkoxy, and fluoroC1-C6alkoxy wherein the alkyl group is fully or partially fluorinated;

When A and A1 have one or more substitutable sp2-hybridized carbon atom, each respective sp2 hybridized carbon atom may be optionally substituted with a Z1 or Z3 substituent;

when A and A1 have one or more substitutable sp3-hybridized carbon atom, each respective sp3 hybridized carbon atom may be optionally substituted with a Z2 or R3 substituent;

when A and A1 have one or more substitutable nitrogen atom, each respective nitrogen atom may be optionally substituted with a Z4 substituent;

each Z1 is independently and individually selected from the group consisting of hydrogen, hydroxyC1-C6alkyl, C1-C6alkoxy, C1-C6alkoxyC1-C6alkyl, (R4)$_2$NC1-C6alkyl, (R4)$_2$NC2-C6alkylN(R4)—(CH$_2$)$_n$, (R4)$_2$NC2-C6alkylO—(CH$_2$)$_n$, (R$^3$)$_2$N—C(=O)—, (R4)$_2$N—C(=O)—, (R4)$_2$N—CO—C1-C6alkyl-, C1-C6alkoxycarbonyl-, -carboxyC1-C6alkyl, C1-C6alkoxycarbonylC1-C6alkyl, (R3)$_2$NSO$_2$—, —SOR3, (R4)$_2$NSO$_2$—, —SO$_2$R3, —SOR4, —C(=O)R6, —C(=NOH)R6, —C(=NOR3)R6, —(CH$_2$)$_n$N(R4)C(O)R8, —(CH$_2$)$_n$-G1, —(CH$_2$)$_n$-G4, phenoxy, —(CH$_2$)$_n$—O—(CH$_2$)$_n$-G1, —(CH$_2$)$_n$—O—(CH$_2$)$_n$-G4, —(CH$_2$)$_n$—NR3—(CH$_2$)$_n$-aryl, —(CH$_2$)$_n$—NR3—(CH$_2$)$_n$-G1, —(CH$_2$)$_n$—NR3—(CH$_2$)$_n$-G4, —S(O)$_2$R5, —N=S(O)R6R8, —S(O)(=NR3)R6, —(CH$_2$)$_n$NHC(O)NHS(O)$_2$R8, —(CH$_2$)$_n$NHS(O)$_2$NHC(O)R8, —C(O)NHS(O)$_2$R8, —S(O)$_2$NHC(O)R8, —(CH$_2$)$_n$NHC(O)(CH$_2$)$_n$R5, —(CH$_2$)$_n$NHS(O)$_2$(CH$_2$)$_n$R5, —(CH$_2$)$_n$C(O)NH(CH$_2$)$_q$R5, —(CH$_2$)$_n$C(O)R5, —(CH$_2$)$_n$OC(O)R5, —(CH$_2$)$_n$S(O)$_2$NH(CH$_2$)$_q$R5, —CH(OH)(CH$_2$)$_p$R5, —CH(OH)CH(OH)R4, —(CH$_2$)$_n$N(R4)$_2$, —(CH$_2$)$_n$R5, —C(=NH)R5, —C(=NH)N(R4)$_2$, —C(=NOR3)R5, —C(=NOR3)N(R4)$_2$, and —NHC(=NH)R8;

in the event that Z1 contains an alkyl or alkylene moiety, such moieties may be further substituted with one or more C1-C6alkyls;

each Z2 is independently and individually selected from the group consisting of hydrogen, aryl, C1-C6alkyl, C3-C8carbocyclyl, hydroxyl, hydroxyC1-C6alkyl-, cyano, (R3)$_2$N—, (R4)$_2$N—, (R4)$_2$NC1-C6alkyl-, (R4)₂NC2-C6alkylN(R4)—(CH₂)ₙ—, (R4)₂NC2-C6alkylO—(CH₂)ₙ—, (R3)₂N—C(=O)—, (R4)₂N—C(=O)—, (R4)₂N—CO—C1-C6alkyl-, carboxyl, carboxyC1-C6alkyl, C1-C6alkoxycarbonyl, C1-C6alkoxycarbonylC1-C6alkyl, (R3)₂NSO₂—, (R4)₂NSO₂—, —SO₂R5, —SO₂R8, —(CH₂)ₙN(R4)C(O)R8, —C(O)R8, =O, =NOH, =N(OR6), —(CH₂)ₙ-G1, —(CH₂)ₙ-G4, —(CH₂)ₙ—O—(CH₂)ₙ-G1, —(CH₂)ₙ—O—(CH₂)ₙ-G4, —(CH₂)ₙ—NR3—(CH₂)ₙ-aryl, —(CH₂)ₙ—NR3—(CH₂)ₙ-G1, —(CH₂)ₙ—NR3—(CH₂)ₙ-G4, —(CH₂)ₙNHC(O)NHS(O)₂R8, —(CH₂)ₙNHS(O)₂NHC(O)R8, —C(O)NHS(O)₂R8, —(CH₂)NHC(O)(CH₂)ₙR5, —(CH₂)ₙNHS(O)₂R5, —(CH₂)ₙC(O)NH(CH₂)qR5, —(CH₂)ₙC(O)R5, —(CH₂)ₙOC(O)R5, and —(CH₂)ₙR5;

in the event that Z2 contains an alkyl or alkylene moiety, such moieties may be further substituted with one or more C1-C6alkyls;

each Z3 is independently and individually selected from the group consisting of H, C1-C6alkyl, branched C3-C7alkyl, C3-C8carbocyclyl, halogen, fluoroalkyl wherein the alkyl moiety can be partially or fully fluorinated, cyano, hydroxyl, methoxy, oxo, (R3)₂N—C(=O)—, (R4)₂N—C(=O)—, —N(R4)—C(=O)R8, (R3)₂NSO₂—, (R4)₂NSO₂—, —N(R4)SO₂R5, —N(R4)SO₂R8, —(CH₂)ₙ—N(R3)₂, —(CH₂)ₙ—N(R4)₂, —O—(CH₂)q—N(R4)₂, —O—CH₂)q—O-alkyl, —N(R3)—(CH₂)q—O-alkyl, —N(R3)—(CH₂)q—N(R4)₂, —O—(CH₂)q—R5, —N(R3)—(CH₂)q—R5, —C(=O)R5, —C(=O)R8, and nitro;

in the event that Z3 contains an alkyl or alkylene moiety, such moieties may be further substituted with one or more C1-C6alkyls;

each Z4 is independently and individually selected from the group consisting of H, C1-C6alkyl, hydroxyC2-C6alkyl, C1-C6alkoxyC2-C6alkyl, (R4)₂N—C2-C6alkyl, (R4)₂N—C2-C6alkylN(R4)-C2-C6alkyl, (R4)₂N—C2-C6alkyl-O—C2-C6alkyl, (R4)₂N—CO—C1-C6alkyl, carboxyC1-C6alkyl, C1-C6alkoxycarbonylC1-C6alkyl, -C2-C6alkylN(R4)C(O)R8, R8-C(=NR3)—, —SO₂R8, —COR8, —(CH₂)ₙ-G1, —(CH₂)ₙ-G4, —(CH₂)q—O—(CH₂)ₙ-G1, —(CH₂)q—O—(CH₂)ₙ-G4, —(CH₂)q—NR3—(CH₂)ₙ-G1, —(CH₂)q—NR3—(CH₂)ₙ-G4, —(CH₂)qNHC(O)(CH₂)ₙR5, —(CH₂)qC(O)NH(CH₂)qR5, —(CH₂)qC(O)R5, —(CH₂)qOC(O)R5, —(CH₂)qR5, —(CH₂)qNR4(CH₂)qR5, and —(CH₂)qO(CH₂)qR5;

in the event that Z4 contains an alkyl or alkylene moiety, such moieties may be further substituted with one or more C1-C6alkyls;

each Z6 is independently and individually selected from the group consisting of H, C1-C6alkyl, branched C3-C7alkyl, hydroxyl, C1-C6alkoxy, —OR4, C1-C6alkylthio, (R3)₂N—, (R4)₂N—, —R5, —N(R3)COR8, —N(R4)COR8, —N(R3)SO₂R6-, —CON(R3)₂, —CON(R4)₂, —COR5, —SO₂N(R4)₂, halogen, fluoroC1-C6alkyl wherein the alkyl is fully or partially fluorinated, cyano, fluoroC1-C6alkoxy wherein the alkyl is fully or partially fluorinated, —O—(CH₂)q—N(R4)₂, —N(R3)—(CH₂)q—N(R4)₂, —O—(CH₂)q—O-alkyl, —N(R3)—(CH₂)q—O-alkyl, —O—(CH₂)q—R5, —N(R3)—(CH₂)q—R5, —(NR3)ᵣ—(CH₂)ₙ—R17, —(O)ᵣ—R17, —(S)ᵣ—R17, and —(CH₂)ₙ—R17;

in the event that Z6 contains an alkyl or alkylene moiety, such moieties may be further substituted with one or more C1-C6alkyls;

wherein each R3 is independently and individually selected from the group consisting of H, C1-C6alkyl, branched C3-C7alkyl, C3-C8carbocyclyl, and Z3-substituted phenyl;

each R4 is independently and individually selected from the group consisting of H, C1-C6alkyl, hydroxyC1-C6alkyl, dihydroxyC1-C6alkyl, C1-C6alkoxyC1-C6alkyl, branched C3-C7alkyl, branched hydroxyC1-C6alkyl, branched C1-C6alkoxyC1-C6alkyl, branched dihydroxyC1-C6alkyl, —(CH₂)p—N(R7)₂, —(CH₂)p—R5, —(CH₂)p—C(O)N(R7)₂, —(CH₂)ₙC(O)R5, —(CH₂)ₙ—C(O)OR3, C3-C8carbocyclyl, hydroxyl substituted C3-C8carbocyclyl, alkoxy substituted C3-C8carbocyclyl, dihydroxy substituted C3-C8carbocyclyl, and —(CH₂)ₙ—R17;

each R5 is independently and individually selected from the group consisting of

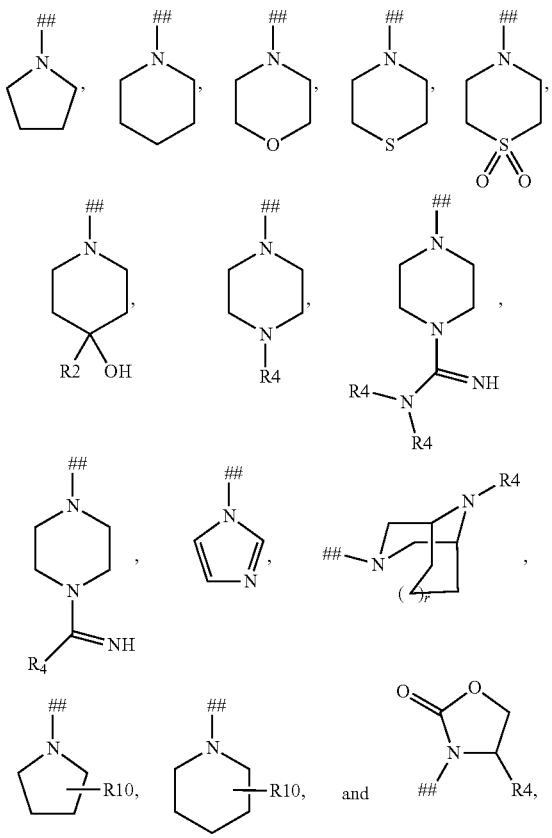

and wherein the symbol (##) is the point of attachment of the R5 moiety;

each R6 is independently and individually selected from the group consisting of C1-C6alkyl, branched C3-C7alkyl, C3-C8carbocyclyl, phenyl, and G1;

each R7 is independently and individually selected from the group consisting of H, C1-C6alkyl, hydroxyC2-C6alkyl, dihydroxyC2-C6alkyl, C1-C6alkoxyC2-C6alkyl, branched C3-C7alkyl, branched hydroxyC2-C6 alkyl, branched C1-C6alkoxyC2-C6alkyl, branched dihydroxyC2-C6alkyl, —(CH₂)q—R5, —(CH₂)ₙ—C(O)R5, —(CH₂)ₙ—C(O)OR3, C3-C8carbocyclyl, hydroxyl substituted C3-C8carbocyclyl, alkoxy substituted C3-C8carbocyclyl, dihydroxy substituted C3-C8carbocyclyl, and —(CH₂)ₙ—R17;

each R8 is independently and individually selected from the group consisting of C1-C6alkyl, branched C3-C7alkyl, fluoroalkyl wherein the alkyl moiety is partially or fully fluorinated, C3-C8carbocyclyl, Z3-substituted phenyl, Z3-substituted phenyl C1-C6alkyl, Z3-substituted G1, Z3-substituted G1-C1-C6alkyl, OH, C1-C6alkoxy, N(R3)$_2$, N(R4)$_2$, and R5;

each R10 is independently and individually selected from the group consisting of CO$_2$H, CO$_2$C1-C6alkyl, CO—N(R4)$_2$, OH, C1-C6alkoxy, and —N(R4)$_2$;

R16 is independently and individually selected from the group consisting of hydrogen, C1-C6alkyl, and halogen;

each R17 is taken from the group comprising phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, oxetanyl, azetadinyl, tetrahydrofuranyl, oxazolinyl, oxazolidinyl, pyranyl, thiopyranyl, tetrahydropyranyl, dioxalinyl, azepinyl, oxepinyl, diazepinyl, pyrrolidinyl, and piperidinyl;

wherein R17 can be further substituted with one or more Z2, Z3 or Z4 moieties;

R19 is H or C1-C6 alkyl;

wherein two R3 or R4 moieties are independently and individually taken from the group consisting of C1-C6alkyl and branched C3-C6alkyl, hydroxyalkyl, and alkoxyalkyl and are attached to the same nitrogen atom, said moieties may cyclize to form a C3-C7 heterocyclyl ring;

and k is 1 or 2; n is 0-6; p is 1-4; q is 2-6; r is 0 or 1; t is 1-3, and salts thereof.

2. Compounds of claim 1 having the formula Ic

3. Compounds of claim 2 having the formula Id wherein A1 is selected from the group consisting of branched C3-C8alkyl, R19 substituted C3-C8carbocyclyl, C1-C6alkyl, fluoroC1-C6alkyl wherein the alkyl is fully or partially fluorinated, Z3-substituted phenyl, and Z3-substituted G1; and wherein R16 is C1-C6alkyl, or halogen.

4. Compounds of claim 3 having the formula Ie

5. Compounds of claim 3 having the formula If wherein R16 is C1-C6alkyl, fluorine or chlorine.

6. Compounds of claim 2 having the formula Ig

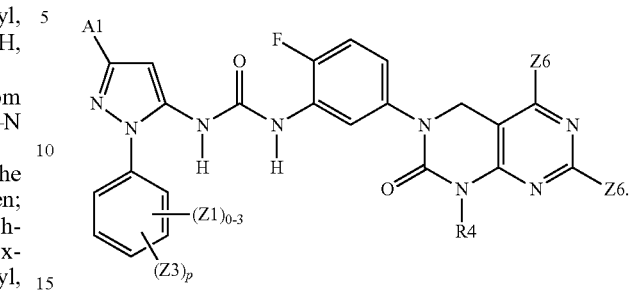

wherein A1 is selected from the group consisting of branched C3-C8alkyl, R19 substituted C3-C8carbocyclyl, C1-C6alkyl, fluoroC1-C6alkyl wherein the alkyl is fully or partially fluorinated, Z3-substituted phenyl, and Z3-substituted G1; and wherein R16 is C1-C6alkyl, or halogen.

7. Compounds of claim 6 having the formula Ih

8. Compounds of claim 6 having the formula Ii

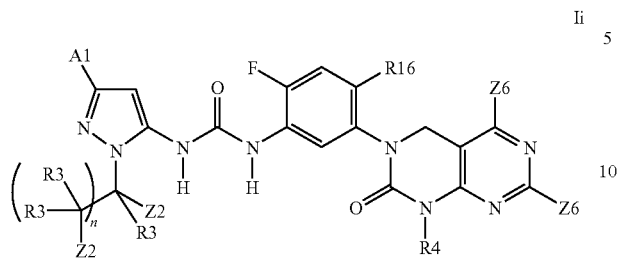

wherein R16 is C1-C6alkyl, fluorine or chlorine.

9. Compounds of claim 1 having formula Ij

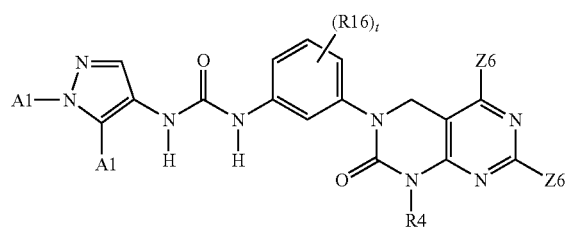

wherein A1 is selected from the group consisting of Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1; and wherein R16 is C1-C6alkyl, or halogen.

10. Compounds of claim 9 having formula Ik

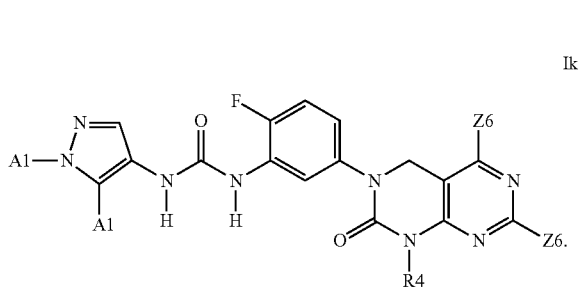

11. Compounds of claim 9 having formula Il

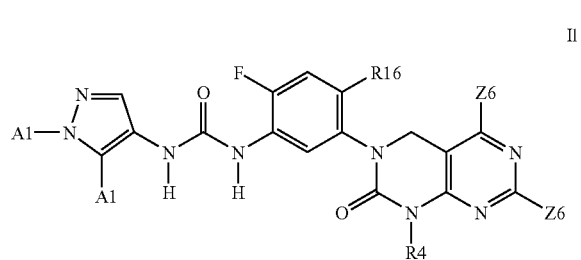

wherein R16 is C1-C6alkyl, fluorine or chlorine.

12. Compounds of claim 1 having formula Im

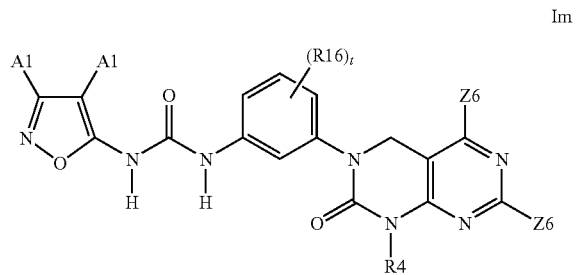

wherein A1 is selected from the group consisting of hydrogen, Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, or halogen.

13. Compounds of claim 12 having formula In

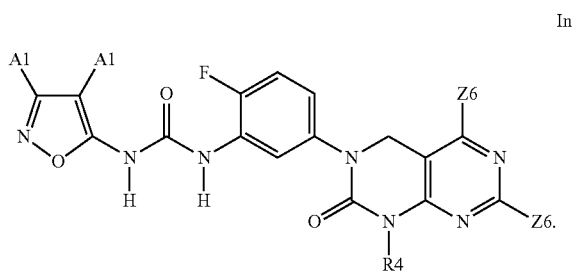

14. Compounds of claim 12 having formula Io

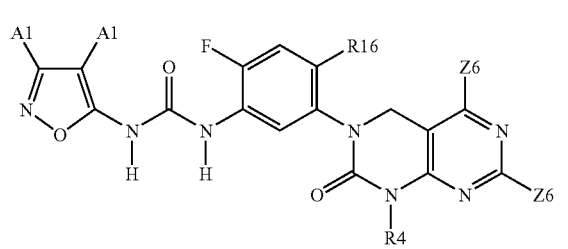

wherein R16 is C1-C6alkyl, fluorine or chlorine.

15. Compounds of claim 1 having formula Ip

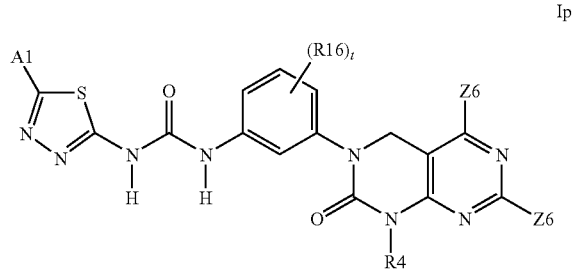

wherein A1 is selected from the group consisting of Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, or halogen.

16. Compounds of claim 15 having formula Iq

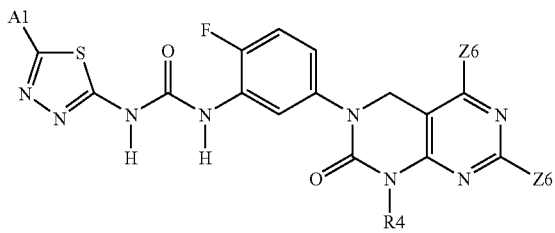

Iq

17. Compounds of claim 15 having formula Ir

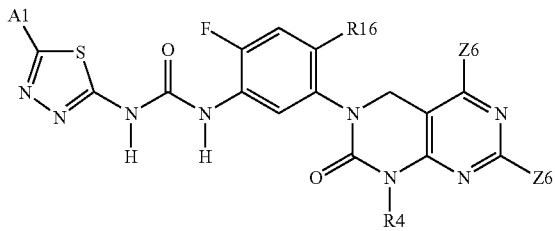

Ir and wherein R16 is C1-C6alkyl, fluorine or chlorine.

18. Compounds of claim 1 having formula Is

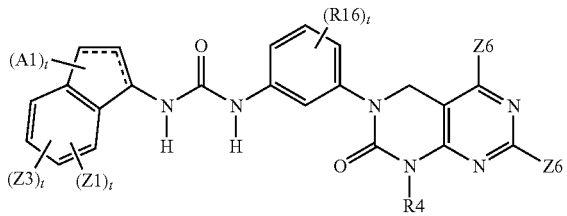

Is wherein the hashed bond is a saturated or unsaturated bond;

and wherein A1 is selected from the group consisting of hydrogen, Z2-substituted branched C3-C8alkyl, R19 substituted C3-C8carbocyclyl, Z2-substituted C1-C6alkyl, halogen, cyano, C1-C6alkoxy, fluoroC1-C6alkoxy, fluoroC1-C6alkyl wherein the alkyl is fully or partially fluorinated, Z3-substituted phenyl, and Z3-substituted G1;

and wherein R16 is C1-C6alkyl, or halogen.

19. Compounds of claim 18 having formula It

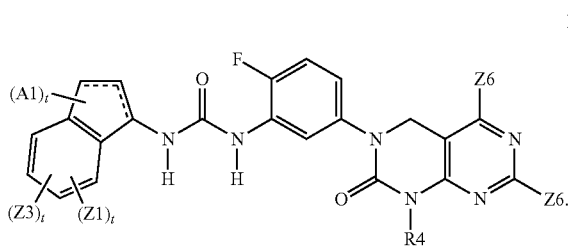

It

20. Compounds of claim 18 having formula Iu

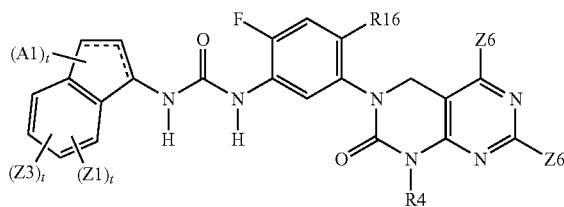

Iu and wherein R16 is C1-C6alkyl, fluorine or chlorine.

21. Compounds of claim 1 having formula Iv

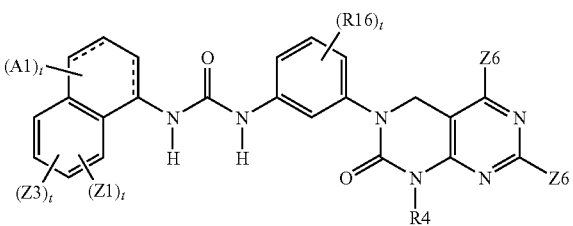

Iv wherein the hashed bond is a saturated or unsaturated bond;

and wherein A1 is selected from the group consisting of hydrogen, Z2-substituted branched C3-C8alkyl, R19 substituted C3-C8carbocyclyl, Z2-substituted C1-C6alkyl, halogen, cyano, C1-C6alkoxy, fluoroC1-C6alkoxy, fluoroC1-C6alkyl wherein the alkyl is fully or partially fluorinated, Z3-substituted phenyl, and Z3-substituted G1;

and wherein R16 is C1-C6alkyl, or halogen.

22. Compounds of claim 21 having formula Iw

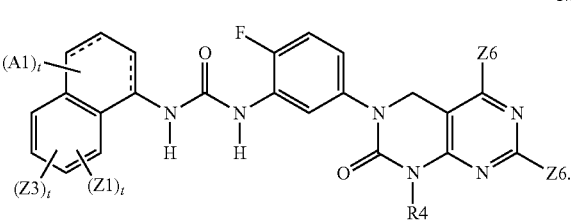

Iw

23. Compounds of claim 21 having formula Ix

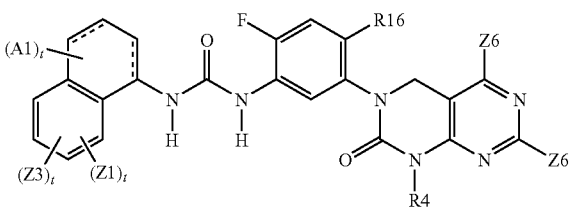

Ix and wherein R16 is C1-C6alkyl, fluorine or chlorine.

24. Compounds of claim 1 having formula Iy

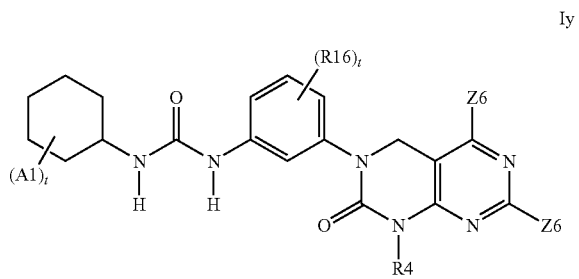

Iy wherein A1 is selected from the group consisting of Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1; and wherein R16 is C1-C6alkyl, or halogen.

25. Compounds of claim 24 having formula Iz

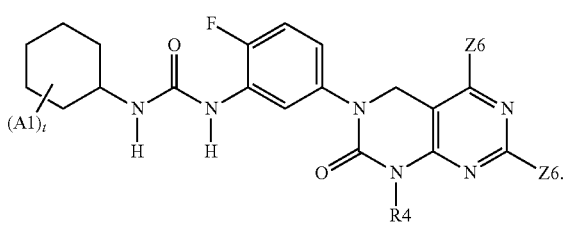

Iz

26. Compounds of claim 24 having formula Iaa

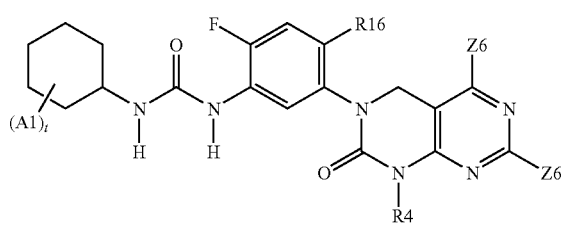

Iaa wherein R16 is C1-C6alkyl, fluorine or chlorine.

27. Compounds of claim 1 having formula Ibb

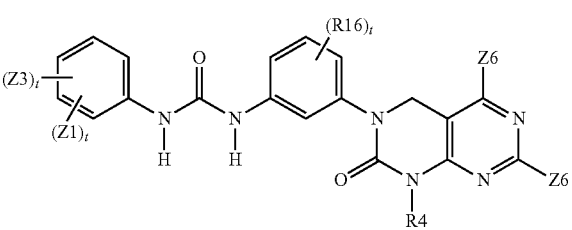

Ibb wherein R16 is C1-C6alkyl, or halogen.

28. Compounds of claim 27 having formula Icc

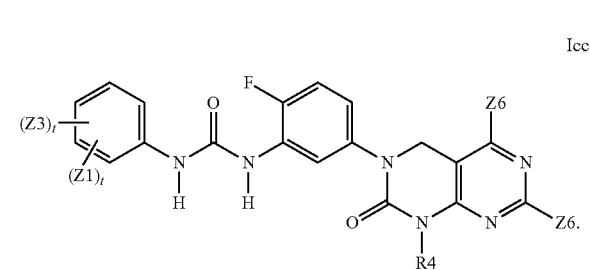

Icc

29. Compounds of claim 27 having formula Idd

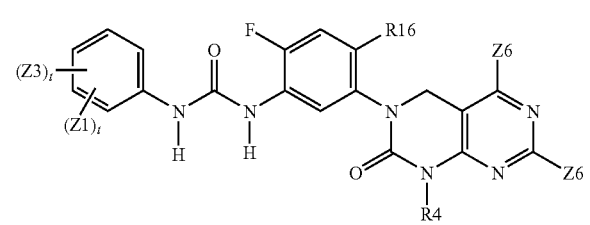

Idd wherein R16 is C1-C6alkyl, fluorine or chlorine.

30. Compounds of claim 1 having formula Iee

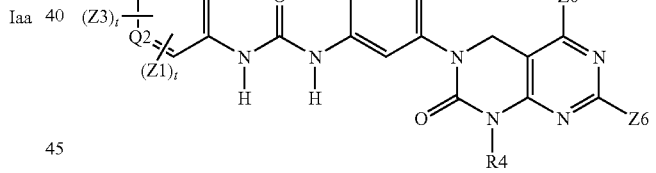

Iee wherein Q1 and Q2 are individually and independently taken from the group consisting of N and CH; and wherein R16 is C1-C6alkyl, or halogen.

31. Compounds of claim 30 having formula Iff

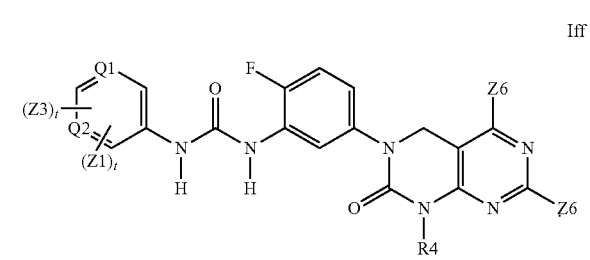

Iff

32. Compounds of claim 30 having formula Igg

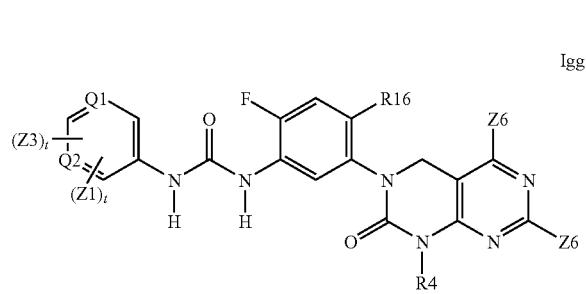

wherein R16 is C1-C6alkyl, fluorine or chlorine.

33. Compounds of claim 1 having formula Ihh

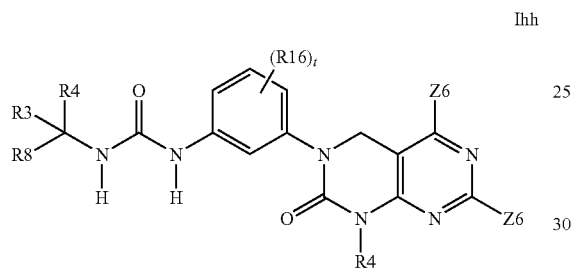

and wherein R16 is C1-C6alkyl, or halogen.

34. Compounds of claim 33 having formula Iii

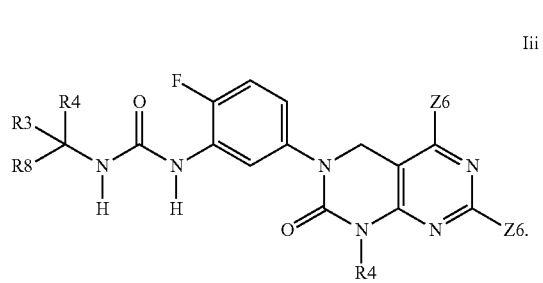

35. Compounds of claim 33 having formula Ijj

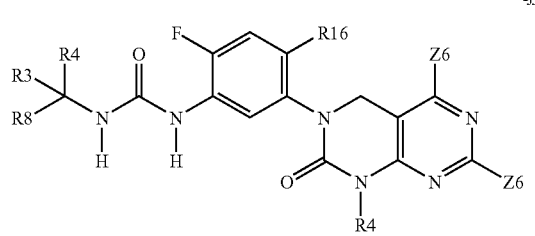

wherein R16 is C1-C6alkyl, fluorine or chlorine.

36. Compounds of claim 1 having formula Ikk

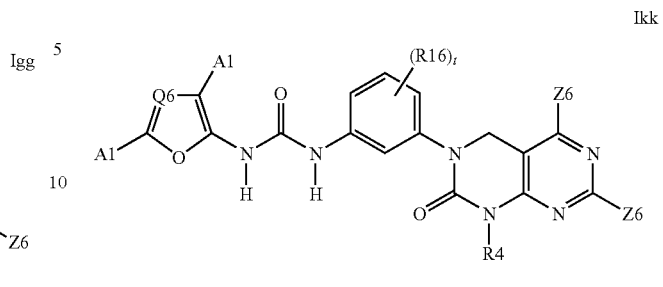

wherein Q6 is N or C-A1;

wherein A1 is selected from the group consisting of hydrogen, Z2-substituted branched C3-C8alkyl, R19 substituted C3-C8carbocyclyl, Z2-substituted C1-C6alkyl, fluoroC1-C 6alkyl wherein the alkyl is fully or partially fluorinated, Z3-substituted phenyl, and Z3-substituted G1;

and wherein R16 is C1-C6alkyl, or halogen.

37. Compounds of claim 36 having formula Ill

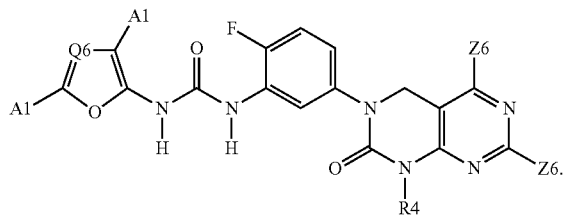

38. Compounds of claim 36 having formula Imm

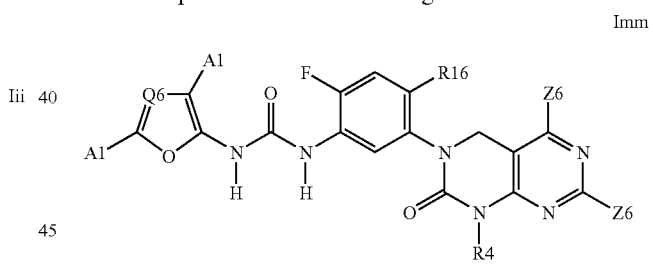

wherein R16 is C1-C6alkyl, fluorine or chlorine.

39. Compounds of claim 1 having formula Inn

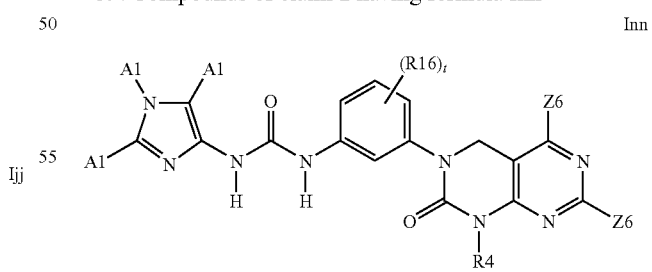

wherein A1 is selected from the group consisting of hydrogen, Z2-substituted branched C3-C8alkyl, R19 substituted C3-C8carbocyclyl, Z2-substituted C1-C6alkyl, fluoroC1-C 6alkyl wherein the alkyl is fully or partially fluorinated, Z3-substituted phenyl, and Z3-substituted G1;

and wherein R16 is C1-C6alkyl, or halogen.

40. Compounds of claim 39 having formula Ioo

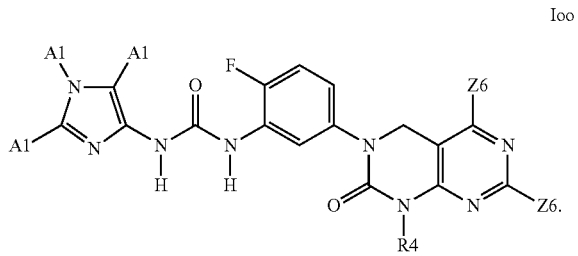

41. Compounds of claim 39 having formula Ipp

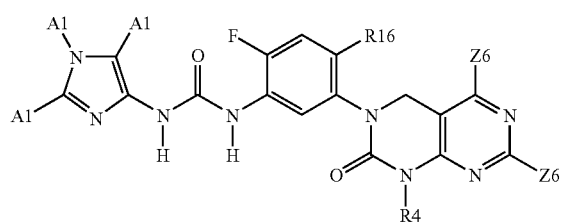

wherein R16 is C1-C6alkyl, fluorine or chlorine.

42. Compounds of claim 1 having formula Iqq

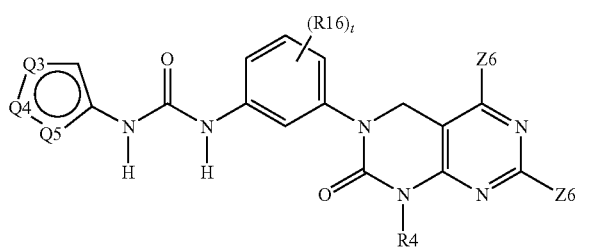

wherein Q3, Q4 and Q5 are selected from the group consisting of N—A1 and C-A1, and only one of Q3, Q4, or Q5 is N—A1;

and wherein A1 is selected from the group consisting of hydrogen, Z2-substituted branched C3-C8alkyl R19 substituted C3-C8carboyclyl, Z2 substituted C1-C6alkyl, flouroC1-C6alkyl wherein the alkyl is fully or partially fluorinated, Z3-substituted phenyl, and Z3-substituted G1;

and wherein R16 is C1-C6alkyl, or halogen.

43. Compounds of claim 42 having formula Irr

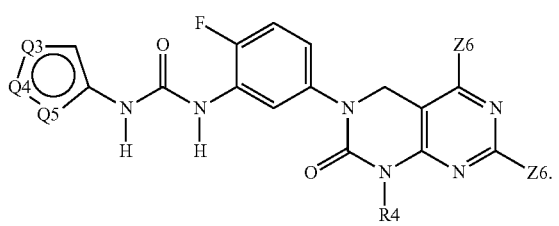

44. Compounds of claim 42 having formula Iss

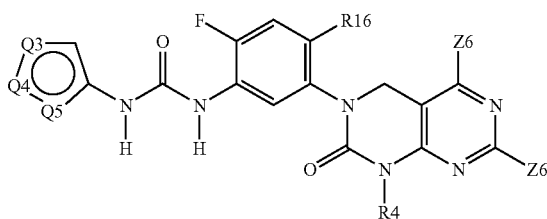

wherein R16 is C1-C6alkyl, fluorine or chlorine.

45. Compounds of the formula IIa'

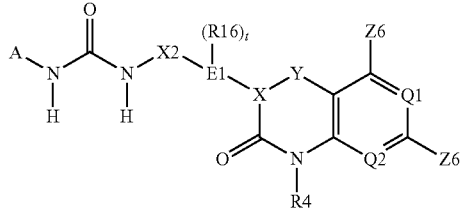

wherein X—Y is N—CH2;
Q1 is N and Q2 is CR3;
X2 is a direct bond;
E1 is phenyl;
A is selected from the group consisting of phenyl, naphthyl, C3-C8carbocyclyl, bicycloheptanyl, bicycloheptenyl, and G1;
G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl;
the A ring may be optionally substituted with one or more —X1-A1 moieties;
X1 is selected from the group consisting of —$(CH_2)_n$—$(O)_r$—$(CH_2)_n$—, —$(CH_2)_n$—$(NR3)_r$—$(CH_2)_n$—, —$(CH_2)_n$—$(S)_r$—$(CH_2)_n$—, —$(CH_2)_n$—$(C=O)_r$—$(CH_2)_n$—, —$(CH_2)_n$—$(C(=O)$—$NR3)_r$—$(CH_2)_n$—, and —$(CH_2)_n$—$(SO_2$—$NR3)_r$—$(CH_2)_n$—, wherein any of the alkylenes may be straight or branched chain;
A1 is selected from the group consisting of hydrogen, aryl, G1 C1-C6 alkyl, branched C3-C8alkyl, R19 substituted C3-C8carbocyclyl, fluoroC1-C6alkyl wherein the alkyl is fully or partially fluorinated, halogen, cyano, hydroxyl, —$N(R4)_2$, —R5, —$C(O)N(R4)_2$, C(O)R5, C1-C6alkoxy, and fluoroC1-C6alkoxy wherein the alkyl group is fully or partially fluorinated;
When A and A1 have one or more substitutable sp2-hybridized carbon atom, each respective sp2 hybridized carbon atom may be optionally substituted with a Z1 or Z3 substituent;
when A and A1 have one or more substitutable sp3-hybridized carbon atom, each respective sp3 hybridized carbon atom may be optionally substituted with a Z2 or R3 substituent;
when A and A1 have one or more substitutable nitrogen atom, each respective nitrogen atom may be optionally substituted with a Z4 substituent;
each Z1 is independently and individually selected from the group consisting of hydrogen, hydroxyC1-C6alkyl, C1-C6alkoxy, C1-C6alkoxyC1-C6alkyl, $(R4)_2$NC1-C6alkyl, $(R4)_2$NC2-C6alkylN(R4)—$(CH_2)_n$, $(R4)_2$ NC2-C6alkylO—(CH$_2$)$_n$—, (R$^3$)$_2$N—C(=O)—, (R4)$_2$N—C(=O)—, (R4)$_2$N—CO—C1-C6alkyl-, C1-C6alkoxycarbonyl-, -carboxyC1-C6alkyl, C1-C6alkoxycarbonylC1-C6alkyl, (R3)$_2$NSO$_2$—, —SOR3, (R4)$_2$NSO$_2$—, —SO$_2$R3, —SOR4, —C(=O)R6, —C(=NOH)R6, —C(=NOR3)R6, —(CH$_2$)$_n$N(R4)C(O)R8, —(CH$_2$)$_n$-G1, —(CH$_2$)$_n$-G4, phenoxy, —(CH$_2$)$_n$—O—(CH$_2$)$_n$-G1, —(CH$_2$)$_n$—O—(CH$_2$)$_n$-G4, —(CH$_2$)$_n$—NR3—(CH$_2$)$_n$-aryl, —(CH$_2$)$_n$—NR3—(CH$_2$)$_n$-G1, —(CH$_2$)$_n$—NR3—(CH$_2$)$_n$-G4, —S(O)$_2$R5, —N=S(O)R6R8, —S(O)(=NR3)R6, —(CH$_2$)$_n$NHC(O)NHS(O)$_2$R8, —(CH$_2$)$_n$NHS(O)$_2$NHC(O)R8, —C(O)NHS(O)$_2$R8, —S(O)$_2$NHC(O)R8, —(CH$_2$)$_n$NHC(O)(CH$_2$)$_n$R5, —(CH$_2$)$_n$NHS(O)$_2$(CH$_2$)$_n$R5, —(CH$_2$)$_n$C(O)NH(CH$_2$)$_q$R5, —(CH$_2$)$_n$C(O)R5, —(CH$_2$)$_n$OC(O)R5, —(CH$_2$)$_n$S(O)$_2$NH(CH$_2$)$_q$R5, —CH(OH)(CH$_2$)$_p$R5, —CH(OH)CH(OH)R4, —(CH$_2$)$_n$N(R4)$_2$, —(CH$_2$)$_n$R5, —C(=NH)R5, —C(=NH)N(R4)$_2$, —C(=NOR3)R5, —C(=NOR3)N(R4)$_2$, and —NHC(=NH)R8;

in the event that Z1 contains an alkyl or alkylene moiety, such moieties may be further substituted with one or more C1-C6alkyls;

each Z2 is independently and individually selected from the group consisting of hydrogen, aryl, C1-C6alkyl, C3-C8carbocyclyl, hydroxyl, hydroxyC1-C6alkyl-, cyano, (R3)$_2$N—, (R4)$_2$N—, (R4)$_2$NC1-C6alkyl-, (R4)$_2$NC2-C6alkylN(R4)—(CH$_2$)$_n$—, (R4)$_2$NC2-C6alkylO—(CH$_2$)$_n$—, (R3)$_2$N—C(=O)—, (R4)$_2$N—C(=O)—, (R4)$_2$N—CO—C1-C6alkyl-, carboxyl, carboxyC1-C6alkyl, C1-C6alkoxycarbonyl, C1-C6alkoxycarbonylC1-C6alkyl, (R3)$_2$NSO$_2$—, (R4)$_2$NSO$_2$—, —SO$_2$R5, —SO$_2$R8, —(CH$_2$)$_n$N(R4)C(O)R8, —C(O)R8, =O, =NOH, =N(OR6), —(CH$_2$)$_n$-G1, —(CH$_2$)$_n$-G4, —(CH$_2$)$_n$—O—(CH$_2$)$_n$-G1, —(CH$_2$)$_n$—O—(CH$_2$)$_n$-G4, —(CH$_2$)$_n$—NR3—(CH$_2$)$_n$-aryl, —(CH$_2$)$_n$—NR3—(CH$_2$)$_n$-G1, —(CH$_2$)$_n$—NR3—(CH$_2$)$_n$-G4, —(CH$_2$)$_n$NHC(O)NHS(O)$_2$R8, —(CH$_2$)$_n$NHS(O)$_2$NHC(O)R8, —C(O)NHS(O)$_2$R8, —(CH$_2$)NHC(O)(CH$_2$)$_n$R5, —(CH$_2$)$_n$NHS(O)$_2$R5, —(CH$_2$)$_n$C(O)NH(CH$_2$)$_q$R5, —(CH$_2$)$_n$C(O)R5, —(CH$_2$)$_n$OC(O)R5, and —(CH$_2$)$_n$R5;

in the event that Z2 contains an alkyl or alkylene moiety, such moieties may be further substituted with one or more C1-C6alkyls;

each Z3 is independently and individually selected from the group consisting of H, C1-C6alkyl, branched C3-C7alkyl, C3-C8carbocyclyl, halogen, fluoroalkyl wherein the alkyl moiety can be partially or fully fluorinated, cyano, hydroxyl, methoxy, oxo, (R3)$_2$N—C(=O)—, (R4)$_2$N—C(=O)—, —N(R4)-C(=O)R8, (R3)$_2$NSO$_2$—, (R4)$_2$NSO$_2$—, —N(R4)SO$_2$R5, —N(R4)SO$_2$R8, —(CH$_2$)$_n$—N(R3)$_2$, —(CH$_2$)$_n$—N(R4)$_2$, —O—(CH$_2$)$_q$—N(R4)$_2$, —O—(CH$_2$)$_q$—O-alkyl, —N(R3)—(CH$_2$)$_q$—O-alkyl, —N(R3)—(CH$_2$)$_q$—N(R4)$_2$, —O—(CH$_2$)$_q$—R5, —N(R3)—(CH$_2$)$_q$—R5, —C(=O)R5, —C(=O)R8, and nitro;

in the event that Z3 contains an alkyl or alkylene moiety, such moieties may be further substituted with one or more C1-C6alkyls;

each Z4 is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C1-C6alkyl, carboxyC1-C6alkyl, C1-C6alkoxycarbonylC1-C6alkyl, —C2-C6alkylN(R4)C(O)R8, R8—C(=NR3)—, —SO$_2$R8, —COR8, —(CH$_2$)$_n$-G1, —(CH$_2$)$_n$-G4, —(CH$_2$)$_q$—O—(CH$_2$)$_n$-G1, —(CH$_2$)$_q$—O—(CH$_2$)$_n$-G 4, —(CH$_2$)$_q$—NR3—(CH$_2$)$_n$-G1, —(CH$_2$)$_q$—NR3—(CH$_2$)$_n$-G4, —(CH$_2$)$_q$NHC(O)(CH$_2$)$_n$R5, —(CH$_2$)$_q$C(O)NH(CH$_2$)$_q$R5, —(CH$_2$)$_q$C(O)R5, —(CH$_2$)$_q$OC(O)R5, —(CH$_2$)$_q$R5, —(CH$_2$)$_q$NR4(CH$_2$)$_q$R5, and —(CH$_2$)$_q$O(CH$_2$)$_q$R5;

in the event that Z4 contains an alkyl or alkylene moiety, such moieties may be further substituted with one or more C1-C6alkyls;

each Z6 is independently and individually selected from the group consisting of H, C1-C6alkyl, branched C3-C7alkyl, hydroxyl, C1-C6alkoxy, —OR4, C1-C6alkylthio, (R3)$_2$N—, (R4)$_2$N—, —R5, —N(R3)COR8, —N(R4)COR8, —N(R3)SO$_2$R6-, —CON(R3)$_2$, —CON(R4)$_2$, —COR5, —SO$_2$N(R4)$_2$, halogen, fluoroC1-C6alkyl wherein the alkyl is fully or partially fluorinated, cyano, fluoroC1-C6alkoxy wherein the alkyl is fully or partially fluorinated, —O—(CH$_2$)$_q$—N(R4)$_2$, —N(R3)—(CH$_2$)$_q$—N(R4)$_2$, —O—(CH$_2$)$_q$—O-alkyl, —N(R3)—(CH$_2$)$_q$—O-alkyl, —O—(CH$_2$)$_q$—R5, —N(R3)—(CH$_2$)$_q$—R5, —(NR3)$_r$—(CH$_2$)$_n$—R17, —(O)$_r$—R17, —(S)$_r$—R17, and —(CH$_2$)$_r$—R17;

in the event that Z6 contains an alkyl or alkylene moiety, such moieties may be further substituted with one or more C1-C6alkyls;

wherein each R3 is independently and individually selected from the group consisting of H, C1-C6alkyl, branched C3-C7alkyl, C3-C8carbocyclyl, and Z3-substituted phenyl;

each R4 is independently and individually selected from the group consisting of H, C1-C6alkyl, hydroxyC1-C6alkyl, dihydroxyC1-C6alkyl, C1-C6alkoxyC1-C6alkyl, branched C3-C7alkyl, branched hydroxyC1-C6alkyl, branched C1-C6alkoxyC1-C6alkyl, branched dihydroxyC1-C6alkyl, —(CH$_2$)$_p$—N(R7)$_2$, —(CH$_2$)$_p$—R5, —(CH$_2$)$_p$—C(O)N(R7)$_2$, —(CH$_2$)$_n$C(O)R5, —(CH$_2$)$_n$—C(O)OR3, C3-C8carbocyclyl, hydroxyl substituted C3-C8carbocyclyl, alkoxy substituted C3-C8carbocyclyl, dihydroxy substituted C3-C8carbocyclyl, and —(CH$_2$)$_n$—R17;

each R5 is independently and individually selected from the group consisting of

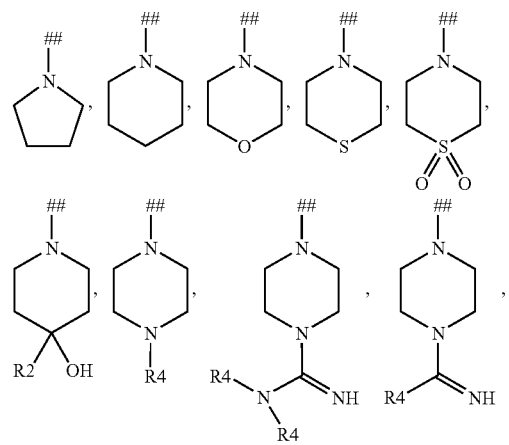

-continued

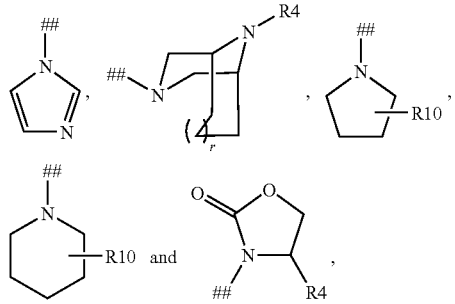

and wherein the symbol (##) is the point of attachment of the R5 moiety;

each R6 is independently and individually selected from the group consisting of C1-C6alkyl, branched C3-C7alkyl, C3-C8carbocyclyl, phenyl, and G1;

each R7 is independently and individually selected from the group consisting of H, C1-C6alkyl, hydroxyC2-C6alkyl, dihydroxyC2-C6alkyl, C1-C6alkoxyC2-C6alkyl, branched C3-C7alkyl, branched hydroxyC2-C6 alkyl, branched C1-C6alkoxyC2-C6alkyl, branched dihydroxyC2-C6alkyl, —$(CH_2)_q$—R5, —$(CH_2)_n$—C(O)R5, —$(CH_2)_n$—C(O)OR3, C3-C8carbocyclyl, hydroxyl substituted C3-C8carbocyclyl, alkoxy substituted C3-C8carbocyclyl, dihydroxy substituted C3-C8carbocyclyl, and —$(CH_2)_n$—R17;

each R8 is independently and individually selected from the group consisting of C1-C6alkyl, branched C3-C7alkyl, fluoroalkyl wherein the alkyl moiety is partially or fully fluorinated, C3-C8carbocyclyl, Z3-substituted phenyl, Z3-substituted phenyl C1-C6alkyl, Z3-substituted G1, Z3-substituted G1-C1-C6alkyl, OH, C1-C6alkoxy, $N(R3)_2$, $N(R4)_2$, and R5;

each R10 is independently and individually selected from the group consisting of $CO_2H$, $CO_2$C1-C6alkyl, CO—N$(R4)_2$, OH, C1-C6alkoxy, and —$N(R4)_2$;

R16 is independently and individually selected from the group consisting of hydrogen, C1-C6alkyl, and halogen;

each R17 is taken from the group comprising phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, oxetanyl, azetadinyl, tetrahydrofuranyl, oxazolinyl, oxazolidinyl, pyranyl, thiopyranyl, tetrahydropyranyl, dioxalinyl, azepinyl, oxepinyl, diazepinyl, pyrrolidinyl, and piperidinyl;

wherein R17 can be further substituted with one or more Z2, Z3 or Z4 moieties;

R19 is H or C1-C6 alkyl;

wherein two R3 or R4 moieties are independently and individually taken from the group consisting of C1-C6alkyl and branched C3-C6alkyl, hydroxyalkyl, and alkoxyalkyl and are attached to the same nitrogen atom, said moieties may cyclize to form a C3-C7 heterocyclyl ring;

and k is 1 or 2; n is 0-6; p is 1-4; q is 2-6; r is 0 or 1; t is 1-3, and salts thereof.

46. Compounds of claim 45 having the formula IIc

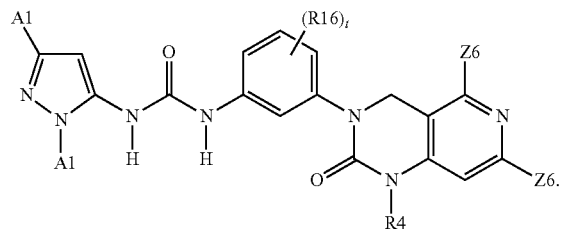

47. Compounds of claim 46 having the formula IId

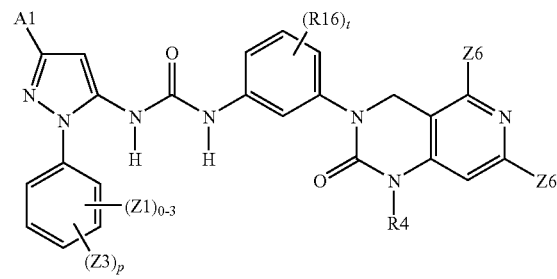

wherein A1 is selected from the group consisting of branched C3-C8alkyl, R19 substituted C3-C8carbocyclyl, C1-C6alkyl, fluoroC1-C6alkyl wherein the alkyl is fully or partially fluorinated, Z3-substituted phenyl, and Z3-substituted G1;

and wherein R16 is C1-C6alkyl, or halogen.

48. Compounds of claim 47 having the formula IIe

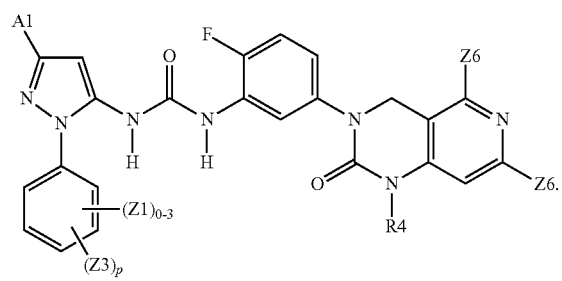

49. Compounds of claim 47 having the formula If

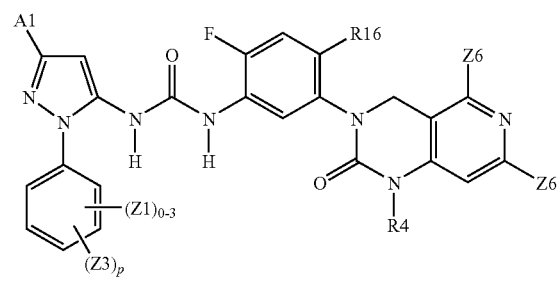

wherein R16 is methyl, fluorine or chlorine.

50. Compounds of claim 46 having the formula IIg

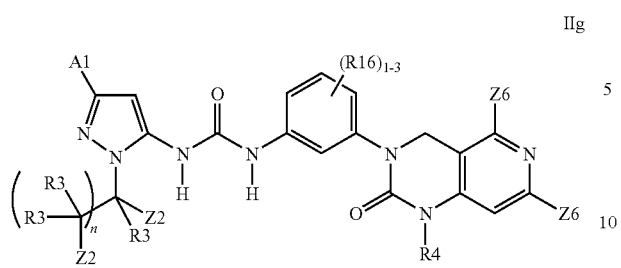

IIg wherein A1 is selected from the group consisting of branched C3-C8alkyl, R19 substituted C3-C8carbocyclyl, C1-C6alkyl, fluoroC1-C6alkyl wherein the alkyl is fully or partially fluorinated, Z3-substituted phenyl, and Z3-substituted G1;
and wherein R16 is C1-C6alkyl, or halogen.

51. Compounds of claim 50 having the formula IIh

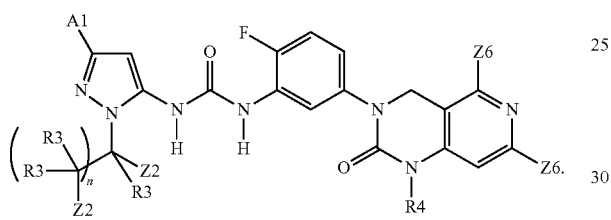

IIh

52. Compounds of claim 50 having the formula IIi

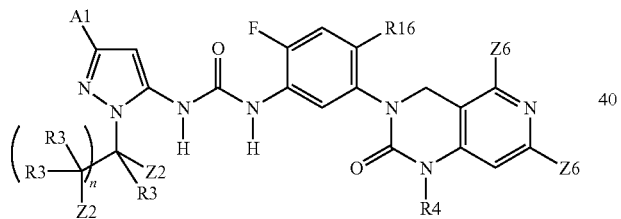

IIi wherein R16 is methyl, fluorine or chlorine.

53. Compounds of claim 45 having formula IIj

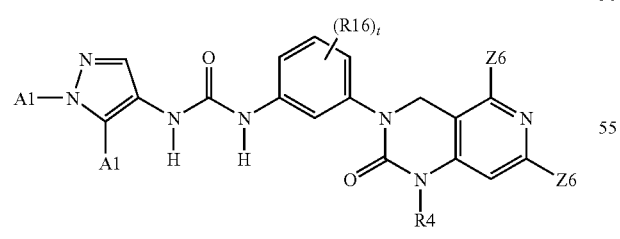

IIj wherein A1 is selected from the group consisting of Z2-substitued branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, or halogen.

54. Compounds of claim 53 having formula IIk

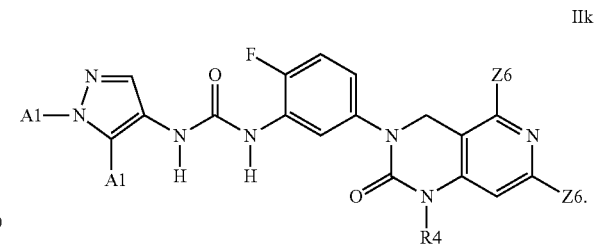

IIk

55. Compounds of claim 53 having formula IIl

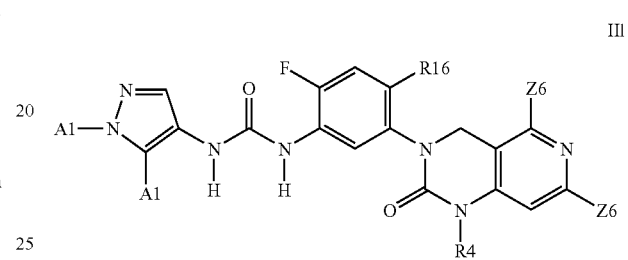

IIl wherein R16 is methyl, fluorine or chlorine.

56. Compounds of claim 45 having formula IIm

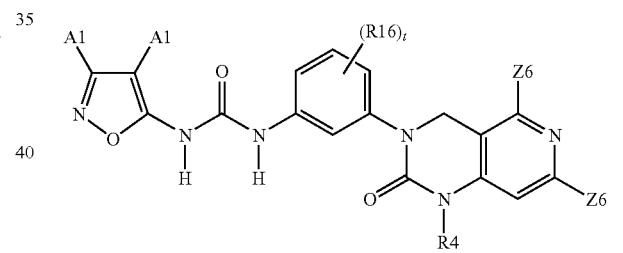

IIm wherein A1 is selected from the group consisting of hydrogen, Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, or halogen.

57. Compounds of claim 56 having formula IIn

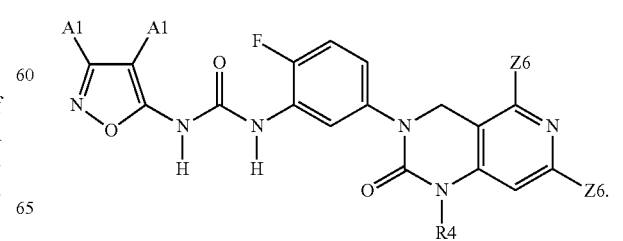

IIn

58. Compounds of claim 56 having formula IIo

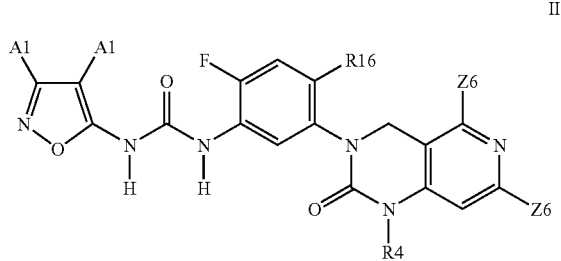

IIo wherein R16 is C1-C6alkyl, fluorine or chlorine.

59. Compounds of claim 45 having formula IIp

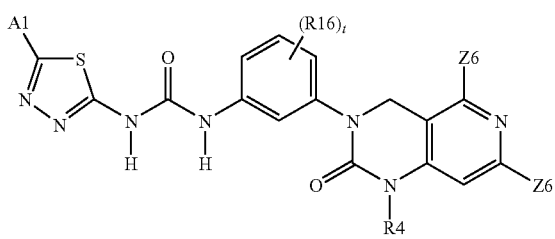

IIp wherein A1 is selected from the group consisting of Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, or halogen.

60. Compounds of claim 50 having formula IIq

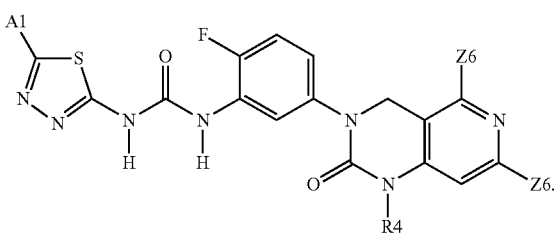

IIq

61. Compounds of claim 50 having formula IIr

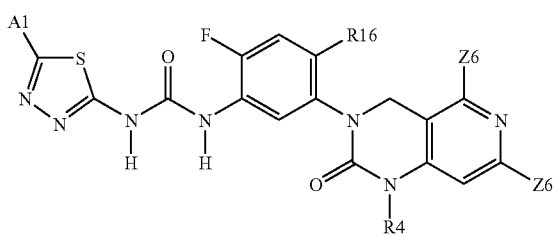

IIr and wherein R16 is methyl, fluorine or chlorine.

62. Compounds of claim 45 having formula IIs

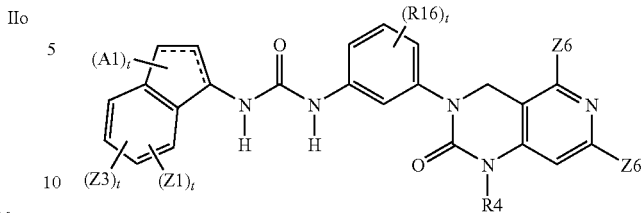

IIs wherein the hashed bond is a saturated or unsaturated bond;

and wherein A1 is selected from the group consisting of hydrogen, Z2-substituted branched C3-C8alkyl, R19 substituted C3-C8carbocyclyl, Z2-substituted C1-C6alkyl, halogen, cyano, C1-C6alkoxy, fluoroC1-C6alkoxy, fluoroC1-C6alkyl wherein the alkyl is fully or partially fluorinated, Z3-substituted phenyl, and Z3-substituted G1;

and wherein R16 is C1-C6alkyl, or halogen.

63. Compounds of claim 62 having formula IIt

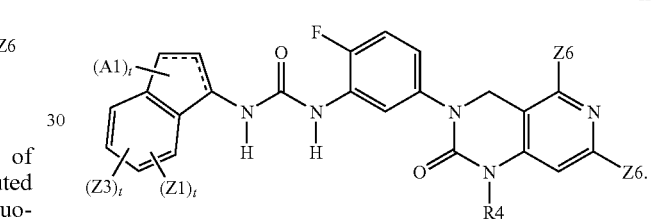

IIt

64. Compounds of claim 62 having formula IIu

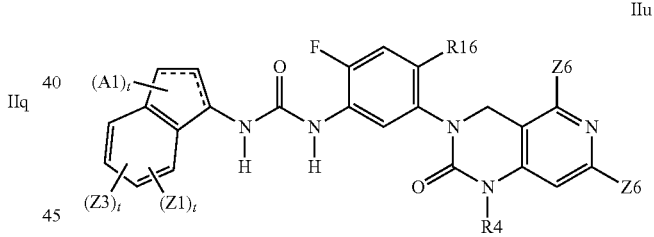

IIu and wherein R16 is C1-C6alkyl, fluorine or chlorine.

65. Compounds of claim 45 having formula IIv

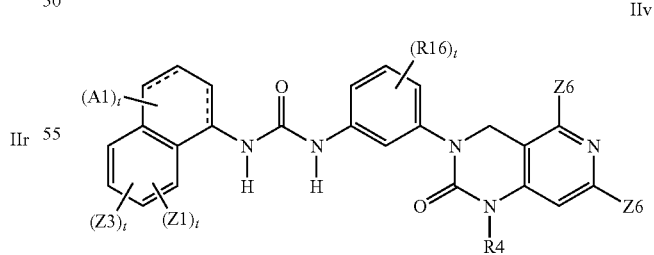

IIv wherein the hashed bond is a saturated or unsaturated bond;

and wherein A1 is selected from the group consisting of hydrogen, Z2-substituted branched C3-C8alkyl, R19 substituted C3-C8carbocyclyl, Z2-substituted C1-C6alkyl, halogen, cyano, C1-C6alkoxy, fluoroC1

-C6alkoxy, fluoroC1-C6alkyl wherein the alkyl is fully or partially fluorinated, Z3-substituted phenyl, and Z3-substituted G1;
and wherein R16 is C1-C6alkyl, or halogen.

66. Compounds of claim 65 having formula IIw

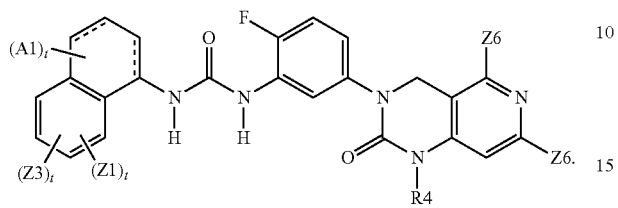

67. Compounds of claim 65 having formula IIx

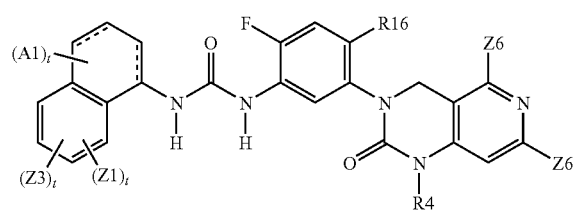

and wherein R16 is C1-C6alkyl, fluorine or chlorine.

68. Compounds of claim 45 having formula IIy

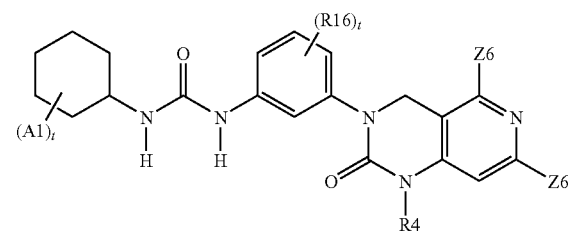

wherein A1 is selected from the group consisting of Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, or halogen.

69. Compounds of claim 68 having formula IIz

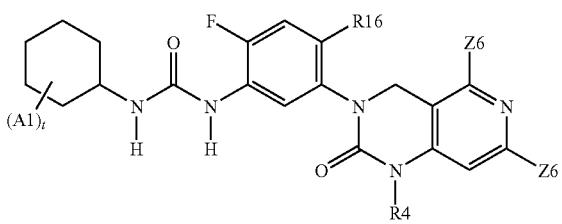

70. Compounds of claim 68 having formula IIaa

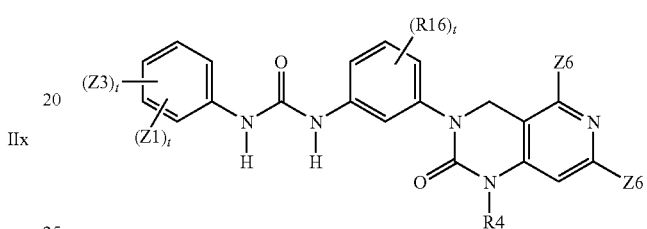

wherein R16 is methyl, fluorine or chlorine.

71. Compounds of claim 45 having formula IIbb

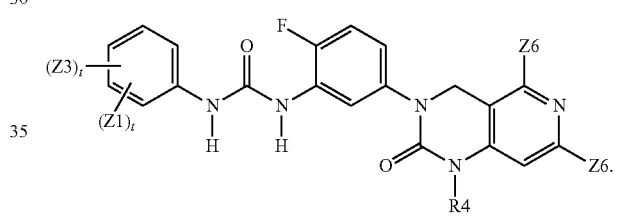

wherein R16 is C1-C6alkyl, or halogen.

72. Compounds of claim 71 having formula IIcc

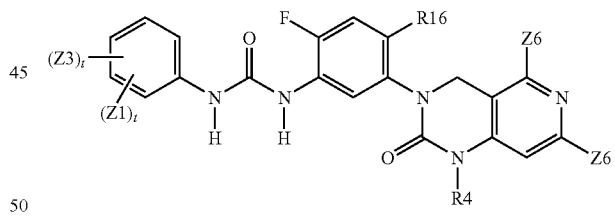

73. Compounds of claim 71 having formula IIdd

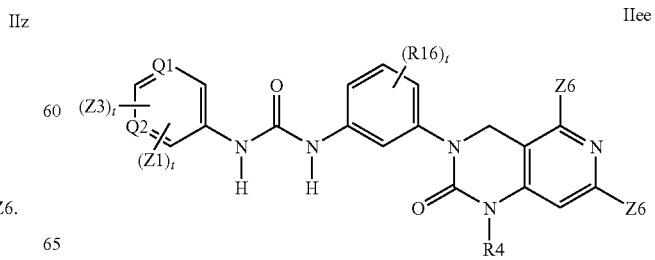

wherein R16 is C1-C6alkyl, fluorine or chlorine.

74. Compounds of claim 45 having formula IIee wherein Q1 and Q2 individually and independently taken from the group consisting of N and CH;
and wherein R16 is C1-C6alkyl, or halogen.

75. Compounds of claim 74 having formula IIff

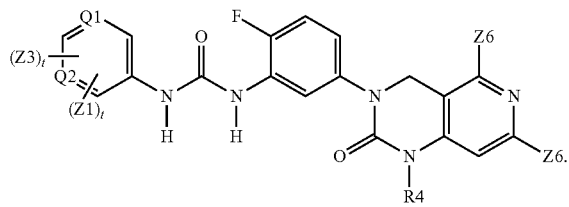

76. Compounds of claim 74 having formula IIgg

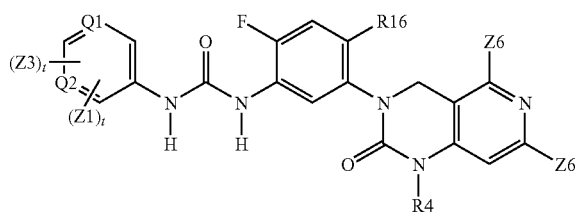

wherein R16 is C1-C6alkyl, fluorine or chlorine.

77. Compounds of claim 45 having formula IIhh

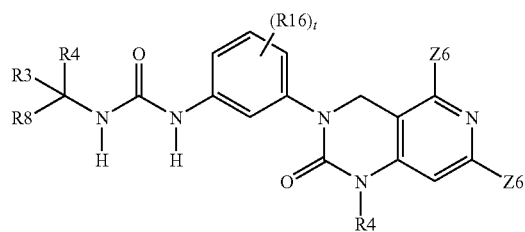

and wherein R16 is C1-C6alkyl, or halogen.

78. Compounds of claim 77 having formula IIii

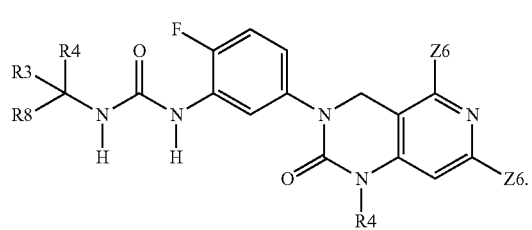

79. Compounds of claim 77 having formula IIjj

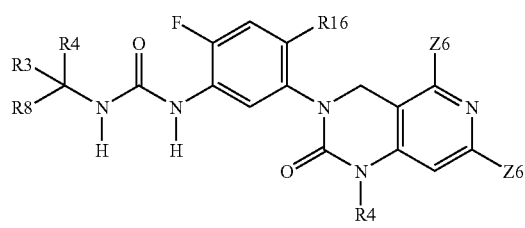

and wherein R16 is methyl, fluorine or chlorine.

80. Compounds of claim 45 having formula IIkk

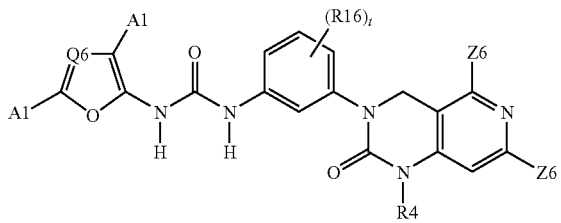

wherein Q6 is N or C-A1;
wherein A1 is selected from the group consisting of hydrogen, Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, or halogen.

81. Compounds of claim 80 having formula IIll

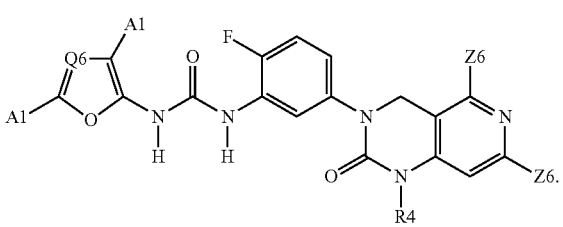

82. Compounds of claim 80 having formula IImm

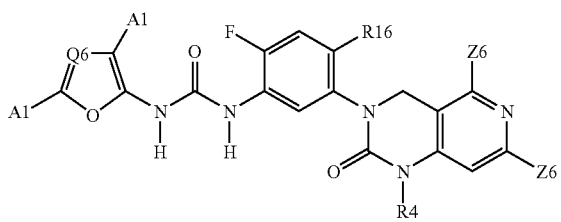

wherein R16 is C1-C6alkyl, fluorine or chlorine.

83. Compounds of claim 45 having formula IInn

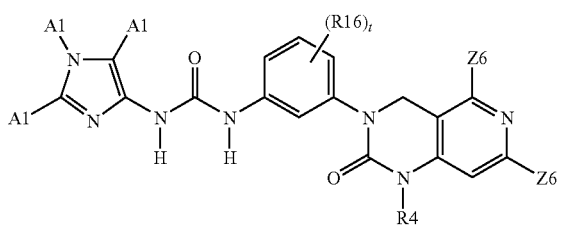

wherein A1 is selected from the group consisting of hydrogen, Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;
and wherein R16 is C1-C6alkyl, or halogen.

84. Compounds of claim 83 having formula IIoo

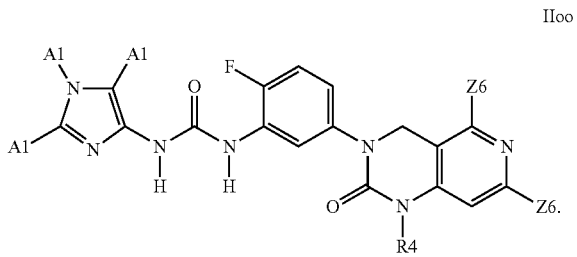

IIoo

85. Compounds of claim 83 having formula IIpp

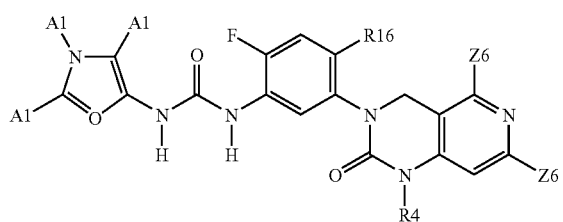

IIpp wherein R16 is C1-C6alkyl, fluorine or chlorine.

86. Compounds of claim 45 having formula IIqq

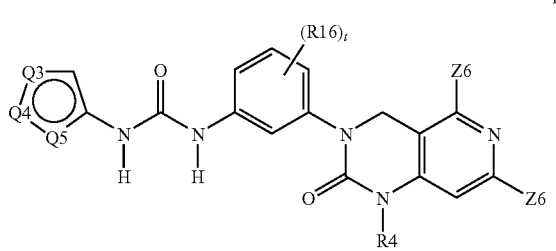

IIqq wherein Q3, Q4 and Q5 are selected from the group consisting of N—A1 and C-A1, and only one of Q3, Q4, or Q5 is N—A1;

wherein A1 is selected from the group consisting of hydrogen, Z2-substituted branched C3-C8alkyl, R19 substituted C3-C8carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, or halogen.

87. Compounds of claim 86 having formula IIrr

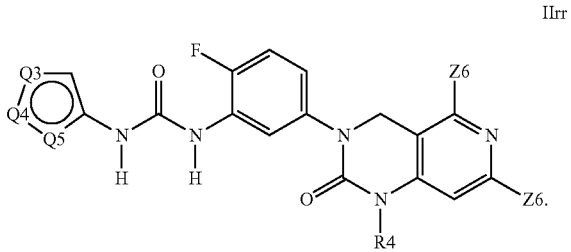

IIrr

88. Compounds of claim 86 having formula IIss

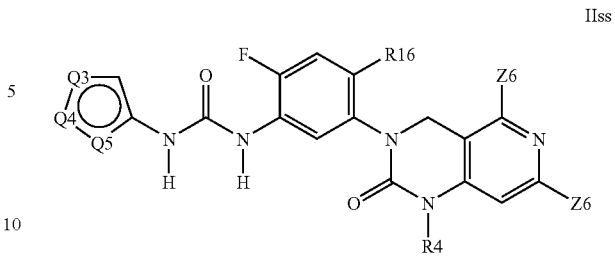

IIss wherein R16 is C1-C6alkyl, fluorine or chlorine.

89. A compound selected from the group consisting of 1-(5-(7-amino-1-methyl-2-oxo-1,2-dihydropyrimido[4,5-d]pyrimidin-3(4H)-yl)-2-fluorophenyl)-3-(3-tert-butyl-1-phenyl-1H-pyrazol-5-yl)urea, 1-(5-(7-amino-1-methyl-2-oxo-1,2-dihydropyrimido[4,5-d]pyrimidin-3(4H)-yl)-2-fluorophenyl)-3-(3-tert-butyl-1-methyl-1H-pyrazol-5-yl)urea, 1-(2-fluoro-5-(1-methyl-7-(methylamino)-2-oxo-1,2-dihydropyrimido[4,5-d]pyrimidin-3(4H)-yl)phenyl)-3-(1-phenyl-3-(trifluoromethyl)-1H-pyrazol-5-yl)urea, 1-(3-tert-butylphenyl)-3-(2-fluoro-5-(1-methyl-7-(methylamino)-2-oxo-1,2-dihydropyrimido[4,5-d]pyrimidin-3(4H)-yl)phenyl)urea, 1-(5-(7-amino-1-methyl-2-oxo-1,2-dihydropyrimido[4,5-d]pyrimidin-3(4H)-yl)-2-fluorophenyl)-3-(3-tert-butyl-1-(quinolin-6-yl)-1H-pyrazol-5-yl)urea, 1-(3-tert-butylisoxazol-5-yl)-3-(2-fluoro-5-(1-methyl-7-(methylamino)-2-oxo-1,2-dihydropyrimido[4,5-d]pyrimidin-3(4H)-yl)phenyl)urea, 1-(5-(1-ethyl-7-(methylamino)-2-oxo-1,2-dihydropyrimido[4,5-d]pyrimidin-3(4H)-yl)-2-fluorophenyl)-3-(1-phenyl-3-(trifluoromethyl)-1H-pyrazol-5-yl)urea, 1-(3-tert-butylisoxazol-5-yl)-3-(5-(1-ethyl-7-(methylamino)-2-oxo-1,2-dihydropyrimido[4,5-d]pyrimidin-3(4H)-yl)-2-fluorophenyl)urea, 1-(5-tert-butylisoxazol-3-yl)-3-(2-fluoro-4-methyl-5-(8-methyl-2-(methylamino)-7-oxo-7,8-dihydropteridin-6-yl)phenyl)urea, 1-(2-fluoro-4-methyl-5-(1-methyl-7-(methylamino)-2-oxo-1,2-dihydropyrimido[4,5-d]pyrimidin-3(4H)-yl)phenyl)-3-(1-phenyl-3-(trifluoromethyl)-1H-pyrazol-5-yl)urea, 1-(3-tert-butylisoxazol-5-yl)-3-(2-fluoro-4-methyl-5-(1-methyl-7-(methylamino)-2-oxo-1,2-dihydropyrimido[4,5-d]pyrimidin-3(4H)-yl)phenyl)urea, 1-(3-tert-butyl-1-methyl-1H-pyrazol-5-yl)-3-(2-fluoro-4-methyl-5-(1-methyl-7-(methylamino)-2-oxo-1,2-dihydropyrimido[4,5-d]pyrimidin-3(4H)-yl)phenyl)urea, 1-(3-tert-butylisoxazol-5-yl)-3-(5-(7-(2-(dimethylamino)ethylamino)-1-methyl-2-oxo-1,2-dihydropyrimido[4,5-d]pyrimidin-3(4H)-yl)-2-fluoro-4-methylphenyl)urea, 1-(5-tert-butylisoxazol-3-yl)-3-(2-fluoro-4-methyl-5-(1-methyl-7-(methylamino)-2-oxo-1,2-dihydropyrimido[4,5-d]pyrimidin-3(4H)-yl)phenyl)urea, 1-(2-fluoro-4-methyl-5-(1-methyl-7-(methylamino)-2-oxo-1,2-dihydropyrimido[4,5-d]pyrimidin-3(4H)-yl)phenyl)-3-(3-(trifluoromethyl)phenyl)urea, 1-(5-tert-butylisoxazol-3-yl)-3-(2-fluoro-5-(1-isopropyl-7-(methylamino)-2-oxo-1,2-dihydropyrimido[4,5-d]pyrimidin-3(4H)-yl)-4-methylphenyl)urea, 1-(3-tert-butylisoxazol-5-yl)-3-(2-fluoro-5-(1-isopropyl-7-(methylamino)-2-oxo-1,2-dihydropyrimido[4,5-d]pyrimidin-3(4H)-yl)-4-methylphenyl)urea, 1-(5-tert-butylisoxazol-3-yl)-3-(2-fluoro-5-(1-isopropyl-7-(methylamino)-2-oxo-1,2-dihydropyrimido[4,5-d]pyrimidin-3(4H)-yl)phenyl)urea, 1-(1-tert-butyl-1H-pyrazol-4-yl)-3-(2-fluoro-5-(1-isopropyl-7-(methylamino)-2-oxo-1,2-dihydropyrimido[4,5-d]pyrimidin-3(4H)-yl)-4-methylphenyl)urea, 1-(1-tert-butyl-1H- pyrazol-4-yl)-3-(2-fluoro-5-(1-isopropyl-7-(methylamino)-2-oxo-1,2-dihydropyrimido[4,5-d]pyrimidin-3(4H)-yl)phenyl)urea, 1-(3-tert-butyl-1-methyl-1H-pyrazol-5-yl)-3-(5-(1-ethyl-7-(methylamino)-2-oxo-1,2-dihydropyrimido[4,5-d]pyrimidin-3(4H)-yl)-2-fluorophenyl)urea, 1-(3-tert-butyl-1-phenyl-1H-pyrazol-5-yl)-3-(2-fluoro-4-methyl-5-(1-methyl-7-(methylamino)-2-oxo-1,2-dihydropyrimido[4,5-d]pyrimidin-3(4H)-yl)phenyl)urea, 1-(3-tert-butyl-1-(quinolin-6-yl)-1H-pyrazol-5-yl)-3-(2-fluoro-4-methyl-5-(1-methyl-7-(methylamino)-2-oxo-1,2-dihydropyrimido[4,5-d]pyrimidin-3(4H)-yl)phenyl)urea, 1-(4-chloro-3-(trifluoromethyl)phenyl)-3-(2-fluoro-5-(1-methyl-7-(methylamino)-2-oxo-1,2-dihydropyrimido[4,5-d]pyrimidin-3(4H)-yl)phenyl)urea, 1-(4-chloro-3-(trifluoromethyl)phenyl)-3-(2-fluoro-5-(1-isopropyl-7-(methylamino)-2-oxo-1,2-dihydropyrimido[4,5-d]pyrimidin-3(4H)-yl)phenyl)urea, 1-(2-fluoro-5-(1-methyl-7-(methylamino)-2-oxo-1,2-dihydropyrimido[4,5-d]pyrimidin-3(4H)-yl)phenyl)-3-(3-isopropyl-1-phenyl-1H-pyrazol-5-yl)urea, 1-(1-tert-butyl-1H-pyrazol-4-yl)-3-(4-chloro-2-fluoro-5-(1-methyl-7-(methylamino)-2-oxo-1,2-dihydropyrimido[4,5-d]pyrimidin-3(4H)-yl)phenyl)urea, 1-(4-chloro-5-(1-ethyl-7-(methylamino)-2-oxo-1,2-dihydropyrimido[4,5-d]pyrimidin-3(4H)-yl)-2-fluorophenyl)-3-(3-(trifluoromethyl)phenyl)urea, 1-(2-fluoro-4-methyl-5-(1-methyl-7-(methylamino)-2-oxo-1,2-dihydropyrimido[4,5-d]pyrimidin-3(4H)-yl)phenyl)-3-(3-(trifluoromethyl)isoxazol-5-yl)urea, 1-(5-(7-(2-(dimethylamino)ethylamino)-1-methyl-2-oxo-1,2-dihydropyrimido[4,5-d]pyrimidin-3(4H)-yl)-2-fluoro-4-methylphenyl)-3-(3-(trifluoromethyl)isoxazol-5-yl)urea, 1-(5-tert-butyl-1,3,4-thiadiazol-2-yl)-3-(2-fluoro-5-(1-methyl-7-(methylamino)-2-oxo-1,2-dihydropyrimido[4,5-d]pyrimidin-3(4H)-yl)phenyl)urea, 1-(2-tert-butyl-4-(piperazin-1-yl)pyrimidin-5-yl)-3-(2-fluoro-5-(1-methyl-7-(methylamino)-2-oxo-1,2-dihydropyrimido[4,5-d]pyrimidin-3(4H)-yl)phenyl)urea, 1-(5-tert-butylisoxazol-3-yl)-3-(2-fluoro-4-methyl-5-(8-methyl-2-(methylamino)-7-oxo-7,8-dihydropteridin-6-yl)phenyl)urea, 1-(3-tert-butyl-1-phenyl-1H-pyrazol-5-yl)-3-(2-fluoro-5-(1-methyl-7-(methylamino)-2-oxo-1,2-dihydropyrimido[4,5-d]pyrimidin-3(4H)-yl)phenyl)urea, 1-(5-(2-amino-8-methyl-7-oxo-7,8-dihydropteridin-6-yl)-2-fluorophenyl)-3-(3-tert-butyl-1-phenyl-1H-pyrazol-5-yl)urea, 1-(5-(2-amino-8-methyl-7-oxo-7,8-dihydropteridin-6-yl)-2-fluorophenyl)-3-(3-tert-butyl-1-methyl-1H-pyrazol-5-yl)urea, 1-(3-tert-butyl-1-phenyl-1H-pyrazol-5-yl)-3-(2-fluoro-5-(8-methyl-2-(methylamino)-7-oxo-7,8-dihydropteridin-6-yl)phenyl)urea, 1-(3-tert-butyl-4-methylisoxazol-5-yl)-3-(2-fluoro-4-methyl-5-(1-methyl-7-(methylamino)-2-oxo-1,2-dihydropyrimido[4,5-d]pyrimidin-3(4H)-yl)phenyl)urea, 1-(3-tert-butyl-4-methylisoxazol-5-yl)-3-(4-chloro-2-fluoro-5-(1-methyl-7-(methylamino)-2-oxo-1,2-dihydropyrimido[4,5-d]pyrimidin-3(4H)-yl)phenyl)urea, 1-(3-tert-butyl-4-methylisoxazol-5-yl)-3-(2,4-difluoro-5-(1-methyl-7-(methylamino)-2-oxo-1,2-dihydropyrimido[4,5-d]pyrimidin-3(4H)-yl)phenyl)urea, 1-(3-tert-butyl-4-fluoroisoxazol-5-yl)-3-(2-fluoro-4-methyl-5-(1-methyl-7-(methylamino)-2-oxo-1,2-dihydropyrimido[4,5-d]pyrimidin-3(4H)-yl)phenyl)urea, 1-(3-tert-butyl-4-chloroisoxazol-5-yl)-3-(2-fluoro-4-methyl-5-(1-methyl-7-(methylamino)-2-oxo-1,2-dihydropyrimido[4,5-d]pyrimidin-3(4H)-yl)phenyl)urea, 1-(1-tert-butyl-1H-imidazol-4-yl)-3-(2-fluoro-4-methyl-5-(1-methyl-7-(methylamino)-2-oxo-1,2-dihydropyrimido[4,5-d]pyrimidin-3(4H)-yl)phenyl)urea, 1-(1-tert-butyl-1H-imidazol-4-yl)-3-(4-chloro-2-fluoro-5-(1-methyl-7-(methylamino)-2-oxo-1,2-dihydropyrimido[4,5-d]pyrimidin-3(4H)-yl)phenyl)urea, 1-(1-tert-butyl-1H-imidazol-4-yl)-3-(5-(1-ethyl-7-(methylamino)-2-oxo-1,2-dihydropyrimido[4,5-d]pyrimidin-3(4H)-yl)-2-fluorophenyl)urea, 1-(1-tert-butyl-5-methyl-1H-imidazol-4-yl)-3-(2-fluoro-4-methyl-5-(1-methyl-7-(methylamino)-2-oxo-1,2-dihydropyrimido[4,5-d]pyrimidin-3(4H)-yl)phenyl)urea, 1-(1-tert-butyl-5-methyl-1H-imidazol-4-yl)-3-(4-chloro-2-fluoro-5-(1-methyl-7-(methylamino)-2-oxo-1,2-dihydropyrimido[4,5-d]pyrimidin-3(4H)-yl)phenyl)urea, 1-(1-tert-butyl-2-methyl-1H-imidazol-4-yl)-3-(2-fluoro-4-methyl-5-(1-methyl-7-(methylamino)-2-oxo-1,2-dihydropyrimido[4,5-d]pyrimidin-3(4H)-yl)phenyl)urea, 1-(5-(1-ethyl-7-(methylamino)-2-oxo-1,2-dihydropyrimido[4,5-d]pyrimidin-3(4H)-yl)-2-fluorophenyl)-3-(5-(trifluoromethyl)pyridin-3-yl)urea, 1-(2-fluoro-4-methyl-5-(1-methyl-7-(methylamino)-2-oxo-1,2-dihydropyrimido[4,5-d]pyrimidin-3(4H)-yl)phenyl)-3-(5-(trifluoromethyl)pyridin-3-yl)urea, 1-(4-chloro-2-fluoro-5-(1-methyl-7-(methylamino)-2-oxo-1,2-dihydropyrimido[4,5-d]pyrimidin-3(4H)-yl)phenyl)-3-(5-(trifluoromethy)pyridin-3-yl)urea, 1-(5-(1-ethyl-7-(methylamino)-2-oxo-1,2-dihydropyrimido[4,5-d]pyrimidin-3(4H)-yl)-2-fluorophenyl)-3-(2-fluoro-5-(trifluoromethyl)phenyl)urea, 1-(5-tert-butyl-1,3,4-thiadiazol-2-yl)-3-(2-fluoro-4-methyl-5-(1-methyl-7-(methylamino)-2-oxo-1,2-dihydropyrimido[4,5-d]pyrimidin-3(4H)-yl)phenyl)urea, 1-(5-(7-amino-l-methyl-2-oxo-1,2-dihydropyrimido[4,5-d]pyrimidin-3(4H)-yl)-2-fluoro-4-methylphenyl)-3-(3-tert-butylisoxazol-5-yl)urea, 1-(5-(7-amino-l-ethyl-2-oxo-1,2-dihydropyrimido[4,5-d]pyrimidin-3(4H)-yl)-2-fluorophenyl)-3-(3-tert-butylisoxazol-5-yl)urea, 1-(3-tert-butylisoxazol-5-yl)-3-(4-chloro-5-(1-ethyl-7-(methylamino)-2-oxo-1,2-dihydropyrimido[4,5-d]pyrimidin-3(4H)-yl)-2-fluorophenyl)urea, 1-(3-tert-butylisoxazol-5-yl)-3-(5-(1-ethyl-7-(methylamino)-2-oxo-1,2-dihydropyrimido[4,5-d]pyrimidin-3(4H)-yl)-2,4-difluorophenyl)urea, 1-(3-tert-butylisoxazol-5-yl)-3-(5-(1-cyclopentyl-7-(methylamino)-2-oxo-1,2-dihydropyrimido[4,5-d]pyrimidin-3(4H)-yl)-2-fluorophenyl)urea, 1-(3-tert-butylisoxazol-5-yl)-3-(2,4-difluoro-5-(7-(methylamino)-2-oxo-l-phenyl-1,2-dihydropyrimido[4,5-d]pyrimidin-3(4H)-yl)phenyl)urea, 1-(5-(1-ethyl-7-(methylamino)-2-oxo-1,2-dihydropyrimido[4,5-d]pyrimidin-3(4H)-yl)-2-fluorophenyl)-3-(3-isopropyl-isoxazol-5-yl)urea, 1-(5-(1-ethyl-7-(methylamino)-2-oxo-1,2-dihydropyrimido[4,5-d]pyrimidin-3(4H)-yl)-2-fluoro-4-methylphenyl)-3-(3-isopropylisoxazol-5-yl)urea, 1-(4-chloro-5-(1-ethyl-7-(methylamino)-2-oxo-1,2-dihydropyrimido[4,5-d]pyrimidin-3(4H)-yl)-2-fluorophenyl)-3-(3-isopropylisoxazol-5-yl)urea, 1-(bicyclo[2.2.1]heptan-2-yl)-3-(2-fluoro-4-methyl-5-(1-methyl-7-(methylamino)-2-oxo-1,2-dihydropyrimido[4,5-d]pyrimidin-3(4H)-yl)phenyl)urea, 1-(bicyclo[2.2.1]hept-5-en-2-yl)-3-(2-fluoro-4-methyl-5-(1-methyl-7-(methylamino)-2-oxo-1,2-dihydropyrimido[4,5-d]pyrimidin-3(4H)-yl)phenyl)urea, and 1-(3-tert-butylisoxazol-5-yl)-3-(5-(1-ethyl-7-(methylamino)-2-oxo-1,2-dihydropyrimido[4,5-d]pyrimidin-3(4H)-yl)-2-fluoro-4-methylphenyl)urea, and salts thereof.

90. A compound selected from the group consisting of 1-(2-fluoro-5-(1-methyl-7-(methylamino)-2-oxo-1,2-dihydropyrido[4,3-d]pyrimidin-3(4H)-yl)phenyl)-3-(1-phenyl-3-(trifluoromethyl)-1H-pyrazol-5-yl)urea, 1-(1-tert-butyl-1H-pyrazol-4-yl)-3-(2-fluoro-5-(1-methyl-7-(methylamino)-2-oxo-1,2-dihydropyrido[4,3-d]pyrimidin-3(4H)-yl)phenyl)urea, 1-(3-tert-butyl-1-methyl-1H-pyrazol-5-yl)-3-(2-fluoro-4-methyl-5-(1-methyl-7-(methylamino)-2-oxo-1,2-dihydropyrido[4,3-d]pyrimidin-3(4H)-yl)phenyl)

urea, 1-(3-tert-butylisoxazol-5-yl)-3-(2-fluoro-4-methyl-5-(1-methyl-7-(methylamino)-2-oxo-1,2-dihydropyrido[4,3-d]pyrimidin-3(4H)-yl)phenyl)urea, 1-(5-tert-butylisoxazol-3-yl)-3-(2-fluoro-4-methyl-5-(1-methyl-7-(methylamino)-2-oxo-1,2-dihydropyrido[4,3-d]pyrimidin-3(4H)-yl)phenyl)urea, 1-(1-tert-butyl-1H-pyrazol-4-yl)-3-(2-fluoro-4-methyl-5-(1-methyl-7-(methylamino)-2-oxo-1,2-dihydropyrido[4,3-d]pyrimidin-3(4H)-yl)phenyl)urea, 1-(3-tert-butylisoxazol-5-yl)-3-(4-chloro-2-fluoro-5-(1-methyl-7-(methylamino)-2-oxo-1,2-dihydropyrido[4,3-d]pyrimidin-3(4H)-yl)phenyl)urea, 1-(5-tert-butylisoxazol1-3-yl)-3-(2-fluoro-5-(1-isopropyl-7-(methylamino)-2-oxo-1,2-dihydropyrido[4,3-d]pyrimidin-3(4H)-yl)-4-methylphenyl)urea, 1-(3-tert-butylisoxazol-5-yl)-3-(2-fluoro-5-(1-isopropyl-7-(methylamino)-2-oxo-1,2-dihydropyrido[4,3-d]pyrimidin-3(4H)-yl)-4-methylphenyl)urea, 1-(1-tert-butyl-1H-pyrazol-4-yl)-3-(2-fluoro-5-(1-isopropyl-7-(methylamino)-2-oxo-1,2-dihydropyrido[4,3-d]pyrimidin-3(4H)-yl)-4-methylphenyl)urea, 1-(4-chloro-2-fluoro-5-(1-methyl-7-(methylamino)-2-oxo-1,2-dihydropyrido[4,3-d]pyrimidin-3(4H)-yl)phenyl)-3-(3-(trifluoromethyl)phenyl)urea,1-(3-tert-butylisoxazol-5-yl)-3-(2-fluoro-5-(1-isopropyl-7-(methylamino)-2-oxo-1,2-dihydropyrido[4,3-d]pyrimidin-3(4H)-yl)phenyl)urea, 1-(4-chloro-2-fluoro-5-(1-methyl-7-(methylamino)-2-oxo-1,2-dihydropyrido[4,3-d]pyrimidin-3(4H)-yl)phenyl)-3-(3-isopropyl-1-phenyl-1H-pyrazol-5-yl)urea, 1-(1-tert-butyl-1H-pyrazol-4-yl)-3-(5-(7-(2-(dimethylamino)ethylamino)-1-methyl-2-oxo-1,2-dihydropyrido[4,3-d]pyrimidin-3(4H)-yl)-2-fluoro-4-methylphenyl)urea, 1-(3-tert-butylisoxazol-5-yl)-3-(5-(1-ethyl-7-(methylamino)-2-oxo-1,2-dihydropyrido[4,3-d]pyrimidin-3(4H)-yl)-2-fluoro-4-methylphenyl)urea, 1-(3-tert-butylisoxazol-5-yl)-3-(4-chloro-5-(1-ethyl-7-(methylamino)-2-oxo-1,2-dihydropyrido[4,3-d]pyrimidin-3(4H)-yl)-2-fluorophenyl)urea, 1-(5-(1-ethyl-7-(methylamino)-2-oxo-1,2-dihydropyrido[4,3-d]pyrimidin-3(4H)-yl)-2-fluoro-4-methylphenyl)-3-(3-(trifluoromethyl)phenyl)urea, 1-(1-tert-butyl-5-methyl-1H-pyrazol-4-yl)-3-(2-fluoro-5-(1-isopropyl-7-(methylamino)-2-oxo-1,2-dihydropyrido[4,3-d]pyrimidin-3(4H)-yl)-4-methylphenyl)urea, 1-(3-tert-butyl-1-methyl-1H-pyrazol-5-yl)-3-(5-(1-ethyl-7-(methylamino)-2-oxo-1,2-dihydropyrido[4,3-d]pyrimidin-3(4H)-yl)-2-fluorophenyl)urea, 1-(3-tert-butylisoxazol-5-yl)-3-(5-(1-ethyl-7-(methylamino)-2-oxo-1,2-dihydropyrido[4,3-d]pyrimidin-3(4H)-yl)-2-fluorophenyl)urea, 1-(1-tert-butyl-1H-pyrazol-4-yl)-3-(5-(1-ethyl-7-(methylamino)-2-oxo-1,2-dihydropyrido[4,3-d]pyrimidin-3(4H)-yl)-2-fluorophenyl)urea, 1-(5-(7-(2-(dimethylamino)ethylamino)-1-methyl-2-oxo-1,2-dihydropyrido[4,3-d]pyrimidin-3(4H)-yl)-2-fluoro-4-methylphenyl)-3-(3-(trifluoromethyl)isoxazol-5-yl)urea, 1-(5-(1-ethyl-7-(methylamino)-2-oxo-1,2-dihydropyrido[4,3-d]pyrimidin-3(4H)-yl)-2-fluoro-4-methylphenyl)-3-(naphthalen-1-yl)urea, 1-(5-(1-ethyl-7-(methylamino)-2-oxo-1,2-dihydropyrido[4,3-d]pyrimidin-3(4H)-yl)-2-fluorophenyl)-3-(naphthalen-1-yl)urea, 1-(4-chloro-5-(1-ethyl-7-(methylamino)-2-oxo-1,2-dihydropyrido[4,3-d]pyrimidin-3(4H)-yl)-2-fluorophenyl)-3-(naphthalen-l-yl)urea, 1-(2-fluoro-5-(1-isopropyl-7-(methylamino)-2-oxo-1,2-dihydropyrido[4,3-d]pyrimidin-3(4H)-yl)phenyl)-3-(3-(trifluoromethyl)phenyl)urea, 1-(4-chloro-3-(trifluoromethyl)phenyl)-3-(2-fluoro-5-(1-methyl-7-(methylamino)-2-oxo-1,2-dihydropyrido[4,3-d]pyrimidin-3(4H)-yl)phenyl)urea, 1-cyclohexyl-3-(5-(1-ethyl-7-(methylamino)-2-oxo-1,2-dihydropyrido[4,3-d]pyrimidin-3(4H)-yl)-2-fluorophenyl)urea, 1-(4-chloro-3-(trifluoromethyl)phenyl)-3-(2-fluoro-5-(1-methyl-7-(methylamino)-2-oxo-1,2-dihydropyrido[4,3-d]pyrimidin-3(4H)-yl)phenyl)urea, 1-cyclohexyl-3-(2-fluoro-5-(1-isopropyl-7-(methylamino)-2-oxo-1,2-dihydropyrido[4,3-d]pyrimidin-3(4H)-yl)phenyl)urea, 1-cyclohexyl-3-(2-fluoro-5-(1-methyl-7-(methylamino)-2-oxo-1,2-dihydropyrido[4,3-d]pyrimidin-3(4H)-yl)phenyl)urea, 1-(5-(1-tert-butyl-7-(methylamino)-2-oxo-1,2-dihydropyrido[4,3-d]pyrimidin-3(4H)-yl)-2-fluorophenyl)-3-(3-tert-butylisoxazol-5-yl)urea, 1-(4-chloro-5-(1-ethyl-7-(methylamino)-2-oxo-1,2-dihydropyrido[4,3-d]pyrimidin-3(4H)-yl)-2-fluorophenyl)-3-(3-(trifluoromethyl)phenyl)urea, 1-(4-chloro-5-(1-ethyl-7-(methylamino)-2-oxo-1,2-dihydropyrido[4,3-d]pyrimidin-3(4H)-yl)-2-fluorophenyl)-3-(2,3-difluorophenyl)urea, 1-(3-tert-butyl-1-methyl-1H-pyrazol-5-yl)-3-(2-fluoro-5-(1-methyl-7-(methylamino)-2-oxo-1,2-dihydropyrimido[4,5-d]pyrimidin-3(4H)-yl)phenyl)urea, 1-(5-(7-amino-l-methyl-2-oxo-1,2-dihydropyrido[4,3-d]pyrimidin-3(4H)-yl)-2-fluorophenyl)-3-(3-tert-butyl-1-phenyl-1H-pyrazol-5-yl)urea, 1-(5-(7-amino-l-methyl-2-oxo-1,2-dihydropyrido[4,3-d]pyrimidin-3(4H)-yl)-2-fluorophenyl)-3-(3-tert-butyl-1-methyl-1H-pyrazol-5-yl)urea, 1-(3-tert-butyl-1-phenyl-1H-pyrazol-5-yl)-3-(2-fluoro-5-(1-methyl-7-(methylamino)-2-oxo-1,2-dihydropyrido[4,3-d]pyrimidin-3(4H)-yl)phenyl)urea, 1-(3-tert-butyl-1-methyl-1H-pyrazol-5-yl)-3-(2-fluoro-5-(1-methyl-7-(methylamino)-2-oxo-1,2-dihydropyrido[4,3-d]pyrimidin-3(4H)-yl)phenyl)urea, 1-(5-(7-amino-1-methyl-2-oxo-1,2-dihydropyrido[4,3-d]pyrimidin-3(4H)-yl)-2-fluorophenyl)-3-(3-tert-butyl-1-phenyl-1H-pyrazol-5-yl)urea, 1-(3-tert-butyl-1-phenyl-1H-pyrazol-5-yl)-3-(2-fluoro-5-(1-methyl-7-(methylamino)-2-oxo-1,2-dihydropyrido[4,3-d]pyrimidin-3(4H)-yl)phenyl)urea, 1-(3-tert-butyl-4-methylisoxazol-5-yl)-3-(2-fluoro-4-methyl-5-(1-methyl-7-(methylamino)-2-oxo-1,2-dihydropyrido[4,3-d]pyrimidin-3(4H)-yl)phenyl)urea, 1-(3-tert-butyl-4-methylisoxazol-5-yl)-3-(4-chloro-2-fluoro-5-(1-methyl-7-(methylamino)-2-oxo-1,2-dihydropyrido[4,3-d]pyrimidin-3(4H)-yl)phenyl)urea, 1-(3-tert-butyl-4-methylisoxazol-5-yl)-3-(2,4-difluoro-5-(1-methyl-7-(methylamino)-2-oxo-1,2-dihydropyrido[4,3-d]pyrimidin-3(4H)-yl)phenyl)urea, 1-(3-tert-butyl-4-fluoroisoxazol-5-yl)-3-(2-fluoro-4-methyl-5-(1-methyl-7-(methylamino)-2-oxo-1,2-dihydropyrido[4,3-d]pyrimidin-3(4H)-yl)phenyl)urea, 1-(3-tert-butyl-4-chloroisoxazol-5-yl)-3-(2-fluoro-4-methyl-5-(1-methyl-7-(methylamino)-2-oxo-1,2-dihydropyrido[4,3-d]pyrimidin-3(4H)-yl)phenyl)urea, 1-(3-tert-butyl-4-fluoroisoxazol-5-yl)-3-(5-(1-ethyl-7-(methylamino)-2-oxo-1,2-dihydropyrido[4,3-d]pyrimidin-3(4H)-yl)-2-fluorophenyl)urea, 1-(3-tert-butyl-4-chloroisoxazol-5-yl)-3-(5-(1-ethyl-7-(methylamino)-2-oxo-1,2-dihydropyrido[4,3-d]pyrimidin-3(4H)-yl)-2-fluorophenyl)urea, 1-(1-tert-butyl-1H-imidazol-4-yl)-3-(2-fluoro-4-methyl-5-(1-methyl-7-(methylamino)-2-oxo-1,2-dihydropyrido[4,3-d]pyrimidin-3(4H)-yl)phenyl)urea, 1-(1-tert-butyl-1H-imidazol-4-yl)-3-(4-chloro-2-fluoro-5-(1-methyl-7-(methylamino)-2-oxo-1,2-dihydropyrido[4,3-d]pyrimidin-3(4H)-yl)phenyl)urea, 1-(1-tert-butyl-1H-imidazol-4-yl)-3-(5-(1-ethyl-7-(methylamino)-2-oxo-1,2-dihydropyrido[4,3-d]pyrimidin-3(4H)-yl)-2-fluorophenyl)urea, 1-(1-tert-butyl-5-methyl-1H-imidazol-4-yl)-3-(2-fluoro-4-methyl-5-(1-methyl-7-(methylamino)-2-oxo-1,2-dihydropyrido[4,3-d]pyrimidin-3(4H)-yl)phenyl)urea, 1-(1-tert-butyl-5-methyl-1H-imidazol-4-yl)-3-(4-chloro-2-fluoro-5-(1-methyl-7-(methylamino)-2-oxo-1,2-dihydropyrido[4,3-d]pyrimidin-3(4H)-yl)phenyl)urea, 1-(1-tert-butyl-2-methyl-1H-imidazol-4-yl)-3-(2-fluoro-4-methyl-5-(1-methyl-7-(methylamino)-2-oxo-1,2-dihydropyrido[4,3-d]pyrimidin-3(4H)-yl)phenyl)urea, 1-(2-fluoro-5-(1-methyl-7-(methylamino)-2-oxo-1,2- dihydropyrido[4,3-d]pyrimidin-3(4H)-yl)phenyl)-3-(5-(trifluoromethyl)pyridin-3-yl)urea, 1-(5-(1-ethyl-7-(methylamino)-2-oxo-1,2-dihydropyrido[4,3-d]pyrimidin-3 (4H)-yl)-2-fluorophenyl)-3-(5-(trifluoromethyl)pyridin-3-yl)urea, (2-fluoro-4-methyl-5-(1-methyl-7-(methylamino)-2-oxo-1,2-dihydropyrido[4,3-d]pyrimidin-3(4H)-yl) phenyl)-3-(5-(trifluoromethyl)pyridin-3-yl)urea, 1-(4-chloro-2-fluoro-5-(1-methyl-7-(methylamino)-2-oxo-1,2-dihydropyrido[4,3-d]pyrimidin-3(4H)-yl)phenyl)-3-(5-(trifluoromethyl)pyridin-3-yl)urea, 1-(2-fluoro-5-(1-(2-hydroxyethyl)-7-(methylamino)-2-oxo-1,2-dihydropyrido [4,3-d]pyrimidin-3(4H)-yl)-4-methylphenyl)-3-(3-(trifluoromethyl)phenyl)urea, 1-(5-(1-ethyl-7-(methylamino)-2-oxo-1,2-dihydropyrido[4,3-d9 pyrimidin-3(4H)-yl)-2-fluorophenyl)-3-(2-fluoro-5-(trifluoromethyl) phenyl)urea, (2-fluoro-4-methyl-5-(1-methyl-7-(methylamino)-2-oxo-1,2-dihydropyrido[4,3-d]pyrimidin-3 (4H)-yl)phenyl)-3-(2-fluoro-5-(trifluoromethyl)phenyl)urea, 1-(4-tert-butylthiophen-2-yl)-3-(2-fluoro-4-methyl-5-(1-methyl-7-(methylamino)-2-oxo-1,2-dihydropyrido[4,3-d] pyrimidin-3(4H)-yl)phenyl)urea, 1-(4-tert-butyl-3-methylthiophen-2-yl)-3-(2-fluoro-4-methyl-5-(1-methyl-7-(methylamino)-2-oxo-1,2-dihydropyrido[4,3-d]pyrimidin-3 (4H)-yl)phenyl)urea, 1-(4-tert-butyl-3-chlorothiophen-2-yl)-3-(2-fluoro-4-methyl-5-(1-methyl-7-(methylamino)-2-oxo-1,2-dihydropyrido[4,3-d]pyrimidin-3(4H)-yl)phenyl) urea, 1-(4-tert-butyl-3-fluorothiophen-2-yl)-3-(2-fluoro-4-methyl-5-(1-methyl-7-(methylamino)-2-oxo-1,2-dihydropyrido[4,3-d]pyrimidin-3(4H)-yl)phenyl)urea, 1-(1-tert-butyl-5-methyl-1H-pyrazol-4-yl)-3-(2-fluoro-4-methyl-5-(1-methyl-7-(methylamino)-2-oxo-1,2-dihydropyrido[4,3-d]pyrimidin-3(4H)-yl)phenyl)urea, 1-(3-tert-butylisoxazol-5-yl)-3-(2-fluoro-5-(1-methyl-7-(methylamino)-2-oxo-1,2-dihydropyrido[4,3-d]pyrimidin-3 (4H)-yl)phenyl)urea, 1-(3-tert-butylisoxazol1-5-yl)-3-(5-(1-cyclopentyl-7-(methylamino)-2-oxo-1,2-dihydropyrido[4,3-d]pyrimidin-3(4H)-yl)-2-fluorophenyl)urea, 1-(3-tert-butylisoxazol-5-yl)-3-(2-fluoro-5-(1-(2-hydroxyethyl)-7-(methylamino)-2-oxo-1,2-dihydropyrido[4,3-d]pyrimidin-3 (4H)-yl)-4-methylphenyl)urea, 1-(3-tert-butylisoxazol-5-yl)-3-(2-fluoro-5-(1-(2-hydroxyethyl)-7-(methylamino)-2-oxo-1,2-dihydropyrido[4,3-d]pyrimidin-3(4H)-yl)phenyl) urea, 1-(3-tert-butylisoxazol-5-yl)-3-(2-fluoro-5-(1-(2-hydroxyethyl)-7-(methylamino)-2-oxo-1,2-dihydropyrimido[4,5-d]pyrimidin-3(4H)-yl)phenyl)urea, 1-(3-tert-butylisoxazol-5-yl)-3-(4-chloro-5-(1-ethyl-7-(methylamino)-2-oxo-1,2-dihydropyrido[4,3-d]pyrimidin-3 (4H)-yl)-2-fluorophenyl)urea, 1-(3-tert-butylisoxazol-5-yl)-3-(5-(1-ethyl-7-(methylamino)-2-oxo-1,2-dihydropyrido[4,3-d]pyrimidin-3(4H)-yl)-2,4-difluorophenyl)urea, 1-(3-tert-butylisoxazol1-5-yl)-3-(5-(1-cyclopentyl-7-(methylamino)-2-oxo-1,2-dihydropyrido[4,3-d]pyrimidin-3(4H)-yl)-2-fluorophenyl)urea, 1-(3-tert-butylisoxazol-5-yl)-3-(2,4-difluoro-5-(7-(methylamino)-2-oxo-l-phenyl-1,2-dihydropyrido[4,3-d]pyrimidin-3(4H)-yl)phenyl)urea, 1-(5-(1-ethyl-7-(methylamino)-2-oxo-1,2-dihydropyrido[4,3-d]pyrimidin-3(4H)-yl)-2-fluorophenyl)-3-(3-isopropylisoxazol-5-yl)urea, 1-(5-(1-ethyl-7-(methylamino)-2-oxo-1,2-dihydropyrido[4,3-d]pyrimidin-3 (4H)-yl)-2-fluoro-4-methylphenyl)-3-(3-isopropylisoxazol-5-yl)urea, 1-(4-chloro-5-(1-ethyl-7-(methylamino)-2-oxo-1,2-dihydropyrido[4,3-d]pyrimidin-3(4H)-yl)-2-fluorophenyl)-3-(3-isopropylisoxazol-5-yl)urea, 1-(1-tert-butyl-2-methyl-1H-pyrrol-3-yl)-3-(2-fluoro-4-methyl-5-(1-methyl-7-(methylamino)-2-oxo-1,2-dihydropyrido[4,3-d] pyrimidin-3(4H)-yl)phenyl)urea, 1-(1-tert-butyl-2-methyl-1H-pyrrol-3-yl)-3-(4-chloro-2-fluoro-5-(1-methyl-7-(methylamino)-2-oxo-1,2-dihydropyrido[4,3-d]pyrimidin-3 (4H)-yl)phenyl)urea, 1-(4-tert-butylfuran-2-yl)-3-(2-fluoro-4-methyl-5-(1-methyl-7-(methylamino)-2-oxo-1,2-dihydropyrido[4,3-d]pyrimidin-3(4H)-yl)phenyl)urea, 1-(2-tert-butyloxazol-5-yl)-3-(2-fluoro-4-methyl-5-(1-methyl-7-(methylamino)-2-oxo-1,2-dihydropyrido[4,3-d]pyrimidin-3 (4H)-yl)phenyl)urea, 1-cyclohexyl-3-(5-(1-ethyl-7-(methylamino)-2-oxo-1,2-dihydropyrido[4,3-d]pyrimidin-3 (4H)-yl)-2-fluoro-4-methylphenyl)urea, 1-(2-fluoro-4-methyl-5-(1-methyl-7-(methylamino)-2-oxo-1,2-dihydropyrido[4,3-d]pyrimidin-3(4H)-yl)phenyl)-3-((1R,2R)-2-methylcyclohexyl)urea, 1-(5-(1-ethyl-7-(methylamino)-2-oxo-1,2-dihydropyrimido[4,5-d] pyrimidin-3(4H)-yl)-2-fluorophenyl)-3-((1S,2S)-2-methylcyclohexyl)urea, 1-cyclohexyl-3-(5-(1-cyclopentyl-7-(methylamino)-2-oxo-1,2-dihydropyrido[4,3-d] pyrimidin-3(4H)-yl)-2-fluorophenyl)urea, 1-cyclopropyl-3-(2-fluoro-4-methyl-5-(1-methyl-7-(methylamino)-2-oxo-1,2-dihydropyrido[4,3-d]pyrimidin-3(4H)-yl)phenyl)urea, 1-(2-fluoro-4-methyl-5-(1-methyl-7-(methylamino)-2-oxo-1,2-dihydropyrido[4,3-d]pyrimidin-3(4H)-yl)phenyl)-3-isopropylurea, 1-(2-fluoro-4-methyl-5-(1-methyl-7-(methylamino)-2-oxo-1,2-dihydropyrido[4,3-d]pyrimidin-3(4H)-yl)phenyl)-3-(1-(pyridin-3-yl)ethyl)urea, (R)-1-(2-fluoro-4-methyl-5-(1-methyl-7-(methylamino)-2-oxo-1,2-dihydropyrido[4,3-d]pyrimidin-3(4H)-yl)phenyl)-3-(1-phenylethyl)urea, and (S)-1-(2-fluoro-4-methyl-5-(1-methyl-7-(methylamino)-2-oxo-1,2-dihydropyrido[4,3-d] pyrimidin-3(4H)-yl)phenyl)-3-(1-phenylethyl)urea, and salts thereof.

91. A pharmaceutical composition comprising a compound of claims 1, 45, 89 or 90 and salts thereof, together with a pharmaceutically acceptable carrier, said carrier including an additive selected from the group including adjuvants, excipients, diluents, and stablilizers.

92. 1-(3-tert-butylisoxazol-5-yl)-3-(5-(1-ethyl-7-(methylamino)-2-oxo-1,2-dihydropyrimido[4,5-d]pyrimidin-3(4H)-yl)-2-fluorophenyl)urea, or a salt thereof.

93. A pharmaceutical composition comprising a compound of claim 92, together with a pharmaceutically acceptable carrier, said carrier including an additive selected from the group including adjuvants, excipients, diluents, and stablilizers.

* * * * *

UNITED STATES PATENT AND TRADEMARK OFFICE
CERTIFICATE OF CORRECTION

PATENT NO. : 7,897,762 B2
APPLICATION NO. : 11/854293
DATED : March 1, 2011
INVENTOR(S) : Daniel L. Flynn et al.

It is certified that error appears in the above-identified patent and that said Letters Patent is hereby corrected as shown below:

First Page, Col. 2, Other Publications, Line 24: Delete "Therpeutics" and insert -- Therapeutics --, therefor.

First Page, Col. 2, Other Publications, Line 32: Delete "Triatylbismuth" and insert -- Triarylbismuth --, therefor.

First Page, Col. 2, Abstract, Line 6: Delete "Preferrably," and insert -- Preferably, --, therefor.

Column 112, Line 41, In Claim 1, delete "$(R^3)_2N$" and insert -- $(R3)_2N$ --, therefor.

Column 112, Line 43, In Claim 1, delete "-carboxyC1-C6alkyl," and insert -- carboxy C1-C6alkyl, --, therefor.

Column 113, Line 4, In Claim 1, delete "C1-C 6alkoxycarbonyl," and insert -- C1-C6alkoxycarbonyl, --, therefor.

Column 113, Line 27, In Claim 1, delete "CH2)q" and insert -- (CH2)q --, therefor.

Column 113, Line 38, In Claim 1, delete "C2-C 6alkylN(R4)" and insert -- C2-C6alkylN(R4) --, therefor.

Column 113, Line 42, In Claim 1, delete "R8-C (=NR3)—," and insert -- R8-C(=NR3)—, --, therefor.

Column 113, Line 44, In Claim 1, delete "$(CH_2)_n$-G 4," and insert -- $(CH_2)_n$-G4,--, therefor.

Column 113, Line 64, In Claim 1, delete "—(S)," and insert -- $—(S)_r$, --, therefor.

Column 113, Line 64, In Claim 1, delete "$—(CH_2)$," and insert -- $—(CH_2)_r$, --, therefor.

Signed and Sealed this
Eighth Day of November, 2011

David J. Kappos
*Director of the United States Patent and Trademark Office*

CERTIFICATE OF CORRECTION (continued)
U.S. Pat. No. 7,897,762 B2

Column 116, Line 17, In Claim 5, delete "1f" and insert -- If--, therefor.

Column 117, Line 33, In Claim 9, delete "C3-C 8alkyl," and insert -- C3-C8alkyl, --, therefor.

Column 124, Line 20, In Claim 36, delete "fluoroC1-C 6alkyl" and insert -- fluoroC1-C6alkyl --, therefor.

Column 124, Line 64, In Claim 39, delete "fluoroC1-C 6alkyl" and insert -- fluoroC1-C6alkyl --, therefor.

Column 125, Line 49, In Claim 42, delete "C3-C8alkyl" and insert -- C3-C8alkyl, --, therefor.

Column 125, Line 50, In Claim 42, delete "C3-C8carboyclyl," and insert -- C3-C8carbocyclyl, --, therefor.

Column 125, Line 50, In Claim 42, delete "Z2 substituted" and insert -- Z2-substituted --, therefor.

Column 126, Line 47, In Claim 45, delete "G1" and insert -- G1, --, therefor.

Column 127, Line 1, In Claim 45, delete "$(R^3)_2N$" and insert -- $(R3)_2N$ --, therefor.

Column 127, Line 3, In Claim 45, delete "-carboxyC1-C6alkyl," and insert -- carboxyC1-C6alkyl, --, therefor.

Column 127, Line 9, In Claim 45, delete "$(CH_2)_n$-aryl ," and insert -- $(CH_2)_n$-aryl, --, therefor.

Column 127, Line 31, In Claim 45, delete "C1-C 6alkoxycarbonyl," and insert -- C1-C6alkoxycarbonyl, --, therefor.

Column 127, Line 34, In Claim 45, delete "=0," and insert -- =O, --, therefor.

Column 127, Line 64, In Claim 45, delete "C2-C 6alkylN(R4)" and insert -- C2-C6alkylN(R4) --, therefor.

Column 127, Line 66, In Claim 45, delete "C 1-C6alkyl," and insert -- C1-C6alkyl, --, therefor.

Column 128, Line 3, In Claim 45, delete "$(CH_2)_n$-G 4," and insert -- $(CH_2)_n$-G4 , --, therefor.

Column 141, Line 16, In Claim 89, delete "2-oxo-1 ,2" and insert -- 2-oxo-1,2 --, therefor.

Column 142, Line 2, In Claim 89, delete "2-oxo-1 ,2" and insert -- 2-oxo-1,2 --, therefor.

Column 143, Line 11, In Claim 90, delete "butylisoxazol1-3-" and insert -- butylisoxazol-3- --, therefor.

CERTIFICATE OF CORRECTION (continued)
U.S. Pat. No. 7,897,762 B2

Column 145, Line 14, In Claim 90, delete "dihydropyrido[4,3-d9 pyrimidin-" and insert -- dihydropyrido[4,3-d]pyrimidin- --, therefor.

Column 145, Line 35, In Claim 90, delete "butylisoxazol1-5-" and insert -- butylisoxazol-5- --, therefor.

Column 145, Line 51, In Claim 90, delete "butylisoxazol1-5-" and insert -- butylisoxazol-5- --, therefor.

Column 146, Line 46, In Claim 91, delete "stablilizers." and insert -- stabilizers. --, therefor.

Column 146, Lines 53-54, In Claim 93, delete "stablilizers." and insert -- stabilizers. --, therefor.